(12) United States Patent
Kim et al.

(10) Patent No.: US 9,073,906 B2
(45) Date of Patent: Jul. 7, 2015

(54) SULFAMIDE DERIVATIVE HAVING AN ADAMANTYL GROUP AND ITS PHARMACEUTICALLY ACCEPTABLE SALT

(75) Inventors: Ki Young Kim, Daejeon (KR); Jin Hee Ahn, Daejeon (KR); Seung Kyu Kang, Daejeon (KR); Sang Dal Rhee, Daejeon (KR); Myung Ae Bae, Daejeon (KR); Sung Hoon Ahn, Seoul (KR); Hee Youn Kim, Daejeon (KR); Won Hoon Jung, Daejeon (KR); Nam Sook Kang, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 14/008,899

(22) PCT Filed: Mar. 30, 2012

(86) PCT No.: PCT/KR2012/002407
§ 371 (c)(1),
(2), (4) Date: Sep. 30, 2013

(87) PCT Pub. No.: WO2012/134233
PCT Pub. Date: Oct. 4, 2012

(65) Prior Publication Data
US 2014/0024636 A1     Jan. 23, 2014

(30) Foreign Application Priority Data

Mar. 31, 2011 (KR) .................. 10-2011-0029829
Jan. 13, 2012 (KR) .................. 10-2012-0004235

(51) Int. Cl.
*C07D 285/16* (2006.01)
*C07D 285/36* (2006.01)
*A61K 31/541* (2006.01)
*C07D 417/04* (2006.01)
*A61K 31/18* (2006.01)
*C07C 307/10* (2006.01)
*C07D 417/10* (2006.01)
*C07D 417/12* (2006.01)
*C07D 285/10* (2006.01)
*C07D 285/14* (2006.01)
*C07D 285/15* (2006.01)

(52) U.S. Cl.
CPC .............. *C07D 417/04* (2013.01); *A61K 31/18* (2013.01); *C07C 307/10* (2013.01); *C07D 417/10* (2013.01); *C07D 417/12* (2013.01); *C07D 285/10* (2013.01); *C07D 285/14* (2013.01); *C07D 285/15* (2013.01); *C07D 285/16* (2013.01); *C07D 285/36* (2013.01); *C07C 2103/74* (2013.01)

(58) Field of Classification Search
USPC .................. 544/5, 8; 548/126, 134; 540/542; 514/211.08, 222.5, 362
See application file for complete search history.

(56) References Cited

U.S. PATENT DOCUMENTS

| | | | |
|---|---|---|---|
| 7,842,707 | B2 | 11/2010 | Royalty et al. |
| 2005/0245534 | A1 | 11/2005 | Link et al. |

FOREIGN PATENT DOCUMENTS

| | | |
|---|---|---|
| JP | 2007-197369 A | 8/2007 |
| WO | 03/065983 A2 | 8/2003 |
| WO | 2004/033427 A1 | 4/2004 |
| WO | 2004/041264 A1 | 5/2004 |
| WO | 2004/065351 A1 | 8/2004 |
| WO | 2004/089380 A2 | 10/2004 |
| WO | 2004/089896 A1 | 10/2004 |
| WO | 2005/108359 A1 | 11/2005 |
| WO | 2005/108361 A1 | 11/2005 |
| WO | 2006/074244 A2 | 7/2006 |
| WO | 2007/057768 A2 | 5/2007 |
| WO | 2007/068330 A1 | 6/2007 |
| WO | 2008/101914 A2 | 8/2008 |
| WO | 2009/026422 A2 | 2/2009 |
| WO | 2011/044370 A1 | 4/2011 |

OTHER PUBLICATIONS

Se Hoan Kim, et al; "Synthesis and Biological Evaluation of Cyclic Sulfamide Derivatives as 11β-Hydroxysteroid Dehydrogenase 1 Inhibitors", ACS Medicinal Chemistry Letters, 2012, vol. 3, Jan. 17, 2012; pp. 88-93.
International Search Report mailed Nov. 12, 2012; PCT/KR2012/002407.

*Primary Examiner* — Kahsay Habte
(74) *Attorney, Agent, or Firm* — Ladas & Parry LLP

(57) ABSTRACT

Provided is a sulfamide derivative having an adamantyl group represented by the following Formula 1, or a pharmaceutically acceptable salt thereof. The sulfamide derivative suppresses the activity of 11β-hydroxysteroid dehydrogenase type 1 (11β-HSD1), and is useful in the treatment of various diseases that are mediated by 11β-HSD1.

Chemical Formula I

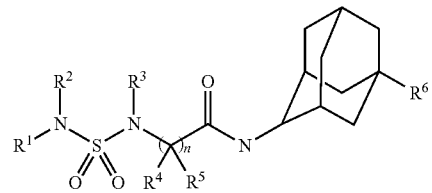

8 Claims, No Drawings

SULFAMIDE DERIVATIVE HAVING AN ADAMANTYL GROUP AND ITS PHARMACEUTICALLY ACCEPTABLE SALT

FIELD OF THE INVENTION

The present invention relates to a sulfamide derivative having an adamantyl group, its pharmaceutically acceptable salt and a pharmaceutical composition comprising the same.

DESCRIPTION OF THE RELATED ART

Recently, patients with obesity, dysglycemia, hypertension, hyperlipidemia and metabolic syndrome implicated with two or more of the risk factors are being increased over the world. Such symptoms are characterized by obesity, particularly visceral obesity, type 2 diabetes, hyperlipidemia, hypertension, atherosclerosis, coronary artery heart disease, chronic kidney failure (C. T. Montague et. al., Diabetes, 49:883-888 (2000)).

Glucocorticoid and 11β-HSD1 (11β-hydroxysteroid dehydrogenase type 1) was reported to play a crucial role in differentiation of adipose stromal cells to mature adipocytes. The level of 11β-HSD1 mRNA in visceral stromal cells of obesity patients was observed to be higher than that in subcutaneous tissue. In addition, transgenic mice overexpressing 11β-HSD1 in adipose showed that 11β-HSD1 was implicated in visceral obesity, insulin resistance, type 2 diabetes, hyperlipidemia and increased level of corticosterone in bulimia (H. Masuzaki et. al., Science, 294:2166-2170 (2001)). Therefore, 11β-HSD1 was suggested to be involved in visceral obesity and metabolic syndrome development.

Cortisol as glucocorticoid hormone binds to glucocorticoid receptor with higher affinity and activates transcription of various genes, thereby decreasing insulin secretion to cause impairment of insulin signaling, triggering gluconeogenesis in liver and increasing differentiation to adipocytes, finally leading to development of various metabolic diseases such as diabetes.

Hydroxysteroid dehydrogenase (HSDs) includes a multitude of isoforms and catalyzes to convert steroid hormones to their inactive metabolites, controlling prevalence and activation of steroid hormones (Nobel et al., Eur. J. Biochem., 268:4113-4125 (2001)).

11β-HSD1 is an enzyme to convert cortisone to cortisol and 11β-HSD2 to convert cortisol to cortisone.

The isoform 1, 11β-HSD1 is ubiquitously expressed in liver, adipose tissue, brain, lung and other glucocorticoid tissues and the isoform 2, 11β-HSD2 is restrictively expressed in tissues expressing mineralocorticoid receptor such as kidney, intestine and placenta. The inhibition of 11β-HSD2 is likely to induce serious adverse effects such as hypertension.

The inhibition of 11β-HSD1 decreases differentiation but increases proliferation of adipose stromal cells. Furthermore, glucocorticoid deficiency (adrenalectomy) leads to enhance potential of insulin and leptin which promotes anorexia and weight loss, and such effects are reverted by administration of glucocorticoid (P. M. Stewart et. al., Trends Endocrin. Metabol, 13:94-96 (2002)).

The excess cortisol is associated with many disorders including diabetes, obesity, dyslipidemia, insulin resistance and hypertension. The administration of 11β-HSD1 inhibitor decreases cortisol and other 11β-hydroxysteroids in target tissues, such that the effects from excess cortisol and 11β-hydroxysteroids are suppressed. In this regard, 11β-HSD1 is understood as a promising therapeutic target for various disorders to be ameliorated by decrease of glucocorticoid effects, and the inhibition of 11β-HSD1 is useful in prevention or treatment of diseases such as diabetes, hypertension and dyslipidemia mediated by abnormal high level of cortisol and other 11β-hydroxysteroids. Furthermore, the inhibition of the 11β-HSD1 activity in brain is useful in treatment or amelioration of anxiety, depression, cognitive impairment and age-related cognitive impairment (Seckl, et al., Endocrinology, 142:1371-1376 (2001)).

Cortisol as anti-inflammatory hormones acts as antagonists to insulin action in liver by decreasing insulin sensitivity, contributing to elevation of glucose level in liver and promotion of gluconeogenesis. The patients with impaired glucose tolerance are very likely to develop type 2 diabetes in the presence of abnormal high-level cortisol (Long et al., J. Exp. Med., 63:465-490 (1936); Houssay, Endocrinology, 30:884-892 (1942)). Furthermore, 11β-HSD1 was well proven to play a crucial role in control of glucose biosynthesis in liver and local glucocorticoid effects (Jamieson et al., J. Endocrinol., 165: 685-692 (2000)). Walker, et al (J. Clin. Endocrinol. Metab., 80: 3155-3159 (1995)) reported that carbenoxolone as non-specific 11β-HSD1 inhibitors improved liver insulin sensitivity of human.

In addition, the estimated action mechanism of 11β-HSD1 for diabetes therapy was further supported by animal experiments using mice and rats. These research results showed that the activity and mRNA level of PEPCK (phosphoenolpyruvate carboxykinase) G6Pase (glucose-6-phosphatase) were reduced by administration of 11β-HSD1 inhibitors. Blood glucose level and liver glucose synthesis were shown to be decreased in 11β-HSD1 knock-out mouse. The collected data from the 11β-HSD1 knock-out mouse demonstrated that PEPCK and G6Pase in the background level were verified to be controlled in an independent manner from glucocorticoid and therefore 11β-HSD1 inhibition were likely to induce hypoglycemia (Kotelevtsev et al., Proc. Natl. Acad. Sci., 94:14924-14929 (1997)).

Accordingly, it would be appreciated that administration of therapeutically effective amounts of 11β-HSD1 inhibitors is effective in treatment and alleviation of diabetes, inter alia, non-insulin dependent diabetes ((NIDDM, type 2 diabetes) and regular administration of therapeutically effective amounts of 11β-HSD1 inhibitors is expected to delay or prevent development of diabetes in human.

The effects caused by elevation of cortisol level may be observed in patients with Cushing's syndrome that is a metabolic disease characterized by high level cortisol in bloodstream. Patients with Cushing's syndrome are often observed to show development of NIDDM.

High level cortisol is associated with obesity through increase of gluconeogenesis in liver by cortisol. Visceral obesity is closely related to glucose resistance, diabetes, hyperinsulinemia, hypertriglyceridemia, hypertension, and other causes of metabolic syndrome such as VLDL elevation and HDL decrease (Montague et al., diabetes, 49: 883-888 (2000)). It was reported that 11β-HSD1 in pre-adipocyte (stromal cell) decreased differentiation to adipocyte probably because of reduction of omental fat depot to decrease central obesity (Bujalska et al., Lancet, 349:1210-1213 (1997)).

Accordingly, it would be understood that administration of therapeutically effective amounts of 11β-HSD1 inhibitors is effective in treatment and control of obesity diabetes and long-term administration of 11β-HSD1 inhibitors along with controlled diet and exercise is expected to delay or prevent onset of obesity.

The inhibition of 11β-HSD1 in mature adipocytes is expected to decrease secretion of plasminogen activator inhibitor 1 (PAI-1) that was reported as one of independent cardiovascular risk factors (Halleux et al., J. Clin. Endocrinol. Metab., 84: 4097-4105 (1999)). The glucocorticoid activity is likely to be correlated with a cardiovascular risk factor and therefore the reduction of the glucocorticoid effects is anticipated to be useful in prevention and treatment of cardiovascular diseases (Walker et al., Hypertension, 31:891-895 (1998); and Fraser et al., Hypertension, 33: 1364-1368 (1999)).

Hypertension and dyslipidemia cause atherosclerosis and the inhibition of the 11β-HSD1 activity and reduction of cortisol level are useful in treatment or control of hypertension. Therefore, administration of therapeutically effective amounts of 11β-HSD1 inhibitors is likely to be effective in treatment, amelioration or prevention of atherosclerosis.

11β-HSD1 involved in appetite control is also expected to show supplementary action in weight-related disorders. Adrenalectomy decreases effects of fasting by increasing both food intake and expression of thalamus neuropeptide Y, addressing that 11β-HSD1 inhibition in brain is suggested to increase a feeling of fullness and decrease food intake since glucocorticoid promotes food intake (Woods et al., Science, 280:1378-1383 (1998)).

Another therapeutic effect accomplished by adjustment of 11β-HSD1 is one related to various pancreatic aliments. It was suggested that 11β-HSD1 inhibition in mouse pancreatic β-cells increased glucose-stimulated insulin secretion (Davani et al., J. Biol. Chem., 275:34841-34844 (2000)), which is coincided with results of previous reports (Billaudel et al., Horm. Metab. Res., 11: 555-560 (1979)). Accordingly, 11β-HSD1 inhibition may exhibit advantageous effects on diabetes therapy as well as fat reduction and efficacies in liver.

The excessive amounts of cortisol in brain may induce neuron loss and function impairment by potentiation of neurotoxins. The administration of effective amounts of 11β-HSD1 inhibitors may alleviate, ameliorate or prevent age-related cognitive impairment and neuron functional impairment. Cognitive impairment is related with senescence and excessive amounts of cortisol in brain (J. R. Seckl and B. R. Walker, Endocrinology, 142:1371-1376 (2001), and references cited herein). 11β-HSD1 adjusts activities of glucocorticoid in brain and therefore contributes to neurotoxins (Rajan et al., Neuroscience, 16:65-70 (1996); Seckl et al., Necroendocrinol., 18:49-99 (2000)). Stress and/or glucocorticoid affects cognitive function (de Quervain et al., Nature, 394: 787-790 (1998)) and rats treated with non-specific 11β-HSD1 inhibitors were revealed to show significantly improved memory ability. Such reports together with well-known glucocorticoid effects in brain urge us to reason that 11β-HSD1 inhibition in brain may lead to therapeutic effects in anxiety, depression and other similar disorders (Tronche et al., Nature Genetics, 23:99-103 (1999)). 11β-HSD1 inactivates 11-dihydro corticosterone into corticosterone in hippocampous cells and increases kinase neurotoxicity, thereby being responsible for age-related learning impairment. Accordingly, selective inhibitors to 11β-HSD1 may suppress decrease in hippocampous functions upon aging (Yau et al., Proc. Natl. Acad. Sci. USA, 98:4716-4721 (2001)). In this regard, 11β-HSD1 inhibition in human brain may ameliorate glucocorticoid-mediated adverse effects on neuron functions such as cognitive impairment, depression and appetite increase.

Furthermore, 11β-HSD1 is expected to exhibit immuno-modulatory actions based on well-known knowledge that glucocorticoid suppresses the immune system.

There is a dynamic interaction between the immune system and HPA (hypothalamic-pituitary-adrenal) axis (Rook, Baillier's Clin. Endocrinol. Metab., 13: 576-581 (2000)). Glucocorticoid contributes to balance between humoral and cell-mediated immune reactions. The elevation of glucocorticoid activity induced by stress is related with humoral reactions and 11β-HSD1 inhibition may stimulate immune reaction toward cell-mediated immune reactions. Higher glucocorticoid activity in certain disease conditions such as tuberculosis, laprosy and psoriasis or excessive stress conditions shifts the immune reaction toward cell-mediated reactions, and at this time the cell-mediated reactions may be advantageous on patients. 11β-HSD1 inhibition and additional glucocorticoid level reduction shifts the immune reaction toward cell-mediated reactions in another aspects (D. Mason, Immunology Today, 12: 57-60 (1991), and G. A. Vt. Rook, Baillier's Clin. Endocrinol. Metab., 13: 576-581 (1999)). The 11β-HSD1 inhibition approach as alternative therapy may supplement temporary immune reactions related with immunization to secure occurrence of cell-mediated immune reactions.

The levels of glucocorticoid target receptor and HSD are related with susceptibility to glaucoma (J. Stokes et al., Invest. Ophthalmol., 41: 1629-1638 (2000)). Furthermore, the correlation between 11β-HSD1 inhibition and intraocular pressure was reported (Walker et al., poster P3-698 at the Endocrine society meeting Jun. 12-15, 1999, San Diego). The administration of carbenoxolone as non-specific 11β-HSD1 inhibitors was shown to decrease intraocular pressure in 20% of patients. 11β-HSD1 in eye is expressed in cells of corneal epithelium, corneal non-pigmented epithelium (region of generation of aqueous humour), ciliaris muscle, and sphincter muscle and dilator muscle of iris. Unlikely, the distant isoenzyme, 11β-HSD is highly expressed in non-pigmented ciliary epithelium and corneal endothelium. Any isoform of 11β-HSDs are not found in trabecular meshwork that is responsible for draining the aqueous humor. Therefore, 11β-HSD1 may be involved in generation of aqueous humour and its inhibition may be useful in decrease of intraocular pressure for glaucoma treatment.

Glucocorticoid plays a crucial role in skeleton development and function but its excessive level is disadvantageous over skeleton development and function. Glucocorticoid-induced bone loss is due partly to suppression of osteoblast proliferation and collagen biosynthesis (C. H. Kim et al., J. Endocrinol., 162:371 379 (1999)). The deleterious effects of glucocorticoid on formation of bone nodule was reported to be reduced by administration of carbenoxolone as non-specific 11β-HSD1 inhibitors (C. G. Bellows et al., Bone, 23:119-125 (1998)). Furthermore, it was suggested that 11β-HSD1 could induce higher glucocorticoid level in osteoclasts to enhance bone resorption (M. S. Cooper et al., Bone, 27:375-381 (2000)). Such research results address that the inhibition of 11β-HSD1 exert advantageous effects on osteoporosis through at least one action mechanism.

11β-HSD1 inhibitors were disclosed, for example, in WO2007/057768, WO2005/108359, WO2009/026422 JP2007197369, WO2005/108361, WO2007/068330, WO0410629, WO03065983, WO04089896, WO04089380, WO04065351, WO04033427, WO04041264, US2005/02405534, WO025108359, WO2006/074244, WO2005/108359, WO2008/101914 and WO2009/026422. However, sulfamide derivatives having an adamantyl group have not been reported yet as 11β-HSD1 inhibitors.

Throughout this application, various patents and publications are referenced and citations are provided in parentheses. The disclosure of these patents and publications in their entities are hereby incorporated by references into this application in order to more fully describe this invention and the state of the art to which this invention pertains.

Technical Problems to be Solved

The present inventors have made intensive researches to develop novel therapeutics to effectively treat various diseases relating to 11β-HSD1 (11β-hydroxysteroid dehydrogenase type 1). As a result, we have found that novel sulfamide derivatives having an adamantyl group have excellent inhibitory activities to 11β-HSD1.

Accordingly, it is an object of this invention to provide a novel sulfamide derivative having an adamantyl group or its pharmaceutically acceptable salt.

It is another object of this invention to provide an inhibitory agent to 11β-HSD1.

It is still another object of this invention to provide a pharmaceutical composition for preventing or treating a 11β-HSD1-related disease.

It is further object of this invention to provide a method for preventing or treating a 11β-HSD1-related disease.

Other objects and advantages of the present invention will become apparent from the detailed description to follow taken in conjugation with the appended claims and drawings.

DETAILED DESCRIPTION OF THIS INVENTION

In one aspect of the present invention, there is provided a sulfamide derivative having an adamantyl group represented by the following Formula 1, or its pharmaceutically acceptable salt:

Chemical Formula 1

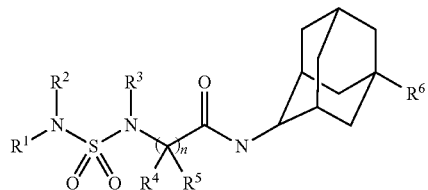

wherein $R^1$ represents H; $C_1$-$C_6$ alkyl; cyano $C_1$-$C_6$ alkyl, $C_3$-$C_8$ cycloalkyl; benzyl unsubstituted or substituted with halogen, $C_1$-$C_6$ alkyl or $OCX_3$ (X is halogen); phenylethyl; $C_1$-$C_6$ alkoxycarbonyl; phenylacetyl; naphthyl; or 5-10 membered aryl substituted with halogen, $C_1$-$C_6$ alkyl, $C_3$-$C_8$ cycloalkyl, $C_1$-$C_6$ alkoxy, $CX_3$ (X is halogen), $OCX_3$ (X is halogen), cyano, nitro, or 5-10 membered aryl or heteroaryl; $R^2$ and $R^3$ independently represent $C_1$-$C_6$ alkyl; or $C_2$-$C_6$ alkenyl; with the proviso that $R^2$ and $R^3$ bind together to form a ring structure, the ring structure is

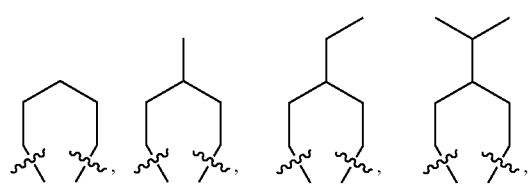

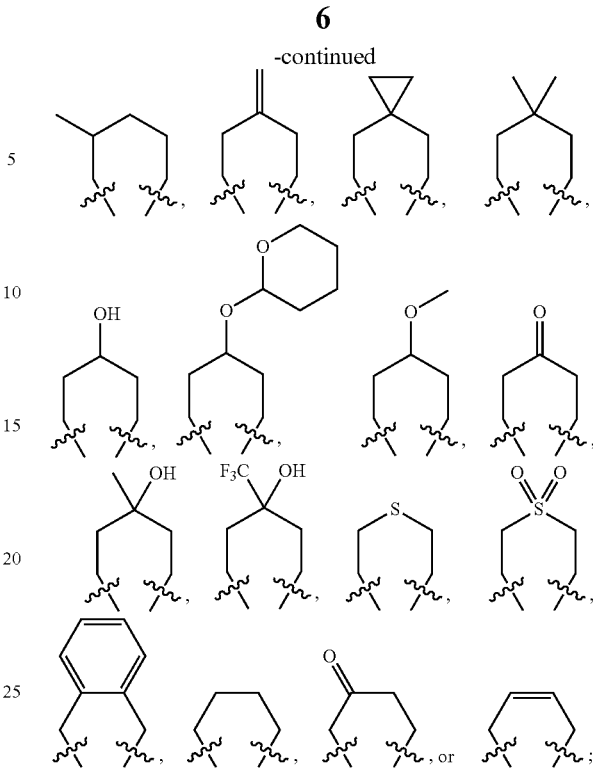

$R^4$ and $R^5$ independently represent H; or $C_1$-$C_6$ alkyl; $R^6$ represents H; OH; $COOR^7$; or $CONR^7R^7$; $R^7$ represents H; or $C_1$-$C_6$ alkyl; and n represents an integer of 1-3.

The present inventors have made intensive researches to develop novel therapeutics to effectively treat various diseases relating to 11β-HSD1. As a result, we have found that novel sulfamide derivatives having an adamantyl group have excellent inhibitory activities to 11β-HSD1.

The compound of the Formula 1 effectively inhibits 11β-HSD1 involved in the production of cortisol as one of glucocorticoid hormones that decreases insulin secretion, causes gluconeogenesis in liver and increase differentiation of adipocytes. Therefore, the compound of the present invention is useful in prevention or treatment of 11β-HSD1-related diseases such as insulin resistance-related metabolic syndromes and obesity.

The term used herein "alkyl" means a linear or branched, saturated hydrocarbon group and includes, for example, methyl, ethyl, propyl, isobutyl, pentyl and hexyl. $C_1$-$C_6$ alkyl means an alkyl group having an alkyl unit of 1 to 6 carbons, excluding the number of carbons of a substituent when the $C_1$-$C_6$ alkyl is substituted. In Formula 1, $C_1$-$C_6$ alkyl at $R^1$ is preferably $C_1$-$C_4$ alkyl, more preferably $C_1$-$C_2$ alkyl.

As used herein, the term "halogen" refers to a halogen element and includes, for example, fluoro, chloro, bromo and iodo.

The term "alkenyl" refers to linear or branched, unsaturated hydrocarbon group having given number of carbons and includes, for example, for example, ethenyl, vinyl, propenyl, allyl, isopropenyl, butenyl, isobutenyl, t-butenyl, n-pentenyl and n-hexenyl. In Formula 1, $C_2$-$C_6$ alkenyl at $R^2$ or $R^3$ means an alkenyl group having an alkenyl unit of 2 to 6 carbons, excluding the number of carbons of a substituent when the $C_2$-$C_6$ alkenyl is substituted.

The term "aryl" refers to a substituted or unsubstituted, monocyclic or polycyclic carbon ring which is entirely or partially unsaturated.

The term "heteroaryl" refers to a heterocyclic aromatic group which contains oxygen, sulfur or nitrogen as a heteroatom. The number of the heteroatom is 1-4, preferably 1-2. In the heteroaryl, the aryl may be specifically monoaryl or biaryl.

The term used herein "alkoxy" means a radical formed by removing hydrogen from alcohol. Where $C_1$-$C_6$ alkoxy is substituted, the number of carbons of a substituent is excluded.

According to a preferred embodiment, $R^1$ in Formula 1 represents phenyl or naphthalene group substituted with halogen, $C_1$-$C_6$ alkyl or $CF_3$, $OCF_3$, cyano, nitro, or 5-10 membered aryl or heteroaryl; n represents an integer of 1.

More preferably, the derivative represented by the Formula 1 is selected from the group consisting of:

(1) N-(adamantan-2-yl)-2-(1,1-dioxido-6-(2-oxo-2-phenylethyl)-1,2,6-thiadiazinan-2-yl)acetamide;
(2) N-(adamantan-2-yl)-2-(1,1-dioxido-6-phenyl-1,2,6-thiadiazinan-2-yl)acetamide;
(3) tert-butyl 6-(2-(adamantan-2-ylamino)-2-oxoethyl)-1,2,6-thiadiazinan-2-carboxylate-1,1-dioxide;
(4) N-(adamantan-2-yl)-2-(1,1-dioxido-1,2,6-thiadiazinan-2-yl)acetamide hydrochloride;
(5) N-(adamantan-2-yl)-2-(6-benzyl-1,1-dioxido-1,2,6-thiadiazinan-2-yl)acetamide;
(6) N-(adamantan-2-yl)-2-(6-(4-fluorobenzyl)-1,1-dioxido-1,2,6-thiadiazinan-2-yl)acetamide;
(7) N-(adamantan-2-yl)-2-(1,1-dioxido-6-(4-(trifluoromethoxy)benzyl)-1,2,6-thiadiazinan-2-yl)acetamide;
(8) N-(adamantan-2-yl)-2-(6-(4-chlorobenzyl)-1,1-dioxido-1,2,6-thiadiazinan-2-yl)acetamide;
(9) N-(adamantan-2-yl)-2-(6-(3-methylbenzyl)-1,1-dioxido-1,2,6-thiadiazinan-2-yl)acetamide;
(10) N-(adamantan-2-yl)-2-(6-(3-chlorobenzyl)-1,1-dioxido-1,2,6-thiadiazinan-2-yl)acetamide;
(11) N-(adamantan-2-yl)-2-(6-(3-fluorobenzyl)-1,1-dioxido-1,2,6-thiadiazinan-2-yl)acetamide;
(12) N-(adamantan-2-yl)-2-(6-(3-methoxybenzyl)-1,1-dioxido-1,2,6-thiadiazinan-2-yl)acetamide;
(13) N-(adamantan-2-yl)-2-(6-(2-chlorobenzyl)-1,1-dioxido-1,2,6-thiadiazinan-2-yl)acetamide;
(14) N-(adamantan-2-yl)-2-(6-(2-fluorobenzyl)-1,1-dioxido-1,2,6-thiadiazinan-2-yl)acetamide;
(15) N-(adamantan-2-yl)-2-(1,1-dioxido-6-phenethyl-1,2,6-thiadiazinan-2-yl)acetamide;
(16) N-(adamantan-2-yl)-2-(6-(3-fluorophenyl)-1,1-dioxido-1,2,6-thiadiazinan-2-yl)acetamide;
(17) N-(adamantan-2-yl)-2-(6-(3-chlorophenyl)-1,1-dioxido-1,2,6-thiadiazinan-2-yl)acetamide;
(18) N-(adamantan-2-yl)-2-(6-(4-fluorophenyl)-1,1-dioxido-1,2,6-thiadiazinan-2-yl)acetamide;
(19) N-(adamantan-2-yl)-2-(6-(4-chlorophenyl)-1,1-dioxido-1,2,6-thiadiazinan-2-yl)acetamide;
(20) N-(adamantan-2-yl)-2-(6-(4-methoxyphenyl)-1,1-dioxido-1,2,6-thiadiazinan-2-yl)acetamide;
(21) N-(adamantan-2-yl)-2-(6-(3-methoxyphenyl)-1,1-dioxido-1,2,6-thiadiazinan-2-yl)acetamide;
(22) N-(adamantan-2-yl)-2-(6-(2-fluorophenyl)-1,1-dioxido-1,2,6-thiadiazinan-2-yl)acetamide;
(23) N-(adamantan-2-yl)-2-(6-(3,4-dichlorophenyl)-1,1-dioxido-1,2,6-thiadiazinan-2-yl)acetamide;
(24) N-(adamantan-2-yl)-2-(1,1-dioxido-6-(p-tolyl)-1,2,6-thiadiazinan-2-yl)acetamide;
(25) N-(adamantan-2-yl)-2-(1,1-dioxido-5-phenyl-1,2,5-thiadiazolidin-2-yl)acetamide;
(26) N-(adamantan-2-yl)-2-(6-methyl-1,1-dioxido-1,2,6-thiadiazinan-2-yl)acetamide;
(27) N-(adamantan-2-yl)-2-(6-(4-chlorophenyl)-1,1-dioxido-1,2,6-thiadiazinan-2-yl)acetamide;
(28) Methyl-4-(2-(6-(4-chlorophenyl)-1,1-dioxido-1,2,6-thiadiazinan-2-yl) acetamido)adamantan-1-carboxylate;
(29) 4-(2-(6-(4-chlorophenyl)-1,1-dioxido-1,2,6-thiadiazinan-2-yl)acetamido) adamantan-1-carboxylic acid;
(30) N-(adamantan-2-yl)-2-(1,1-dioxido-6-(4-(trifluoromethyl)phenyl)-1,2,6-thiadiazinan-2-yl)acetamide;
(31) N-(adamantan-2-yl)-2-(6-(4-cyanophenyl)-1,1-dioxido-1,2,6-thiadiazinan-2-yl)acetamide;
(32) N-(adamantan-2-yl)-2-(6-(naphthalene-2-yl)-1,1-dioxido-1,2,6-thiadiazinan-2-yl)acetamide;
(33) Methyl-4-(2-(1,1-dioxido-6-phenyl-1,2,6-thiadiazinan-2-yl)acetamido)adamantan-1-carboxylate;
(34) 4-(2-(6-(4-chlorophenyl)-1,1-dioxido-1,2,6-thiadiazinan-2-yl)acetamido)adamantan-1-carboxamide;
(35) N-(adamantan-2-yl)-2-(6-cyclohexyl-1,1-dioxido-1,2,6-thiadiazinan-2-yl)acetamide;
(36) 4-(2-(1,1-dioxido-6-phenyl-1,2,6-thiadiazinan-2-yl)acetamido)adamantan-1-carboxylic acid;
(37) 2-(6-(4-chlorophenyl)-1,1-dioxido-1,2,6-thiadiazinan-2-yl)-N-(5-hydroxyadamantan-2-yl)acetamide;
(38) 2-(1,1-dioxido-6-phenyl-1,2,6-thiadiazinan-2-yl)-N-(5-hydroxyadamantan-2-yl)acetamide;
(39) 2-(1,1-dioxido-6-phenyl-1,2,6-thiadiazinan-2-yl)-N-(5-hydroxyadamantan-2-yl)acetamide;
(40) 2-(6-(4-fluorophenyl)-1,1-dioxido-1,2,6-thiadiazinan-2-yl)-N-(5-hydroxyadamantan-2-yl)acetamide;
(41) 2-(6-(2-fluorophenyl)-1,1-dioxido-1,2,6-thiadiazinan-2-yl)-N-(5-hydroxyadamantan-2-yl)acetamide;
(42) 4-(2-(6-(2-fluorophenyl)-1,1-dioxido-1,2,6-thiadiazinan-2-yl)acetamido)adamantan-1-carboxamide;
(43) 4-(2-(6-(2-fluorophenyl)-1,1-dioxido-1,2,6-thiadiazinan-2-yl)acetamido)adamantan-1-carboxamide;
(44) 4-(2-(6-(4-fluorophenyl)-1,1-dioxido-1,2,6-thiadiazinan-2-yl)acetamido)adamantan-1-carboxamide;
(45) 4-(2-(6-(4-fluorophenyl)-1,1-dioxido-1,2,6-thiadiazinan-2-yl)acetamido)adamantan-1-carboxamide;
(46) 2-(6-(3,4-dichlorophenyl)-1,1-dioxido-1,2,6-thiadiazinan-2-yl)-N-(5-hydroxyadamantan-2-yl)acetamide;
(47) 2-(6-(3-chlorophenyl)-1,1-dioxido-1,2,6-thiadiazinan-2-yl)-N-(5-hydroxyadamantan-2-yl)acetamide;
(48) N-(adamantan-2-yl)-2-(6-ethyl-1,1-dioxido-1,2,6-thiadiazinan-2-yl)acetamide;
(49) 4-(2-(6-(3,4-dichlorophenyl)-1,1-dioxido-1,2,6-thiadiazinan-2-yl)-acetamido)adamantan-1-carboxamide;
(50) 4-(2-(6-(3,4-dichlorophenyl)-1,1-dioxido-1,2,6-thiadiazinan-2-yl)-acetamido)adamantan-1-carboxamide;
(51) N-(adamantan-2-yl)-2-(1,1-dioxido-6-(prop-2-yn-1-yl)-1,2,6-thiadiazinan-2-yl)acetamide;
(52) 4-(2-(6-(3-methoxyphenyl)-1,1-dioxido-1,2,6-thiadiazinan-2-yl)-acetamido)adamantan-1-carboxamide;
(53) 4-(2-(6-(3-methoxyphenyl)-1,1-dioxido-1,2,6-thiadiazinan-2-yl)-acetamido)adamantan-1-carboxamide;
(54) 4-(2-(1,1-dioxido-6-(p-tolyl)-1,2,6-thiadiazinan-2-yl) acetamido)adamantan-1-carboxamide;
(55) 4-(2-(1,1-dioxido-6-(p-tolyl)-1,2,6-thiadiazinan-2-yl) acetamido)adamantan-1-carboxamide;
(56) 4-(2-(6-(3-chlorophenyl)-1,1-dioxido-1,2,6-thiadiazinan-2-yl)-acetamido)adamantan-1-carboxamide;
(57) N-(5-hydroxyadamantan-2-yl)-2-(6-(napthalene-2-yl)-1,1-dioxido-1,2,6-thiadiazinan-2-yl)acetamide;
(58) 2-(6-(4-cyanophenyl)-1,1-dioxido-1,2,6-thiadiazinan-2-yl)-N-(5-hydroxyadamantan-2-yl)acetamide;
(59) 4-(2-(6-(2-fluorophenyl)-1,1-dioxido-1,2,6-thiadiazinan-2-yl)-acetamido)adamantan-1-carboxamide;

(60) 4-(2-(1,1-dioxido-6-phenyl-1,2,6-thiadiazinan-2-yl)acetamido)adamantan-1-carboxamide;
(61) 4-(2-(1,1-dioxido-5-phenyl-1,2,5-thiadiazolidin-2-yl)acetamido)adamantan-1-carboxamide;
(62) 4-(2-(1,1-dioxido-6-(4-trifluoromethyl)phenyl-1,2,6-thiadiazinan-2-yl)acetamido)adamantan-1-carboxamide;
(63) 4-(2-(6-(napthalene-2-yl)-1,1-dioxido-1,2,6-thiadiazinan-2-yl)acetamido)adamantan-1-carboxamide;
(64) 4-(2-(5-(2-fluorophenyl)-1,1-dioxido-1,2,5-thiadiazolidin-2-yl)acetamido)adamantan-1-carboxamide;
(65) 4-(2-(5-(2-chlorophenyl)-1,1-dioxido-1,2,5-thiadiazolidin-2-yl)acetamido)adamantan-1-carboxamide;
(66) 4-(2-(5-(4-fluorophenyl)-1,1-dioxido-1,2,5-thiadiazolidin-2-yl)acetamido)adamantan-1-carboxamide;
(67) N-(adamantan-2-yl)-2-(5-(2-chlorophenyl)-1,1-dioxido-1,2,5-thiadiazolidin-2-yl)acetamide;
(68) N-(adamantan-2-yl)-2-(5-(4-fluorophenyl)-1,1-dioxido-1,2,5-thiadiazolidin-2-yl)acetamide;
(69) 4-(2-(6-(3-fluorophenyl)-1,1-dioxido-1,2,6-thiadiazinan-2-yl)acetamido)adamantan-1-carboxamide;
(70) 4-(2-(6-(4-methoxyphenyl)-1,1-dioxido-1,2,6-thiadiazinan-2-yl)acetamido)adamantan-1-carboxamide;
(71) 4-(2-(6-(4-cyanophenyl)-1,1-dioxido-1,2,6-thiadiazinan-2-yl)acetamido)adamantan-1-carboxamide;
(72) 4-(2-(6-(4-chlorophenyl)-1,1-dioxido-1,2,6-thiadiazinan-2-yl)propaneamido)adamantan-1-carboxamide;
(73) 4-(2-(6-(4-chloronaphthalene-1-yl)-1,1-dioxido-1,2,6-thiadiazinan-2-yl)acetamido)adamantan-1-carboxamide;
(74) 4-(2-(6-(3,4-dichlorophenyl)-1,1-dioxido-1,2,6-thiadiazinan-2-yl)propaneamido)adamantan-1-carboxamide;
(75) 4-(2-(6-(2,4-difluorophenyl)-1,1-dioxido-1,2,6-thiadiazinan-2-yl)acetamido)adamantan-1-carboxamide;
(76) 4-(2-(6-(3,4-difluorophenyl)-1,1-dioxido-1,2,6-thiadiazinan-2-yl)acetamido)adamantan-1-carboxamide;
(77) 4-(2-(1,1-dioxido-5-(o-tolyl)-1,2,5-thiadiazolidin-2-yl)acetamido)adamantan-1-carboxamide;
(78) 4-(2-(5-(benzo[d][1,3]dioxol-5-yl)-1,1-dioxido-1,2,5-thiadiazolidin-2-yl)acetamido)adamantan-1-carboxamide;
(79) 4-(2-(6-(3,4-difluorophenyl)-1,1-dioxido-1,2,6-thiadiazinan-2-yl)propaneamido)adamantan-1-carboxamide;
(80) 4-(2-(6-(2,4-difluorophenyl)-1,1-dioxido-1,2,6-thiadiazinan-2-yl)propaneamido)adamantan-1-carboxamide;
(81) 4-(2-(6-(benzo[d][1,3]dioxol-5-yl)-1,1-dioxido-1,2,6-thiadiazinan-2-yl)acetamido)adamantan-1-carboxamide;
(82) 4-(2-(6-(benzo[d][1,3]dioxol-5-yl)-1,1-dioxido-1,2,6-thiadiazinan-2-yl)propaneamido)adamantan-1-carboxamide;
(83) 4-(2-(6-(2-fluorophenyl)-1,1-dioxido-1,2,6-thiadiazinan-2-yl)acetamido)adamantan-1-carboxamide;
(84) 4-(2-(6-(2-fluorophenyl)-1,1-dioxido-1,2,6-thiadiazinan-2-yl)acetamido)adamantan-1-carboxamide;
(85) 4-(2-(6-(2,5-difluorophenyl)-1,1-dioxido-1,2,6-thiadiazinan-2-yl)acetamido) adamantan-1-carboxamide;
(86) 4-(2-(6-(2,5-difluorophenyl)-1,1-dioxido-1,2,6-thiadiazinan-2-yl)acetamido) adamantan-1-carboxamide;
(87) 4-(2-(1,1-dioxido-6-(2,4,6-trichlorophenyl)-1,2,6-thiadiazinan-2-yl)acetamido)adamantan-1-carboxamide;
(88) 4-(2-(1,1-dioxido-6-(2,4,6-trichlorophenyl)-1,2,6-thiadiazinan-2-yl)acetamido)adamantan-1-carboxamide;
(89) 4-(2-(1,1-dioxido-6-(2,4,6-trifluorophenyl)-1,2,6-thiadiazinan-2-yl)acetamido)adamantan-1-carboxamide;
(90) 4-(2-(1,1-dioxido-6-(2,4,6-trifluorophenyl)-1,2,6-thiadiazinan-2-yl)acetamido)adamantan-1-carboxamide;
(91) 4-(2-(6-(2-chlorophenyl)-1,1-dioxido-1,2,6-thiadiazinan-2-yl)acetamido)adamantan-1-carboxamide;
(92) 4-(2-(6-(2-chlorophenyl)-1,1-dioxido-1,2,6-thiadiazinan-2-yl)acetamido)adamantan-1-carboxamide;
(93) 4-(2-(6-(2-fluorophenyl)-1,1-dioxido-1,2,6-thiadiazinan-2-yl)propaneamido)adamantan-1-carboxamide;
(94) 4-(2-(6-(2-fluorophenyl)-1,1-dioxido-1,2,6-thiadiazinan-2-yl)propaneamido)adamantan-1-carboxamide;
(95) 4-(2-(6-(2-bromophenyl)-1,1-dioxido-1,2,6-thiadiazinan-2-yl)acetamido)adamantan-1-carboxamide;
(96) 4-(2-(1,1-dioxido-6-(2,4,5-trifluorophenyl)-1,2,6-thiadiazinan-2-yl)acetamido)adamantan-1-carboxamide;
(97) 4-(2-(6-(2-fluorophenyl)-1,1-dioxido-1,2,6-thiadiazinan-2-yl)methylpropaneamido)adamantan-1-carboxamide;
(98) 4-(2-(6-(2-fluorophenyl)-1,1-dioxido-1,2,6-thiadiazinan-2-yl)methylpropaneamido)adamantan-1-carboxamide;
(99) 4-(2-(6-(2,5-dichlorophenyl)-1,1-dioxido-1,2,6-thiadiazinan-2-yl)acetamido)adamantan-1-carboxamide;
(100) 4-(2-(1,1-dioxido-6-(2,4,5-trichlorophenyl)-1,2,6-thiadiazinan-2-yl)acetamido)adamantan-1-carboxamide;
(101) 4-(2-(1,1-dioxido-6-(2,4,5-trichlorophenyl)-1,2,6-thiadiazinan-2-yl)acetamido)adamantan-1-carboxamide;
(102) 4-(2-(6-(2,6-difluorophenyl)-1,1-dioxido-1,2,6-thiadiazinan-2-yl)acetamido)adamantan-1-carboxamide;
(103) 4-(2-(6-(2,6-difluorophenyl)-1,1-dioxido-1,2,6-thiadiazinan-2-yl)acetamido)adamantan-1-carboxamide;
(104) 4-(2-(6-(2-chloro-4-fluorophenyl)-1,1-dioxido-1,2,6-thiadiazinan-2-yl)acetamido)adamantan-1-carboxamide;
(105) 4-(2-(6-(4-chloro-2-fluorophenyl)-1,1-dioxido-1,2,6-thiadiazinan-2-yl)acetamido)adamantan-1-carboxamide;
(106) 4-(2-(6-(4-chloro-2-fluorophenyl)-1,1-dioxido-1,2,6-thiadiazinan-2-yl)acetamido)adamantan-1-carboxamide;
(107) 4-(2-(6-(2,5-dichlorophenyl)-1,1-dioxido-1,2,6-thiadiazinan-2-yl)acetamido)adamantan-1-carboxamide;
(108) 4-(2-(6-(2-bromophenyl)-1,1-dioxido-1,2,6-thiadiazinan-2-yl)acetamido)adamantan-1-carboxamide;
(109) 4-(2-(1,1-dioxido-6-(2,4,5-trifluorophenyl)-1,2,6-thiadiazinan-2-yl)acetamido)adamantan-1-carboxamide;
(110) 4-(2-(6-(2-chloro-4-fluorophenyl)-1,1-dioxido-1,2,6-thiadiazinan-2-yl)acetamido)adamantan-1-carboxamide;
(111) 4-(2-(1,1-dioxido-6-(2,3,5,6-tetrafluorophenyl)-1,2,6-thiadiazinan-2-yl)acetamido)adamantan-1-carboxamide;
(112) 4-(2-(1,1-dioxido-6-(2,3,5,6-tetrafluorophenyl)-1,2,6-thiadiazinan-2-yl)acetamido)adamantan-1-carboxamide;
(113) 4-(2-(6-(2,4-dichlorophenyl)-1,1-dioxido-1,2,6-thiadiazinan-2-yl)acetamido)adamantan-1-carboxamide;
(114) 4-(2-(6-(2,4-dichlorophenyl)-1,1-dioxido-1,2,6-thiadiazinan-2-yl)acetamido)adamantan-1-carboxamide;
(115) 4-(2-(6-(2-chloro-5-(trifluoromethyl)phenyl)-1,1-dioxido-1,2,6-thiadiazinan-2-yl)acetamido)adamantan-1-carboxamide;
(116) 4-(2-(6-(2-chloro-5-(trifluoromethyl)phenyl)-1,1-dioxido-1,2,6-thiadiazinan-2-yl)acetamido)adamantan-1-carboxamide;
(117) 4-(2-(6-(4-chloro-2-(trifluoromethyl)phenyl)-1,1-dioxido-1,2,6-thiadiazinan-2-yl)acetamido)adamantan-1-carboxamide;
(118) 4-(2-(6-(4-chloro-2-(trifluoromethyl)phenyl)-1,1-dioxido-1,2,6-thiadiazinan-2-yl)acetamido)adamantan-1-carboxamide;
(119) 4-(2-(6-(2,3-dichlorophenyl)-1,1-dioxido-1,2,6-thiadiazinan-2-yl)acetamido)adamantan-1-carboxamide;
(120) 4-(2-(6-(2,3-dichlorophenyl)-1,1-dioxido-1,2,6-thiadiazinan-2-yl)acetamido)adamantan-1-carboxamide;
(121) 4-(2-(6-(2,6-dichlorophenyl)-1,1-dioxido-1,2,6-thiadiazinan-2-yl)acetamido)adamantan-1-carboxamide;
(122) 4-(2-(1,1-dioxido-7-(2,4,6-trichlorophenyl)-1,2,7-thiadiazepane-2-yl)acetamido)adamantan-1-carboxamide;
(123) 4-(2-(methyl(N-methyl-N-(2,4,6-trichlorophenyl)sulfamoyl)amino)acetamido)adamantan-1-carboxamide;

(124) 4-(2-(1,1-dioxido-5-(2,4,6-trichlorophenyl)-1,2,5-thiadiazolidin-2-yl)acetamido)adamantan-1-carboxamide;
(125) 4-(2-(1,1-dioxido-5-(2,4,6-trichlorophenyl)-1,2,5-thiadiazolidin-2-yl)acetamido)adamantan-1-carboxamide;
(126) 4-(2-(ethyl(N-ethyl-N-(2,4,6-trichlorophenyl)sulfamoyl)amino)acetamido) adamantan-1-carboxamide;
(127) 4-(2-(methyl(N-methyl-N-(2,4,5-trichlorophenyl)sulfamoyl)amino)acetamido)adamantan-1-carboxamide;
(128) 4-(2-(3-methyl-1,1-dioxido-6-(2,4,6-trichlorophenyl)-1,2,6-thiadiazinan-2-yl)acetamido)adamantan-1-carboxamide;
(129) 4-(2-((N-(2-fluorophenyl)-N-methylsulfamoyl)(methyl)amino)acetamido) adamantan-1-carboxamide;
(130) 4-(2-(methyl(N-methyl-N-(2,4,6-trifluorophenyl)sulfamoyl)amino)acetamido)adamantan-1-carboxamide;
(131) 4-(2-(1,1-dioxido-6-(o-tolyl)-1,2,6-thiadiazinan-2-yl)acetamido)adamantan-1-carboxamide;
(132) 4-(2-(6-(2-ethylphenyl)-1,1-dioxido-1,2,6-thiadiazinan-2-yl)acetamido)adamantan-1-carboxamide;
(133) 4-(2-(6-(3-chloro-2-methylphenyl)-1,1-dioxido-1,2,6-thiadiazinan-2-yl)acetamido)adamantan-1-carboxamide;
(134) 4-(2-(6-(4-chloro-2-methylphenyl)-1,1-dioxido-1,2,6-thiadiazinan-2-yl)acetamido)adamantan-1-carboxamide;
(135) 4-(2-(6-(3-fluoro-2-methylphenyl)-1,1-dioxido-1,2,6-thiadiazinan-2-yl)acetamido)adamantan-1-carboxamide;
(136) 4-(2-(6-(4-fluoro-2-methylphenyl)-1,1-dioxido-1,2,6-thiadiazinan-2-yl)acetamido)adamantan-1-carboxamide;
(137) 4-(2-(6-(2-fluoro-6-methylphenyl)-1,1-dioxido-1,2,6-thiadiazinan-2-yl)acetamido)adamantan-1-carboxamide;
(138) 4-(2-(6-(2,6-dichloro-3-methylphenyl)-1,1-dioxido-1,2,6-thiadiazinan-2-yl) acetamido)adamantan-1-carboxamide;
(139) 4-(2-(1,1-dioxido-6-(3,4,5-trichlorophenyl)-1,2,6-thiadiazinan-2-yl)acetamido)adamantan-1-carboxamide;
(140) 4-(2-(6-(2-chloro-4,6-dimethylphenyl)-1,1-dioxido-1,2,6-thiadiazinan-2-yl) acetamido)adamantan-1-carboxamide;
(141) 4-(2-(6-(2-fluorophenyl)-1,1-dioxido-4-((tetrahydro-2H-pyran-2-yl)oxy)-1,2,6-thiadiazinan-2-yl)acetamido)adamantan-1-carboxamide;
(142) 4-(2-(6-(2-fluorophenyl)-4-hydroxy-1,1-dioxido-1,2,6-thiadiazinan-2-yl)acetamido)adamantan-1-carboxamide;
(143) 4-(2-(6-mesityl-1,1-dioxido-1,2,6-thiadiazinan-2-yl) acetamido)adamantan-1-carboxamide;
(144) 4-(2-(6-(2,5-dimethylphenyl)-1,1-dioxido-1,2,6-thiadiazinan-2-yl)acetamido)adamantan-1-carboxamide;
(145) 4-(2-(6-(2,4-dimethylphenyl)-1,1-dioxido-1,2,6-thiadiazinan-2-yl)acetamido)adamantan-1-carboxamide;
(146) 4-(2-(6-([1,1'-biphenyl]-2-yl)-1,1-dioxido-1,2,6-thiadiazinan-2-yl)acetamido)adamantan-1-carboxamide;
(147) 4-(2-(6-(2-methoxy-6-methylphenyl)-1,1-dioxido-1,2,6-thiadiazinan-2-yl)acetamido)adamantan-1-carboxamide;
(148) 4-(2-(6-(4-methoxy-2,6-dimethylphenyl)-1,1-dioxido-1,2,6-thiadiazinan-2-yl)acetamido)adamantan-1-carboxamide;
(149) 4-(2-(6-(2-cyanophenyl)-1,1-dioxido-1,2,6-thiadiazinan-2-yl)acetamido) adamantan-1-carboxamide;
(150) 4-(2-(6-(2,6-dibromo-4-methylphenyl)-1,1-dioxido-1,2,6-thiadiazinan-2-yl)acetamido)adamantan-1-carboxamide;
(151) 4-(2-(6-(2,4-dichloro-6-methylphenyl)-1,1-dioxido-1,2,6-thiadiazinan-2-yl)acetamido)adamantan-1-carboxamide;
(152) 4-(2-(6-(4-bromo-2-chloro-6-methylphenyl)-1,1-dioxido-1,2,6-thiadiazinan-2-yl)acetamido)adamantan-1-carboxamide;
(153) 4-(2-(6-(2,4-dimethoxyphenyl)-1,1-dioxido-1,2,6-thiadiazinan-2-yl)acetamido)adamantan-1-carboxamide;
(154) 4-(2-(6-(2-acetamidophenyl)-1,1-dioxido-1,2,6-thiadiazinan-2-yl)acetamido)adamantan-1-carboxamide;
(155) 4-(2-(6-(2,3-dihydro-1H-inden-4-yl)-1,1-dioxido-1,2,6-thiadiazinan-2-yl)acetamido)adamantan-1-carboxamide;
(156) 4-(2-(4-methyl-1,1-dioxido-6-(2,4,6-trichlorophenyl)-1,2,6-thiadiazinan-2-yl)acetamido)adamantan-1-carboxamide;
(157) 4-(2-(6-(4-bromo-2,6-dimethylphenyl)-1,1-dioxido-1,2,6-thiadiazinan-2-yl)acetamido)adamantan-1-carboxamide;
(158) 4-(2-(6-(2-bromo-4,6-dimethylphenyl)-1,1-dioxido-1,2,6-thiadiazinan-2-yl)acetamido)adamantan-1-carboxamide;
(159) 4-(2-(6-(2,6-dibromo-4-fluorophenyl)-1,1-dioxido-1,2,6-thiadiazinan-2-yl)acetamido)adamantan-1-carboxamide;
(160) 4-(2-(6-(2-bromo-6-chloro-4-fluorophenyl)-1,1-dioxido-1,2,6-thiadiazinan-2-yl)acetamido)adamantan-1-carboxamide;
(161) 4-(2-(6-(2-bromo-6-chloro-4-fluorophenyl)-1,1-dioxido-1,2,6-thiadiazinan-2-yl)acetamido)adamantan-1-carboxamide;
(162) 4-(2-(1,1-dioxido-6-(2,4,6-trichlorophenyl)-1,4,2,6-dithiadiazinan-2-yl)acetamido)adamantan-1-carboxamide;
(163) 4-(2-(1,1,4,4-tetraoxido-6-(2,4,6-trichlorophenyl)-1,4,2,6-dithiadiazinan-2-yl)acetamido)adamantan-1-carboxamide;
(164) 4-(2-(4-chloro-1,1-dioxido-6-(2,4,6-trichlorophenyl)-1,2,6-thiadiazinan-2-yl)acetamido)adamantan-1-carboxamide;
(165) 4-(2-(6-(2-bromo-4-chloro-6-fluorophenyl)-1,1-dioxido-1,2,6-thiadiazinan-2-yl)acetamido)adamantan-1-carboxamide;
(166) 4-(2-(6-(2-bromo-4,6-dichlorophenyl)-1,1-dioxido-1,2,6-thiadiazinan-2-yl)acetamido)adamantan-1-carboxamide;
(167) 4-(2-(4-hydroxy-1,1-dioxido-6-(2,4,6-trichlorophenyl)-1,2,6-thiadiazinan-2-yl)acetamido)adamantan-1-carboxamide;
(168) 4-(2-(1,1-dioxido-4-oxo-6-(2,4,6-trichlorophenyl)-1,2,6-thiadiazinan-2-yl)acetamido)adamantan-1-carboxamide;
(169) 4-(2-(4-methoxy-1,1-dioxido-6-(2,4,6-trichlorophenyl)-1,2,6-thiadiazinan-2-yl)acetamido)adamantan-1-carboxamide;
(170) 4-(2-(6-(2,6-dichloro-4-(trifluoromethoxy)phenyl)-1,1-dioxido-1,2,6-thiadiazinan-2-yl)acetamido)adamantan-1-carboxamide;
(171) 4-(2-(6-(2,6-dichloro-4-(trifluoromethyl)phenyl)-1,1-dioxido-1,2,6-thiadiazinan-2-yl)acetamido)adamantan-1-carboxamide;
(172) 4-(2-(4,4-difluoro-1,1-dioxido-6-(2,4,6-trichlorophenyl)-1,2,6-thiadiazinan-2-yl)acetamido)adamantan-1-carboxamide;
(173) 4-(2-(4-hydroxy-4-methyl-1,1-dioxido-6-(2,4,6-trichlorophenyl)-1,2,6-thiadiazinan-2-yl)acetamido)adamantan-1-carboxamide;
(174) 4-(2-(4-hydroxy-1,1-dioxido-6-(2,4,6-trichlorophenyl)-4-(trifluoromethyl)-1,2,6-thiadiazinan-2-yl)acetamido)adamantan-1-carboxamide;

(175) 4-(2-(4-methylene-1,1-dioxido-6-(2,4,6-trichlorophenyl)-1,2,6-thiadiazinan-2-yl)acetamido)adamantan-1-carboxamide;
(176) 4-(2-(6,6-dioxido-7-(2,4,6-trichlorophenyl)-6-thia-5,7-diazaspiro[2,5]octane-5-yl)acetamido)adamantan-1-carboxamide;
(177) 4-(2-(4,4-dimethyl-1,1-dioxido-6-(2,4,6-trichlorophenyl)-1,2,6-thiadiazinan-2-yl)acetamido)adamantan-1-carboxamide;
(178) 4-(2-(6-(2-chloro-4-(trifluoromethyl)phenyl)-1,1-dioxido-1,2,6-thiadiazinan-2-yl)acetamido)adamantan-1-carboxamide;
(179) 4-(2-(6-(4-bromo-2-(chlorophenyl)-1,1-dioxido-1,2,6-thiadiazinan-2-yl)acetamido)adamantan-1-carboxamide;
(180) 4-(2-(6-(2-bromo-4-(chlorophenyl)-1,1-dioxido-1,2,6-thiadiazinan-2-yl)acetamido)adamantan-1-carboxamide;
(181) 4-(2-(4-methyl-1,1-dioxido-6-phenyl-1,2,6-thiadiazinan-2-yl)acetamido)adamantan-1-carboxamide;
(182) 4-(2-(6-(2-bromo-4-chloro-6-fluorophenyl)-4-methyl-1,1-dioxido-1,2,6-thiadiazinan-2-yl)acetamido)adamantan-1-carboxamide;
(183) 4-(2-(6-(2,6-dichloro-4-(trifluoromethyl)phenyl)-4-methyl-1,1-dioxido-1,2,6-thiadiazinan-2-yl)acetamido)adamantan-1-carboxamide;
(184) 4-(2-(6-(2,6-dichloro-4-(trifluoromethyl)phenyl)-4-methylene-1,1-dioxido-1,2,6-thiadiazinan-2-yl)acetamido)adamantan-1-carboxamide;
(185) 4-(2-(4-methylene-1,1-dioxido-6-phenyl-1,2,6-thiadiazinan-2-yl)acetamido)adamantan-1-carboxamide;
(186) 4-(2-(6-(2-bromo-4-chloro-6-fluorophenyl)-4-methylene-1,1-dioxido-1,2,6-thiadiazinan-2-yl)acetamido)adamantan-1-carboxamide;
(187) 4-(2-(6-(4-chloro-2-iodophenyl)-4-methyl-1,1-dioxido-1,2,6-thiadiazinan-2-yl)acetamido)adamantan-1-carboxamide;
(188) 4-(2-(6-(2-iodophenyl)-4-methyl-1,1-dioxido-1,2,6-thiadiazinan-2-yl)acetamido)adamantan-1-carboxamide;
(189) 4-(2-(1,1-dioxido-4-oxo-5-(2,4,6-trichlorophenyl)-1,2,5-thiadiazolidin-2-yl) acetamido)adamantan-1-carboxamide;
(190) 4-(3-(4-methyl-1,1-dioxido-6-(2,4,6-trichlorophenyl)-1,2,6-thiadiazinan-2-yl)propaneamido)adamantan-1-carboxamide;
(191) 4-(2-(1,1-dioxido-5-oxo-6-(2,4,6-trichlorophenyl)-1,2,6-thiadiazinan-2-yl)acetamido)adamantan-1-carboxamide;
(192) 4-(2-(6-(2-chloro-4-nitrophenyl)-4-methyl-1,1-dioxido-1,2,6-thiadiazinan-2-yl)acetamido)adamantan-1-carboxamide;
(193) 4-(2-(6-(4-chloro-2-nitrophenyl)-4-methyl-1,1-dioxido-1,2,6-thiadiazinan-2-yl)acetamido)adamantan-1-carboxamide;
(194) 4-(2-(2,2-dioxidobenzo[c][1,2,5]thiadiazol-1(3H)-yl)acetamido)adamantan-1-carboxamide;
(195) 4-(2-((S)-6-(2,6-dichloro-4-(trifluoromethyl)phenyl)-4-methyl-1,1-dioxido-1,2,6-thiadiazinan-2-yl)acetamido)adamantan-1-carboxamide;
(196) 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide;
(197) 4-(2-(6-(2-chloro-4-(methylsulfonamido)phenyl)-4-methyl-1,1-dioxido-1,2,6-thiadiazinan-2-yl)acetamido)adamantan-1-carboxamide;
(198) 4-(2-(6-(4-acetamido-2-chlorophenyl)-4-methyl-1,1-dioxido-1,2,6-thiadiazinan-2-yl)acetamido)adamantan-1-carboxamide;
(199) 4-(2-(6-(2-chloro-4-(3-ethylureido)phenyl)-4-methyl-1,1-dioxido-1,2,6-thiadiazinan-2-yl)acetamido)adamantan-1-carboxamide;
(200) 4-(2-(1,1-dioxido-7-(2,4,6-trichlorophenyl)-6,7-dihydro-1,2,7-thiadiazepine-2(3H)-yl)acetamido)adamantan-1-carboxamide;
(201) 4-(2-(allyl(N-allyl-N-(2,6-dichloro-4-(trifluoromethyl)phenyl)sulfamoyl)amino)acetamido)adamantan-1-carboxamide;
(202) 4-(2-(6-(2,6-dichloro-4-(trifluoromethyl)phenyl)-4-isopropyl-1,1-dioxido-1,2,6-thiadiazinan-2-yl)acetamido)adamantan-1-carboxamide;
(203) 4-(2-((S)-4-methyl-1,1-dioxido-6-(2,4,6-trichlorophenyl)-1,2,6-thiadiazinan-2-yl)acetamido)adamantan-1-carboxamide;
(204) 4-(2-((R)-4-methyl-1,1-dioxido-6-(2,4,6-trichlorophenyl)-1,2,6-thiadiazinan-2-yl)acetamido)adamantan-1-carboxamide;
(205) 4-(2-(6-(2,6-dichloro-4-(trifluoromethyl)phenyl)-4-ethyl-1,1-dioxido-1,2,6-thiadiazinan-2-yl)acetamido)adamantan-1-carboxamide;
(206) 4-(2-(4-methyl-1,1-dioxido-6-(pyridine-2-yl)-1,2,6-thiadiazinan-2-yl)acetamido)adamantan-1-carboxamide;
(207) 4-(2-(4-methyl-6-(5-nitropyridine-2-yl)-1,1-dioxido-1,2,6-thiadiazinan-2-yl)acetamido)adamantan-1-carboxamide;
(208) 4-(2-(4-methyl-1,1-dioxido-6-(5-(trifluoromethyl)pyridine-2-yl)-1,2,6-thiadiazinan-2-yl)acetamido)adamantan-1-carboxamide;
(209) 4-(2-(6-(4-bromo-2,6-dichlorophenyl)-4-methyl-1,1-dioxido-1,2,6-thiadiazinan-2-yl)acetamido)adamantan-1-carboxamide;
(210) 4-(2-(6-(3,5-dichloro-[1,1'-biphenyl]-4-yl)-4-methyl-1,1-dioxido-1,2,6-thiadiazinan-2-yl)acetamido)adamantan-1-carboxamide;
(211) 4-(2-(6-(3,5-dichloro-2',4'-difluoro-[1,1'-biphenyl]-4-yl)-4-methyl-1,1-dioxido-1,2,6-thiadiazinan-2-yl)acetamido)adamantan-1-carboxamide;
(212) 4-(2-(6-(2,6-dichloro-4-(furan-2-yl)phenyl)-4-methyl-1,1-dioxido-1,2,6-thiadiazinan-2-yl)acetamido)adamantan-1-carboxamide;
(213) 4-(2-(6-(2,6-dichloro-4-cyanophenyl)-4-methyl-1,1-dioxido-1,2,6-thiadiazinan-2-yl)acetamido)adamantan-1-carboxamide;
(214) 4-(2-(6-(2,6-dichloro-4-methylphenyl)-4-methyl-1,1-dioxido-1,2,6-thiadiazinan-2-yl)acetamido)adamantan-1-carboxamide;
(215) 4-(2-(6-(2,6-dichloro-4-propylphenyl)-4-methyl-1,1-dioxido-1,2,6-thiadiazinan-2-yl)acetamido)adamantan-1-carboxamide; and
(216) 4-(2-(6-(2,6-dichloro-4-cyclopropylphenyl)-4-methyl-1,1-dioxido-1,2,6-thiadiazinan-2-yl)acetamido)adamantan-1-carboxamide.

Still more preferably, the derivative represented by the Formula 1 is selected from the group consisting of 4-(2-(6-(3-fluorophenyl)-1,1-dioxido-1,2,6-thiadiazinan-2-yl)acetamido)adamantan-1-carboxamide; 4-(2-(1,1-dioxido-6-(2,4,6-trichlorophenyl)-1,2,6-thiadiazinan-2-yl)acetamido)adamantan-1-carboxamide (E); 4-(2-(1,1-dioxido-7-(2,4,6-trichlorophenyl)-1,2,7-thiadiazepane-2-yl)acetamido)adamantan-1-carboxamide; 4-(2-(methyl(N-methyl-N-(2,4,6-trichlorophenyl)sulfamoyl)amino)acetamido)adamantan-1-carboxamide; 4-(2-(4-methyl-1,1-dioxido-6-(2,4,6-trichlorophenyl)-1,2,6-thiadiazinan-2-yl)acetamido)adamantan-1-carboxamide; 4-(2-(4-methyl-1,1-dioxido-6-(2,4,6-trichlorophenyl)-1,2,6-thiadiazinan-2-yl)acetamido)adamantan-1-carboxamide; 4-(2-(6-(2,6-dichloro-4-

(trifluoromethyl)phenyl)-4-methyl-1,1-dioxido-1,2,6-thiadiazinan-2-yl)acetamido)adamantan-1-carboxamide; 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide; 4-(2-((S)-4-methyl-1,1-dioxido-6-(2,4,6-trichlorophenyl)-1,2,6-thiadiazinan-2-yl) acetamido) adamantan-1-carboxamide; and 4-(2-((R)-4-methyl-1,1-dioxido-6-(2,4,6-trichlorophenyl)-1,2,6-thiadiazinan-2-yl) acetamido)adamantan-1-carboxamide.

The present invention includes not only sulfamide derivatives having an adamantyl group represented by the Formula 1 but also their pharmaceutically acceptable salts.

The pharmaceutically acceptable salt of the derivatives represented by the Formula 1 includes acid addition salts formed with pharmaceutically acceptable free acids.

The acid addition salts may be formed using inorganic acids such as hydrochloride, nitric acid, phosphoric acid, sulfuric acid, hydrobromic acid, hydroiodic acid, nitrous acid and phosphorous acid; or organic acids aliphatic mono- and dicarboxylate, phenyl-substituted alkanoate, hydroxy alkanoate and alkandioate, aromatic acids, nontoxic organic acids such as aliphatic and aromatic sulfonic acids, acetic acid, benzoic acid, citric acid, lactic acid, maleic acid, gluconic acid, methanesulfonic acid, 4-toluenesulfonic acid, tartaric acid and fumaric acid. Such pharmaceutically nontoxic salts include sulfate, pyrosulfate, bisulfate, sulfite, bisulfate, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylenesulfonate, phenyl acetate, phenylpropionate, phenylbutyrate, citrate, lactate, hydroxybutyrate, glycolate, malate, tartrate, methane sulfonate, propane sulfonate, naphthalene-1-sulfonate, naphthalene-2-sulfonate or mandelate.

Preferably, the pharmaceutically acceptable salt of this invention includes hydrochloric acid salt, sulfuric acid salt, acetic acid salt, trifluoroacetic acid salt, phosphoric acid salt, fumaric acid salt, maleic acid salt, citric acid salt, methane sulfonic acid salt or lactic acid salt.

According to the present invention, the acid addition salts may be prepared through conventional methods. For example, acid addition salts may be prepared by dissolving the derivative of the Formula 1 in an excessive amount of organic solvent such as methanol, ethanol, acetone, methylene chloride or acetonitrile, and precipitating the salt in organic or inorganic acid, followed by filtration and drying, or distillation under reduced pressure and drying, or crystallization in organic solvent.

Further, a pharmaceutically acceptable metal salt may be produced using a base. An alkali metal salt or an alkaline earth metal salt may be obtained, for example, by dissolving a compound in an excessive amount of alkali metal hydroxide or alkaline earth metal hydroxide solution, filtering the undissolved salt, and then evaporating and drying the filtrate. In respects to metal salts, sodium, potassium, or calcium salt is pharmaceutically preferable, and the corresponding silver salt may be obtained by reacting an alkali metal salt or alkaline earth metal salt with a suitable silver salt (e.g., silver nitrate).

The present invention includes not only sulfamide derivatives having an adamantyl group represented by the Formula 1 or their pharmaceutically acceptable salt but also their solvates, hydrates and stereoisomers.

In another aspect of this invention, there is provided an inhibitory agent to 11β-HSD1 (11β-hydroxysteroid dehydrogenase type 1), which comprises as an active ingredient the sulfamide derivative having an adamantyl group or its pharmaceutically acceptable salt described above.

The inhibitory agent comprises the sulfamide derivative having an adamantyl group or its pharmaceutically acceptable salt. Therefore, in the interest of avoiding unnecessary redundancy, the common descriptions between them are not being repeated.

The compound used effectively inhibits the activity of 11β-HSD1 catalyzing conversion of cortisone cortisol. The term used herein "inhibition" refers to significant decrease in in vivo expression level or biological activity.

In still another aspect of this invention, there is provided a pharmaceutical composition for preventing or treating a 11β-HSD1-related disease, which comprises as an active ingredient the sulfamide derivative having an adamantyl group or its pharmaceutically acceptable salt described above.

In further aspect of this invention, there is provided a method for preventing or treating a 11β-HSD1-related disease, which comprises administering to a subject the a pharmaceutical composition for preventing or treating a 11β-HSD1-related disease.

According to the present invention, the compound of the present invention effectively inhibits 11β-HSD1 involved in the production of cortisol as one of glucocorticoid hormones that decreases insulin secretion, causes gluconeogenesis in liver and increase differentiation of adipocytes. Therefore, the compound of the present invention is useful in prevention or treatment of 11β-HSD1-related diseases such as insulin resistance-related metabolic syndromes, obesity, bone diseases and brain diseases by decreasing in vivo cortisol level.

The term used herein "prevent" refers to suppression or progression delay of 11β-HSD1-related diseases by administration of the present composition.

The term used herein "treat" refers to suppression of development of 11β-HSD1-related diseases; alleviation of 11β-HSD1-related diseases; or removal of 11β-HSD1-related diseases.

The term used "subject" means all animals such as human having or to have 11β-HSD1-related diseases.

The term used "11β-HSD1-related disease" refers to diseases caused by high expression level or high activity of 11β-HSD1, or diseases to be prevented, treated, ameliorated or alleviated by inhibition of expression or activity of 11β-HSD1. 11β-HSD1-related diseases include all pathological conditions caused by 11β-HSD1, for example, diabetes, arthritis, obesity, hypertension, dyslipidemia, arteriolosclerosis, osteoporosis and impaired glucose resistance, but not limited to.

Preferably, the 11β-HSD1-related disease to be prevented or treated by the compound of the present invention is selected from the group consisting of diabetes, obesity, dyslipidemia, hypertension, cognitive impairment, arthritis, osteoporosis, glaucoma and diseases caused by hypoimmunity.

The term "diabetes" means chronic diseases caused by relative or absolute insulin insufficiency leading to glucose-intolerance. The term "diabetes" is used to intend to encompass all types of diabetes, e.g., Type 1 diabetes, Type 2 diabetes and hereditary diabetes. Type 1 diabetes is insulin-dependent diabetes caused mainly by β-cell disruption. Type 2 diabetes is insulin-independent diabetes caused by insufficient insulin secretion after diet or insulin resistance.

The term "dyslipidemia" means abnormal lipid conditions including hyperlipidemia, hypercholesterolemia, hypertriglyceridemia, low HDL-cholesterol (hypoalphalipoproteinemia) and dysmetabolic lipoproteins.

The term "cognitive impairment" means diseases with malfunction of cognition (e.g., memory processing, perception and problem solving) caused by impairment of cranial nerve tissues. The excess of cortisol in brain is likely to cause loss or malfunction of neurons through activation of neurotoxins. Therefore, the inhibitors to 11β-HSD1 may suppress cognitive impairment and malfunction of neurons which may be associated with senescence. In this regard, the composition of the present invention is considerably useful in prevention or treatment of cognitive impairment.

The term "arthritis" means diseases caused by inflammation in joint tissues for joint movement or loss of cartilage tissues. Arthritis to be prevented or treated by the present composition includes degenerative arthritis and rheumatoid arthritis.

The term used herein "diseases caused by hypoimmunity" refers to diseases caused by abnormal reduction of immunity or diseases to be treated by elevation of immune reactions, for example, including tumors, infection diseases by bacteria or viruses, inflammatory diseases, cough, arthritis, inflammatory osteolysis and immunodeficiency diseases, not limited to.

When the composition of the present disclosure is prepared into a pharmaceutical composition, the pharmaceutical composition of the present disclosure comprises a pharmaceutically acceptable carrier. The pharmaceutically acceptable carrier included in the pharmaceutical composition of the present disclosure may be a commonly used one, including lactose, dextrose, sucrose, sorbitol, mannitol, starch, gum *acacia*, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

The pharmaceutical composition of the present disclosure may be administered orally or parenterally. When administered parenterally, it may be administered intravenously, subcutaneously, intramuscularly, intraabdominally, transdermally, or the like.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

Effects of the Invention

The features and advantages of the present disclosure may be summarized as follows:

(a) The present invention provides novel sulfamide derivatives having an adamantyl group or their pharmaceutically acceptable salts, an inhibitory agent to 11β-HSD1 (11β-hydroxysteroid dehydrogenase type 1) comprising as an active ingredient the sulfamide derivative having an adamantyl group represented by the following Formula 1 or its pharmaceutically acceptable salt, a pharmaceutical composition for preventing or treating a 11β-HSD1-related disease and a method for preventing or treating a 11β-HSD1-related disease.

(b) The sulfamide derivatives having an adamantyl group effectively inhibits the activity of 11β-HSD1 such that they are very useful in prevention or treatment of 11β-HSD1-related disease such as diabetes, obesity, dyslipidemia, hypertension, cognitive impairment, arthritis, osteoporosis, glaucoma and diseases caused by hypoimmunity.

EXAMPLES FOR PERFORMING THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

The chemical structures, IUPAC nomenclatures and NMR values of compounds synthesized in the present invention were summarized in Tables 1-32:

TABLE 1

| No | Structure | IUPAC Name | NMR |
|---|---|---|---|
| 1 | 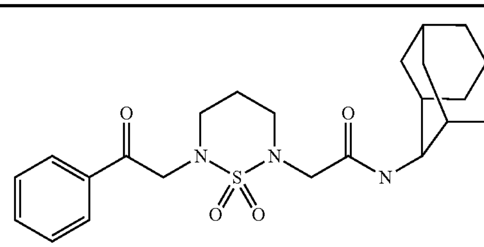 | N-(adamantan-2-yl)-2-(1,1-dioxido-6-(2-oxo-2-phenylethyl)-1,2,6-thiadiazinan-2-yl)acetamide | $^1$H NMR (300 MHz, CDCl$_3$), 7.97 (d, J = 7.5 Hz, 2H), 7.62 (t, J = 7.5 Hz, 1H), 7.50 (t, J = 7.8 Hz, 2H), 7.01 (d, J = 8.1 Hz, 1H), 4.53 (s, 2H), 4.08 (d, J = 8.4 Hz, 1H), 3.84 (t, J = 5.7 Hz, 2H), 3.64 (t, J = 5.7 Hz, 2H), 3.50 (t, J = 5.7 Hz, 2H), 1.95-1.59 (m, 16H) |

TABLE 1-continued

| No | Structure | IUPAC Name | NMR |
|----|-----------|------------|-----|
| 2 | 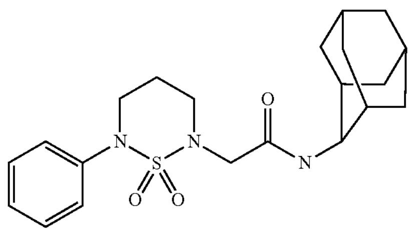 [SMILES: O=C(CN1CCCN(c2ccccc2)S1(=O)=O)NC1C2CC3CC(C2)CC1C3] | N-(adamantan-2-yl)-2-(1,1-dioxido-6-phenyl-1,2,6-thiadiazinan-2-yl)acetamide | $^1$H NMR (300 MHz, CDCl$_3$) 7.41-7.26 (m, 5H), 7.02-6.99 (m, 1H), 4.07 (m, 1H), 3.94 (s, 2H), 3.81-3.74 (m, 4H), 2.03-1.94 (m, 4H), 1.85-1.74 (m, 10H), 1.66-1.60 (m, 3H) |
| 3 | 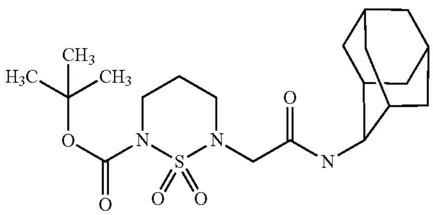 [SMILES: CC(C)(C)OC(=O)N1CCCN(CC(=O)NC2C3CC4CC(C3)CC2C4)S1(=O)=O] | tert-butyl 6-(2-(adamantan-2-yl amino)-2-oxoethyl)-1,2,6-thiadiazinan-2-carboxylate-1,1-dioxide | $^1$H NMR (300 MHz, CDCl$_3$) δ 6.90 (brd, 1H), 4.06 (m, 1H), 4.00 (t, J = 5.8 Hz, 2H), 3.83 (s, 2H), 3.66 (t, J = 5.8 Hz, 2H), 1.92~1.63 (m, 15H), 1.52 (s, 9H) |
| 4 | 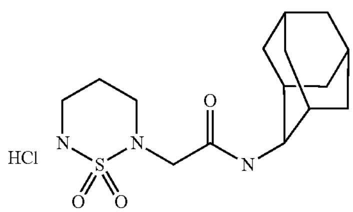 [SMILES: Cl ; O=C(CN1CCCNS1(=O)=O)NC1C2CC3CC(C2)CC1C3] | N-(adamantan-2-yl)-2-(1,1-dioxido-1,2,6-thiadiazinan-2-yl)acetamide hydrochloride | $^1$H NMR (300 MHz, CDCl$_3$): 7.59 (d, J = 7.6 Hz, 1H), 6.98 (s, 1H), 3.84-3.82 (m, 1H), 3.59 (s, 2H), 3.33-3.24 (m, 4H), 1.90-1.48 (m, 16H) |

TABLE 2

| No | Structure | IUPAC Name | NMR |
|----|-----------|------------|-----|
| 5 | 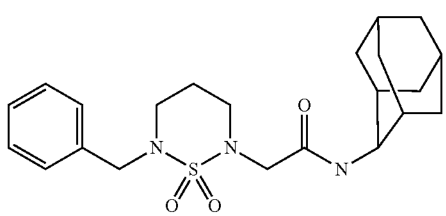 [SMILES: O=C(CN1CCCN(Cc2ccccc2)S1(=O)=O)NC1C2CC3CC(C2)CC1C3] | N-(adamantan-2-yl)-2-(6-benzyl-1,1-dioxido-1,2,6-thiadiazinan-2-yl)acetamide | δ 7.72~7.69 (brd, 1H), 7.39~7.28 (m, 5H), 4.17 (s, 2H), 3.86~3.83 (m, 1H), 3.79 (s, 2H), 3.46~3.42 (m, 2H), 3.17~3.14 (m, 2H), 1.93~1.89 (m, 2H), 1.80~1.67 (m, 12H), 1.52~1.48 (m, 2H) |
| 6 | 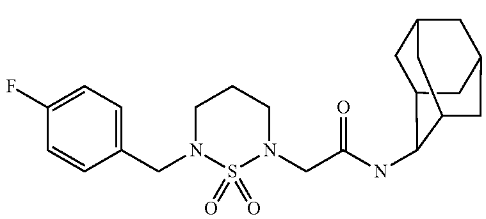 [SMILES: O=C(CN1CCCN(Cc2ccc(F)cc2)S1(=O)=O)NC1C2CC3CC(C2)CC1C3] | N-(adamantan-2-yl)-2-(6-(4-fluorobenzyl)-1,1-dioxido-1,2,6-thiadiazinan-2-yl)acetamide | δ 7.71~7.69 (brd, 1H), 7.40~7.35 (m, 2H), 7.21~7.15 (m, 2H), 4.16 (s, 2H), 3.86~3.83 (m, 1H), 3.78 (s, 2H), 3.46~3.42 (m, 2H), 3.18~3.14 (m, 2H), 1.93~1.89 (m, 2H), 1.80~1.68 (m, 12H), 1.52~1.48 (m, 2H) |
| 7 | 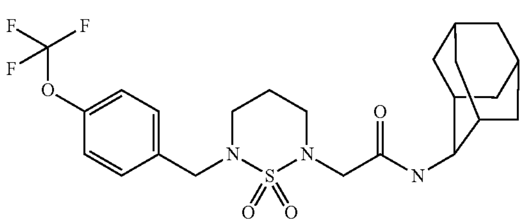 [SMILES: O=C(CN1CCCN(Cc2ccc(OC(F)(F)F)cc2)S1(=O)=O)NC1C2CC3CC(C2)CC1C3] | N-(adamantan-2-yl)-2-(1,1-dioxido-6-(4-(trifluoromethoxy)benzyl)-1,2,6-thiadiazinan-2-yl)acetamide | δ 7.72~7.69 (brd, 1H), 7.48~7.45 (m, 2H), 7.36~7.34 (m, 2H), 4.22 (s, 2H), 3.86~3.83 (m, 1H), 3.78 (s, 2H), 3.46~3.42 (m, 2H), 3.21~3.14 (m, 2H), 1.93~1.89 (m, 2H), 1.80~1.67 (m, 12H), 1.52~1.48 (m, 2H) |

TABLE 2-continued

| No | Structure | IUPAC Name | NMR |
|---|---|---|---|
| 8 | 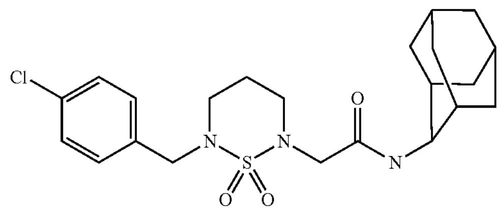 [SMILES: O=C(CN1CCCN(Cc2ccc(Cl)cc2)S1(=O)=O)NC1C2CC3CC(C2)CC1C3] | N-(adamantan-2-yl)-2-(6-(4-chlorobenzyl)-1,1-dioxido-1,2,6-thiadiazinan-2-yl)acetamide | δ 7.71~7.69 (brd, 1H), 7.43~7.34 (m, 4H), 4.17 (s, 2H), 3.85~3.83 (m, 1H), 3.78 (s, 2H), 3.46~3.42 (m, 2H), 3.19~3.15 (m, 2H), 1.93~1.89 (m, 2H), 1.80~1.67 (m, 12H), 1.52~1.48 (m, 2H) |
| 9 | 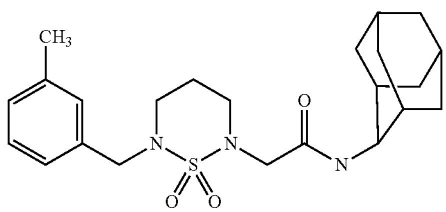 [SMILES: Cc1cccc(CN2CCCN(CC(=O)NC3C4CC5CC(C4)CC3C5)S2(=O)=O)c1] | N-(adamantan-2-yl)-2-(6-(3-methylbenzyl)-1,1-dioxido-1,2,6-thiadiazinan-2-yl)acetamide | δ 7.71~7.69 (brd, 1H), 7.26~7.21 (m, 1H), 7.13~7.09 (m, 3H), 4.13 (s, 2H), 3.86~3.84 (m, 1H), 3.78 (s, 2H), 3.45~3.41 (s, 2H), 3.17~3.13 (m, 2H), 2.29 (s, 3H), 1.93~1.89 (m, 2H), 1.80~1.68 (m, 12H), 1.52~1.48 (m, 2H) |
| 10 | 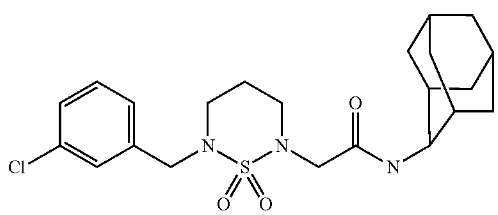 [SMILES: O=C(CN1CCCN(Cc2cccc(Cl)c2)S1(=O)=O)NC1C2CC3CC(C2)CC1C3] | N-(adamantan-2-yl)-2-(6-(3-chlorobenzyl)-1,1-dioxido-1,2,6-thiadiazinan-2-yl)acetamide | LCMS MH+ 452 |
| 11 | 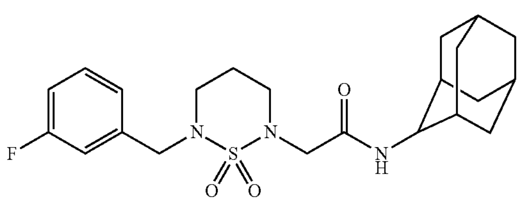 [SMILES: O=C(CN1CCCN(Cc2cccc(F)c2)S1(=O)=O)NC1C2CC3CC(C2)CC1C3] | N-(adamantan-2-yl)-2-(6-(3-fluorobenzyl)-1,1-dioxido-1,2,6-thiadiazinan-2-yl)acetamide | LCMS MH+ 436 |

TABLE 3

| No | Structure | IUPAC Name | NMR |
|---|---|---|---|
| 12 | 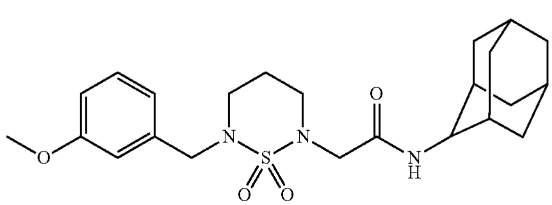 | N-(adamantan-2-yl)-2-(6-(3-methoxybenzyl)-1,1-dioxido-1,2,6-thiadiazinan-2-yl)acetamide | LCMS MH+ 188 |
| 13 | 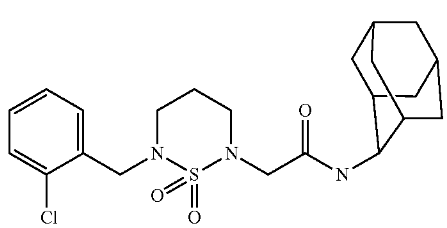 [SMILES: O=C(CN1CCCN(Cc2ccccc2Cl)S1(=O)=O)NC1C2CC3CC(C2)CC1C3] | N-(adamantan-2-yl)-2-(6-(2-chlorobenzyl)-1,1-dioxido-1,2,6-thiadiazinan-2-yl)acetamide | δ 7.48~7.45 (m, 1H), 7.40~7.37 (m, 1H), 7.33~7.23 (m, 2H), 7.08~7.05 (brd, 1H), 4.44 (s, 2H), 4.10~4.07 (m, 1H), 3.85 (s, 2H), 3.58~3.55 (m, 2H), 3.38~3.34 (m, 2H), 1.94~1.64 (m, 14H) |

TABLE 3-continued

| No | Structure | IUPAC Name | NMR |
|----|-----------|------------|-----|
| 14 | 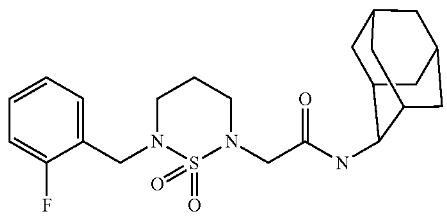 [SMILES: O=C(CN1CCCN(Cc2ccccc2F)S1(=O)=O)NC1C2CC3CC(C2)CC1C3] | N-(adamantan-2-yl)-2-(6-(2-fluorobenzyl)-1,1-dioxido-1,2,6-thiadiazinan-2-yl)acetamide | δ 7.44~7.39 (m, 1H), 7.35~7.27 (m, 1H), 7.19~7.14 (m, 1H), 7.10~7.03 (m, 2H), 4.35 (s, 2H), 4.09~4.07 (m, 1H), 3.85 (s, 2H), 3.58~3.54 (m, 2H), 3.36~3.32 (m, 2H), 1.94~1.66 (m, 14H) |
| 15 | 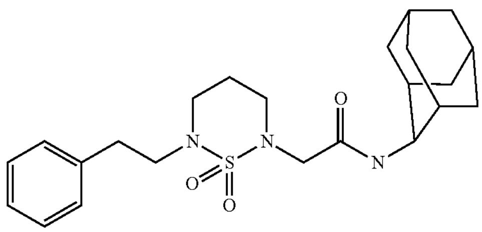 [SMILES: O=C(CN1CCCN(CCc2ccccc2)S1(=O)=O)NC1C2CC3CC(C2)CC1C3] | N-(adamantan-2-yl)-2-(1,1-dioxido-6-phenethyl-1,2,6-thiadiazinan-2-yl)acetamide | δ 7.33~7.19 (m, 5H), 7.01~6.98 (brd, 1H), 4.06~4.047 (m, 1H), 3.71 (s, 2H), 3.53~3.49 (m, 2H), 3.38~3.33 (m, 4H), 2.94~2.87 (m, 2H), 1.92~1.60 (m, 14H) |
| 16 | 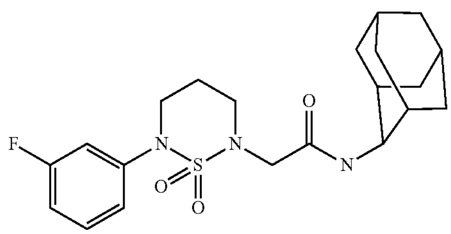 [SMILES: O=C(CN1CCCN(c2cccc(F)c2)S1(=O)=O)NC1C2CC3CC(C2)CC1C3] | N-(adamantan-2-yl)-2-(6-(3-fluorophenyl)-1,1-dioxido-1,2,6-thiadiazinan-2-yl)acetamide | $^1$H NMR (300 MHz, CDCl$_3$): δ 7.38-7.30 (m, 1H), 7.17-6.95 (m, 4H), 4.08-4.05 (m, 1H), 3.93 (s, 2H), 3.80-3.74 (m, 4H), 2.04-1.59 (m, 16H) |
| 17 | 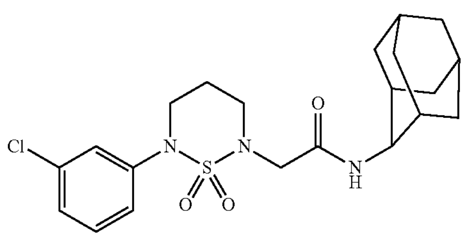 [SMILES: O=C(CN1CCCN(c2cccc(Cl)c2)S1(=O)=O)NC1C2CC3CC(C2)CC1C3] | N-(adamantan-2-yl)-2-(6-(3-chlorophenyl)-1,1-dioxido-1,2,6-thiadiazinan-2-yl)acetamide | $^1$H NMR (300 MHz, CDCl$_3$): 7.36-7.24 (m, 4H), 6.95 (d, J = 7.9 Hz, 1H), 4.08-4.05 (m, 1H), 3.92 (s, 2H), 3.79-3.74 (m, 4H), 2.01-1.58 (m, 16H) |
| 18 | 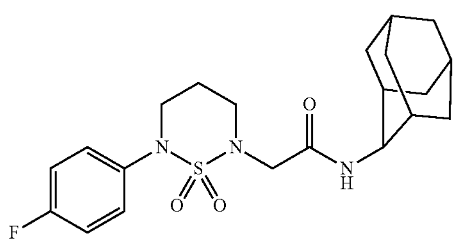 [SMILES: O=C(CN1CCCN(c2ccc(F)cc2)S1(=O)=O)NC1C2CC3CC(C2)CC1C3] | N-(adamantan-2-yl)-2-(6-(4-fluorophenyl)-1,1-dioxido-1,2,6-thiadiazinan-2-yl)acetamide | $^1$H NMR (300 MHz, CDCl$_3$): δ 7.36-7.32 (m, 2H), 7.09-7.03 (m, 2H), 6.97 (d, J = 8.2 Hz, 1H), 4.08-4.05 (m, 1H), 3.93 (s, 2H), 3.78-3.71 (m, 4H), 2.04-1.60 (m, 16H) |

TABLE 4

| No | Structure | IUPAC Name | NMR |
|----|-----------|------------|-----|
| 19 | 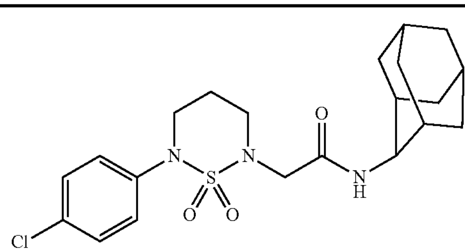 | N-(adamantan-2-yl)-2-(6-(4-chlorophenyl)-1,1-dioxido-1,2,6-thiadiazinan-2-yl)acetamide | $^1$H NMR (300 MHz, CDCl$_3$): δ 7.36-7.26 (m, 4H), 6.96 (d, J = 8.1 Hz, 1H), 4.08-4.05 (m, 1H), 3.92 (s, 2H), 3.77-3.73 (m, 4H), 2.03-1.60 (m, 16H) |

TABLE 4-continued

| No | Structure | IUPAC Name | NMR |
|---|---|---|---|
| 20 | 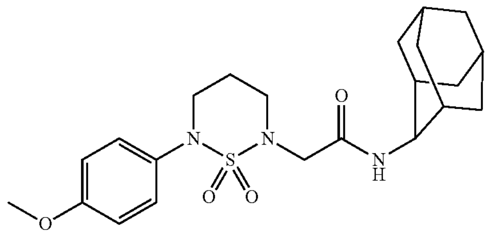 [SMILES: COc1ccc(N2CCCN(CC(=O)NC3C4CC5CC(C4)CC3C5)S2(=O)=O)cc1] | N-(adamantan-2-yl)-2-(6-(4-methoxyphenyl)-1,1-dioxido-1,2,6-thiadiazinan-2-yl)acetamide | $^1$H NMR (300 MHz, CDCl$_3$): δ 7.32-7.25 (m, 2H), 7.01 (d, J = 7.5 Hz, 1H), 6.91-6.86 (m, 2H), 4.08-4.03 (m, 1H), 3.93 (s, 2H), 3.80 (s, 3H), 3.76-3.70 (m, 4H), 1.99-1.60 (m, 16H) |
| 21 | 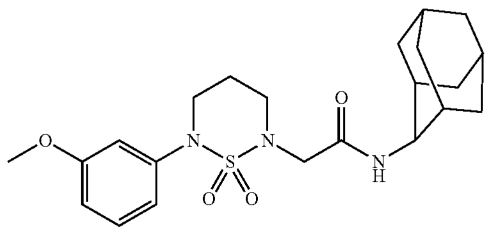 [SMILES: COc1cccc(N2CCCN(CC(=O)NC3C4CC5CC(C4)CC3C5)S2(=O)=O)c1] | N-(adamantan-2-yl)-2-(6-(3-methoxyphenyl)-1,1-dioxido-1,2,6-thiadiazinan-2-yl)acetamide | $^1$H NMR (300 MHz, CDCl$_3$): δ 7.30-7.25 (m, 1H), 7.00 (d, J = 8.2 Hz, 1H), 6.97-6.82 (m, 3H), 4.08-4.04 (m, 1H), 3.93 (s, 2H), 3.81 (s, 3H), 3.79-3.73 (m, 4H), 2.04-1.61 (m, 16H) |
| 22 | 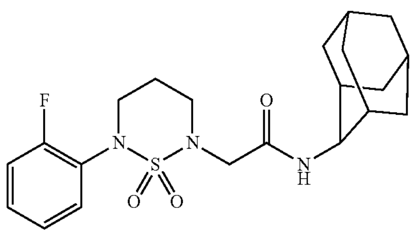 [SMILES: O=C(CN1CCCN(c2ccccc2F)S1(=O)=O)NC1C2CC3CC(C2)CC1C3] | N-(adamantan-2-yl)-2-(6-(2-fluorophenyl)-1,1-dioxido-1,2,6-thiadiazinan-2-yl)acetamide | $^1$H NMR (300 MHz, CDCl$_3$): δ 7.47-7.41 (m, 1H), 7.33-7.28 (m, 2H), 7.17-7.11(m, 2H), 7.00(d, J = 7.7 Hz, 1H), 4.08-4.06 (m, 1H), 3.95 (s, 2H), 3.81-3.77 (m, 4H), 2.04-1.66 (m, 16H) |
| 23 | 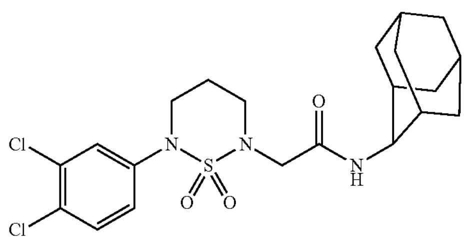 [SMILES: O=C(CN1CCCN(c2ccc(Cl)c(Cl)c2)S1(=O)=O)NC1C2CC3CC(C2)CC1C3] | N-(adamantan-2-yl)-2-(6-(3,4-dichlorophenyl)-1,1-dioxido-1,2,6-thiadiazinan-2-yl)acetamide | $^1$H NMR (300 MHz, CDCl$_3$): δ 7.46-7.43 (m, 2H), 7.24-7.20 (m, 1H), 6.92 (d, J = 7.6 Hz, 1H), 4.08-4.05 (m, 1H), 3.92 (s, 2H), 3.78-3.72 (m, 4H), 2.04-1.58 (m, 16H) |
| 24 | 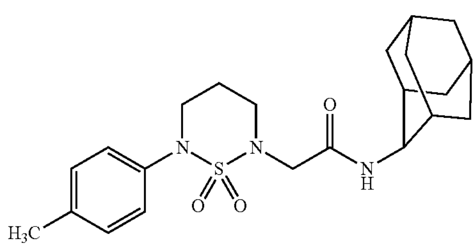 [SMILES: Cc1ccc(N2CCCN(CC(=O)NC3C4CC5CC(C4)CC3C5)S2(=O)=O)cc1] | N-(adamantan-2-yl)-2-(1,1-dioxido-6-(p-tolyl)-1,2,6-thiadiazinan-2-yl)acetamide | $^1$H NMR (300 MHz, CDCl$_3$): d 7.26-7.23 (m, 2H), 7.18-7.16 (m, 2H), 7.01 (d, J = 7.5 Hz, 1H), 4.08-4.06 (m, 1H), 3.93 (s, 2H), 3.77-3.72 (m, 4H), 2.34 (s, 3H), 2.01-1.61 (m, 16H) |
| 25 | 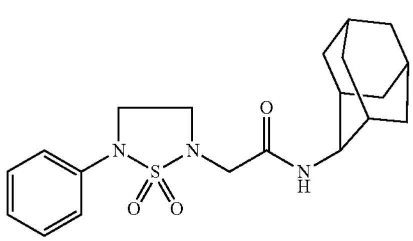 [SMILES: O=C(CN1CCN(c2ccccc2)S1(=O)=O)NC1C2CC3CC(C2)CC1C3] | N-(adamantan-2-yl)-2-(1,1-dioxido-5-phenyl-1,2,5-thiadiazolidin-2-yl)acetamide | $^1$H NMR (300 MHz, CDCl$_3$): d 7.45-7.39(m, 2H), 7.32-7.20 (m, 3H), 7.11 (d, J = 7.5 Hz, 1H), 4.11-4.09(m, 1H), 3.94-3.92(m, 2H), 3.90(s, 2H), 3.69-3.64(m, 2H), 1.94-1.64(m, 14H) |

TABLE 5

| No | Structure | IUPAC Name | NMR |
|---|---|---|---|
| 26 | 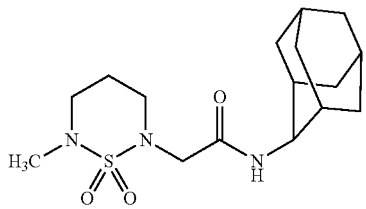 [SMILES: CN1CCCN(CC(=O)NC2C3CC4CC(C3)CC2C4)S1(=O)=O] | N-(adamantan-2-yl)-2-(6-methyl-1,1-dioxido-1,2,6-thiadiazinan-2-yl)acetamide | ¹H NMR (300 MHz, CDCl₃): d 7.02 (d, J = 7.0 Hz, 1H), 4.08-4.05 (m, 1H), 3.79 (s, 2H), 3.55-3.51 (m, 2H), 3.40-3.36 (m, 2H), 2.82 (s, 3H), 1.93-1.63 (m, 16H) |
| 27 | 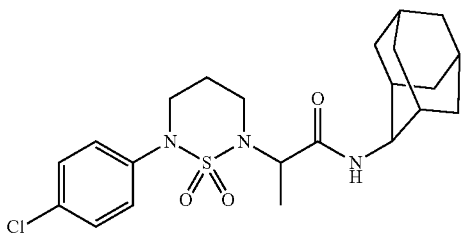 [SMILES: CC(C(=O)NC1C2CC3CC(C2)CC1C3)N1CCCN(c2ccc(Cl)cc2)S1(=O)=O] | N-(adamantan-2-yl)-2-(6-(4-chlorophenyl)-1,1-dioxido-1,2,6-thiadiazinan-2-yl)acetamide | ¹H NMR (300 MHz, CDl₃): δ 7.34-7.31 (m, 4H), 6.75 (d, J = 7.7 Hz, 1H), 4.55 (q, J = 7.1 Hz, 1H), 4.06-4.03 (m, 1H), 3.90-3.86 (m, 2H), 3.60-3.56 (m, 2H), 2.01-1.93 (m, 2H), 1.90-1.60 (m, 14H), 1.52 (d, J = 7.1 Hz, 3H) |
| 28 | 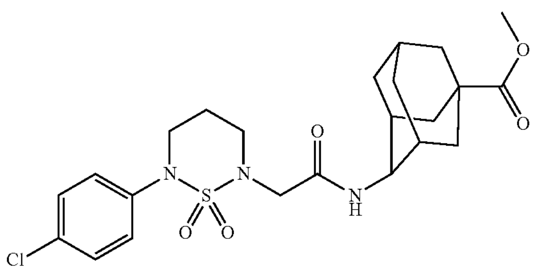 [SMILES: COC(=O)C12CC3CC(C1)C(NC(=O)CN1CCCN(c4ccc(Cl)cc4)S1(=O)=O)C(C3)C2] | Methyl 4-(2-(6-(4-chlorophenyl)-1,1-dioxido-1,2,6-thiadiazinan-2-yl)acetamido)adamantan-1-carboxylate | ¹H NMR (300 MHz, CDCl₃): δ 7.36-7.26 (m, 4H), 6.93-6.84 (m, 1H), 4.06-4.00 (m, 1H), 3.92 (s, 2H), 3.78-3.73 (m, 4H), 3.66 (s, 3H), 2.08-1.60 (m, 15H) |
| 29 | 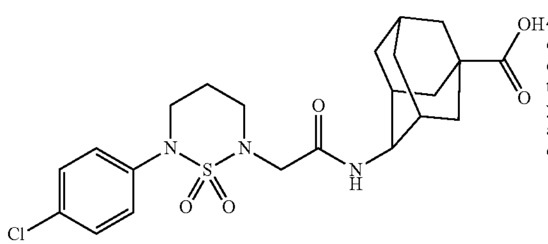 | 4-(2-(6-(4-chlorophenyl)-1,1-dioxido-1,2,6-thiadiazinan-2-yl)acetamido)adamantan-1-carboxylic acid | ¹H NMR (300 MHz, DMSO-d₆,): δ 12.04 (s, 1H), 7.87-7.75 (m, 1H), 7.45 (d, J = 8.7 Hz, 2H), 7.37 (d, J = 8.7 Hz, 2H), 3.89 (s, 2H), 3.81-3.78 (m, 1H), 3.68-3.59 (m, 4H), 1.97-1.41 (m, 15H) |
| 30 | 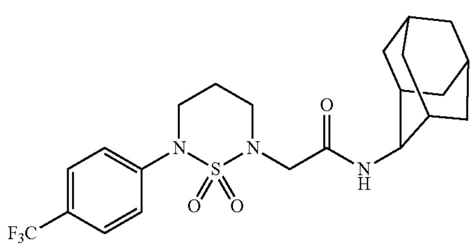 [SMILES: O=C(CN1CCCN(c2ccc(C(F)(F)F)cc2)S1(=O)=O)NC1C2CC3CC(C2)CC1C3] | N-(adamantan-2-yl)-2-(1,1-dioxido-6-(4-(trifluoromethyl)phenyl)-1,2,6-thiadiazinan-2-yl)acetamide | ¹H NMR (300 MHz, CDCl₃): δ 7.64 (d, J = 8.7 Hz, 2H), 7.46 (d, J = 8.7 Hz, 2H), 6.94 (d, J = 7.8 Hz, 1H), 4.08-4.06 (m, 1H), 3.94 (s, 2H), 3.85-3.76 (m, 4H), 2.06-1.98 (m, 2H), 1.93-1.59 (m, 14H) |
| 31 | 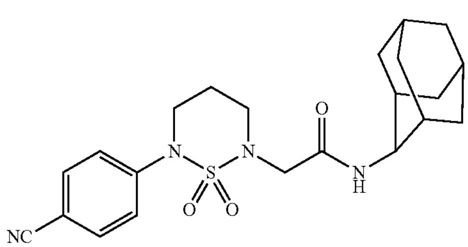 [SMILES: N#Cc1ccc(N2CCCN(CC(=O)NC3C4CC5CC(C4)CC3C5)S2(=O)=O)cc1] | N-(adamantan-2-yl)-2-(6-(4-cyanophenyl)-1,1-dioxido-1,2,6-thiadiazinan-2-yl)acetamide | ¹H NMR (300 MHz, CDCl₃): δ 7.68 (d, J = 8.5 Hz, 2H), 7.45 (d, J = 8.5 Hz, 2H), 6.90 (d, J = 7.8 Hz, 1H), 4.08-4.05 (m, 1H), 3.92 (s, 2H), 3.86-3.77 (m, 4H), 2.06-1.98 (m, 2H), 1.93-1.62 (m, 14H) |

TABLE 5-continued

| No | Structure | IUPAC Name | NMR |
|---|---|---|---|
| 32 | 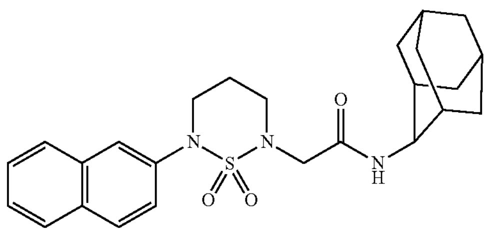 [SMILES: O=C(CN1CCCN(c2ccc3ccccc3c2)S1(=O)=O)NC1C2CC3CC(C2)CC1C3] | N-(adamantan-2-yl)-2-(6-(naphthalene-2-yl)-1,1-dioxido-1,2,6-thiadiazinan-2-yl)acetamide | $^1$H NMR (300 MHz, CDCl$_3$): δ 7.86- 7.81(m, 4H), 7.53-7.45 (m, 3H), 7.02 (d, J = 7.8 Hz, 1H), 4.10-4.06 (m, 1H), 3.99 (s, 2H), 3.91-3.88 (m, 2H), 3.82-3.78 (m, 2H), 2.10- 2.00 (m, 2H), 2.00-1.61 (m, 14H) |

TABLE 6

| No | Structure | IUPAC Name | NMR |
|---|---|---|---|
| 33 | 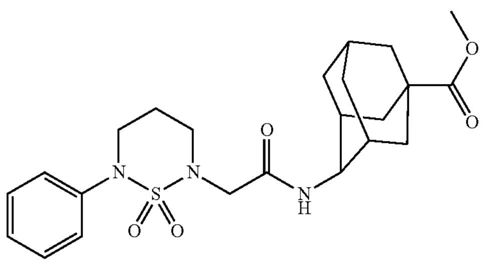 [SMILES: COC(=O)C12CC3CC(C1)C(NC(=O)CN1CCCN(c4ccccc4)S1(=O)=O)C(C3)C2] | Methyl 4-(2-(1,1-dioxido-6-phenyl-1,2,6-thiadiazinan-2-yl)acetamido)adamantan-1-carboxylate | $^1$H NMR (300 MHz, CDCl$_3$): δ 7.41-7.27 (m, 5H), 6.99-6.88 (m, 1H), 4.06-4.01 (m, 1H), 3.94 (s, 2H), 3.82-3.73 (m, 4H), 3.66 (s, 3H), 2.05-1.57 (m, 13H) |
| 34 | 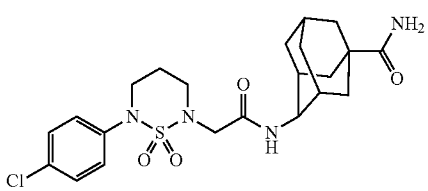 [SMILES: NC(=O)C12CC3CC(C1)C(NC(=O)CN1CCCN(c4ccc(Cl)cc4)S1(=O)=O)C(C3)C2] | 4-(2-(6-(4-chlorophenyl)-1,1-dioxido-1,2,6-thiadiazinan-2-yl)acetamido)adamantan-1-carboxamide | $^1$H NMR (300 MHz, CDCl$_3$): δ 7.37-7.27 (m, 4H), 6.85-6.83 (m, 1H), 5.70-5.52 (m, 1H), 5.29~5.15 (m, 1H), 4.35 (s, 2H), 4.07-3.98 (m, 1H), 3.82-3.67 (m, 4H), 4.08-3.98 (m, 1H), 2.21-1.65 (m, 15H) |
| 35 | 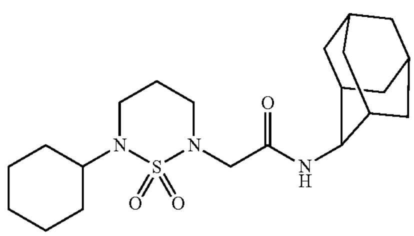 [SMILES: O=C(CN1CCCN(C2CCCCC2)S1(=O)=O)NC1C2CC3CC(C2)CC1C3] | N-(adamantan-2-yl)-2-(6-cyclohexyl-1,1-dioxido-1,2,6-thiadiazinan-2-yl)acetamide | LCMS MH+ 410 |
| 36 | 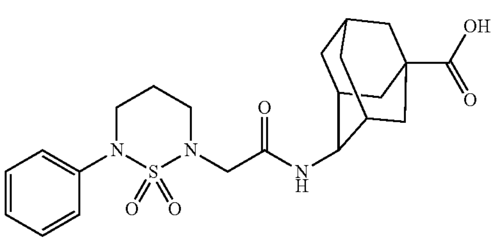 [SMILES: O=C(CN1CCCN(c2ccccc2)S1(=O)=O)NC1C2CC3CC1CC(C(=O)O)(C3)C2] | 4-(2-(1,1-dioxido-6-phenyl-1,2,6-thiadiazinan-2-yl)acetamido)adamantan-1-carboxylic acid | $^1$H NMR (300 MHz, DMSO-d$_6$): δ 12.04 (s, 1H), 7.89-7.76 (m, 1H), 7.44-7.27 (m, 5H), 3.92 (s, 2H), 3.84-3.82 (m, 1H), 3.71-3.62 (m, 4H), 2.05-1.45 (m, 15H) |
| 37 | 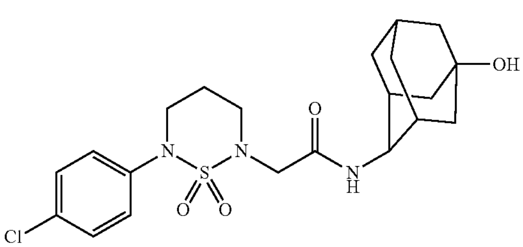 [SMILES: O=C(CN1CCCN(c2ccc(Cl)cc2)S1(=O)=O)NC1C2CC3CC1CC(O)(C3)C2] | 2-(6-(4-chlorophenyl)-1,1-dioxido-1,2,6-thiadiazinan-2-yl)-N-(5-hydroxyadamantan-2-yl)acetamide | $^1$H NMR (300 MHz, CDCl$_3$): δ 9.80 (s, 1H), 7.37-7.27 (m, 4H), 6.85 (d, J = 7.0 Hz, 1H), 4.35 (s, 2H), 3.93-3.92 (m, 1H), 3.82-3.67 (m, 4H), 3.28-3.19 (m, 2H), 2.35-2.31 (m, 2H), 2.20-1.59 (m, 11H) |

TABLE 6-continued

| No | Structure | IUPAC Name | NMR |
|---|---|---|---|
| 38 | 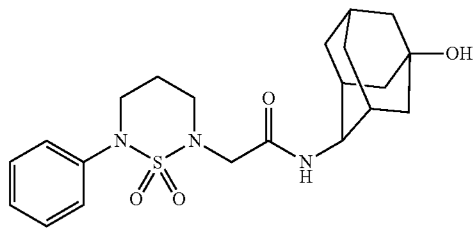 [SMILES: O=C(CN1CCCN(c2ccccc2)S1(=O)=O)NC1C2CC3CC1CC(O)(C3)C2] | 2-(1,1-dioxido-6-phenyl-1,2,6-thiadiazinan-2-yl)-N-(5-hydroxyadamantan-2-yl)acetamide (Z) | $^1$H NMR (300 MHz, CDCl$_3$): δδ 7.44-7.27 (m, 5H), 6.90 (d, J = 6.5 Hz, 1H), 3.94-3.91 (m, 1H), 3.93 (s, 2H), 3.83-3.70 (m, 4H), 2.38-1.11 (m, 15H) |
| 39 | 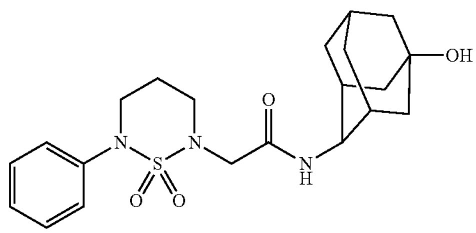 [SMILES: O=C(CN1CCCN(c2ccccc2)S1(=O)=O)NC1C2CC3CC1CC(O)(C3)C2] | 2-(1,1-dioxido-6-phenyl-1,2,6-thiadiazinan-2-yl)-N-(5-hydroxyadamantan-2-yl)acetamide (E) | $^1$H NMR (300 MHz, CDCl$_3$): δδ 7.42-7.16 (m, 5H), 6.90 (d, J = 7.6 Hz, 1H), 4.05-4.01 (m, 1H), 3.93 (s, 2H), 3.91-3.74 (m, 4H), 2.25-1.47 (m, 15H) |

TABLE 7

| No | Structure | IUPAC Name | NMR |
|---|---|---|---|
| 40 | 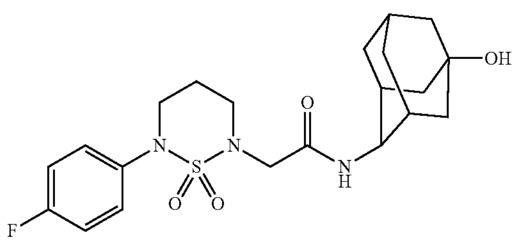 [SMILES: O=C(CN1CCCN(c2ccc(F)cc2)S1(=O)=O)NC1C2CC3CC1CC(O)(C3)C2] | 2-(6-(4-fluorophenyl)-1,1-dioxido-1,2,6-thiadiazinan-2-yl)-N-(5-hydroxyadamantan-2-yl)acetamide | $^1$H NMR (300 MHz, CDCl$_3$): δδ 7.36-7.31 (m, 2H), 7.10-7.04 (m, 2H), 6.87 (d, J = 7.5 Hz, 1H), 4.04-4.01 (m, 1H), 3.94-3.92 (m, 2H), 3.78-3.69 (m, 4H), 2.03-1.95 (m, 2H), 2.21-1.25 (m, 13H) |
| 41 | 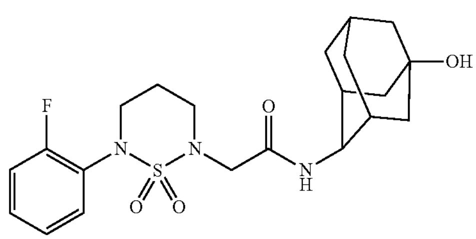 [SMILES: O=C(CN1CCCN(c2ccccc2F)S1(=O)=O)NC1C2CC3CC1CC(O)(C3)C2] | 2-(6-(2-fluorophenyl)-1,1-dioxido-1,2,6-thiadiazinan-2-yl)-N-(5-hydroxyadamantan-2-yl)acetamide | $^1$H NMR (300 MHz, CDCl$_3$): δδ 7.46-7.40 (m, 1H), 7.34-7.28 (m, 1H), 7.17-7.11 (m, 2H), 6.90 (d, J = 7.7 Hz, 1H), 4.04-4.01 (m, 1H), 3.96-3.94 (m, 2H), 3.80-3.77 (m, 4H), 2.21-1.48 (m, 13H), 2.03-1.95 (m, 2H) |
| 42 | 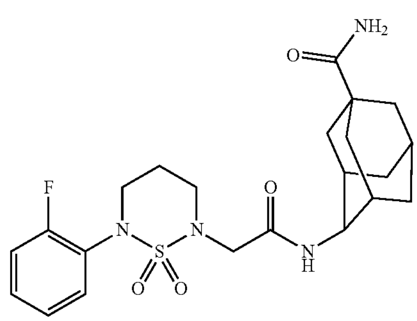 [SMILES: NC(=O)C12CC3CC(C1)C(NC(=O)CN1CCCN(c4ccccc4F)S1(=O)=O)C(C3)C2] | 4-(2-(6-(2-fluorophenyl)-1,1-dioxido-1,2,6-thiadiazinan-2-yl)acetamido)adamantan-1-carboxamide (Z) | $^1$H NMR (300 MHz, CDCl$_3$): δδ 7.47-7.41 (m, 1H), 7.34-7.27 (m, 1H), 7.19-7.11 (m, 2H), 6.97 (d, J = 7.8 Hz, 1H), 5.58 (s, 1H), 5.33 (s, 1H), 4.07-4.04 (m, 1H), 3.95 (s, 2H), 3.81-3.77 (m, 4H), 2.09-1.59 (m, 15H) |

TABLE 7-continued

| No | Structure | IUPAC Name | NMR |
|---|---|---|---|
| 43 | 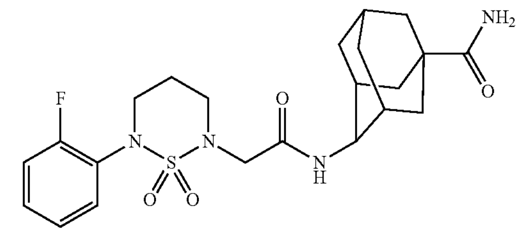 [SMILES: NC(=O)C12CC3CC(C1)C(NC(=O)CN1CCCN(c4ccccc4F)S1(=O)=O)C(C3)C2] | 4-(2-(6-(2-fluorophenyl)-1,1-dioxido-1,2,6-thiadiazinan-2-yl)acetamido)adamantan-1-carboxamide (E) | $^1$H NMR (300 MHz, CDCl$_3$): δδ 7.47 -7.41 (m, 1H), 7.34-7.27 (m, 1H), 7.19-7.11 (m, 2H), 6.97 (d, J = 7.8 Hz, 1H), 5.58 (s, 1H), 5.33 (s, 1H), 4.07-4.04 (m, 1H), 3.95 (s, 2H), 3.81-3.77 (m, 4H), 2.09-1.59 (m, 15H) |
| 44 | 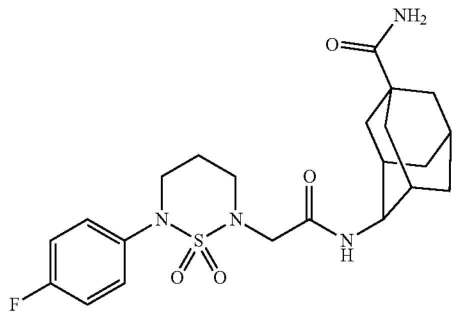 [SMILES: NC(=O)C12CC3CC(C1)C(NC(=O)CN1CCCN(c4ccc(F)cc4)S1(=O)=O)C(C3)C2] | 4-(2-(6-(4-fluorophenyl)-1,1-dioxido-1,2,6-thiadiazinan-2-yl)acetamido)adamantan-1-carboxamide (Z) | $^1$H NMR (300 MHz, CDCl$_3$): δδ 7.43-7.30 (m, 2H), 7.10-7.03 (m, 2H), 6.90-9.95 (m, 1H), 4.04-4.02 (m, 1H), 3.79-3.64 (m, 6H), 2.15-1.12 (m, 15H) |
| 45 | 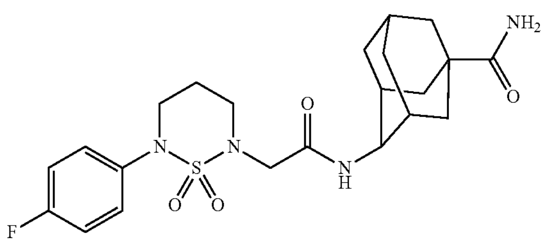 [SMILES: NC(=O)C12CC3CC(C1)C(NC(=O)CN1CCCN(c4ccc(F)cc4)S1(=O)=O)C(C3)C2] | 4-(2-(6-(4-fluorophenyl)-1,1-dioxido-1,2,6-thiadiazinan-2-yl)acetamido)adamantan-1-carboxamide (E) | $^1$H NMR (300 MHz, CDCl$_3$): δδ 7.43-7.32 (m, 2H), 7.10-7.01 (m, 2H), 6.90-9.95 (m, 1H), 4.04-4.02 (m, 1H), 3.82-3.64 (m, 6H), 2.36-1.12 (m, 15H) |
| 46 | 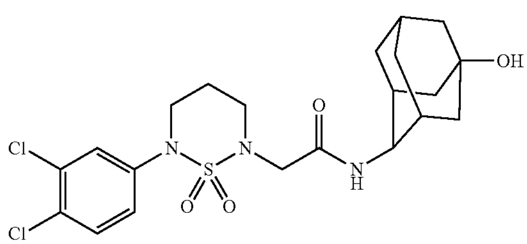 [SMILES: O=C(CN1CCCN(c2ccc(Cl)c(Cl)c2)S1(=O)=O)NC1C2CC3CC1CC(O)(C3)C2] | 2-(6-(3,4-dichlorophenyl)-1,1-dioxido-1,2,6-thiadiazinan-2-yl)-N-(5-hydroxyadamantan-2-yl)acetamide | $^1$H NMR (300 MHz, CDCl$_3$): δδ 7.46-7.44 (m, 2H), 7.23-7.19 (m, 1H), 6.82 (d, J = 7.2 Hz, 1H), 4.05-4.00 (m, 1H), 3.93-3.91 (m, 2H), 3.79-3.70 (m, 4H), 2.21-1.23 (m, 15H) |

TABLE 8

| No | Structure | IUPAC Name | NMR |
|---|---|---|---|
| 47 | 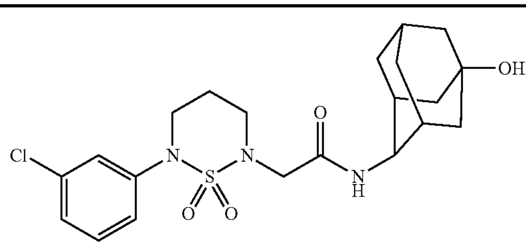 | 2-(6-(3-chlorophenyl)-1,1-dioxido-1,2,6-thiadiazinan-2-yl)-N-(5-hydroxyadamantan-2-yl)acetamide | $^1$H NMR (300 MHz, CDCl$_3$): δδ 7.36-7.23 (m, 4H), 6.86 (d, J = 7.2 Hz, 1H), 3.95-3.94 (m, 1H), 3.92 (s, 2H), 3.78-3.74 (m, 4H), 2.21-1.60 (m, 15H) |

TABLE 8-continued

| No | Structure | IUPAC Name | NMR |
|---|---|---|---|
| 48 | 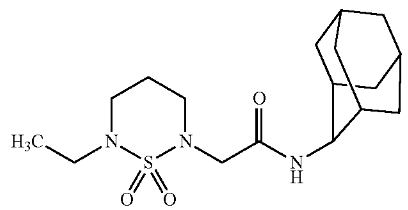 [SMILES: CCN1CCCN(CC(=O)NC2C3CC4CC(C3)CC2C4)S1(=O)=O] | N-(adamantan-2-yl)-2-(6-ethyl-1,1-dioxido-1,2,6-thiadiazinan-2-yl)acetamide | $^1$H NMR (300 MHz, CDCl$_3$): δδ 7.03 (d, J = 8.5 Hz, 1H), 4.07-4.04 (m, 1H), 3.76 (s, 2H), 3.55-3.51 (m, 2H), 3.43-3.39 (m, 2H), 3.21 (q, J = 7.2 Hz, 2H), 1.93-1.58 (m, 16H), 1.20 (t, J = 7.2 Hz, 3H) |
| 49 | 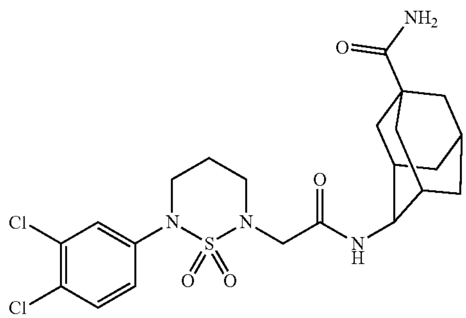 [SMILES: NC(=O)C12CC3CC(C1)C(NC(=O)CN1CCCN(c4ccc(Cl)c(Cl)c4)S1(=O)=O)C(C3)C2] | 4-(2-(6-(3,4-dichlorophenyl)-1,1-dioxido-1,2,6-thiadiazinan-2-yl)-acetamido)adamantan-1-carboxamide (Z) | $^1$H NMR (300 MHz, CDCl$_3$): δδ 7.47-7.44 (m, 2H), 7.24-7.21 (m, 1H), 6.87 (d, J = 7.1 Hz, 1H), 5.63 (s, 1H), 5.20 (s, 1H), 4.01-3.99 (m, 1H), 3.90 (s, 2H), 3.79-3.73 (m, 4H), 2.15-1.61 (m, 15H) |
| 50 | 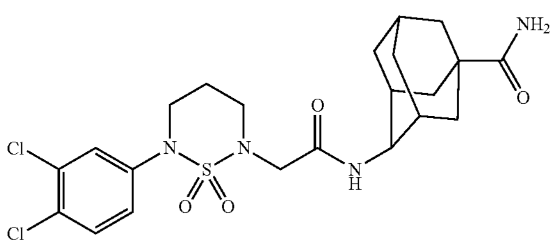 [SMILES: NC(=O)C12CC3CC(C1)C(NC(=O)CN1CCCN(c4ccc(Cl)c(Cl)c4)S1(=O)=O)C(C3)C2] | 4-(2-(6-(3,4-dichlorophenyl)-1,1-dioxido-1,2,6-thiadiazinan-2-yl)-acetamido)adamantan-1-carboxamide (E) | $^1$H NMR (300 MHz, CDCl$_3$): δδ 7.47-7.44 (m, 2H), 7.24-7.21 (m, 1H), 6.87 (d, J = 7.1 Hz, 1H), 5.63 (s, 1H), 5.20 (s, 1H), 4.01-3.99 (m, 1H), 3.90 (s, 2H), 3.79-3.73 (m, 4H), 2.15-1.61 (m, 15H) |
| 51 | 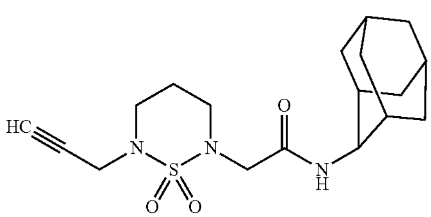 [SMILES: C#CCN1CCCN(CC(=O)NC2C3CC4CC(C3)CC2C4)S1(=O)=O] | N-(adamantan-2-yl)-2-(1,1-dioxido-6-(prop-2-yn-1-yl)-1,2,6-thiadiazinan-2-yl)acetamide | $^1$H NMR (300 MHz, CDCl$_3$): δδ 6.94 (d, J = 7.4 Hz, 1H), 4.07-4.03 (m, 1H), 3.97 (s, 2H), 3.96 (s, 1H), 3.80 (s, 2H), 3.62-3.52 (m, 4H), 1.94-1.61 (m, 16H) |
| 52 | 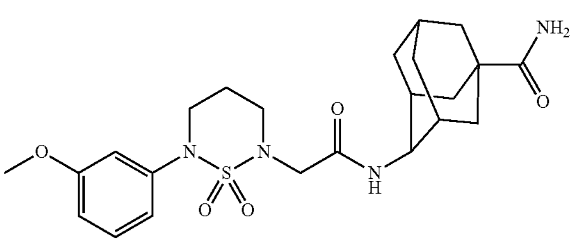 [SMILES: COc1cccc(N2CCCN(CC(=O)NC3C4CC5CC3CC(C(N)=O)(C5)C4)S2(=O)=O)c1] | 4-(2-(6-(3-methoxyphenyl)-1,1-dioxido-1,2,6-thiadiazinan-2-yl)-acetamido)adamantan-1-carboxamide (Z) | $^1$H NMR (300 MHz, CDCl$_3$): δδ 7.32-7.27 (m, 1H), 6.98-6.95 (m, 2H), 6.89-6.84 (m, 2H), 5.67-5.57 (m, 1H), 5.26-5.18 (s, 1H), 4.07-3.98 (m, 1H), 3.94-3.92 (m, 2H), 3.82 (s, 3H), 3.81-3.75 (m, 4H), 2.18-1.61 (m, 15H) |
| 53 | 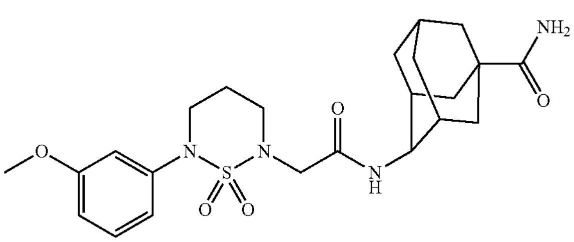 [SMILES: COc1cccc(N2CCCN(CC(=O)NC3C4CC5CC3CC(C(N)=O)(C5)C4)S2(=O)=O)c1] | 4-(2-(6-(3-methoxyphenyl)-1,1-dioxido-1,2,6-thiadiazinan-2-yl)-acetamido)adamantan-1-carboxamide (E) | $^1$H NMR (300 MHz, CDCl$_3$): δδ 7.31-7.25 (m, 1H), 6.99-6.94 (m, 2H), 6.90-6.83 (m, 2H), 5.56 (s, 1H), 5.26 (s, 1H), 4.07-4.04 (m, 1H), 3.95 (s, 2H), 3.81 (s, 3H), 3.80-3.74 (m, 4H), 2.09-1.60 (m, 15H) |

TABLE 9

| No | Structure | IUPAC Name | NMR |
|---|---|---|---|
| 54 | (structure) | 4-(2-(1,1-dioxido-6-(p-tolyl)-1,2,6-thiadiazinan-2-yl)acetamido)adamantan-1-carboxamide (E, Z mixture) | $^1$H NMR (300 MHz, CDCl$_3$): δδ 7.26-7.16 (m, 4H), 7.00-6.97 (s, 1H), 5.65-5.55 (m, 1H), 5.21-4.13 (m, 1H), 4.06-3.97 (m, 1H), 3.93-3.91 (m, 2H), 3.77-3.73 (m, 4H), 2.34 (s, 3H), 2.17-1.58 (m, 15H) |
| 55 | (structure) | 4-(2-(1,1-dioxido-6-(p-tolyl)-1,2,6-thiadiazinan-2-yl)acetamido)adamantan-1-carboxamide (E) | $^1$H NMR (300 MHz, CDCl$_3$): δδ 7.26-7.16 (m, 4H), 6.99 (d, J = 7.9 Hz, 1H), 5.57 (s, 1H), 5.27 (s, 1H), 4.06-4.04 (m, 1H), 3.93 (s, 2H), 3.77-3.73 (m, 4H), 2.34 (s, 3H), 2.09-1.61 (m, 15H) |
| 56 | (structure) | 4-(2-(6-(3-chlorophenyl)-1,1-dioxido-1,2,6-thiadiazinan-2-yl)-acetamido)adamantan-1-carboxamide | $^1$H NMR (300 MHz, CDCl$_3$): δδ 7.36-7.24 (m, 4H), 6.94-6.89 (s, 1H), 5.64-5.57 (m, 1H), 5.30-5.21 (m, 1H), 4.08-3.99 (m, 1H), 3.93-3.91 (m, 2H), 3.79-3.76 (m, 4H), 2.15-1.60 (m, 15H) |
| 57 | (structure) | N-(5-hydroxyadamantan-2-yl)-2-(6-(napthalene-2-yl)-1,1-dioxido-1,2,6-thiadiazinan-2-yl)acetamide | $^1$H NMR (300 MHz, CDCl$_3$): δδ 7.86-7.81 (m, 4H), 7.53-7.45 (m, 3H), 6.92 (d, J = 7.3 Hz, 1H), 4.04-3.27 (m, 7H), 2.20-1.45 (m, 15H) |
| 58 | (structure) | 2-(6-(4-cyanophenyl)-1,1-dioxido-1,2,6-thiadiazinan-2-yl)-N-(5-hydroxyadamantan-2-yl)acetamide | $^1$H NMR (300 MHz, CDCl$_3$): δ 7.68 (d, J = 8.5 Hz, 2H), 7.44 (d, J = 8.5 Hz, 2H), 6.81 (d, J = 7.6 Hz, 1H), 4.04-4.04 (m, 1H), 3.92-3.91 (m, 2H), 3.85-3.76 (m, 4H), 2.20-1.53 (m, 15H) |
| 59 | (structure) | 4-(2-(6-(2-fluorophenyl)-1,1-dioxido-1,2,6-thiadiazinan-2-yl)-acetamido)adamantan-1-carboxamide | $^1$H NMR (300 MHz, CDCl$_3$): δδ 7.46-7.41 (m, 1H), 7.34-7.26 (m, 1H), 7.18-7.12 (m, 1H), 6.98-6.94 (m, 1H), 5.67-5.59 (m, 1H), 5.34-5.26 (s, 1H), 4.07-3.96 (m, 1H), 3.95-3.92 (m, 2H), 3.81-3.77 (m, 4H), 2.17-1.58 (m, 15H) |

TABLE 9-continued

| No | Structure | IUPAC Name | NMR |
|---|---|---|---|
| 60 | 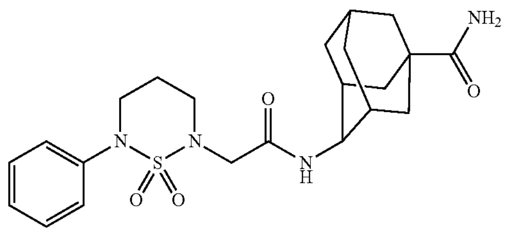 [SMILES: NC(=O)C12CC3CC(C1)C(NC(=O)CN1CCCN(c4ccccc4)S1(=O)=O)C(C3)C2] | 4-(2-(1,1-dioxido-6-phenyl-1,2,6-thiadiazinan-2-yl)acetamido)adamantan-1-carboxamide | $^1$H NMR (300 MHz, CDCl$_3$): δδ 7.41-7.30 (m, 5H), 6.96 (d, J = 7.1 Hz, 1H), 5.69 (s, 1H), 5.25 (s, 1H), 4.00-3.98 (m, 1H), 3.94-3.92 (m, 2H), 3.81-3.74 (m, 4H), 2.17-1.68 (m, 15H) |

TABLE 10

| No | Structure | IUPAC Name | NMR |
|---|---|---|---|
| 61 | 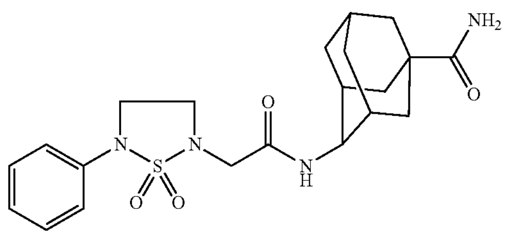 [SMILES: NC(=O)C12CC3CC(C1)C(NC(=O)CN1CCN(c4ccccc4)S1(=O)=O)C(C3)C2] | 4-(2-(1,1-dioxido-5-phenyl-1,2,5-thiadiazolidin-2-yl)acetamido)adamantan-1-carboxamide | $^1$H NMR (300 MHz, CDCl$_3$): δδ 7.44-7.38 (m, 2H), 7.31-7.20 (m, 3H), 7.12 (d, J = 7.8 Hz, 1H), 5.57 (s, 1H), 5.30 (s, 1H), 4.09-4.06 (m, 1H), 3.93-3.89 (m, 2H), 3.71-3.65 (m, 2H), 2.08-1.62 (m, 15H) |
| 62 | 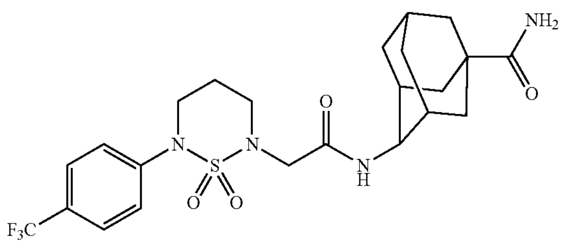 [SMILES: NC(=O)C12CC3CC(C1)C(NC(=O)CN1CCCN(c4ccc(C(F)(F)F)cc4)S1(=O)=O)C(C3)C2] | 4-(2-(1,1-dioxido-6-(4-trifluoromethyl)phenyl-1,2,6-thiadiazinan-2-yl)acetamido)adamantan-1-carboxamide | $^1$H NMR (300 MHz, CDCl$_3$): δδ 7.65 (d, J = 8.5 Hz, 2H), 7.47 (d, J = 8.5 Hz, 2H), 6.91 (d, J = 7.8 Hz, 1H), 5.57 (s, 1H), 5.32 (s, 1H), 4.07-4.05 (m, 1H), 3.94-3.92 (m, 2H), 3.85-3.78 (m, 4H), 2.09-1.59 (m, 15H) |
| 63 | 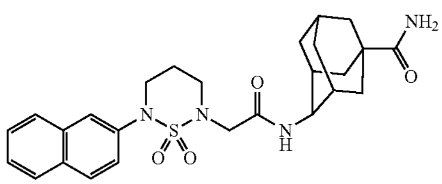 [SMILES: NC(=O)C12CC3CC(C1)C(NC(=O)CN1CCCN(c4ccc5ccccc5c4)S1(=O)=O)C(C3)C2] | 4-(2-(6-(napthalene-2-yl)-1,1-dioxido-1,2,6-thiadiazinan-2-yl)acetamido)adamantan-1-carboxamide | $^1$H NMR (300 MHz, CDCl$_3$): δδ 7.86-7.81 (m, 4H), 7.52-7.45 (m, 3H), 6.99 (d, J = 7.6 Hz, 1H), 5.57 (s, 1H), 5.30 (s, 1H), 4.07-4.05 (m, 1H), 3.99 (s, 2H), 3.92-3.88 (m, 2H), 3.83-3.78 (m, 2H), 2.09-1.56 (m, 15H) |
| 64 | 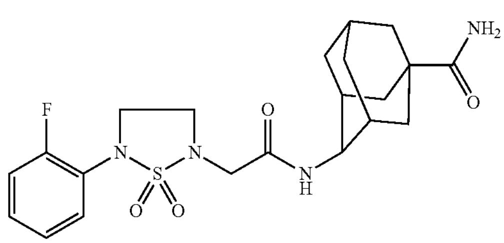 [SMILES: NC(=O)C12CC3CC(C1)C(NC(=O)CN1CCN(c4ccccc4F)S1(=O)=O)C(C3)C2] | 4-(2-(5-(2-fluorophenyl)-1,1-dioxido-1,2,5-thiadiazolidin-2-yl)acetamido)adamantan-1-carboxamide | $^1$H NMR (300 MHz, CDCl$_3$): δδ 7.73-7.16 (m, 4H), 7.01 (d, J = 7.8 Hz, 1H), 5.58 (s, 1H), 5.27 (s, 1H), 4.31-4.25 (m, 1H), 4.09-3.90 (m, 6H), 2.24-0.81 (m, 15H) |
| 65 | 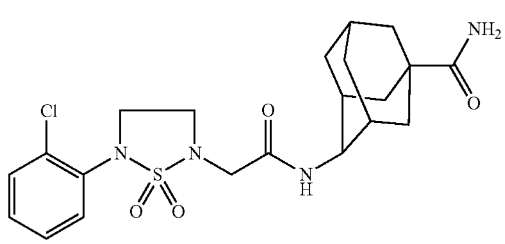 [SMILES: NC(=O)C12CC3CC(C1)C(NC(=O)CN1CCN(c4ccccc4Cl)S1(=O)=O)C(C3)C2] | 4-(2-(5-(2-chlorophenyl)-1,1-dioxido-1,2,5-thiadiazolidin-2-yl)acetamido)adamantan-1-carboxamide | $^1$H NMR (300 MHz, CDCl$_3$): δδ 7.68-7.62 (m, 1H), 7.54-7.48 (m, 1H), 7.38-7.32 (m, 2H), 7.19 (d, J = 7.9 Hz, 1H), 5.60 (s, 1H), 5.37 (s, 1H), 4.10-4.08 (m, 1H), 3.95-3.91 (m, 2H), 3.91 (s, 2H), 3.73-3.68 (m, 2H), 2.17-1.60 (m, 15H) |

TABLE 10-continued

| No | Structure | IUPAC Name | NMR |
|---|---|---|---|
| 66 | 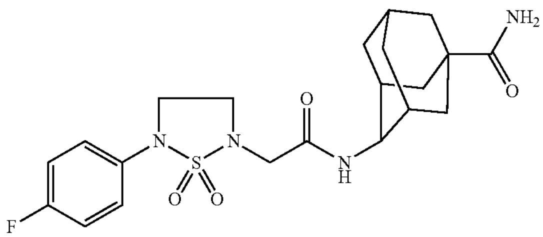 [SMILES: NC(=O)C12CC3CC(C1)C(NC(=O)CN1CCN(c4ccc(F)cc4)S1(=O)=O)C(C3)C2] | 4-(2-(5-(4-fluorophenyl)-1,1-dioxido-1,2,5-thiadiazolidin-2-yl)acetamido)adamantan-1-carboxamide | $^1$H NMR (300 MHz, CDCl$_3$): δδ 7.67-7.63 (m, 1H), 7.52-7.48 (m, 1H), 7.37-7.31 (m, 2H), 7.16 (d, J = 7.3 Hz, 1H), 4.13-4.08 (m, 1H), 3.95-3.90 (m, 2H), 3.89 (s, 2H), 3.71-3.67 (m, 2H), 1.95-1.58 (m, 14H) |
| 67 | 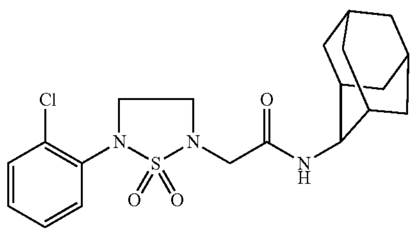 [SMILES: O=C(CN1CCN(c2ccccc2Cl)S1(=O)=O)NC1C2CC3CC(C2)CC1C3] | N-(adamantan-2-yl)-2-(5-(2-chlorophenyl)-1,1-dixoxido-1,2,5-thiadiazolidin-2-yl)acetamide | $^1$H NMR (300 MHz, CDCl$_3$): δδ 8.42 (s, 1H), 7.43-7.19 (m, 12H), 7.06-7.03 (m, 1H), 6.77-6.74 (m, 1H), 5.04 (s, 2H), 3.97 (s, 2H), 3.92-3.88 (m, 2H), 3.70-3.65 (m, 2H) |

TABLE 11

| No | Structure | IUPAC Name | NMR |
|---|---|---|---|
| 68 | 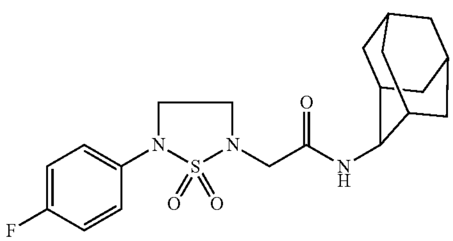 [SMILES: O=C(CN1CCN(c2ccc(F)cc2)S1(=O)=O)NC1C2CC3CC(C2)CC1C3] | N-(adamantan-2-yl)-2-(5-(4-fluorophenyl)-1,1-dioxido-1,2,5-thiadiazolidin-2-yl)acetamide | LCMS MH+ 408 |
| 69 | 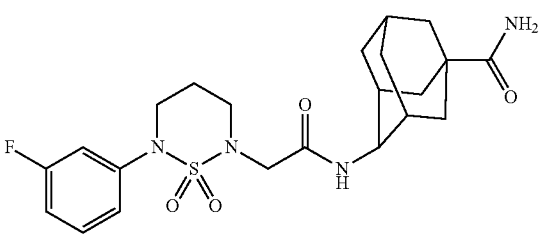 [SMILES: NC(=O)C12CC3CC(C1)C(NC(=O)CN1CCCN(c4cccc(F)c4)S1(=O)=O)C(C3)C2] | 4-(2-(6-(3-fluorophenyl)-1,1-dioxido-1,2,6-thiadiazinan-2-yl)acetamido)adamantan-1-carboxamide | $^1$H NMR (300 MHz, CDCl$_3$): δδ 7.38-7.31 (m, 1H), 7.16-6.99 (m, 3H), 6.94 (d, J = 7.8 Hz, 1H), 5.58 (s, 1H), 5.35 (s, 1H), 4.07-3.99 (m, 1H), 3.93-3.91 (m, 2H), 3.80-3.75 (m, 4H), 2.15-1.58 (m, 15H) |
| 70 | 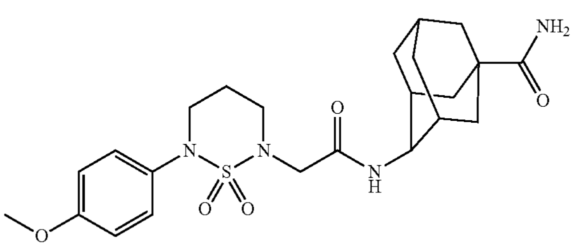 [SMILES: COc1ccc(N2CCCN(CC(=O)NC3C4CC5CC3CC(C(N)=O)(C5)C4)S2(=O)=O)cc1] | 4-(2-(6-(4-methoxyphenyl)-1,1-dioxido-1,2,6-thiadiazinan-2-yl)acetamido)adamantan-1-carboxamide | $^1$H NMR (300 MHz, CDCl$_3$): δδ 7.29 (d, J = 8.8 Hz, 2H), 7.00-6.95 (m, 1H), 6.89 (d, J = 8.8 Hz, 2H), 5.66-5.56 (m, 1H), 5.23-5.15 (m, 1H), 4.07-3.99 (m, 1H), 3.93-3.90 (m, 2H), 3.80 (s, 3H), 3.77-3.70 (m, 4H), 2.15-1.57 (m, 15H) |

TABLE 11-continued

| No | Structure | IUPAC Name | NMR |
|---|---|---|---|
| 71 | 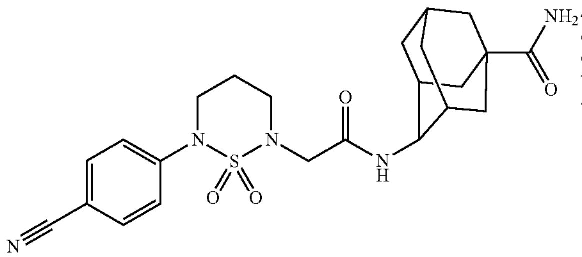 [SMILES: N#Cc1ccc(N2CCCN(CC(=O)NC3C4CC5CC3CC(C(N)=O)(C5)C4)S2(=O)=O)cc1] | 4-(2-(6-(4-cyanophenyl)-1,1-dioxido-1,2,6-thiadiazinan-2-yl)acetamido)adamantan-1-carboxamide | $^1$H NMR (300 MHz, CDCl$_3$): δδ 7.68 (d, J = 8.3 Hz, 2H), 7.45 (d, J = 8.3 Hz, 2H), 6.87 (d, J = 7.8 Hz, 1H), 5.56 (s, 1H), 5.27 (s, 1H), 4.07-4.04 (m, 1H), 3.92 (s, 2H), 3.85-3.78 (m, 4H), 2.09-1.25 (m, 15H) |
| 72 | 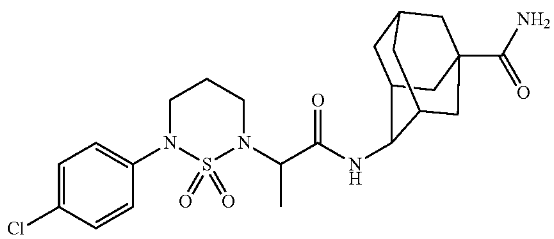 [SMILES: CC(C(=O)NC1C2CC3CC1CC(C(N)=O)(C3)C2)N1CCCN(c2ccc(Cl)cc2)S1(=O)=O] | 4-(2-(6-(4-chlorophenyl)-1,1-dioxido-1,2,6-thiadiazinan-2-yl)propaneamido)adamantan-1-carboxamide | $^1$H NMR (300 MHz, CDCl$_3$): δδ 7.45 (d, J = 7.9 Hz, 2H), 7.33 (d, J = 7.9 Hz, 2H), 6.79 (d, J = 7.5 Hz, 1H), 6.45 (s, 1H), 5.70 (s, 1H), 4.74 (q, J = 6.6 Hz, 1H), 4.02-3.94 (m, 1H), 3.84-3.75 (m, 1H), 3.63-3.60 (m, 2H), 2.10-1.71 (m, 16H), 1.55 (d, J = 6.6 Hz, 3H) |
| 73 | 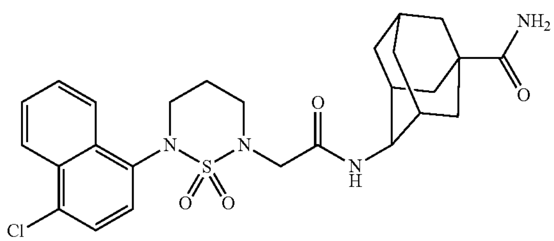 [SMILES: NC(=O)C12CC3CC(C1)C(NC(=O)CN1CCCN(c4ccc(Cl)c5ccccc45)S1(=O)=O)C(C3)C2] | 4-(2-(6-(4-chloronaphthalene-1-yl)-1,1-dioxido-1,2,6-thiadiazinan-2-yl)acetamido)adamantan-1-carboxamide | $^1$H NMR (300 MHz, CDCl$_3$): δδ 8.34-8.29 (m, 1H), 8.26-8.22 (m, 1H), 7.70-7.65 (m, 3H), 7.60-7.56 (m, 1H), 6.99 (d, J = 7.8 Hz, 1H), 5.55 (s, 1H), 5.30 (s, 1H), 4.43-3.82 (m, 4H), 3.57-3.51 (m, 2H), 2.43-2.28 (m, 1H), 2.17-1.55 (m, 15H) |
| 74 | 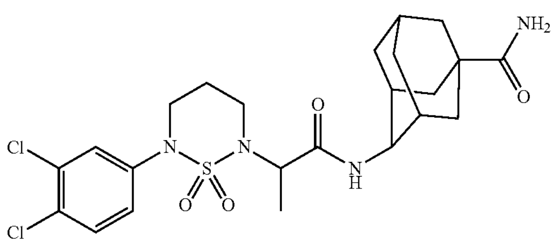 [SMILES: CC(C(=O)NC1C2CC3CC1CC(C(N)=O)(C3)C2)N1CCCN(c2ccc(Cl)c(Cl)c2)S1(=O)=O] | 4-(2-(6-(3,4-dichlorophenyl)-1,1-dioxido-1,2,6-thiadiazinan-2-yl)propaneamido)adamantan-1-carboxamide | $^1$H NMR (300 MHz, CDCl$_3$): δδ 7.62-7.24 (m, 3H), 6.69 (d, J = 7.2 Hz, 1H), 6.55 (s, 1H), 5.73 (s, 1H), 4.52 (q, J = 7.1 Hz, 1H), 4.04-3.60 (m, 4H), 2.04-1.25 (m, 16H), 1.53 (d, J = 7.1 Hz, 3H) |

TABLE 12

| No | Structure | IUPAC Name | NMR |
|---|---|---|---|
| 75 | 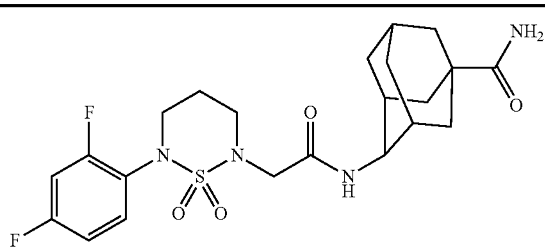 | 4-(2-(6-(2,4-difluorophenyl)-1,1-dioxido-1,2,6-thiadiazinan-2-yl)acetamido)adamantan-1-carboxamide | $^1$H NMR (300 MHz, CDCl$_3$): δδ 7.47-7.38 (m, 1H), 6.94-6.87 (m, 3H), 5.63-5.57 (m, 1H), 5.30-5.26 (m, 1H), 4.07-3.99 (m, 1H), 3.94-3.92 (m, 2H), 3.82-3.73 (m, 4H), 2.15-1.60 (m, 15H) |

TABLE 12-continued

| No | Structure | IUPAC Name | NMR |
|---|---|---|---|
| 76 | 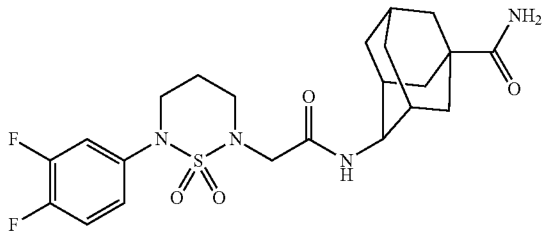 [SMILES: NC(=O)C12CC3CC(C1)C(NC(=O)CN1CCCN(c4ccc(F)c(F)c4)S1(=O)=O)C(C3)C2] | 4-(2-(6-(3,4-difluorophenyl)-1,1-dioxido-1,2,6-thiadiazinan-2-yl)acetamido)adamantan-1-carboxamide | $^1$H NMR (300 MHz, CDCl$_3$): δδ 7.26-7.08 (m, 3H), 6.92-6.88 (s, 1H), 5.65-5.58 (s, 1H), 5.30-5.23 (m, 1H), 4.07-3.99 (m, 1H), 3.93-3.90 (m, 2H), 3.79-3.70 (m, 4H), 2.15-1.59 (m, 15H) |
| 77 | 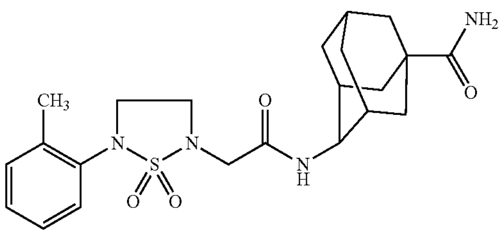 [SMILES: Cc1ccccc1N1CCN(CC(=O)NC2C3CC4CC2CC(C(N)=O)(C4)C3)S1(=O)=O] | 4-(2-(1,1-dioxido-5-(o-tolyl)-1,2,5-thiadiazolidin-2-yl)acetamido)adamantan-1-carboxamide | $^1$H NMR (300 MHz, CDCl$_3$): δδ 7.47-7.19 (m, 4H), 6.99-6.97 (m, 1H), 5.58~5.57 (m, 1H), 5.28 (s, 1H), 4.11-4.03 (m, 1H), 3.91-3.90 (m, 2H), 3.84-3.80 (m, 2H), 3.71-3.64 (m, 2H), 2.43-2.42 (m, 3H), 2.28-1.60 (m, 13H) |
| 78 | 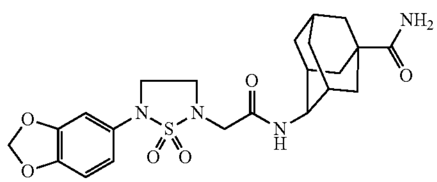 [SMILES: NC(=O)C12CC3CC(C1)C(NC(=O)CN1CCN(c4ccc5c(c4)OCO5)S1(=O)=O)C(C3)C2] | 4-(2-(5-(benzo[d][1,3]dioxol-5-yl)-1,1-dioxido-1,2,5-thiadiazolidin-2-yl)acetamido)adamantan-1-carboxamide | $^1$H NMR (300 MHz, CDCl$_3$): δδ 7.22-7.13 (m, 1H), 6.93-6.90 (m, 1H), 6.85-6.77 (m, 2H), 6.02-6.00 (m, 2H), 5.84-5.59 (m, 1H), 5.33-5.19 (m, 1H), 4.14-3.99 (m, 1H), 3.90(s, 2H), 3.86-3.80 (m, 2H), 3.67-3.60 (m, 2H), 2.11-1.58 (m, 13H) |
| 79 | 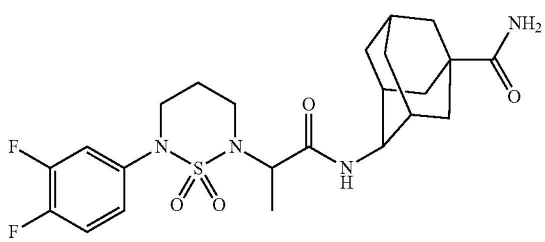 [SMILES: CC(C(=O)NC1C2CC3CC1CC(C(N)=O)(C3)C2)N1CCCN(c2ccc(F)c(F)c2)S1(=O)=O] | 4-(2-(6-(3,4-difluorophenyl)-1,1-dioxido-1,2,6-thiadiazinan-2-yl)propaneamido)adamantan-1-carboxamide | $^1$H NMR (300 MHz, CDCl$_3$): δδ 7.34-7.24 (m, 1H), 7.21-7.14 (m, 2H), 6.81-6.68 (m, 1H), 5.74-5.28 (m, 1H), 4.56-4.48 (m, 1H), 4.06-3.98 (m, 1H), 3.95-3.74 (m, 2H), 3.70-3.53 (m, 2H), 2.12-1.59 (m, 15H), 1.54-1.50 (m, 3H) |
| 80 | 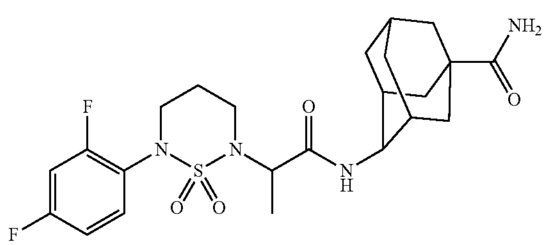 [SMILES: CC(C(=O)NC1C2CC3CC1CC(C(N)=O)(C3)C2)N1CCCN(c2ccc(F)cc2F)S1(=O)=O] | 4-(2-(6-(2,4-difluorophenyl)-1,1-dioxido-1,2,6-thiadiazinan-2-yl)propaneamido)adamantan-1-carboxamide | $^1$H NMR (300 MHz, CDCl$_3$): δδ 7.58-7.47 (m, 1H), 6.95-6.85 (m, 2H), 6.78 (d, J = 8.1 Hz, 1H), 5.57 (s, 1H), 5.26 (s, 1H), 4.58-4.51 (m, 1H), 4.06-4.00 (m, 1H), 3.91-3.56 (m, 4H), 2.08-1.64 (m, 15H), 1.56-1.52 (m, 3H) |
| 81 | 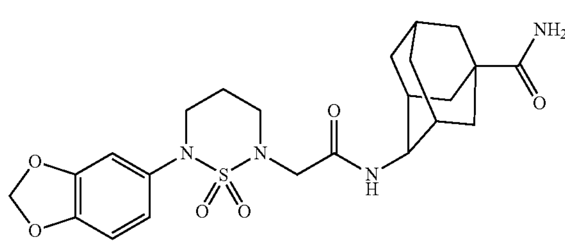 [SMILES: NC(=O)C12CC3CC(C1)C(NC(=O)CN1CCCN(c4ccc5c(c4)OCO5)S1(=O)=O)C(C3)C2] | 4-(2-(6-(benzo[d][1,3]dioxol-5-yl)-1,1-dioxido-1,2,6-thiadiazinan-2-yl)acetamido)adamantan-1-carboxamide | $^1$H NMR (300 MHz, CDCl$_3$): δδ 6.98-6.93 (s, 1H), 6.86-6.77 (m, 3H), 5.99 (s, 2H), 5.66-5.58 (s, 1H), 5.30-5.23 (m, 1H), 4.07-3.97 (m, 1H), 3.92-3.89 (m, 2H), 3.76-3.68 (m, 4H), 2.15-1.58 (m, 15H) |

TABLE 13

| No | Structure | IUPAC Name | NMR |
|---|---|---|---|
| 82 | 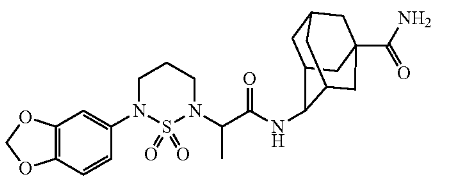 [SMILES: CC(C(=O)NC1C2CC3CC1CC(C(N)=O)(C3)C2)N1CCCN(c2ccc3c(c2)OCO3)S1(=O)=O] | 4-(2-(6-(benzo[d][1,3]dioxol-5-yl)-1,1-dioxido-1,2,6-thiadiazinan-2-yl)propaneamido)adamitan-1-carboxamide | ¹H NMR (300 MHz, CDCl₃): δ 6.93-6.76 (m, 4H), 5.99-5.97 (m, 2H), 5.80-5.28 (m, 1H), 4.58-4.50 (m, 1H), 4.05-3.99 (m, 1H), 3.90-3.72 (m, 2H), 3.58-3.55 (m, 2H), 2.06-1.59 (m, 15H), 1.54-1.51 (m, 3H) |
| 83 | 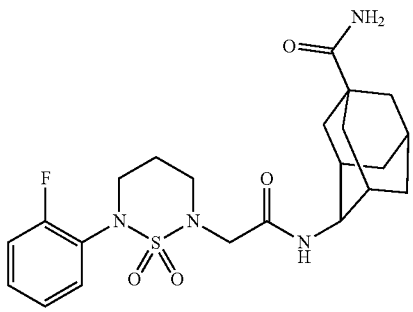 [SMILES: NC(=O)C12CC3CC(C1)C(NC(=O)CN1CCCN(c4ccccc4F)S1(=O)=O)C(C3)C2] | 4-(2-(6-(2-fluorophenyl)-1,1-dioxido-1,2,6-thiadiazinan-2-yl)acetamido)adamantan-1-carboxamide (Z) | LCMS MH+ 465 |
| 84 | 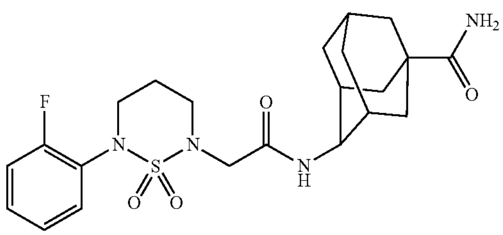 [SMILES: NC(=O)C12CC3CC(C1)C(NC(=O)CN1CCCN(c4ccccc4F)S1(=O)=O)C(C3)C2] | 4-(2-(6-(2-fluorophenyl)-1,1-dioxido-1,2,6-thiadiazinan-2-yl)acetamido)adamantan-1-carboxamide (E) | LCMS MH+ 465 |
| 85 | 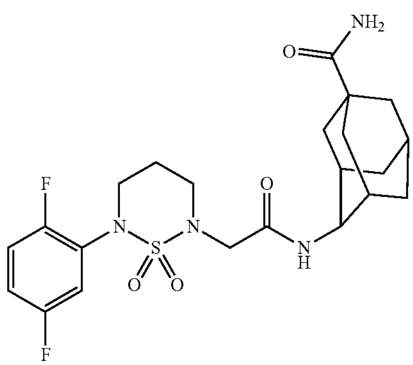 [SMILES: NC(=O)C12CC3CC(C1)C(NC(=O)CN1CCCN(c4cc(F)ccc4F)S1(=O)=O)C(C3)C2] | 4-(2-(6-(2,5-difluorophenyl)-1,1-dioxido-1,2,6-thiadiazinan-2-yl)acetamido)adamantan-1-carboxamide (Z) | ¹H NMR (300 MHz, CDCl₃): δδ 7.21-6.97 (m, 3H), 6.90 (d, J = 7.1 Hz, 1H), 5.64 (s, 1H), 5.21 (s, 1H), 4.01-3.99 (m, 1H), 3.92 (s, 2H), 3.81-3.76 (m, 4H), 2.15-1.73 (m, 15H) |
| 86 | 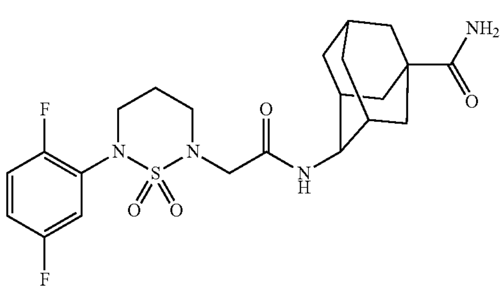 [SMILES: NC(=O)C12CC3CC(C1)C(NC(=O)CN1CCCN(c4cc(F)ccc4F)S1(=O)=O)C(C3)C2] | 4-(2-(6-(2,5-difluorophenyl)-1,1-dioxido-1,2,6-thiadiazinan-2-yl)acetamido)adamantan-1-carboxamide (E) | ¹H NMR (300 MHz, CDCl₃): δδ 7.21-6.97 (m, 3H), 6.93 (d, J = 8.2 Hz, 1H), 5.58 (s, 1H), 5.28 (s, 1H), 4.08-4.04 (m, 1H), 3.94 (s, 2H), 3.82-3.75 (m, 4H), 2.10-1.59 (m, 15H) |

TABLE 13-continued

| No | Structure | IUPAC Name | NMR |
|---|---|---|---|
| 87 | 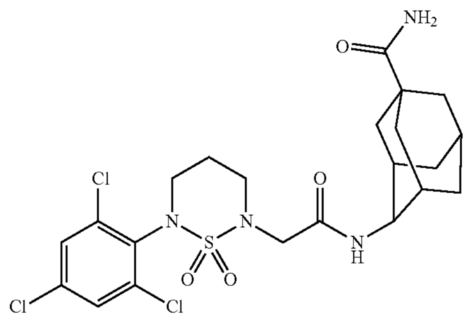 [SMILES: NC(=O)C12CC3CC(C1)C(NC(=O)CN1CCCN(c4c(Cl)cc(Cl)cc4Cl)S1(=O)=O)C(C3)C2] | 4-(2-(1,1-dioxido-6-(2,4,6-trichlorophenyl)-1,2,6-thiadiazinan-2-yl)acetamido)adamantan-1-carboxamide(Z) | ¹H NMR (300 MHz, CDCl₃): δδ 7.41 (s, 2H), 6.94 (d, J = 7.0 Hz, 1H), 5.56 (s, 1H), 5.22 (s, 1H), 4.18-4.14 (m, 1H), 4.00 (s, 2H), 3.87-3.82 (m, 2H), 3.71-3.41 (m, 2H), 2.14-1.61 (m, 15H) |
| 88 | 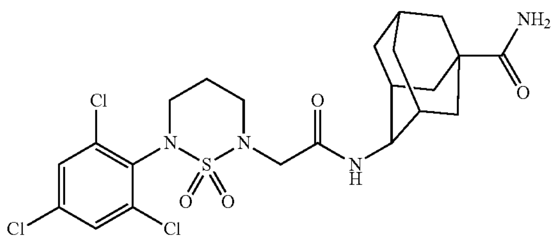 [SMILES: NC(=O)C12CC3CC(C1)C(NC(=O)CN1CCCN(c4c(Cl)cc(Cl)cc4Cl)S1(=O)=O)C(C3)C2] | 4-(2-(1,1-dioxido-6-(2,4,6-trichlorophenyl)-1,2,6-thiadiazinan-2-yl)acetamido)adamantan-1-carboxamide(E) | ¹H NMR (300 MHz, CDCl₃): δδ 7.41 (s, 2H), 6.97 (d, J = 7.8 Hz, 1H), 5.57 (s, 1H), 5.25 (s, 1H), 4.15-4.03 (m, 3H), 3.87-3.83 (m, 4H), 2.09-1.42 (m, 15H) |

TABLE 14

| No | Structure | IUPAC Name | NMR |
|---|---|---|---|
| 89 | 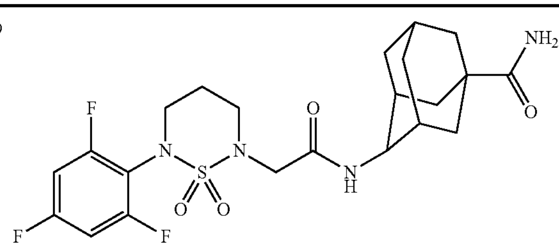 | 4-(2-(1,1-dioxido-6-(2,4,6-trifluorophenyl)-1,2,6-thiadiazinan-2-yl)acetamido)adamantan-1-carboxamide | ¹H NMR (300 MHz, CDCl₃): δδ 6.95 (d, J = 7.9 Hz, 1H), 6.78-6.72 (m, 2H), 5.57 (s, 1H), 5.28 (s, 1H), 4.07-4.04 (m, 1H), 3.93 (s, 2H), 3.87-3.81 (m, 4H), 2.09-1.61 (m, 15H) |
| 90 | 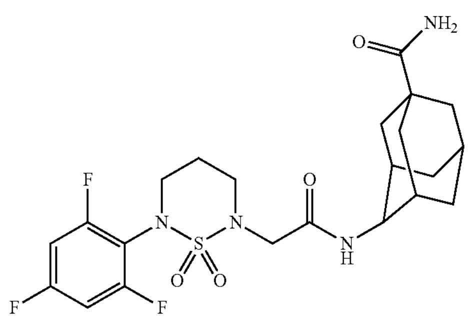 [SMILES: NC(=O)C12CC3CC(C1)C(NC(=O)CN1CCCN(c4c(F)cc(F)cc4F)S1(=O)=O)C(C3)C2] | 4-(2-(1,1-dioxido-6-(2,4,6-trifluorophenyl)-1,2,6-thiadiazinan-2-yl)acetamido)adamantan-1-carboxamide | ¹H NMR (300 MHz, CDCl₃): δ 6.91 (d, J = 7.0 Hz, 1H), 6.79-6.72 (m, 2H), 5.65 (s, 1H), 5.23 (s, 1H), 4.01-3.98 (m, 1H), 3.90 (s, 2H), 3.87-3.80 (m, 4H), 2.17-1.73 (m, 15H) |
| 91 | 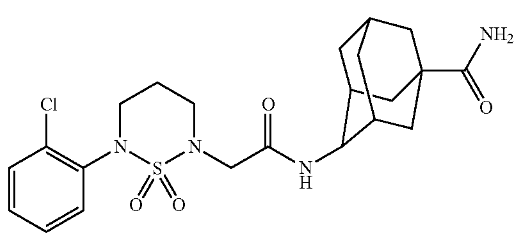 [SMILES: NC(=O)C12CC3CC(C1)C(NC(=O)CN1CCCN(c4ccccc4Br)S1(=O)=O)C(C3)C2] | 4-(2-(6-(2-chlorophenyl)-1,1-dioxido-1,2,6-thiadiazinan-2-yl)acetamido)adamantan-1-carboxamide | ¹H NMR(300 MHz, CDCl₃): δ 7.58-7.54(m, 1H), 7.49-7.45(m, 1H), 7.32-7.25(m, 2H), 6.97(d, J = 7.8 Hz, 1 H), 5.57(s, 1H), 5.29 (s, 1H), 4.37-4.31 (m, 1H), 4.23-4.14 (m, 1H), 4.07-4.04 (m, 1H), 3.93-3.86(m, 1H), 3.72-3.66 (m, 1H), 3.49-3.45 (m, 2H), 2.35-2.32(m, 1H), 2.09-1.54 (m, 14H) |

TABLE 14-continued

| No | Structure | IUPAC Name | NMR |
|---|---|---|---|
| 92 | (structure) | 4-(2-(6-(2-chlorophenyl)-1,1-dioxido-1,2,6-thiadiazinan-2-yl)acetamido)adamantan-1-carboxamide | $^1$H NMR (300 MHz, CDCl$_3$): δ 7.58-7.54 (m, 1H), 7.49-7.46 (m, 1H), 7.33-7.26 (m, 2H), 6.93 (d, J = 7.6 Hz, 1H), 5.67 (s, 1H), 5.21 (s, 1H), 4.35-4.29 (m, 1H), 4.21-4.12 (m, 1H), 4.00-3.98 (m, 1H), 3.91-3.84 (m, 1H), 3.69-3.63 (m, 1H), 3.51-3.46 (m, 2H), 2.32-1.64 (m, 15H) |
| 93 | (structure) | 4-(2-(6-(2-fluorophenyl)-1,1-dioxido-1,2,6-thiadiazinan-2-yl)propaneamido)adamantan-1-carboxamide | $^1$H NMR (300 MHz, CDCl$_3$): δ 7.55-7.50 (m, 1H), 7.33-7.28 (m, 1H), 7.17-7.11 (m, 2H), 6.86 (d, J = 7.7 Hz, 1H), 5.58 (s, 1H), 5.30 (s, 1H), 4.57 (q, J = 7.1 Hz, 1H), 4.06-4.03 (m, 1H), 3.95-3.79 (m, 2H), 3.64-3.59 (m, 2H), 2.08-1.57 (m, 15H), 1.54 (d, J = 7.1 Hz, 3H) |
| 94 | (structure) | 4-(2-(6-(2-fluorophenyl)-1,1-dioxido-1,2,6-thiadiazinan-2-yl)propaneamido)adamantan-1-carboxamide | $^1$H NMR (300 MHz, CDCl$_3$): δ 7.56-7.51 (m, 1H), 7.33-7.26 (m, 2H), 7.18-7.11 (m, 1H), 6.92 (d, J = 8.0 Hz, 1H), 5.77 (s, 1H), 5.21 (s, 1H), 4.55 (q, J = 7.1 Hz, 1H), 4.04-4.03 (m, 1H), 3.97-3.78 (m, 2H), 3.62-3.58 (m, 2H), 2.15-1.67 (m, 15H), 1.54 (d, J = 7.1 Hz, 3H) |
| 95 | (structure) | 4-(2-(6-(2-bromophenyl)-1,1-dioxido-1,2,6-thiadiazinan-2-yl)acetamido)adamantan-1-carboxamide | $^1$H NMR (300 MHz, CDCl$_3$): δ 7.68-7.65 (m, 1H), 7.61-7.57 (m, 1H), 7.38-7.32 (m, 1H), 7.24-7.18 (m, 1H), 6.96 (d, J = 7.8 Hz, 1H), 5.57 (s, 1H), 5.27 (s, 1H), 4.42-4.37 (m, 1H), 4.26-4.15 (m, 1H), 4.07-4.04 (m, 1H), 3.91-3.82 (m, 1H), 3.72-3.67 (m, 1H), 3.48-3.42 (m, 2H), 2.11-1.55 (m, 15H) |

TABLE 15

| No | Structure | IUPAC Name | NMR |
|---|---|---|---|
| 96 | (structure) | 4-(2-(1,1-dioxido-6-(2,4,5-trifluorophenyl)-1,2,6-thiadiazinan-2-yl)acetamido)adamantan-1-carboxamide | $^1$H NMR (300 MHz, CDCl$_3$): δ 7.35-7.27 (m, 1H), 7.07-6.99 (m, 1H), 6.89 (d, J = 7.9 Hz, 1H), 5.57 (s, 1H), 5.28 (s, 1H), 4.07-4.04 (m, 1H), 3.93 (s, 2H), 3.82-3.78 (m, 2H), 3.75-3.71 (m, 2H), 2.10-1.62 (m, 15H) |

| No | Structure | IUPAC Name | NMR |
|---|---|---|---|
| 97 | 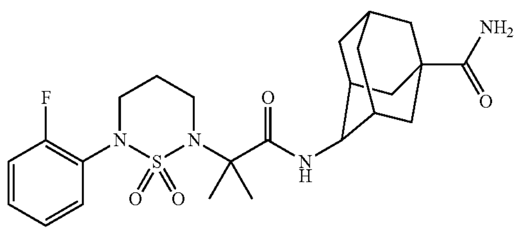 [SMILES: CC(C)(C(=O)NC1C2CC3CC1CC(C(N)=O)(C3)C2)N1CCCN(c2ccccc2F)S1(=O)=O] | 4-(2-(6-(2-fluorophenyl)-1,1-dioxido-1,2,6-thiadiazinan-2-yl)methylpropaneamido)adamantan-1-carboxamide | $^1$H NMR (300 MHz, CDCl$_3$): δ 7.54-7.48(m, 1H), 7.32-7.24(m, 1H), 7.16-7.09 (m, 2H), 6.89 (d, J = 8.1 Hz, 1H), 5.59(s, 1H), 5.27(s, 1H), 4.00-3.97(m, 1H), 3.85-3.81(m, 2H), 3.77-3.73(m, 2H), 2.04-1.57(m, 15H), 1.67(s, 6H) |
| 98 | 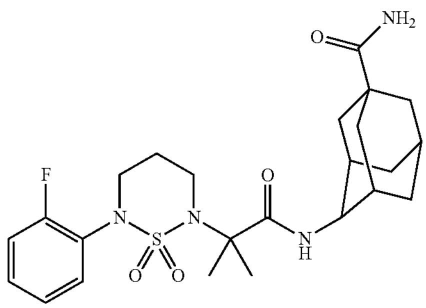 [SMILES: CC(C)(C(=O)NC1C2CC3CC1CC(C(N)=O)(C3)C2)N1CCCN(c2ccccc2F)S1(=O)=O] | 4-(2-(6-(2-fluorophenyl)-1,1-dioxido-1,2,6-thiadiazinan-2-yl)methylpropaneamido)adamantan-1-carboxamide | $^1$H NMR (300 MHz, CDCl$_3$): δ 7.51-7.46 (m, 1H), 7.32-7.25 (m, 1H), 7.17-7.09 (m, 2H), 6.86 (d, J = 7.2 Hz, 1H), 5.88 (s, 1H), 5.19 (s, 1H), 3.93-3.91 (m, 1H), 3.84-3.79 (m, 4H), 2.09-1.73 (m, 15H), 1.68 (s, 6H) |
| 99 | 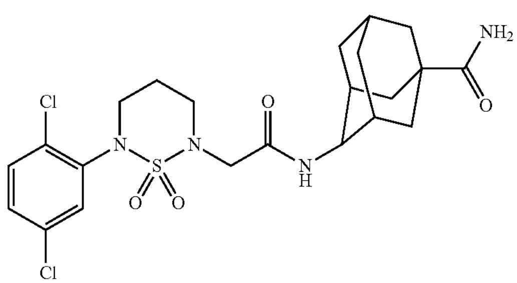 [SMILES: NC(=O)C12CC3CC(C1)C(NC(=O)CN1CCCN(c4cc(Cl)ccc4Cl)S1(=O)=O)C(C3)C2] | 4-(2-(6-(2,5-dichlorophenyl)-1,1-dioxido-1,2,6-thiadiazinan-2-yl)acetamido)adamantan-1-carboxamide | $^1$H NMR (300 MHz, CDCl$_3$): δδ 7.56-7.54 (m, 1H), 7.43-7.40 (m, 1H), 7.29-7.28 (m, 1H), 6.93 (d, J = 7.9 Hz, 1H), 5.58 (s, 1H), 5.29 (s, 1H), 4.35-4.11 (m, 2H), 4.07-4.04 (m, 1H), 3.92-3.82 (m, 1H), 3.75-3.65(m, 1H), 3.50-3.42(m, 2H), 2.35-1.62 (m, 15H) |
| 100 | 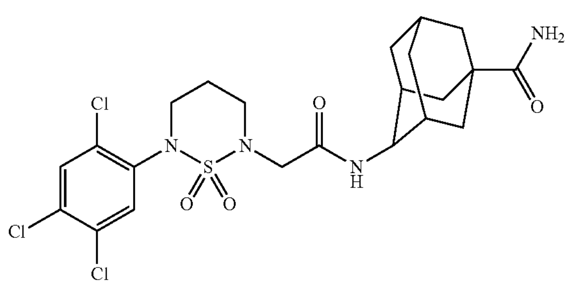 [SMILES: NC(=O)C12CC3CC(C1)C(NC(=O)CN1CCCN(c4cc(Cl)c(Cl)cc4Cl)S1(=O)=O)C(C3)C2] | 4-(2-(1,1-dioxido-6-(2,4,5-trichlorophenyl)-1,2,6-thiadiazinan-2-yl)acetamido)adamantan-1-carboxamide | $^1$H NMR (300 MHz, CDCl$_3$): δ 7.65 (s, 1H), 7.60 (s, 1H), 6.89 (d, J = 8.4 Hz, 1H), 5.56 (s, 1H), 5.21 (s, 1H), 4.34-3.44 (m, 7H), 2.17-1.58 (m, 15H) |
| 101 | 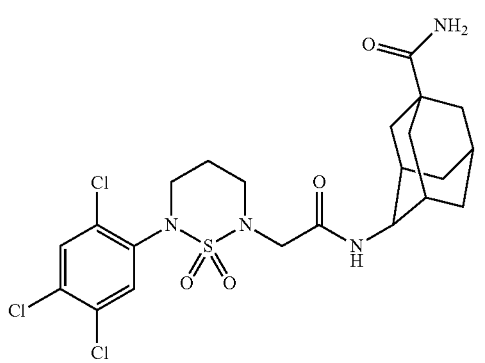 [SMILES: NC(=O)C12CC3CC(C1)C(NC(=O)CN1CCCN(c4cc(Cl)c(Cl)cc4Cl)S1(=O)=O)C(C3)C2] | 4-(2-(1,1-dioxido-6-(2,4,5-trichlorophenyl)-1,2,6-thiadiazinan-2-yl)acetamido)adamantan-1-carboxamide | $^1$H NMR (300 MHz, CDCl$_3$): δ 7.65 (s, 1H), 7.60 (s, 1H), 6.85 (d, J = 7.2 Hz, 1H), 5.65 (s, 1H), 5.23 (s, 1H), 4.32-3.46 (m, 7H), 2.17-1.65 (m, 15H) |

TABLE 15-continued

| No | Structure | IUPAC Name | NMR |
|---|---|---|---|
| 102 | 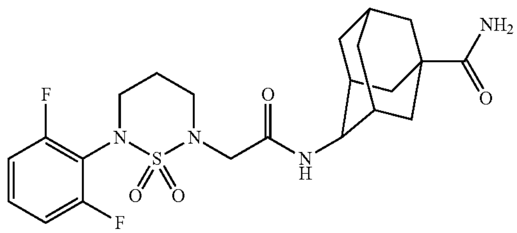 [SMILES: NC(=O)C12CC3CC(C1)C(NC(=O)CN1CCCN(c4c(F)cccc4F)S1(=O)=O)C(C3)C2] | 4-(2-(6-(2,6-difluorophenyl)-1,1-dioxido-1,2,6-thiadiazinan-2-yl)acetamido)adamantan-1-carboxamide | ¹H NMR (300 MHz, CDCl₃): δ 7.31-7.23 (m, 1H), 7.00-6.94 (m, 3H), 5.57 (s, 1H), 5.30 (s, 1H), 4.07-4.04 (m, 1H), 3.94 (s, 2H), 3.90-3.78 (m, 4H), 2.17-1.59 (m, 15H) |

TABLE 16

| No | Structure | IUPAC Name | NMR |
|---|---|---|---|
| 103 | 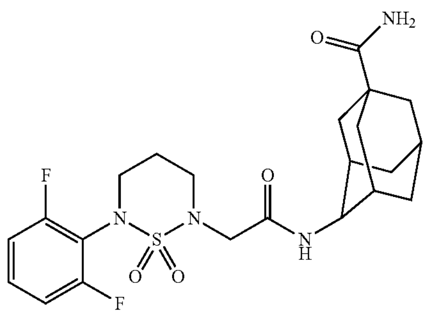 [SMILES: NC(=O)C12CC3CC(C1)C(NC(=O)CN1CCCN(c4c(F)cccc4F)S1(=O)=O)C(C3)C2] | 4-(2-(6-(2,6-difluorophenyl)-1,1-dioxido-1,2,6-thiadiazinan-2-yl)acetamido)adamantan-1-carboxamide | ¹H NMR(300 MHz, CDCl₃): δ 7.32-7.26(m, 1H), 7.00-6.93(m, 3H), 5.69(s, 1H), 5.24(s, 1H), 4.01-3.98(m, 1H), 3.92(s, 2H), 3.90-3.81(m, 4H), 2.17-1.65(m, 15H) |
| 104 | 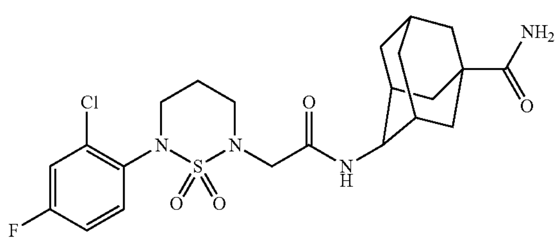 [SMILES: NC(=O)C12CC3CC(C1)C(NC(=O)CN1CCCN(c4ccc(F)cc4Cl)S1(=O)=O)C(C3)C2] | 4-(2-(6-(2-chloro-4-fluorophenyl)-1,1-dioxido-1,2,6-thiadiazinan-2-yl)acetamido)adamantan-1-carboxamide | ¹H NMR (300 MHz, CDCl₃): δ 7.57-7.52 (m, 1H), 7.25-7.21 (m, 1H), 7.05-6.99 (m, 1H), 6.94 (d, J = 8.0 Hz, 1H), 5.58 (s, 1H), 5.29 (s, 1H), 4.35-4.30 (m, 1H), 4.23-4.13 (m, 1H), 4.07-4.04 (m, 1H), 3.92-3.83 (m, 1H), 3.71-3.66 (m, 1H), 3.48-3.40 (m, 2H), 2.10-1.55 (m, 15H) |
| 105 | 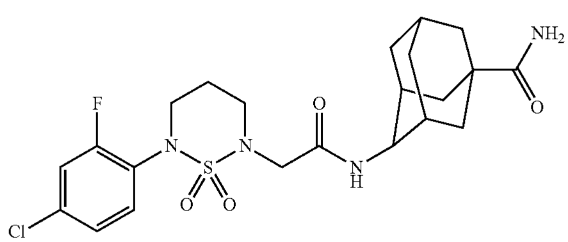 | 4-(2-(6-(4-chloro-2-fluorophenyl)-1,1-dioxido-1,2,6-thiadiazinan-2-yl)acetamido)adamantan-1-carboxamide | ¹H NMR (300 MHz, CDCl₃): δ 7.40-7.34 (m, 1H), 7.20-7.12 (m, 2H), 6.89 (d, J = 7.3 Hz, 1H), 5.50 (s, 1H), 5.20 (s, 1H), 4.06-4.04 (m, 1H), 3.92 (s, 2H), 3.81-3.73 (m, 4H), 2.09~1.53 (m, 15H) |
| 106 | 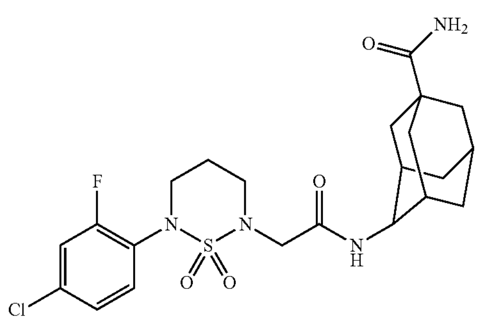 [SMILES: NC(=O)C12CC3CC(C1)C(NC(=O)CN1CCCN(c4ccc(Cl)cc4F)S1(=O)=O)C(C3)C2] | 4-(2-(6-(4-chloro-2-fluorophenyl)-1,1-dioxido-1,2,6-thiadiazinan-2-yl)acetamido)adamantan-1-carboxamide | ¹H NMR (300 MHz, CDCl₃): δ 7.41-7.35 (m, 1H), 7.20-7.13 (m, 2H), 6.88 (d, J = 7.1 Hz, 1H), 5.64 (s, 1H), 5.21 (s, 1H), 4.01-3.99 (m, 1H), 3.90 (s, 2H), 3.81-3.74 (m, 4H), 2.16-1.62 (m, 15H) |

TABLE 16-continued

| No | Structure | IUPAC Name | NMR |
|---|---|---|---|
| 107 | 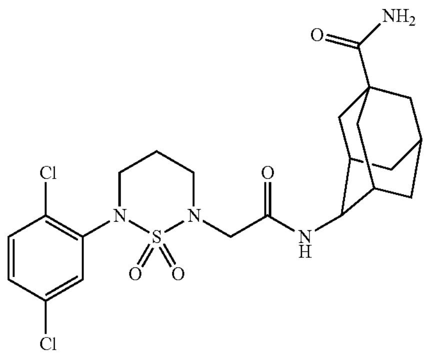 [SMILES: NC(=O)C12CC3CC(C1)C(NC(=O)CN1CCCN(c4cc(Cl)ccc4Cl)S1(=O)=O)C(C3)C2] | 4-(2-(6-(2,5-dichlorophenyl)-1,1-dioxido-1,2,6-thiadiazinan-2-yl)acetamido)adamantan-1-carboxamide | ¹H NMR(300 MHz, CDCl₃): δ 7.56-7.55 (m, 1H), 7.43-7.40 (m, 1H), 7.29-7.28 (m, 1H), 6.93 (d, J = 7.9 Hz, 1H), 5.58(s, 1H), 5.29(s, 1H), 4.35-4.11 (m, 2H), 4.07-4.04(m, 1H), 3.92-3.82(m, 1H), 3.75-3.65(m, 1H), 3.50-3.42(m, 2H), 2.35-1.62(m, 15H) |
| 108 | 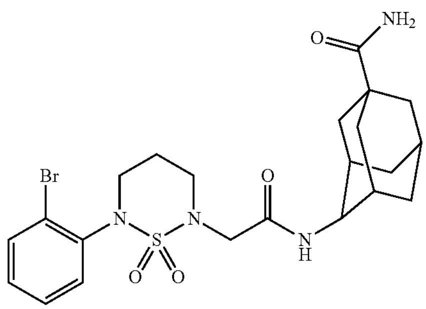 | 4-(2-(6-(2-bromophenyl)-1,1-dioxido-1,2,6-thiadiazinan-2-yl)acetamido)adamantan-1-carboxamide | ¹H NMR(300 MHz, CDCl₃): δ 7.68-7.65 (m, 1H), 7.60-7.57 (m, 1H), 7.38-7.32 (m, 1H), 7.24-7.18 (m, 1H), 6.92 (d, J = 7.4 Hz, 1H), 5.67 (s, 1H), 5.21 (s, 1H), 4.41-4.35 (m, 1H), 4.23-4.13 (m, 1H), 4.01-3.98 (m, 1H), 3.90-3.81 (m, 1H), 3.69-3.63(m, 1H), 3.50-3.43(m, 2H), 2.19-1.67(m, 15H) |
| 109 | 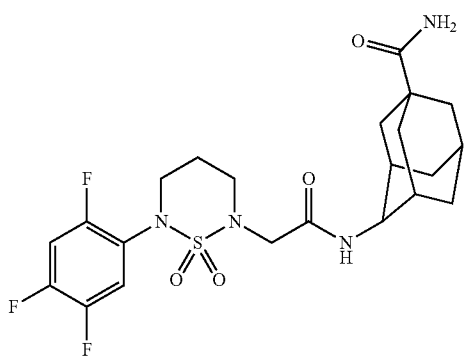 [SMILES: NC(=O)C12CC3CC(C1)C(NC(=O)CN1CCCN(c4cc(F)c(F)cc4F)S1(=O)=O)C(C3)C2] | 4-(2-(1,1-dioxido-6-(2,4,5-trifluorophenyl)-1,2,6-thiadiazinan-2-yl)acetamido)adamantan-1-carboxamide | ¹H NMR (300 MHz, CDCl₃): δ 7.36-7.28 (m, 1H), 7.08-6.99 (m, 1H), 6.87 (d, J = 7.5 Hz, 1H), 5.64 (s, 1H), 5.26 (s, 1H), 4.02-3.99 (m, 1H), 3.91 (s, 2H), 3.81-3.77 (m, 2H), 3.75-3.72 (m, 2H), 2.17-1.65 (m, 15H) |

TABLE 17

| No | Structure | IUPAC Name | NMR |
|---|---|---|---|
| 110 | 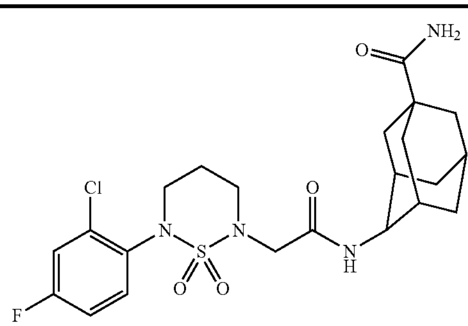 | 4-(2-(6-(2-chloro-4-fluorophenyl)-1,1-dioxido-1,2,6-thiadiazinan-2-yl)acetamido)adamantan-1-carboxamide | ¹H NMR (300 MHz, CDCl₃): δ 7.57-7.52 (m, 1H), 7.24-7.21 (m, 1H), 7.06-6.99 (m, 1H), 6.90 (d, J = 6.6 Hz, 1H), 5.66 (s, 1H), 5.22(s, 1H), 4.34-4.28(m, 1H), 4.20-4.11 (m, 1H), 4.01-3.99 (m, 1H), 3.90-3.81(m, 1H), 3.68-3.62(m, 1H), 3.52-3.43(m, 1H), 2.18-1.65(m, 15H) |

TABLE 17-continued

| No | Structure | IUPAC Name | NMR |
|---|---|---|---|
| 111 | 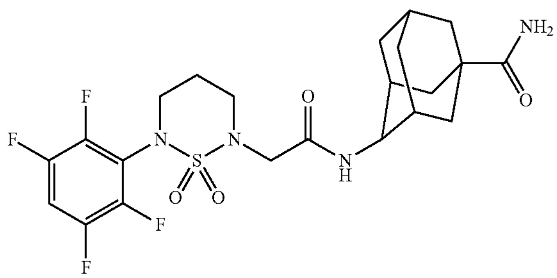 [SMILES: NC(=O)C12CC3CC(C1)C(NC(=O)CN1CCCN(c4c(F)c(F)cc(F)c4F)S1(=O)=O)C(C3)C2] | 4-(2-(1,1-dioxido-6-(2,4,5,6-tetrafluorophenyl)-1,2,6-thiadiazinan-2-yl)acetamido)adamantan-1-carboxamide | $^1$H NMR (300 MHz, CDCl$_3$): δ 7.16-7.05 (m, 1H), 6.90 (d, J = 7.8 Hz, 1H), 5.58 (s, 1H), 5.34 (s, 1H), 4.08-4.05 (m, 1H), 3.93-3.90 (m, 4H), 3.87-3.84 (m, 2H), 2.10-1.60 (m, 15H) |
| 112 | 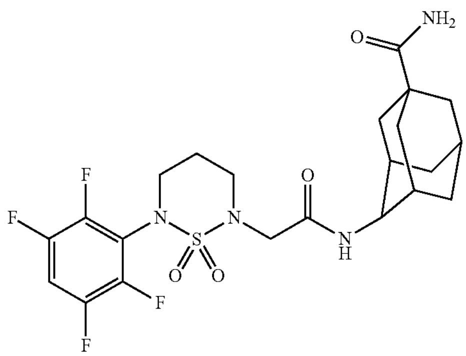 [SMILES: NC(=O)C12CC3CC(C1)C(NC(=O)CN1CCCN(c4c(F)c(F)cc(F)c4F)S1(=O)=O)C(C3)C2] | 4-(2-(1,1-dioxido-6-(2,4,5,6-tetrafluorophenyl)-1,2,6-thiadiazinan-2-yl)acetamido)adamantan-1-carboxamide | $^1$H NMR (300 MHz, CDCl$_3$): δ 7.16-7.05 (m, 1H), 6.87 (d, J = 6.6 Hz, 1H), 5.65 (s, 1H), 5.26(s, 1H), 4.01-3.99(m, 1H), 3.92-3.84(m, 6H), 2.18-1.65(m, 15H) |
| 113 | 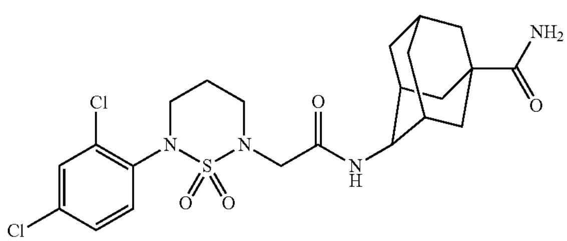 [SMILES: NC(=O)C12CC3CC(C1)C(NC(=O)CN1CCCN(c4ccc(Cl)cc4Cl)S1(=O)=O)C(C3)C2] | 4-(2-(6-(2,4-dichlorophenyl)-1,1-dioxido-1,2,6-thiadiazinan-2-yl)acetamido)adamantan-1-carboxamide | $^1$H NMR (300 MHz, CDCl$_3$): δ 7.51-7.48 (m, 2H), 7.30-7.26 (m, 1H), 6.92 (d, J = 7.7 Hz, 1H), 5.57 (s, 1H), 5.31 (s, 1H), 4.33-4.28 (m, 1H), 4.23-4.13 (m, 1H), 4.07-4.04 (m, 1H), 3.92-3.82 (m, 1H), 3.71-3.65(m, 1H), 3.48-3.43(m, 2H), 2.35-2.30(m, 1H), 2.10-1.56(m, 14H) |
| 114 | 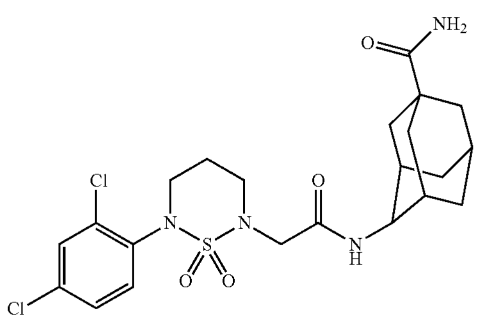 [SMILES: NC(=O)C12CC3CC(C1)C(NC(=O)CN1CCCN(c4ccc(Cl)cc4Cl)S1(=O)=O)C(C3)C2] | 4-(2-(6-(2,4-dichlorophenyl)-1,1-dioxido-1,2,6-thiadiazinan-2-yl)acetamido)adamantan-1-carboxamide | $^1$H NMR (300 MHz, CDCl$_3$): δ 7.51-7.49 (m, 2H), 7.30-7.26 (m, 1H), 6.90(d, J = 7.9 Hz, 1H), 5.66 (s, 1H), 5.25(s, 1H), 4.32-4.27 (m, 1H), 4.19-4.12(m, 1H), 4.04-3.99(m, 1H), 3.89-3.80(m, 1H), 3.68-3.62(m, 1H), 3.49-3.44(m, 2H), 2.34-2.25(m, 1H), 2.17-1.68(m, 14H) |
| 115 | 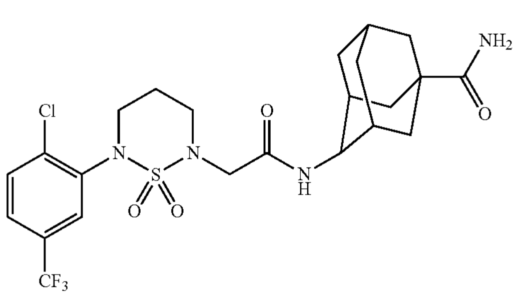 [SMILES: NC(=O)C12CC3CC(C1)C(NC(=O)CN1CCCN(c4cc(C(F)(F)F)ccc4Cl)S1(=O)=O)C(C3)C2] | 4-(2-(6-(2-chloro-5-trifluoromethyl)phenyl)-1,1-dioxido-1,2,6-thiadiazinan-2-yl)acetamido)adamantan-1-carboxamide | $^1$H NMR (300 MHz, CDCl$_3$): δ 7.80 (d, J = 1.7 Hz, 1H), 7.62 (d, J = 8.4 Hz, 1H), 7.55 (dd, J = 8.4 Hz, 1.7 Hz, 1H), 6.91(d, J = 7.9 Hz, 1H), 5.57 (s, 1H), 5.29 (s, 1H), 4.37-4.31 (m, 1H), 4.28-4.15 (m, 1H), 4.07-4.04 (m, 1H), 3.98-3.88 (m, 1H), 3.73-3.67 (m, 1H), 3.50-3.45(m, 2H), 2.38-2.33(m, 1H), 2.10-1.61(m, 14H) |

TABLE 17-continued

| No | Structure | IUPAC Name | NMR |
|---|---|---|---|
| 116 | 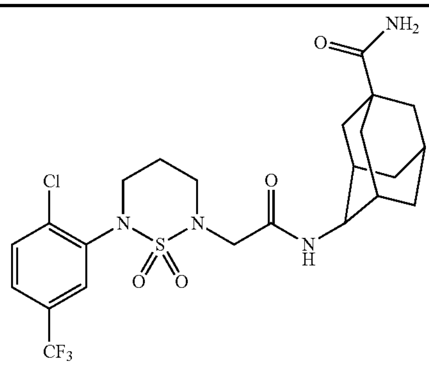 | 4-(2-(6-(2-chloro-5-trifluoromethyl)phenyl)-1,1-dioxido-1,2,6-thiadiazinan-2-yl)acetamido)adamantan-1-carboxamide | $^1$H NMR (300 MHz, CDCl$_3$): δ 7.79-7.78 (m, 1H), 7.64-7.61 (m, 1H), 7.56-7.53 (m, 1H), 6.88 (d, J = 6.9 Hz, 1H), 5.66 (s, 1H), 5.25 (s, 1H), 4.35-4.16 (m, 2H), 4.02-3.99 (m, 1H), 3.97-3.87 (m, 1H), 3.71-3.65 (m, 1H), 3.53-3.44 (m, 2H), 2.38-1.69 (m, 15H) |

TABLE 18

| No | Structure | IUPAC Name | NMR |
|---|---|---|---|
| 117 | 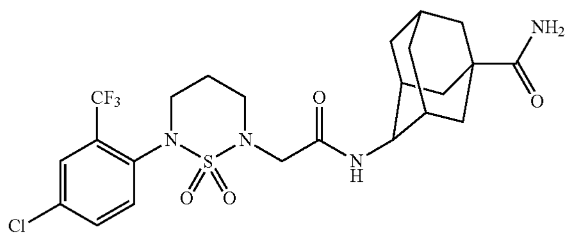 [SMILES: NC(=O)C12CC3CC(C1)C(NC(=O)CN1CCCN(c4ccc(Cl)cc4C(F)(F)F)S1(=O)=O)C(C3)C2] | 4-(2-(6-(4-chloro-2-trifluoromethyl)phenyl)-1,1-dioxido-1,2,6-thiadiazinan-2-yl)acetamido)adamantan-1-carboxamide | $^1$H NMR(300 MHz, CDCl$_3$): δ 7.75-7.68 (m, 2H), 7.60-7.56(m, 1H), 6.85(d, J = 7.5 Hz, 1H), 5.55(s, 1H), 5.23(s, 1H), 4.30-4.25 (m, 1H), 4.21-4.15 (m, 1H), 4.07-4.04(m, 1H), 3.90-3.79(m, 1H), 3.67-3.61(m, 1H), 3.44-3.32 (m, 2H), 2.35-2.25 (m, 1H), 2.09-1.58 (m, 14H) |
| 118 | 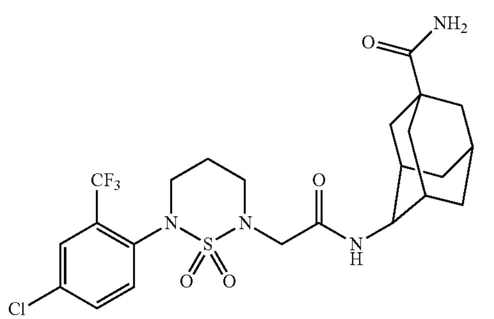 [SMILES: NC(=O)C12CC3CC(C1)C(NC(=O)CN1CCCN(c4ccc(Cl)cc4C(F)(F)F)S1(=O)=O)C(C3)C2] | 4-(2-(6-(4-chloro-2-trifluoromethyl)phenyl)-1,1-dioxido-1,2,6-thiadiazinan-2-yl)acetamido)adamantan-1-carboxamide | $^1$H NMR(300 MHz, CDCl$_3$): δ 7.74-7.69(m, 2H), 7.60-7.57 (m, 1H), 6.82(s, 1H), 5.60 (s, 1H), 5.25(s, 1H), 4.29-3.34(m, 7H), 2.30-2.24 (m, 1H), 2.17-1.56 (m, 14H) |
| 119 | 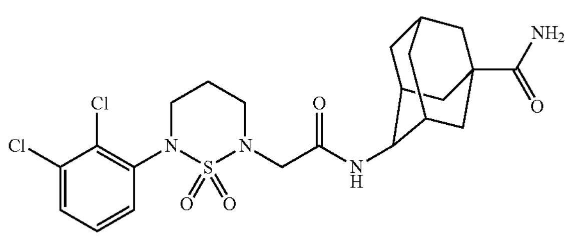 [SMILES: NC(=O)C12CC3CC(C1)C(NC(=O)CN1CCCN(c4cccc(Cl)c4Cl)S1(=O)=O)C(C3)C2] | 4-(2-(6-(2,3-dichlorophenyl)-1,1-dioxido-1,2,6-thiadiazinan-2-yl)acetamido)adamantan-1-carboxamide | $^1$H NMR (300 MHz, CDCl$_3$): δ7.51 (dd, J = 8.0 Hz, 1.4 Hz, 1H), 7.46(dd, J = 8.0 Hz, 1.4 Hz, 1H), 7.24(dd, J = 8.0 Hz, 1H), 6.92(d, J = 7.9 Hz, 1H), 5.56(s, 1H), 5.28(s, 1H), 4.34-4.28(m, 1H), 4.23-4.13(m, 1H), 4.07-4.04(m, 1H), 3.91-3.82(m, 1H), 3.72-3.66(m, 1H), 3.50-3.44 (m, 2H), 2.41-2.27(m, 1H), 2.11-1.57(m, 14H) |

TABLE 18-continued

| No | Structure | IUPAC Name | NMR |
|---|---|---|---|
| 120 | 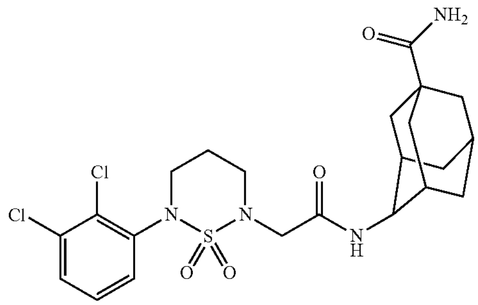 [SMILES: NC(=O)C12CC3CC(C1)C(NC(=O)CN1CCCN(c4cccc(Cl)c4Cl)S1(=O)=O)C(C3)C2] | 4-(2-(6-(2,3-dichlorophenyl)-1,1-dioxido-1,2,6-thiadiazinan-2-yl)acetamido)adamantan-1-carboxamide | $^1$H NMR (300 MHz, CDCl$_3$): δ 7.51 (dd, J = 8.0 Hz, 1.4 Hz, 1H), 7.46 (dd, J = 8.0 Hz, 1.4 Hz, 1H), 7.24 (d, J = 8.0 Hz, 1H), 6.89 (s, 1H), 5.65 (s, 1H), 5.21 (s, 1H), 4.33-4.27 (m, 1H), 4.21-4.12 (m, 1H), 4.01-3.99 (m, 1H), 3.90-3.81 (m, 1H), 3.69-3.63 (m, 1H), 3.52-3.45 (m, 2H), 2.35-2.26 (m, 1H), 2.18-1.63 (m, 14H) |
| 121 | 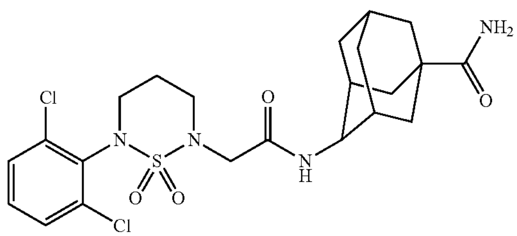 [SMILES: NC(=O)C12CC3CC(C1)C(NC(=O)CN1CCCN(c4c(Cl)cccc4Cl)S1(=O)=O)C(C3)C2] | 4-(2-(6-(2,6-dichlorophenyl)-1,1-dioxido-1,2,6-thiadiazinan-2-yl)acetamido)adamantan-1-carboxamide | $^1$H NMR (300 MHz, CDCl$_3$): δ 7.41-7.38 (m, 2H), 7.25-7.20 (m, 1H), 7.02 (d, J = 8.1 Hz, 1H), 5.57 (s, 1H), 5.26 (s, 1H), 4.05 (s, 3H), 3.89-3.83 (m, 4H), 2.10-1.61 (m, 15H) |
| 122 | 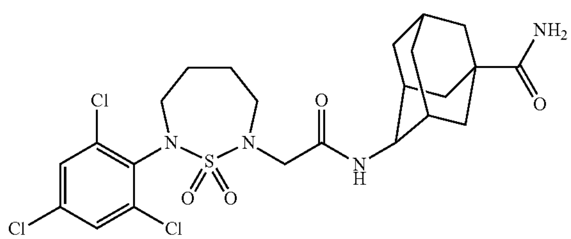 [SMILES: NC(=O)C12CC3CC(C1)C(NC(=O)CN1CCCCN(c4c(Cl)cc(Cl)cc4Cl)S1(=O)=O)C(C3)C2] | 4-(2-(1,1-dioxido-7-(2,4,6-trichlorophenyl)-1,2,7-thiadiazepane-2-yl)acetamido)adamantan-1-carboxamide | $^1$H NMR (300 MHz, CDCl$_3$): δ 7.43 (s, 2H), 6.94 (d, J = 8.0 Hz, 1H), 5.57 (s, 1H), 5.30 (s, 1H), 4.04-4.01 (m, 1H), 3.95 (s, 2H), 3.55-3.52 (m, 2H), 3.42-3.38 (m, 2H), 2.23-2.17 (m, 2H), 2.04-1.55 (m, 15 H) |
| 123 | 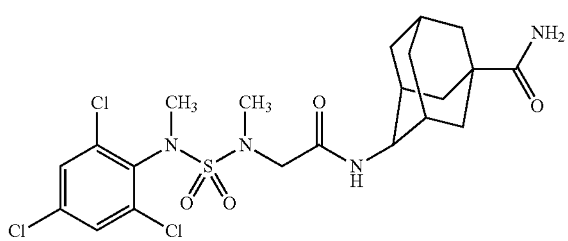 [SMILES: CN(CC(=O)NC1C2CC3CC1CC(C(N)=O)(C3)C2)S(=O)(=O)N(C)c1c(Cl)cc(Cl)cc1Cl] | 4-(2-(methyl(N-methyl-N-(2,4,6-trichlorophenyl)sulfamoyl)amino)acetamido)adamantan-1-carboxamide | $^1$H NMR (300 MHz, CDCl$_3$): δ 7.43 (s, 2H), 6.85 (d, J = 7.8 Hz, 1H), 5.57 (s, 1H), 5.27 (s, 1H), 4.05-4.02 (m, 1H), 3.92 (s, 2H), 3.22 (s, 3H), 3.09 (s, 3H), 2.16-1.57 (m, 13H) |

TABLE 19

| No | Structure | IUPAC Name | NMR |
|---|---|---|---|
| 124 | 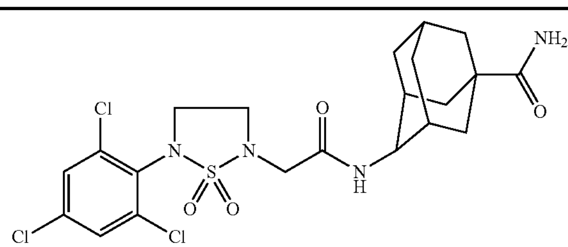 | 4-(2-(1,1-dioxido-5-(2,4,6-trichlorophenyl)-1,2,5-thiadiazolidin-2-yl)acetamido)adamantan-1-carboxamide | $^1$H NMR (300 MHz, CDCl$_3$): δδ 7.46 (s, 2H), 7.16 (d, J = 7.7 Hz, 1H), 5.56 (s, 1H), 5.22 (s, 1H), 4.10-4.07 (m, 1H), 3.98-3.89 (m, 2H), 3.87 (s, 2H), 3.79-3.74 (m, 2H), 2.10-1.57 (m, 13H) |

TABLE 19-continued

| No | Structure | IUPAC Name | NMR |
|---|---|---|---|
| 125 | 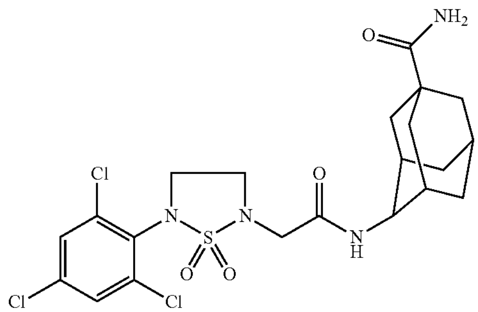 [SMILES: NC(=O)C12CC3CC(C1)C(NC(=O)CN1CCN(c4c(Cl)cc(Cl)cc4Cl)S1(=O)=O)C(C3)C2] | 4-(2-(1,1-dioxido-5-(2,4,6-trichlorophenyl)-1,2,5-thiadiazolidin-2-yl)acetamido)adamantan-1-carboxamide | $^1$H NMR (300 MHz, CDCl$_3$): δ 7.46 (s, 2H), 7.26-7.22 (m, 1H), 5.79 (s, 1H), 5.12 (s, 1H), 4.06-4.02 (m, 1H), 3.95-3.91 (m, 2H), 3.89 (s, 2H), 3.80-3.76 (m, 2H), 2.17-1.62 (m, 13H) |
| 126 | 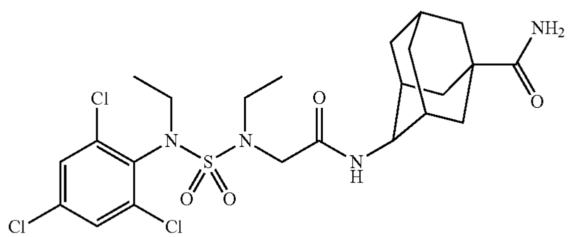 [SMILES: CCN(CC(=O)NC1C2CC3CC1CC(C(N)=O)(C3)C2)S(=O)(=O)N(CC)c1c(Cl)cc(Cl)cc1Cl] | 4-(2-(ethyl(N-ethyl-N-(2,4,6-trichlorophenyl)sulfamoyl)amino)acetamido)adamantan-1-carboxamide | $^1$H NMR (300 MHz, CDCl$_3$): δ 7.44 (s, 2H), 7.02 (d, J = 7.7 Hz, 1H), 5.56 (s, 1H), 5.24 (s, 1H), 4.05-4.03 (m, 1H), 3.93 (s, 2H), 3.71 (q, J = 7.1 Hz, 2H), 3.49 (q, J = 7.1 Hz, 2H), 2.03-1.56 (m, 13H), 1.24 (t, J = 7.1 Hz 3H), 1.13 (t, J = 7.1 Hz, 3H) |
| 127 | 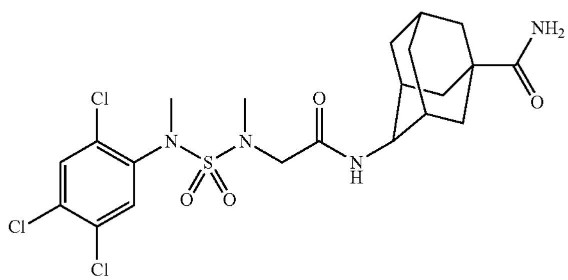 [SMILES: CN(CC(=O)NC1C2CC3CC1CC(C(N)=O)(C3)C2)S(=O)(=O)N(C)c1cc(Cl)c(Cl)cc1Cl] | 4-(2-(methyl(N-methyl-N-(2,4,5-trichlorophenyl)sulfamoyl)amino)acetamido)adamantan-1-carboxamide | $^1$H NMR (300 MHz, CDCl$_3$): δ 7.70 (s, 1H), 7.59 (s, 1H), 6.78 (d, J = 7.9 Hz, 1H), 5.55 (s, 1H), 5.25 (s, 1H), 4.05-4.02 (m, 1H), 3.87 (s, 2H), 3.17 (s, 3H), 3.01 (s, 3H), 2.06-1.25 (m, 13H) |
| 128 | 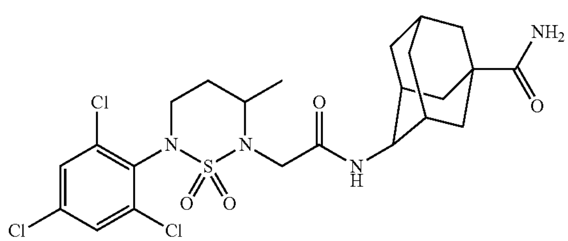 [SMILES: CC1CCN(c2c(Cl)cc(Cl)cc2Cl)S(=O)(=O)N1CC(=O)NC1C2CC3CC1CC(C(N)=O)(C3)C2] | 4-(2-(3-methyl-1,1-dioxido-6-(2,4,6-trichlorophenyl)-1,2,6-thiadiazinan-2-yl)acetamido)adamantan-1-carboxamide | $^1$H NMR(300 MHz, CDCl$_3$): δ7.42(d, J = 2.4 Hz, 1H), 7.39(d, J = 2.4 Hz, 1H), 6.99(d, J = 7.7 Hz, 1H), 5.56(s, 1H), 5.22(s, 1H), 4.61-4.50(m, 1H), 4.28-4.18(m, 2H), 4.05-4.02(m, 1H), 3.65-3.59(m, 1H), 3.31-3.24(m, 1H), 2.14-1.54(m, 15H), 1.33(d, J = 6.9 Hz, 3H) |
| 129 | 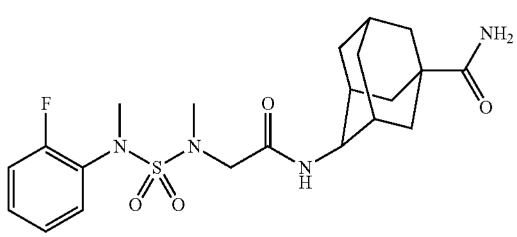 [SMILES: CN(CC(=O)NC1C2CC3CC1CC(C(N)=O)(C3)C2)S(=O)(=O)N(C)c1ccccc1F] | 4-(2-((N-(2-fluorophenyl)-N-methylsulfamoyl)(methyl)amino)acetamido)adamantan-1-carboxamide | $^1$H NMR (300 MHz, CDCl$_3$): δ7.54-7.48 (m, 1H), 7.38-7.30 (m, 1H), 7.21-7.12 (m, 2H), 6.87 (d, J = 7.8 Hz, 1H), 5.55 (s, 1H), 5.29 (s, 1H), 4.03-4.01 (m, 1H), 3.77 (s, 2H), 3.29 (s, 3H), 2.94 (s, 3H), 2.05-1.56 (m, 13H) |
| 130 | 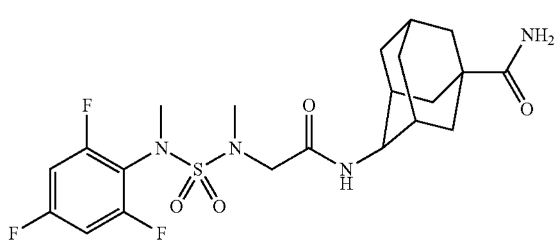 [SMILES: CN(CC(=O)NC1C2CC3CC1CC(C(N)=O)(C3)C2)S(=O)(=O)N(C)c1c(F)cc(F)cc1F] | 4-(2-(methyl(N-methyl-N-(2,4,6-trifluorophenyl)sulfamoyl)amino)acetamido)adamantan-1-carboxamide | $^1$H NMR (300 MHz, CDCl$_3$): δ 6.84 (d, J = 7.6 Hz, 1H), 6.82-6.74 (m, 2H), 5.55 (s, 1H), 5.30 (s, 1H) 4.05-4.03 (m, 1H), 3.88 (s, 2H), 3.22 (s, 3H), 3.02 (s, 3H), 2.17-1.25 (m, 13H) |

TABLE 20

| No | Structure | IUPAC Name | NMR |
|---|---|---|---|
| 131 | 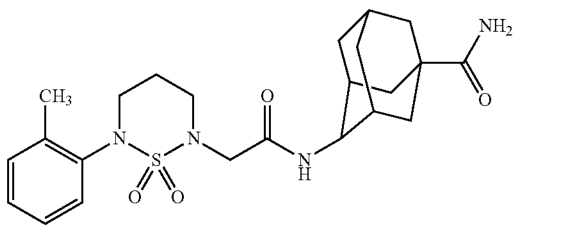 [SMILES: Cc1ccccc1N1CCCN(CC(=O)NC2C3CC4CC2CC(C(N)=O)(C4)C3)S1(=O)=O] | 4-(2-(1,1-dioxido-6-(o-tolyl)-1,2,6-thiadiazinan-2-yl)acetamido)adamantan-1-carboxamide | $^1$H NMR (300 MHz, CDCl$_3$): δ 7.48-7.44 (m, 1H), 7.26-7.21 (m, 3H), 7.00 (d, J = 7.7 Hz, 1H), 5.56(s, 1H), 5.26(s, 1H), 4.30-4.25(m, 1H), 4.16-4.05(m, 2H), 3.94-3.85(m, 1H), 3.71-3.65(m, 1H), 3.48-3.37(m, 2H), 2.38(s, 3H), 2.23-1.58(m, 15H) |
| 132 | 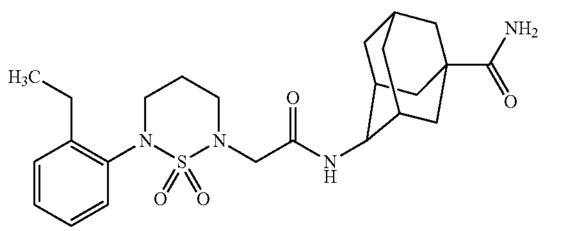 [SMILES: CCc1ccccc1N1CCCN(CC(=O)NC2C3CC4CC2CC(C(N)=O)(C4)C3)S1(=O)=O] | 4-(2-(6-(2-ethylphenyl)-1,1-dioxido-1,2,6-thiadiazinan-2-yl)acetamido)adamantan-1-carboxamide | $^1$H NMR(300 MHz, CDCl$_3$): δ 7.51-7.48(m, 1H), 7.30-7.21(m, 3H), 7.00(d, J = 7.8 Hz, 1H), 5.56 (s, 1H), 5.34(s, 1H), 4.30-4.25 (m, 1H), 4.18-4.05(m, 2H), 3.95-3.86(m, 1H), 3.71-3.65(m, 1H), 3.47-3.35(m, 2H), 2.84-2.68(m, 2H), 2.28-1.56(m, 15H), 1.24(t, J = 7.5 Hz, 3H) |
| 133 | 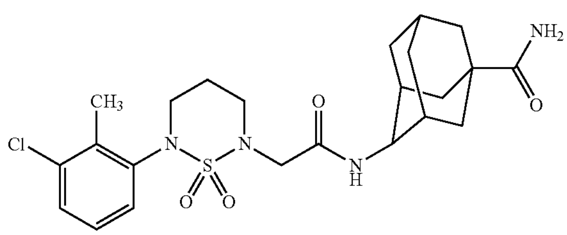 [SMILES: Cc1c(Cl)cccc1N1CCCN(CC(=O)NC2C3CC4CC2CC(C(N)=O)(C4)C3)S1(=O)=O] | 4-(2-(6-(3-chloro-2-methylphenyl)-1,1-dioxido-1,2,6-thiadiazinan-2-yl)acetamido)adamantan-1-carboxamide | $^1$H NMR(300 MHz,CDCl$_3$): δ7.43-7.41(m, 1H), 7.37-7.35(m, 1H), 7.19-7.13(m, 1H), 6.95(d, J = 7.9 Hz, 1H), 5.55 (s, 1H), 5.25(s, 1H), 4.29-4.24(m, 1H), 4.19-4.13(m, 1H), 4.08-4.05(m, 1H), 3.92-3.83(m, 1H), 3.78-3.67(m, 1H), 3.55-3.35(m, 2H), 2.42(s, 3H), 2.29-1.57(m, 15H) |
| 134 | 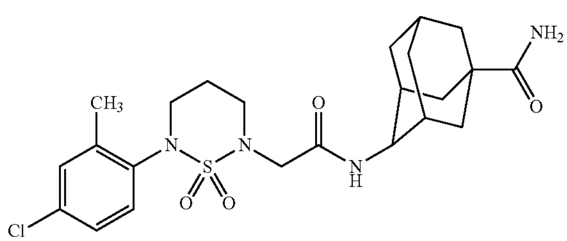 [SMILES: Cc1cc(Cl)ccc1N1CCCN(CC(=O)NC2C3CC4CC2CC(C(N)=O)(C4)C3)S1(=O)=O] | 4-(2-(6-(4-chloro-2-methylphenyl)-1,1-dioxido-1,2,6-thiadiazinan-2-yl)acetamido)adamantan-1-carboxamide | $^1$H NMR (300 MHz, CDCl$_3$): δ 7.41-7.38 (m, 1H), 7.26-7.18 (m, 2H), 6.95 (d, J = 7.7 Hz, 1H), 5.55 (s, 1H), 5.25 (s, 1H), 4.28-4.22 (m, 1H), 4.17-4.04 (m, 2H), 3.91-3.83 (m, 1H), 3.70-3.64 (m, 1H), 3.48-3.32 (m, 2H), 2.35 (s, 3H), 2.27-1.58 (m, 15H) |
| 135 | 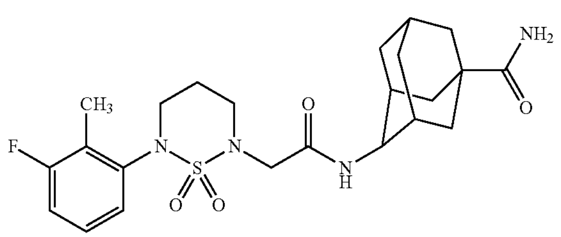 [SMILES: Cc1c(F)cccc1N1CCCN(CC(=O)NC2C3CC4CC2CC(C(N)=O)(C4)C3)S1(=O)=O] | 4-(2-(6-(3-fluoro-2-methylphenyl)-1,1-dioxido-1,2,6-thiadiazinan-2-yl)acetamido)adamantan-1-carboxamide | $^1$H NMR(300 MHz,CDCl$_3$): δ7.31-7.15 (m, 2H), 7.06-7.01(m, 1H), 6.96(d, J = 7.5 Hz, 1H), 5.57(s, 1H), 5.30(s, 1H), 4.30-4.25(m, 1H), 4.19-4.13 (m, 1H), 4.08-4.05(m, 1H), 3.94-3.86 (m, 1H), 3.73-3.67 (m, 1H), 3.53-3.36 (m, 2H), 2.29(s, 3H), 2.17-1.60(m, 15H) |
| 136 | 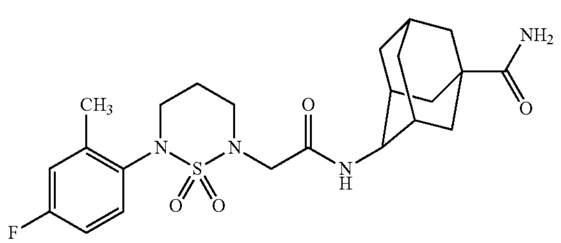 [SMILES: Cc1cc(F)ccc1N1CCCN(CC(=O)NC2C3CC4CC2CC(C(N)=O)(C4)C3)S1(=O)=O] | 4-(2-(6-(4-fluoro-2-methylphenyl)-1,1-dioxido-1,2,6-thiadiazinan-2-yl)acetamido)adamantan-1-carboxamide | $^1$HNMR(300 MHz,CDCl$_3$): δ7.46-7.41(m, 1H), 6.98-6.88(m, 3H), 5.55(s, 1H), 5.20(s, 1H), 4.29-4.23(m, 1H), 4.18-4.13(m, 1H), 4.09-4.04(m, 1H), 3.92-3.83(m, 1H), 3.70-3.65(m, 1H), 3.47-3.32(m, 2H), 2.37(s, 3H), 2.25-1.61 (m, 15H) |

TABLE 20-continued

| No | Structure | IUPAC Name | NMR |
|---|---|---|---|
| 137 | 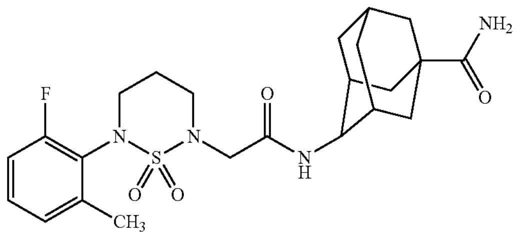 [SMILES: Cc1cccc(F)c1N1CCCN(CC(=O)NC2C3CC4CC2CC(C(N)=O)(C4)C3)S1(=O)=O] | 4-(2-(6-(2-fluoro-6-methylphenyl)-1,1-dioxido-1,2,6-thiadiazinan-2-yl)acetamido)adamantan-1-carboxamide | $^1$H NMR(300 MHz, CDCl$_3$): δ 7.32-7.29 (m, 1H), 7.16-7.12(m, 2H), 7.02(d, J = 7.7 Hz, 1H), 5.55(s, 1H), 5.24(s, 1H), 4.23-4.17 (m, 1H), 4.12-3.98 (m, 3H), 3.87-3.82 (m, 1H), 3.61-3.54 (m, 2H), 2.50 (s, 3H), 2.41-2.29 (m, 1H), 2.09-1.58 (m, 14H) |

TABLE 21

| No | Structure | IUPAC Name | NMR |
|---|---|---|---|
| 138 | 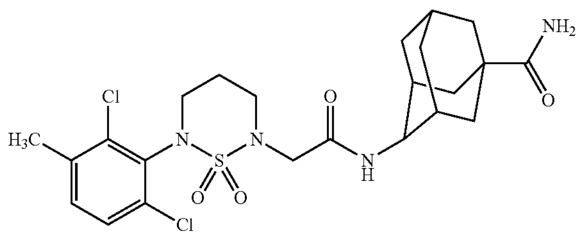 [SMILES: Cc1ccc(Cl)c(N2CCCN(CC(=O)NC3C4CC5CC3CC(C(N)=O)(C5)C4)S2(=O)=O)c1Cl] | 4-(2-(6-(2,6-dichloro-3-methylphenyl)-1,1-dioxido-1,2,6-thiadiazinan-2-yl)acetamido)adamantan-1-carboxamide | $^1$H NMR (300 MHz, CDCl$_3$): δ 7.28 (d, J = 8.3 Hz, 1H), 7.17 (d, J = 8.3 Hz, 1H), 7.02 (d, J = 7.8 Hz, 1H), 5.54 (s, 1H), 5.19 (s, 1H), 4.05-4.04 (m, 3H), 3.89-3.82 (m, 4H), 2.38 (s, 3H), 2.09-1.56 (m, 15H) |
| 139 | 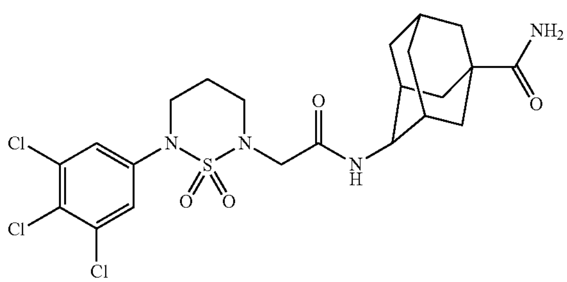 [SMILES: NC(=O)C12CC3CC(C1)C(NC(=O)CN1CCCN(c4cc(Cl)c(Cl)c(Cl)c4)S1(=O)=O)C(C3)C2] | 4-(2-(1,1-dioxido-6-(3,4,5-trichlorophenyl)-1,2,6-thiadiazinan-2-yl)acetamido)adamantan-1-carboxamide | $^1$H NMR (300 MHz, CDCl$_3$): δ 7.40 (s, 2H), 6.86 (d, J = 7.8 Hz, 1H), 5.57 (s, 1H), 5.30 (s, 1H), 4.08-4.05 (m, 1H), 3.92 (s, 2H), 3.80-3.72 (m, 4H), 2.10-1.60 (m, 15H) |
| 140 | 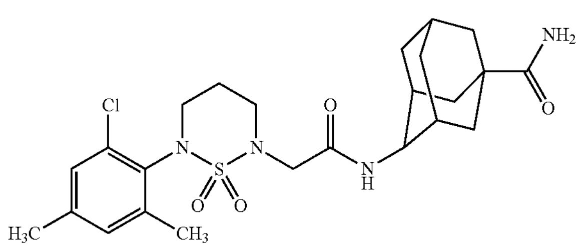 [SMILES: Cc1cc(C)c(N2CCCN(CC(=O)NC3C4CC5CC3CC(C(N)=O)(C5)C4)S2(=O)=O)c(Cl)c1] | 4-(2-(6-(2-chloro-4,6-dimethylphenyl)-1,1-dioxido-1,2,6-thiadiazinan-2-yl)acetamido)adamantan-1-carboxamide | $^1$H NMR(300 MHz, CDCl$_3$): δ7.12 (s, 1H), 7.04-7.01(s, 1H), 6.94 (s, 1H), 5.57(s, 1H), 5.27(s, 1H), 4.22-4.16(m, 1H), 4.10-3.95(m, 3H), 3.87-3.81(m, 1H), 3.60-3.51 (m, 2H), 2.44 (s, 3H), 2.41-2.30(m, 1H), 2.28-2.26(m, 3H), 2.09-1.57(m, 14H) |
| 141 | 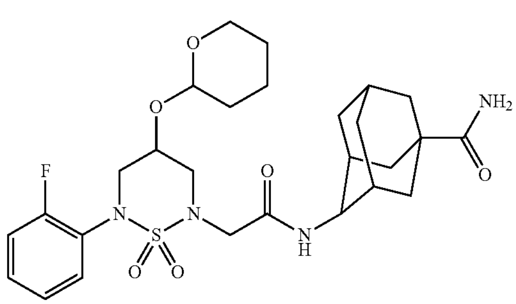 [SMILES: NC(=O)C12CC3CC(C1)C(NC(=O)CN1CC(OC4CCCCO4)CN(c4ccccc4F)S1(=O)=O)C(C3)C2] | 4-(2-(6-(2-fluorophenyl)-1,1-dioxido-4-((tetrahydro-2H-pyran-2-yl)oxy)-1,2,6-thiadiazinan-2-yl)acetamido)adamantan-1-carboxamide | $^1$H NMR (300 MHz, CDCl$_3$): δ 7.50-7.43 (m, 1H), 7.34-7.28 (m, 1H), 7.18-7.10 (m, 2H), 6.98-6.93 (m, 1H), 5.60 (s, 1H), 5.36 (s, 1H), 4.76-4.66 (m, 1H), 4.17-3.66 (m, 9H), 3.54-3.42 (m, 1H), 2.11-1.51 (m, 19H) |

TABLE 21-continued

| No | Structure | IUPAC Name | NMR |
|---|---|---|---|
| 142 | 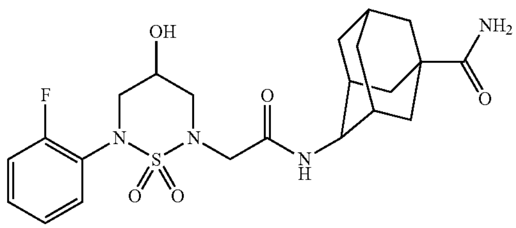 [SMILES: NC(=O)C12CC3CC(C1)C(NC(=O)CN1CC(O)CN(c4ccccc4F)S1(=O)=O)C(C3)C2] | 4-(2-(6-(2-fluorophenyl)-4-hydroxy-1,1-dioxido-1,2,6-thiadiazinan-2-yl)acetamido)adamantan-1-carboxamide | $^1$H NMR (300 MHz, CDCl$_3$): δ 7.59-7.46 (m, 1H), 7.35-7.27 (m, 1H), 7.18-7.00 (m, 3H), 4.30-4.03 (m, 6H), 3.70-3.60 (m, 2H), 2.10-1.55 (m, 13H) |
| 143 | 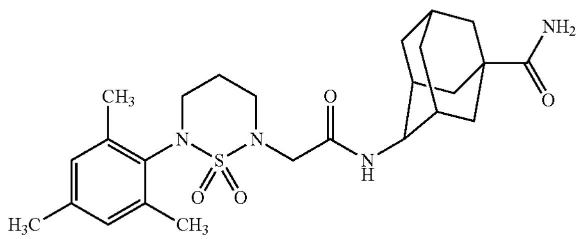 [SMILES: Cc1cc(C)c(N2CCCN(CC(=O)NC3C4CC5CC3CC(C(N)=O)(C5)C4)S2(=O)=O)c(C)c1] | 4-(2-(6-mesityl-1,1-dioxido-1,2,6-thiadiazinan-2-yl)acetamido)adamantan-1-carboxamide | $^1$H NMR (300 MHz, CDCl$_3$): δ 7.06-7.03 (s, 1H), 6.88 (s, 2H), 5.55 (s, 1H), 5.18 (s, 1H), 4.07-4.05 (m, 1H), 3.97 (s, 2H), 3.79-3.72 (m, 4H), 2.41 (s, 6H), 2.25 (s, 3H), 2.17-1.59 (m, 15H) |
| 144 | 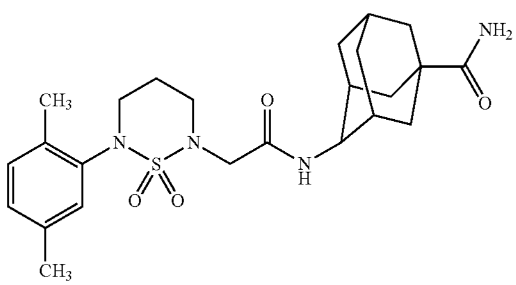 [SMILES: Cc1ccc(C)c(N2CCCN(CC(=O)NC3C4CC5CC3CC(C(N)=O)(C5)C4)S2(=O)=O)c1] | 4-(2-(6-(2,5-dimethylphenyl)-1,1-dioxido-1,2,6-thiadiazinan-2-yl)acetamido)adamantan-1-carboxamide | $^1$H NMR (300 MHz, CDCl$_3$): δ 7.15-7.13 (m, 1H), 7.06-7.00 (m, 3H), 5.58 (s, 1H), 5.30 (s, 1H), 4.31-4.25 (m, 1H), 4.20-4.05 (m, 2H), 3.95-3.86 (m, 1H), 3.72-3.66 (m, 1H), 3.47-3.34 (m, 2H), 2.32-1.24 (m, 21H) |

TABLE 22

| No | Structure | IUPAC Name | NMR |
|---|---|---|---|
| 145 | 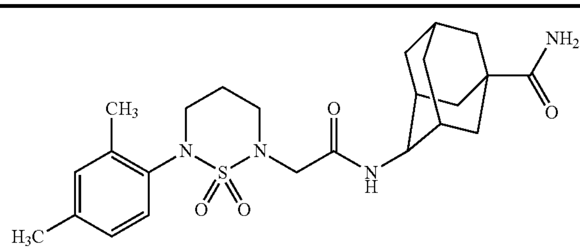 | 4-(2-(6-(2,4-dimethylphenyl)-1,1-dioxido-1,2,6-thiadiazinan-2-yl)acetamido)adamantan-1-carboxamide | $^1$H NMR (300 MHz, CDCl$_3$): δ 7.36-7.33(m, 1H), 7.07-7.01 (m, 3H), 5.57(s, 1H), 5.24(s, 1H), 4.30-4.24 (m, 1H), 4.16-4.04 (m, 2H), 3.92-3.83(m, 1H), 3.71-3.65 (m, 1H), 3.47-3.35 (m, 2H), 2.33(s, 3H), 2.31(s, 3H), 2.27-1.61 (m, 15 H) |
| 146 | 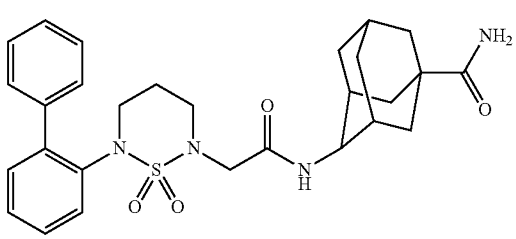 [SMILES: NC(=O)C12CC3CC(C1)C(NC(=O)CN1CCCN(c4ccccc4-c4ccccc4)S1(=O)=O)C(C3)C2] | 4-(2-(6-([1,1'-biphenyl]-2-yl)-1,1-dioxido-1,2,6-thiadiazinan-2-yl)acetamido)adamantan-1-carboxamide | $^1$H NMR(300 MHz, CDCl$_3$): δ7.63-7.61 (m, 1H), 7.49-7.35 (m, 8H), 6.84-6.81 (s, 1H), 5.56(s, 1H), 5.21(s, 1H), 4.13-3.06 (m, 7H), 2.05-1.60(m, 15H) |

| No | Structure | IUPAC Name | NMR |
|----|-----------|------------|-----|
| 147 | 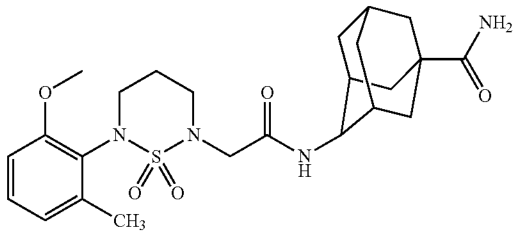 [SMILES: COc1cccc(C)c1N1CCCN(CC(=O)NC2C3CC4CC2CC(C(N)=O)(C4)C3)S1(=O)=O] | 4-(2-(6-(2-methoxy-6-methylphenyl)-1,1-dioxido-1,2,6-thiadiazinan-2-yl)acetamido)adamantan-1-carboxamide | $^1$H NMR (300 MHz, CDCl$_3$): δ 7.20-7.15(m, 1H), 7.10-7.07 (s, 1H), 6.83-6.76(m, 2H), 5.57 (s, 1H), 5.25(s, 1H), 4.07-3.67 (m, 10H), 2.40(s, 3H), 2.16-1.62 (m, 15H) |
| 148 | 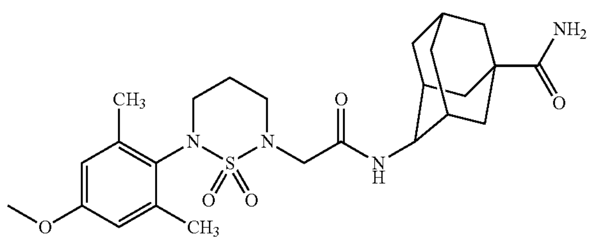 [SMILES: COc1cc(C)c(N2CCCN(CC(=O)NC3C4CC5CC3CC(C(N)=O)(C5)C4)S2(=O)=O)c(C)c1] | 4-(2-(6-(4-methoxy-2 6-dimethylphenyl)-1,1-dioxido-1,2,6-thiadiazinan-2-yl)acetamido) adamantan-1-carboxamide | $^1$H NMR(300 MHz, CDCl$_3$): δ 7.39-7.37(m, 1H), 7.02-7.00(s, 1H), 6.78-6.72(m, 2H), 5.57 (s, 1H), 5.23(s, 1H), 4.30-4.24(m, 1H), 4.16-4.05(m, 2H), 3.91-3.82(m, 1H), 3.78(s, 3H), 3.70-3.65(m, 1H), 3.47-3.32(m, 2H), 2.35 (s, 3H), 2.23-1.59(m, 15H) |
| 149 | 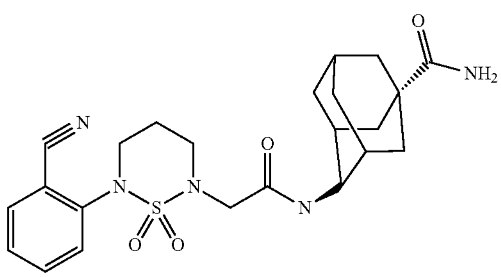 | 4-(2-(6-(2-cyanophenyl)-1,1-dioxido-1,2,6-thiadiazinan-2-yl)acetamido)adamantan-1-carboxamide | $^1$H NMR(300 MHz, CDCl$_3$): δ 7.74-7.71(m, 1H), 7.68-7.60 (m, 2H), 7.47-7.42(m, 1H), 6.85-6.82(s, 1H), 5.56(s, 1H), 5.21 (s, 1H), 4.06 (m, 3H), 3.85-3.78 (m, 4H), 2.17-1.63 (m, 15H) |
| 150 | 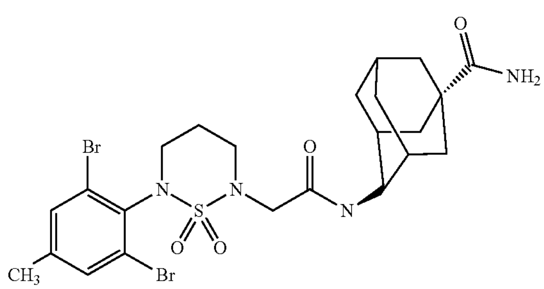 | 4-(2-(6-(2,6-dibromo-4-methylphenyl)-1,1-dioxido-1,2,6-thiadiazinan-2-yl)acetamido)adamantan-1-carboxamide | $^1$H NMR (300 MHz, CDCl$_3$): δ 7.43 (s, 2H), 7.04-7.01(m, 1H), 5.57 (s, 1H), 5.28 (s, 1H), 4.09(s, 2H), 4.09-4.04 (m, 1H), 3.89-3.86 (m, 2H), 3.83-3.79 (m, 2H), 2.31 (s, 3H), 2.09-1.61 (m, 15H) |
| 151 | 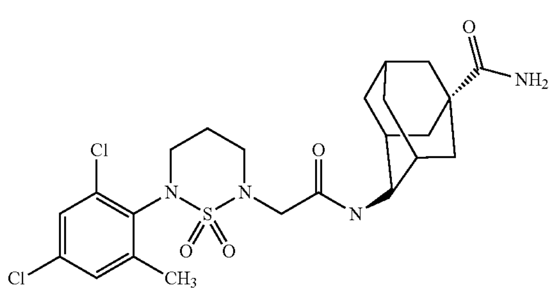 | 4-(2-(6-(2,4-dichloro-6-methylphenyl)-1,1-dioxido-1,2,6-thiadiazinan-2-yl)acetamido)adamantan-1-carboxamide | $^1$H NMR(300 MHz, CDCl$_3$): δ7.32 (d, J = 2.4 Hz, 1H), 7.15 (d, J = 2.4 Hz, 1H), 6.99-6.97 (s, 1H), 5.56(s, 1H), 5.25 (s, 1H), 4.21-4.15 (m, 1H), 4.13-3.95 (m, 3H), 3.85-3.80 (m, 1H), 3.62-3.51 (m, 2H), 2.47(s, 3H), 2.36-2.26(m, 1H), 2.09-1.61(m, 14H) |

TABLE 23

| No | Structure | IUPAC Name | NMR |
|---|---|---|---|
| 152 | 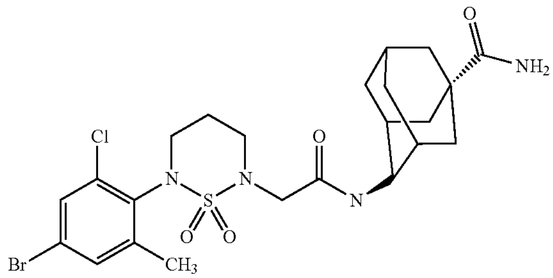 | 4-(2-(6-(4-bromo-2-chloro-6-methylphenyl)-1,1-dioxido-1,2,6-thiadiazinan-2-yl)acetamido)adamantan-1-carboxamide | ¹H NMR(300 MHz, CDCl₃): δ 7.48-7.47 (m, 2H), 7.31-7.30 (m, 2H), 6.99-6.96 (m, 1H), 5.56(s, 1H), 5.25 (s, 1H), 4.21-3.79 (m, 5H), 3.62-3.51 (m, 2H), 2.47 (s, 3H), 2.38-2.26 (m, 1H), 2.10-1.59(m, 14 H) |
| 153 | 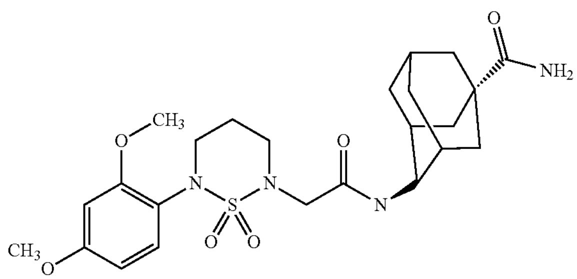 | 4-(2-(6-(2,4-dimethylphenyl)-1,1-dioxido-1,2,6-thiadiazinan-2-yl)acetamido)adamantan-1-carboxamide | ¹H NMR(300 MHz, CDCl₃): δ 7.28-7.26 (m, 1H), 7.06-7.03 (s, 1H), 6.49-6.41 (m, 2H), 5.56 (s, 1H), 5.26 (s, 1H), 4.06-4.02 (m, 1H), 3.95-3.67 (m, 6H), 3.84 (s, 3H), 3.79 (s, 3H), 2.08-1.57 (m, 15H) |
| 154 | 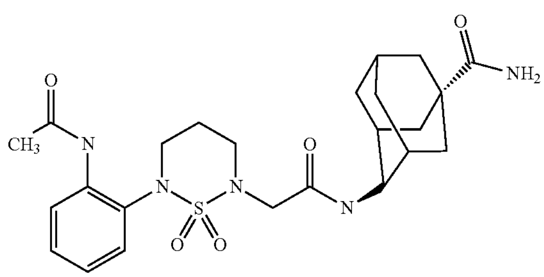 | 4-(2-(6-(2-acetamidophenyl)-1,1-dioxido-1,2,6-thiadiazinan-2-yl)acetamido)adamantan-1-carboxamide | ¹H NMR(300 MHz, CDCl₃): δ 9.56 (s, 1H), 8.12 (d, J = 7.7 Hz, 1H), 8.01(d, J = 7.7 Hz, 1H), 7.45 (d, J = 7.7 Hz, 1H), 7.29 (t, J = 6.3 Hz, 1H), 7.12 (t, J = 6.3 Hz, 1H), 6.99 (s, 1H), 6.72 (s, 1H), 3.98-3.52 (m, 6H), 2.16 (s, 3H), 2.10-1.22 (m, 15H) |
| 155 | 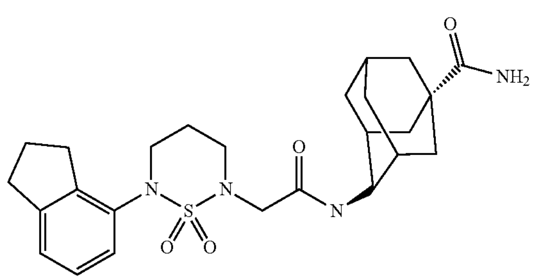 | 4-(2-(6-(2,3-dihydro-1H-inden-4-yl)-1,1-dioxido-1,2,6-thiadiazinan-2-yl)acetamido)adamantan-1-carboxamide | ¹H NMR(300 MHz, CDCl₃): δ 7.74 (d, J = 7.0 Hz, 1H), 7.17 (s, 3H), 6.98 (s, 1H), 6.71 (s, 1H), 3.89 (s, 2H), 3.83-3.80 (m, 1H), 3.63-3.54 (m, 4H), 2.96-2.86 (m, 4H), 2.02-1.74 (m, 15H), 1.43-1.39 (m, 2H) |
| 156 | 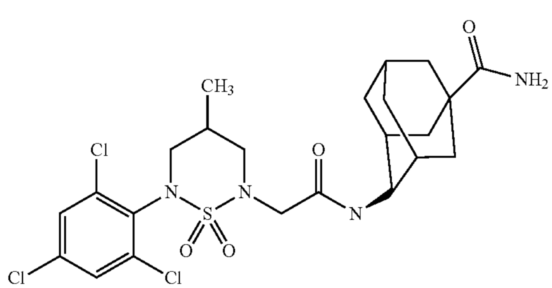 | 4-(2-(4-methyl-1,1-dioxido-6-(2,4,6-trichlorophenyl)-1,2,6-thiadiazinan-2-yl)acetamido)adamantan-1-carboxamide | ¹H NMR(300 MHz, CDCl₃): δ 7.42 (d, J = 2.4 Hz, 1H), 7.39 (d, J = 2.4 Hz, 1H), 6.96 (d, J = 7.3 Hz, 1H), 5.56 (s, 1H), 5.25 (s, 1H), 4.33 (d, J = 17 Hz, 1H), 4.09-3.87 (m, 3H), 3.33-3.17 (m, 2H), 2.63-2.54 (m, 13H), 0.95(d, J = 6.6 Hz, 3H) |

TABLE 23-continued

| No | Structure | IUPAC Name | NMR |
|---|---|---|---|
| 157 | 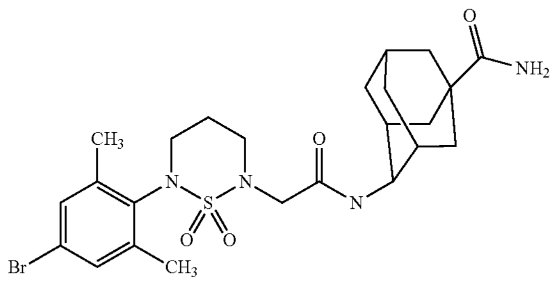 [SMILES: Cc1cc(Br)cc(C)c1N1CCCN(CC(=O)NC2C3CC4CC2CC(C(N)=O)(C4)C3)S1(=O)=O] | 4-(2-(6-(4-bromo-2,6-dimethylphenyl)-1,1-dioxido-1,2,6-thiadiazinan-2-yl)acetamido)adamantan-1-carboxamide | ¹H NMR (300 MHz, CDCl₃): δ 7.23 (s, 2H), 7.00 (d, J = 7.9 Hz, 1H), 5.56(s, 1H), 5.28 (s, 1H), 4.07-4.05(m, 1H), 3.96 (s, 2H), 3.81-3.71(m, 4H), 2.42(s, 6H), 2.09-1.76(m, 15H) |
| 158 | 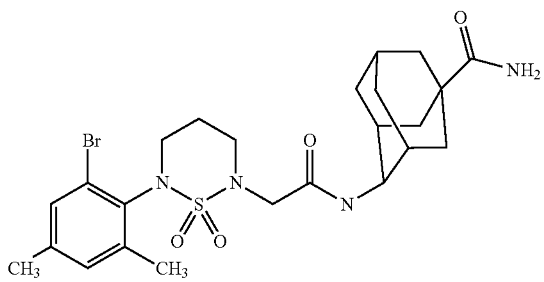 [SMILES: Cc1cc(C)c(N2CCCN(CC(=O)NC3C4CC5CC3CC(C(N)=O)(C5)C4)S2(=O)=O)c(Br)c1] | 4-(2-(6-(2-bromo-4,6-dimethylphenyl)-1,1-dioxido-1,2,6-thiadiazinan-2-yl)acetamido)adamantan-1-carboxamide | ¹H NMR (300 MHz, CDCl₃): δ 7.31 (s, 1H), 7.01 (d, J = 7.8 Hz, 1H), 6.98 (s, 1H), 5.57 (s, 1H), 5.27 (s, 1H), 4.30 (d, J = 17 Hz, 1H), 4.15-3.99 (m, 4H), 3.82(d, J = 17 Hz, 1H), 3.56-3.47(m, 2H), 2.48(s, 3H), 2.27 (s, 3H), 2.09-1.53(m, 14H) |

TABLE 24

| No | Structure | IUPAC Name | NMR |
|---|---|---|---|
| 159 | 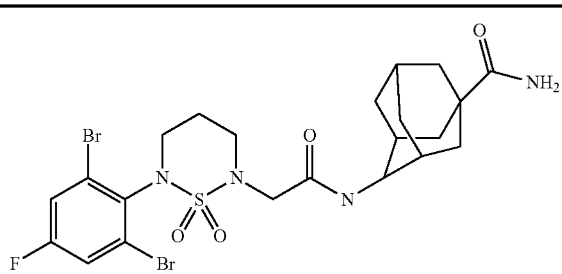 | 4-(2-(6-(2,6-dibromo-4-fluorophenyl)-1,1-dioxido-1,2,6-thiadiazinan-2-yl)acetamido)adamantan-1-carboxamide | ¹H NMR (300 MHz, CDCl₃): δδ 7.43 (s, 2H), 7.03 (d, J = 7.9Hz, 1H), 5.56 (s, 1H), 5.22 (s, 1H), 4.10-4.03 (m, 3H), 3.89-3.78 (m, 4H), 2.31 (s, 3H), 2.12-1.61 (m, 13H) |
| 160 | 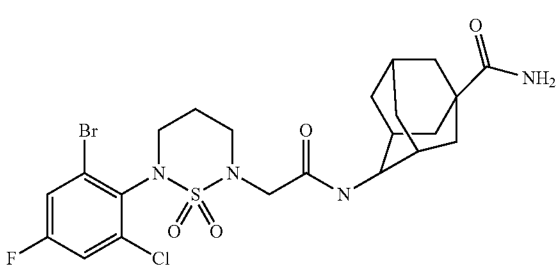 [SMILES: NC(=O)C12CC3CC(C1)C(NC(=O)CN1CCCN(c4c(Cl)cc(F)cc4Br)S1(=O)=O)C(C3)C2] | 4-(2-(6-(2-bromo-6-chloro-4-fluorophenyl)-1,1-dioxido-1,2,6-thiadiazinan-2-yl)acetamido)adamantan-1-carboxamide | ¹H NMR (300MHz, CDCl₃): δ 7.35 (dd, J = 7.4, 2.4Hz, 1H), 7.21 (dd, J = 7.4, 2.4Hz, 1H), 6.98 (d, J = 4.0 Hz, 1H), 5.57 (s, 1H), 5.28 (s, 1H), 4.15 (d, J = 17.1Hz, 1H), 4.07-4.05 (m, 1H), 3.99-3.87 (m, 3H), 3.84-3.74 (m, 22H), 2.15-1.58 (m, 15H) |
| 161 | 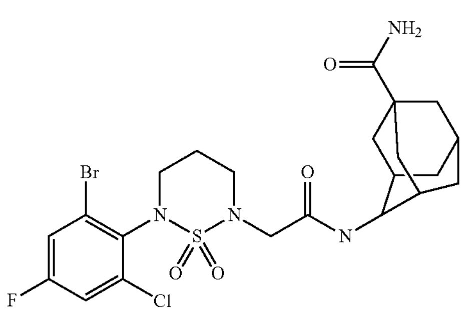 [SMILES: NC(=O)C12CC3CC(C1)C(NC(=O)CN1CCCN(c4c(Cl)cc(F)cc4Br)S1(=O)=O)C(C3)C2] | 4-(2-(6-(2-bromo-6-chloro-4-fluorophenyl)-1,1-dioxido-1,2,6-thiadiazinan-2-yl)acetamido)adamantan-1-carboxamide | ¹H NMR (300 MHz, CDCl₃): δ 7.48 (t, J = 1.8Hz, 1H), 7.17 (dd, J = 9.4, 2.4Hz, 1H), 6.94 (d, J = 4.0Hz, 1H), 5.56 (s, 1H), 5.22 (s, 1H), 4.26 (d, J = 17.4Hz, 1H), 4.07-4.00 (m, 3H), 3.79 (d, J = 17.4Hz, 1H), 3.69-3.56 (m, 2H), 2.41-1.50 (m, 15H) |

TABLE 24-continued

| No | Structure | IUPAC Name | NMR |
|---|---|---|---|
| 162 | 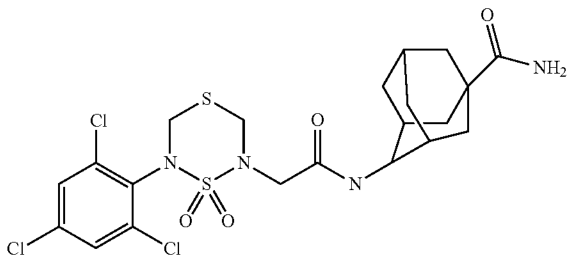 [SMILES: NC(=O)C12CC3CC(C1)C(NC(=O)CN1CSCN(c4c(Cl)cc(Cl)cc4Cl)S1(=O)=O)C(C3)C2] | 4-(2-(1,1-dioxido-6-(2,4,6-trichlorophenyl)-1,4,2,6-dithiadiazinan-2-yl)acetamido)adamantan-1-carboxamide | $^1$H NMR (300 MHz, CDCl$_3$): δ 7.43 (s, 2H), 6.73 (d, J = 7.4Hz, 1H), 5.58 (s, 1H), 5.34 (s, 1H), 5.06 (s, 2H), 4.91 (s, 2H), 4.21 (s, 2H), 4.05 (m, 1H), 2.09-1.26 (m, 13H) |
| 163 | 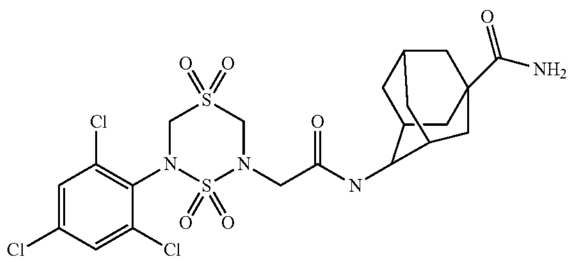 [SMILES: NC(=O)C12CC3CC(C1)C(NC(=O)CN1CS(=O)(=O)CN(c4c(Cl)cc(Cl)cc4Cl)S1(=O)=O)C(C3)C2] | 4-(2-(1,1,4,4-tetraoxido-6-(2,4,6-trichlorophenyl)-1,4,2,6-dithiadiazinan-2-yl)acetamido)adamantan-1-carboxamide | $^1$H NMR (300 MHz, DMSO-d6): δ 7.95 (d, J = 6.9Hz, 1H), 7.86 (s, 2H), 6.98 (s, 1H), 6.71 (s, 1H), 5.37 (s, 2H), 5.28 (s, 2H), 4.39 (s, 2H), 3.79 (m, 1H), 1.92-1.38 (m, 13H) |
| 164 | 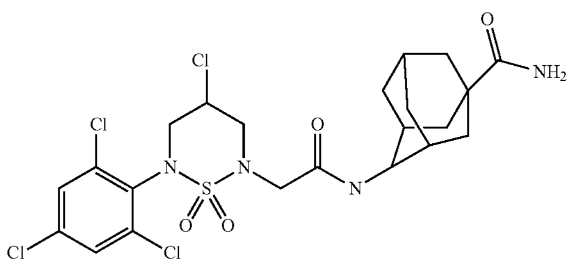 [SMILES: NC(=O)C12CC3CC(C1)C(NC(=O)CN1CC(Cl)CN(c4c(Cl)cc(Cl)cc4Cl)S1(=O)=O)C(C3)C2] | 4-(2-(4-chloro-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δ 7.44 (s, 2H), 6.83 (d, J = 7.4Hz, 1H), 5.60 (s, 1H), 5.32 (s, 1H), 4.57-3.77 (m, 8H), 2.15-1.56 (m, 13H) |
| 165 | 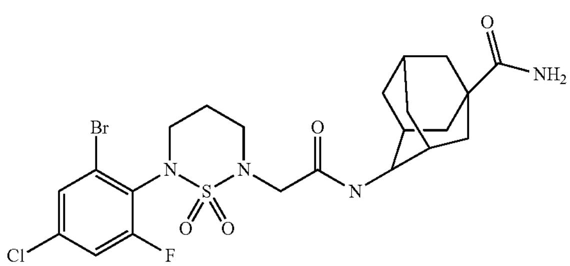 | 4-(2-(6-(2-bromo-4-chloro-6-fluorophenyl)-1,1-dioxido-1,2,6-thiadiazinan-2-yl)acetamido)adamantan-1-carboxamide | $^1$H NMR (300 MHz, CDCl$_3$): δ 7.48 (t, J = 1.8Hz, 1H), 7.17 (dd, J = 9.4, 2.4Hz, 1H), 6.94 (d, J = 4.0Hz, 1H), 5.56 (s, 1H), 5.22 (s, 1H), 4.26 (d, J = 17.4Hz, 1H), 4.07-4.00 (m, 3H), 3.79 (d, J = 17.4Hz, 1H), 3.69-3.56 (m, 2H), 2.41-1.50 (m, 15H) |

TABLE 25

| No | Structure | IUPAC Name | NMR |
|---|---|---|---|
| 166 | 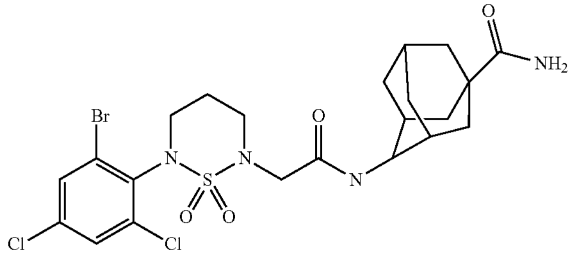 [SMILES: NC(=O)C12CC3CC(C1)C(NC(=O)CN1CCCN(c4c(F)cc(Cl)cc4Br)S1(=O)=O)C(C3)C2] | 4-(2-(6-(2-bromo-4,6-dichlorophenyl)-1,1-dioxido-1,2,6-thiadiazinan-2-yl)acetamido)adamantan-1-carboxamide | $^1$H NMR (300 MHz, CDCl$_3$): δδ 7.59 (s, 1H), 7.45 (s, 1H), 6.97 (d, J = 6.9Hz, 1H), 5.58 (s, 1H), 5.31 (s, 1H), 4.15 (d, J = 16.7Hz, 1H), 4.09-3.88 (m, 4H), 3.77-3.74 (m, 2H), 2.25-1.24 (m, 15H) |

TABLE 25-continued

| No | Structure | IUPAC Name | NMR |
|---|---|---|---|
| 167 | 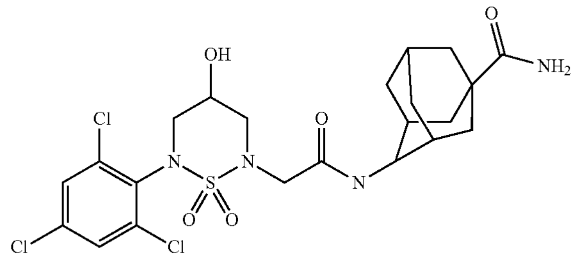 | 4-(2-(4-hydroxy-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δδ 7.43 (s, 2H), 6.93 (d, J = 7.9Hz, 1H), 5.65 (s, 1H), 5.35 (s, 1H), 4.34-4.26 (m, 2H), 4.17-3.93 (m, 4H), 3.72-3.59 (m, 2H), 2.12-1.58 (m, 13H) |
| 168 | 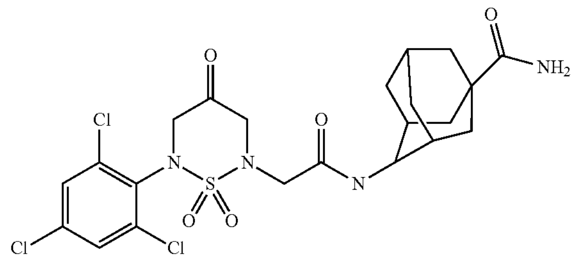 [SMILES: NC(=O)C12CC3CC(C1)C(NC(=O)CN1CC(=O)CN(c4c(Cl)cc(Cl)cc4Cl)S1(=O)=O)C(C3)C2] | 4-(2-(1,1-dioxido-4-oxo-6-(2,4,6-trichlorophenyl)-1,2,6-thiadiazinan-2-yl)acetamido)adamantan-1-carboxamide | $^1$H NMR (300 MHz, CDCl$_3$): δδ 7.46 (s, 2H), 6.49 (d, J = 7.6Hz, 1H), 5.60 (s, 1H), 5.37 (s, 1H), 4.35 (s, 2H), 4.32 (s, 2H), 4.08 (s, 2H), 4.04 (m, 1H), 2.09-1.59 (m, 13H) |
| 169 | 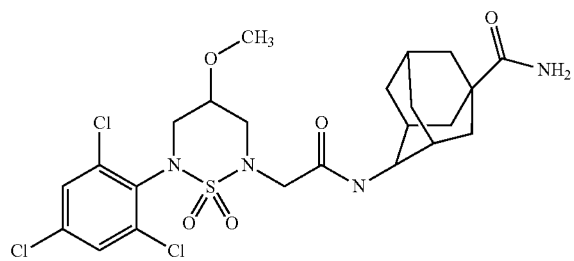 [SMILES: COC1CN(CC(=O)NC2C3CC4CC2CC(C(N)=O)(C4)C3)S(=O)(=O)N(c2c(Cl)cc(Cl)cc2Cl)C1] | 4-(2-(4-methoxy-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δδ 7.43 (s, 1H), 7.41 (s, 1H), 6.98 (d, J = 7.7Hz, 1H), 5.57 (s, 1H), 5.26 (s, 1H), 4.29-3.97 (m, 5H), 3.74-3.57 (m, 3H), 3.37 (s, 3H), 2.15-1.22 (m, 13H) |
| 170 | 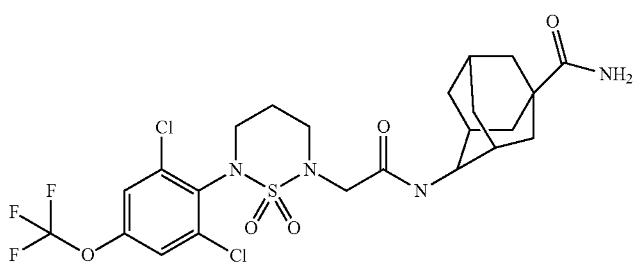 [SMILES: NC(=O)C12CC3CC(C1)C(NC(=O)CN1CCCN(c4c(Cl)cc(OC(F)(F)F)cc4Cl)S1(=O)=O)C(C3)C2] | 4-(2-(6-(2,6-dichloro-4-(trifluoromethoxy)phenyl)-1,1-dioxido-1,2,6-thiadiazinan-2-yl)acetamido)adamantan-1-carboxamide | $^1$H NMR (300 MHz, CDCl$_3$): δ 7.28 (d, J = 0.8Hz, 2H), 6.96 (d, J = 7.7Hz, 1H), 5.57 (s, 1H), 5.29 (s, 1H), 4.06-4.03 (m, 3H), 3.86 (t, J = 5.7Hz, 4H), 2.09-1.53 (m, 15H) |
| 171 | 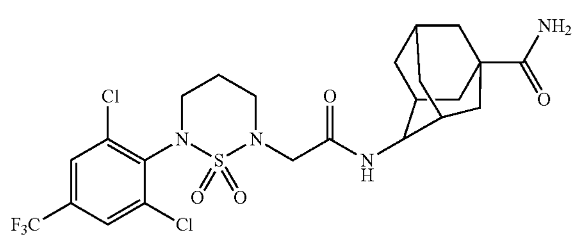 [SMILES: NC(=O)C12CC3CC(C1)C(NC(=O)CN1CCCN(c4c(Cl)cc(C(F)(F)F)cc4Cl)S1(=O)=O)C(C3)C2] | 4-(2-(6-(2,6-dichloro-4-(trifluoromethyl)phenyl)-1,1-dioxido-1,2,6-thiadiazinan-2-yl)acetamido)adamantan-1-carboxamide | $^1$H NMR (300 MHz, CDCl$_3$): δ 7.66 (s, 2H), 6.95 (d, J = 7.8Hz, 1H), 5.57 (s, 1H), 5.29 (s, 1H), 4.07-4.04 (m, 3H), 3.88 (t, J = 5.7Hz, 4H), 2.21-1.56 (m, 15H) |
| 172 | 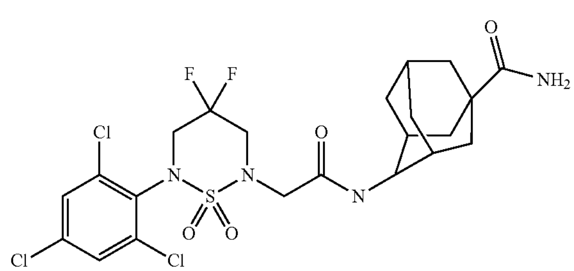 [SMILES: NC(=O)C12CC3CC(C1)C(NC(=O)CN1CC(F)(F)CN(c4c(Cl)cc(Cl)cc4Cl)S1(=O)=O)C(C3)C2] | 4-(2-(4,4--difluoro-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δ 7.44 (s, 2H), 6.67 (d, J = 8.0Hz, 1H), 5.54 (brs, 1H), 5.24 (brs, 1H), 4.21 (s, 2H), 4.14-4.01 (m, 5H), 2.10-1.56 (m, 13H) |

TABLE 26

| No | Structure | IUPAC Name | NMR |
|---|---|---|---|
| 173 | 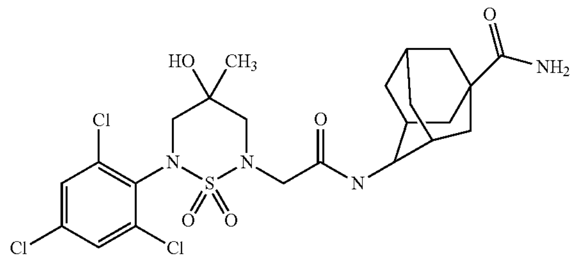 [SMILES: CC1(O)CN(CC(=O)NC2C3CC4CC2CC(C(N)=O)(C4)C3)S(=O)(=O)N(c2c(Cl)cc(Cl)cc2Cl)C1] | 4-(2-(4-hydroxy-4-methyl-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δ 7.51 (d, J = 6.8Hz, 1H), 7.40 (s 2H), 5.84 (s, 1H), 5.25 (s, 1H), 4.74 (s, 1H), 4.48-4.43 (m, 1H), 4.34-4.29 (m, 1H), 4.05 (m, 1H), 3.80-3.76 (m, 1H), 3.58-3.52 (m, 1H), 3.26-3.16 (m, 2H), 2.30-1.56 (m, 13H), 1.33 (s, 3H) |
| 174 | 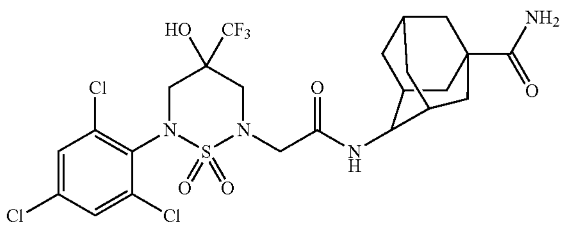 [SMILES: NC(=O)C12CC3CC(C1)C(NC(=O)CN1CC(O)(C(F)(F)F)CN(c4c(Cl)cc(Cl)cc4Cl)S1(=O)=O)C(C3)C2] | 4-(2-(4-hydroxy-1,1-dioxido-6-(2,4,6-trichlorophenyl)-4-(trifluoromethyl)-1,2,6-thiadiazinan-2-yl)acetamido)adamantan-1-carboxamide | $^1$H NMR (300 MHz, CDCl$_3$): δ 7.43 (s, 2H), 6.68 (d, J = 7.7Hz, 1H), 5.57 (s, 1H), 5.26-5.24 (m, 2H), 4.69-4.64 (m, 1H), 4.09-4.23 (m, 3H), 4.01 (m, 1H), 3.62-3.46 (m, 2H), 2.10-1.24 (m, 13H) |
| 175 | 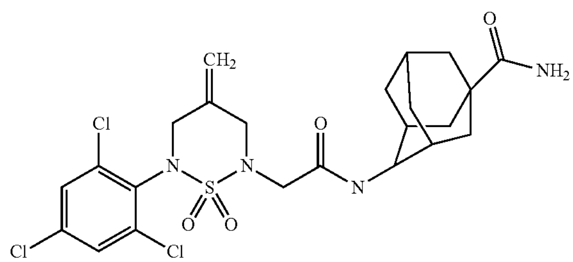 [SMILES: C=C1CN(CC(=O)NC2C3CC4CC2CC(C(N)=O)(C4)C3)S(=O)(=O)N(c2c(Cl)cc(Cl)cc2Cl)C1] | 4-(2-(4-methylene-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δ 7.42 (s, 2H), 6.93 (d, J = 8.0Hz, 1H), 5.58 (s, 1H), 5.29-5.27 (m, 2H), 5.21 (s, 1H), 4.29 (s, 2H), 4.26 (s, 2H), 4.06-4.05 (m, 1H), 3.97 (s, 2H), 2.17-1.58 (m, 13H) |
| 176 | 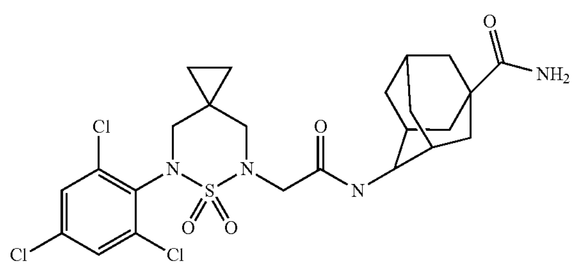 [SMILES: NC(=O)C12CC3CC(C1)C(NC(=O)CN1CC4(CC4)CN(c4c(Cl)cc(Cl)cc4Cl)S1(=O)=O)C(C3)C2] | 4-(2-(6,6-dioxido-7-(2,4,6-trichlorophenyl)-6-thia-5,7-diazaspiro[2,5]octane-5-yl)acetamido)adamantan-1-carboxamide | $^1$H NMR (300 MHz, CDCl$_3$): δ 7.40 (s, 2H), 6.91 (d, J = 8.1 Hz, 1H), 5.55 (s, 1H), 5.23 (s, 1H), 4.23 (s, 2H), 4.04-4.03 (m, 1H), 3.62 (s, 2H), 3.59 (s, 2H), 2.08-1.25 (m, 13H), 0.71-0.69 (m, 4H) |
| 177 | 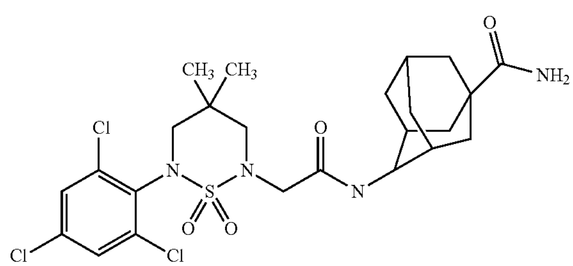 [SMILES: CC1(C)CN(CC(=O)NC2C3CC4CC2CC(C(N)=O)(C4)C3)S(=O)(=O)N(c2c(Cl)cc(Cl)cc2Cl)C1] | 4-(2-(4,4-dimethyl-1,1-dioxido-6-(2,4,6-trichlorophenyl)-1,2,6-thiadiazinan-2-yl)acetamido)adamantan-1-carboxamide | $^1$H NMR (300 MHz, CDCl$_3$): δ 7.40 (s, 2H), 7.00 (d, J = 8.0Hz 1H), 5.55 (s, 1H), 5.23 (s, 1H), 4.07 (s, 2H), 4.05-4.04 (m, 1H), 3.68 (s, 2H), 3.46 (s, 2H), 2.09-1.25 (m, 13H), 1.24 (s, 6H) |
| 178 | 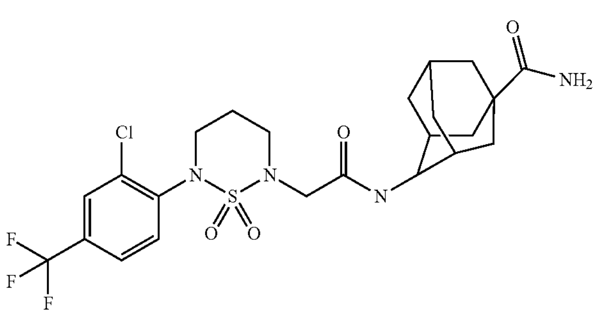 [SMILES: NC(=O)C12CC3CC(C1)C(NC(=O)CN1CCCN(c4ccc(C(F)(F)F)cc4Cl)S1(=O)=O)C(C3)C2] | 4-(2-(6-(2-chloro-4-(trifluoromethyl)phenyl)-1,1-dioxido-1,2,6-thiadiazinan-2-yl)acetamido)adamantan-1-carboxamide | $^1$H NMR (300 MHz, CDCl$_3$): δ 7.76 (d, J = 1.8Hz, 1H), 7.70 (d, J = 8.3Hz, 1H), 7.57 (dd, J = 8.3Hz, 1.5Hz, 1H), 6.90 (d, J = 8.1Hz, 1H), 5.56 (s, 1H), 5.27 (s, 1H), 4.19-4.18 (m, 2H), 4.06-4.05 (m, 1H) 3.91-3.45 (m, 4H), 2.36-2.32 (m, 1H), 2.10-1.26 (m, 14H) |

TABLE 26-continued

| No | Structure | IUPAC Name | NMR |
|---|---|---|---|
| 179 | 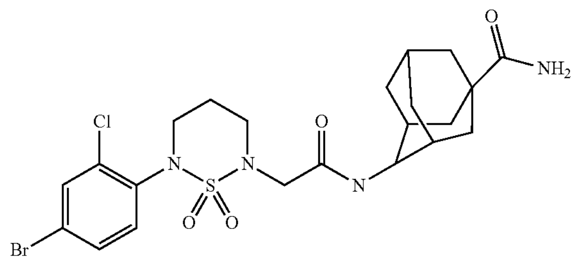 [SMILES: NC(=O)C12CC3CC(C1)C(NC(=O)CN1CCCN(c4ccc(Cl)cc4Br)S1(=O)=O)C(C3)C2] | 4-(2-(6-(4-bromo-2-chlorophenyl)-1,1-dioxido-1,2,6-thiadiazinan-2-yl)acetamido)adamantan-1-carboxamide | ¹H NMR (300MHz, CDCl₃): δ 7.75 (s, 1H), 7.35-7.34 (m, 2H) 6.92 (d, J = 7.8Hz, 1H), 5.57 (s, 1H), 5.28 (s, 1H), 4.35-4.13 (m, 2H), 4.06-4.05 (m, 1H), 3.89-3.41 (m, 4H), 2.32-2.31 (m, 1H), 2.11-1.60 (m, 14H) |

TABLE 27

| No | Structure | IUPAC Name | NMR |
|---|---|---|---|
| 180 | 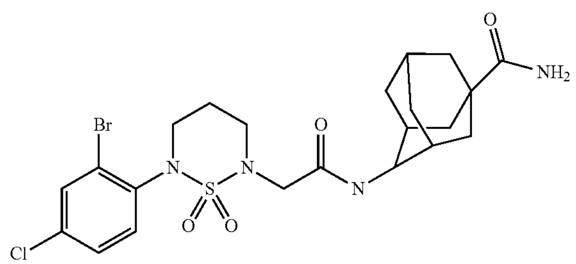 | 4-(2-(6-(2-bromo-4-chlorophenyl)-1,1-dioxido-1,2,6-thiadiazinan-2-yl)acetamido)adamantan-1-carboxamide | ¹H NMR (300 MHz, CDCl₃): δ 7.67 (d, J = 2.2Hz, 1H), 7.52 (d, J = 8.6Hz, 1H), 7.33 (dd, J = 8.6Hz, 2.3 Hz, 1H), 6.92 (d, J = 7.5Hz, 1H), 5.56 (s, 1H), 5.24 (s,1H), 4.40-4.13 (m, 2H), 4.05-4.04 (m, 1H), 3.88-3.80 (m, 4H), 2.35-2.34 (m, 1H), 2.12-1.59 (m, 14H) |
| 181 | 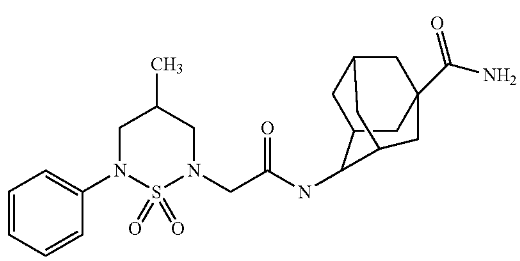 [SMILES: CC1CN(CC(=O)NC2C3CC4CC2CC(C(N)=O)(C4)C3)S(=O)(=O)N(c2ccccc2)C1] | 4-(2-(4-methyl-1,1-dioxido-6-phenyl-1,2,6-thiadiazinan-2-yl)acetamido)adamantan-1-carboxamide | ¹H NMR (300 MHz, CDCl₃): δ 7.38-7.26 (m, 5H), 6.95 (d, J = 7.1 Hz, 1H), 5.54 (s, 1H), 5.22 (s, 1H), 4.24-4.18 (m, 1H), 4.05-4.04 (m, 1H), 3.84-3.67 (m, 3H), 3.46-3.24 (m, 2H), 2.46- 2.45 (m, 1H), 2.14-1.54 (m, 13H), 0.97 (d, J = 6.3 Hz, 3H) |
| 182 | 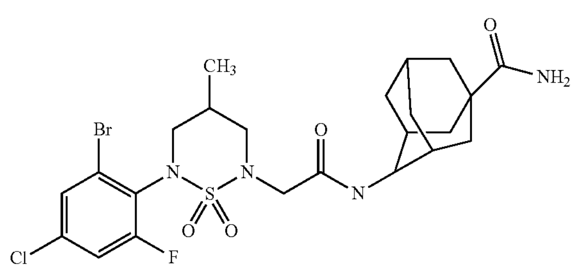 [SMILES: CC1CN(CC(=O)NC2C3CC4CC2CC(C(N)=O)(C4)C3)S(=O)(=O)N(c2c(F)cc(Cl)cc2Br)C1] | 4-(2-(6-(2-bromo-4-chloro-6-fluorophenyl)-4-methyl-1,1-dioxido-1,2,6-thiadiazinan-2-yl)acetamido)adamantan-1-carboxamide | ¹H NMR (300 MHz, CDCl₃): δ 7.48 (s, 1H), 7.18 (d, J = 9.3Hz, 1H), 6.92 (d, J = 8.2Hz, 1H), 5.58 (s, 1H), 5.32 (s, 1H), 4.48-4.43 (m, 1H), 4.05-4.04 (m, 1H), 4.04- 3.69 (m, 3H), 3.33-3.21 (m, 2H), 2.61-2.60 (m, 1H), 2.14-1.56 (m, 13H), 0.95 (d, J = 6.6Hz, 3H) |
| 183 | 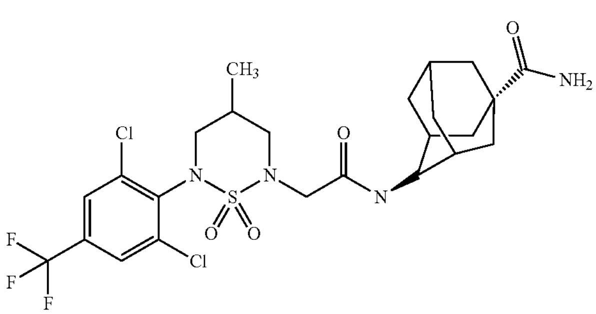 | (E) 4-(2-(6-(2,6-dichloro-4-(trifluoromethyl)phenyl)-4-methyl-1,1-dioxido-1,2,6-thiadiazinan-2-yl) acetamido)adamantan-1-carboxamide | ¹H NMR (300 MHz, CDCl₃): δ 7.69 (s, 1H), 7.65 (s, 1H), 6.95 (d, J = 6.8Hz, 1H), 5.58 (s, 1H), 5.29 (s, 1H), 4.40-4.34 (m, 1H), 4.12-3.90 (m, 3H), 3.78-3.72 (m, 1H), 3.33-3.21 (m, 2H), 2.62-2.61 (m, 1H), 2.14-1.58 (m, 13H), 0.97 (d, J = 6.0 Hz, 3H) |

TABLE 27-continued

| No | Structure | IUPAC Name | NMR |
|---|---|---|---|
| 184 | 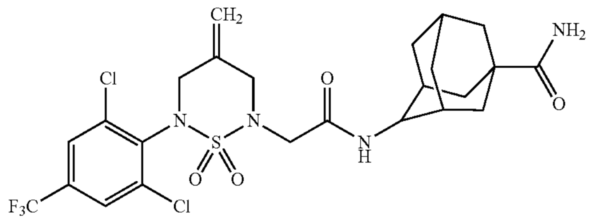 [SMILES: C=C1CN(CC(=O)NC2C3CC4CC2CC(C(N)=O)(C4)C3)S(=O)(=O)N(c2c(Cl)cc(C(F)(F)F)cc2Cl)C1] | 4-(2-(6-(2,6-dichloro-4-(trifluoromethyl)phenyl)-4-methylene-1,1-dioxido-1,2,6-thiadiazinan-2-yl)acetamido)adamantan-1-carboxamide | $^1$H NMR (300 MHz, CDCl$_3$): δ 7.39-7.29 (m, 5H), 6.92 (d, J = 8.0Hz, 1H), 5.56 (s, 1H), 5.29-5.27 (m, 2H), 5.21 (s, 1H), 4.29 (s, 2H), 4.19 (s, 2H), 4.05-4.04 (m, 1H), 3.82 (s, 2H), 2.10-1.55 (m, 13H) |
| 185 | 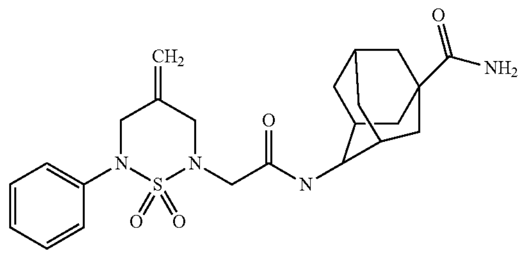 [SMILES: C=C1CN(CC(=O)NC2C3CC4CC2CC(C(N)=O)(C4)C3)S(=O)(=O)N(c2ccccc2)C1] | 4-(2-(4-methylene-1,1-dioxido-6-phenyl-1,2,6-thiadiazinan-2-yl)acetamido)adamantan-1-carboxamide | $^1$H NMR (300 MHz, CDCl$_3$): δ 7.48 (t, J = 2.1Hz, 1H), 7.20 (dd, J = 9.5Hz, 2.3Hz, 1H), 6.90 (d, J = 6.8Hz, 1H), 5.55 (s, 1H), 5.30 (s, 1H), 5.21-5.20 (m, 2H), 4.57-4.43 (m, 2H), 4.19-3.90 (m, 4H), 3.77-3.72 (m, 1H), 2.12-1.77 (m, 13H) |

TABLE 28

| No | Structure | IUPAC Name | NMR |
|---|---|---|---|
| 186 | 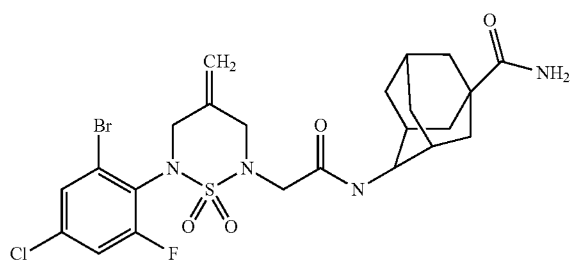 | 4-(2-(6-(2-bromo-4-chloro-6-fluorophenyl)-4-methylene-1,1-dioxido-1,2,6-thiadiazinan-2-yl)acetamido)adamantan-1-carboxamide | $^1$H NMR (300 MHz, CDCl$_3$): δ 7.48 (t, J = 2.1Hz, 1H), 7.20 (dd, J = 9.5Hz, 2.3Hz, 1H), 6.90 (d, J = 6.8Hz, 1H), 5.55 (s, 1H), 5.30 (s, 1H), 5.21-5.20 (m, 2H), 4.57-4.43 (m, 2H), 4.19-3.90 (m, 4H), 3.77-3.72 (m, 1H), 2.12-1.77 (m, 13H) |
| 187 | 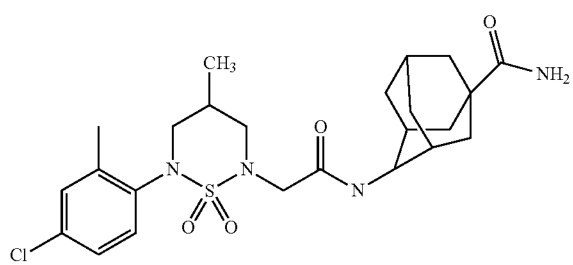 [SMILES: Cc1cc(Cl)ccc1N1CC(C)CN(CC(=O)NC2C3CC4CC2CC(C(N)=O)(C4)C3)S1(=O)=O] | 4-(2-(6-(4-chloro-2-iodophenyl)-4-methyl-1,1-dioxido-1,2,6-thiadiazinan-2-yl)acetamido)adamantan-1-carboxamide | $^1$H NMR (300 MHz, CDCl$_3$): δ 7.90 (d, J = 2.3Hz, 1H), 7.50 (d, J = 8.5 Hz, 1H), 7.38 (dd, J = 8.5Hz, 2.3 Hz, 1H), 6.90 (d, J = 7.9Hz, 1H) 5.55 (s, 1H), 5.20 (s, 1H), 4.53-4.48 (m, 1H), 4.04-4.03 (m, 1H), 3.93-3.85 (m, 1H), 3.76-3.70 (m, 1H), 3.52-3.44 (m, 1H), 3.28-3.19 (m, 2H), 2.63-2.62 (m, 1H), 2.12-1.54 (m, 13H), 0.95 (d, J = 6.7 Hz, 3H) |
| 188 | 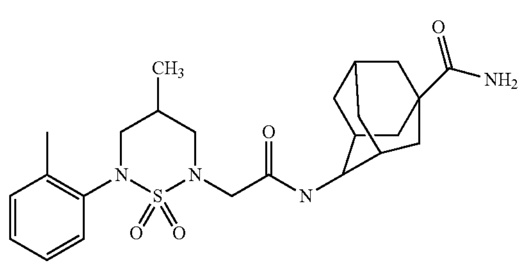 [SMILES: Cc1ccccc1N1CC(C)CN(CC(=O)NC2C3CC4CC2CC(C(N)=O)(C4)C3)S1(=O)=O] | 4-(2-(6-(2-iodophenyl)-4-methyl-1,1-dioxido-1,2,6-thiadiazinan-2-yl)acetamido)adamantan-1-carboxamide | $^1$H NMR (300 MHz, CDCl$_3$): δ 7.92 (d, J = 8.0Hz, 1H), 7.58 (d, J = 7.9Hz, 1H), 7.39 (t, J = 7.9Hz, 1H), 7.07 (t, J = 7.9Hz, 1H), 6.94 (d, J = 7.1Hz, 1H), 5.57 (s, 1H), 5.25 (s, 1H), 4.57-4.51 (m, 1H), 4.07-4.06 (m, 1H), 3.95-3.86 (m, 1H), 3.77-3.72 (m, 1H), 3.55-3.47 (m, 1H), 3.31-3.23 (m, 2H), 2.66-2.65 (m, 1H), 2.17-1.56 (m, 13H), 0.95 (d, J = 6.7Hz, 3H) |

TABLE 28-continued

| No | Structure | IUPAC Name | NMR |
|---|---|---|---|
| 189 | 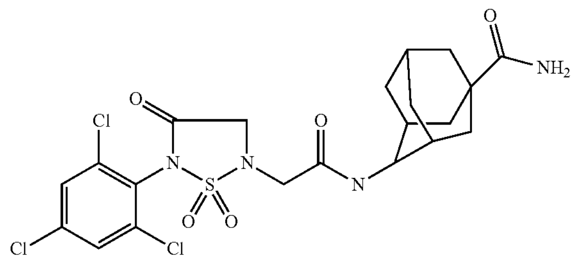 [SMILES: NC(=O)C12CC3CC(C1)C(NC(=O)CN1CC(=O)N(c4c(Cl)cc(Cl)cc4Cl)S1(=O)=O)C(C3)C2] | 4-(2-(1,1-dioxido-4-oxo-5-(2,4,6-trichlorophenyl)-1,2,5-thiadiazolidin-2-yl)acetamido)adamantan-1-carboxamide | ¹H NMR (300 MHz, CDCl₃): δ 7.52 (s, 2H), 6.61 (d, J = 6.5Hz, 1H), 5.61 (s, 1H), 5.37 (s, 1H), 4.54 (s, 2H), 4.41 (s, 2H), 4.08-4.07 (m, 1H), 2.10-1.57 (m, 13H) |
| 190 | 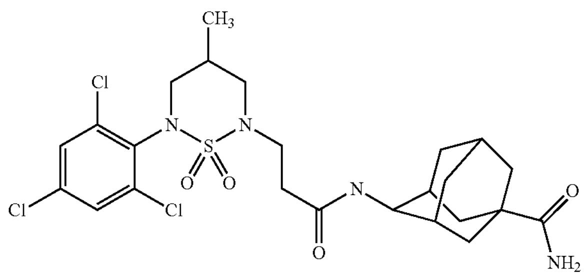 [SMILES: CC1CN(CCC(=O)NC2C3CC4CC2CC(C(N)=O)(C4)C3)S(=O)(=O)N(c2c(Cl)cc(Cl)cc2Cl)C1] | 4-(3-(4-methyl-1,1-dioxido-6-(2,4,6-trichlorophenyl)-1,2,6-thiadiazinan-2-yl)propaneamido)adamantan-1-carboxamide | ¹H NMR (300 MHz, CDCl₃): δ 7.37 (s, 2H), 6.05 (d, J = 6.5Hz, 1H), 5.63 (s, 1H), 5.38 (s, 1H), 4.07-3.95 (m, 3H), 3.85-3.74 (m, 1H), 3.46-3.34 (m, 2H), 3.21-3.12 (m, 1H), 2.60-2.49 (m, 3H), 2.12-1.53 (m, 13H), 0.91 (d, J = 6.5Hz, 3H) |
| 191 | 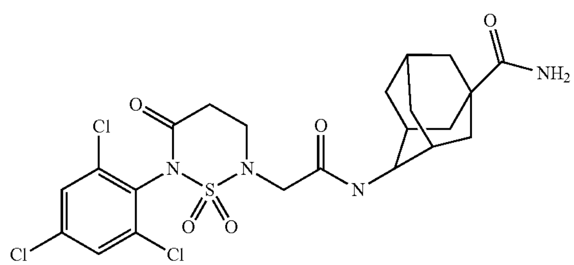 [SMILES: NC(=O)C12CC3CC(C1)C(NC(=O)CN1CCC(=O)N(c4c(Cl)cc(Cl)cc4Cl)S1(=O)=O)C(C3)C2] | 4-(2-(1,1-dioxido-5-oxo-6-(2,4,6-trichlorophenyl)-1,2,6-thiadiazinan-2-yl)acetamido)adamantan-1-carboxamide | ¹H NMR (300 MHz, CDCl₃): δ 7.48 (s, 2H), 5.88 (d, J = 7.9Hz, 1H), 5.58 (s, 1H) 5.29 (s, 1H), 4.41 (s, 2H), 4.14-4.09 (m, 3H), 2.75 (t, J = 7.1Hz, 2H), 2.12-1.45 (m, 13H). |
| 192 | 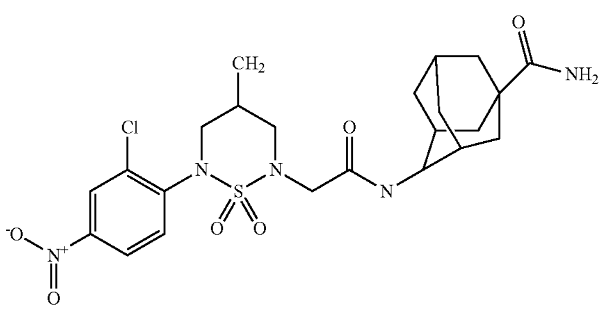 | 4-(2-(6-(2-chloro-4-nitrophenyl)-4-methyl-1,1-dioxido-1,2,6-thiadiazinan-2-yl)acetamido)adamantan-1-carboxamide | ¹H NMR (300 MHz, CDCl₃): δ 7.85 (dd, J = 2.1Hz, 1H), 7.63-7.61 (m, 2H), 6.76 (d, J = 7.7Hz, 1H), 5.58 (s, 1H), 5.26 (s, 1H), 4.06-4.02 (m, 2H), 3.90-3.79 (m, 1H), 3.69-3.57 (m, 2H), 3.50-3.41 (m, 1H), 3.35-3.28 (m, 1H), 2.57 (m, 1H), 2.14-1.52 (m, 13H), 0.97 (d, J = 6.7Hz, 3H) |

TABLE 29

| No | Structure | IUPAC Name | NMR |
|---|---|---|---|
| 193 | 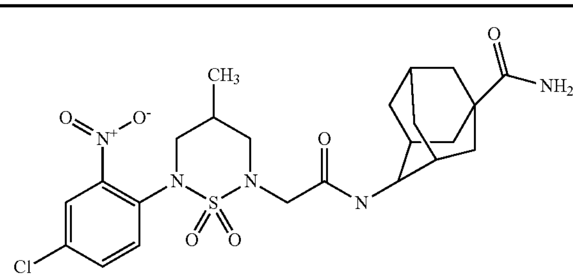 | 4-(2-(6-(4-chloro-2-nitrophenyl)-4-methyl-1,1-dioxido-1,2,6-thiadiazinan-2-yl)acetamido)adamantan-1-carboxamide | ¹H NMR (300MHz, CDCl₃): δ 8.37 (dd, J = 2.6Hz, 1H), 8.19-8.15 (dd, J = 8.8Hz, 2.6 Hz, 1H), 7.74 (d, J = 8.7Hz, 1H), 6.86 (d, J = 7.8Hz, 1H), 5.59 (s, 1H), 5.36 (s, 1H), 4.40-3.28 (m, 1H), 4.06 (m, 1H), 3.99-3.86 (m, 1H), 3.76-3.56 (m, 2H), 3.42-3.28 (m, 2H), 2.61 (m, 1H), 2.15-1.55 (m, 13H), 0.98 (d, J = 6.7Hz, 3H) |

TABLE 29-continued

| No | Structure | IUPAC Name | NMR |
|---|---|---|---|
| 194 | 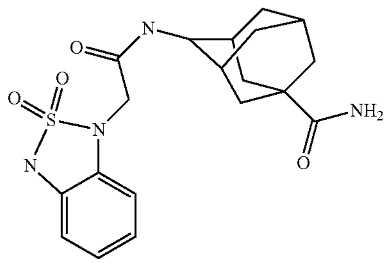 [SMILES: NC(=O)C12CC3CC(C1)C(NC(=O)CN1c4ccccc4NS1(=O)=O)C(C3)C2] | 4-(2-(2,2-dioxidobenzo[c][1,2,5]thiadiazol-1(3H)-yl)acetamido)adamantan-1-carboxamide | ¹H NMR (300 MHz, DMSO) δ 8.06 (d, J = 7.2Hz 1H), 6.99-6.95 (m, 4H), 6.90-6.88 (m, 1H), 6.73-6.88 (m, 1H), 6.73-6.74 (m, 1H), 4.48 (s, 2H), 3.82-3.80 (m, 1H), 1.95-1.76 (m, 1H), 1.45-1.41 (m, 2H) |
| 195 | 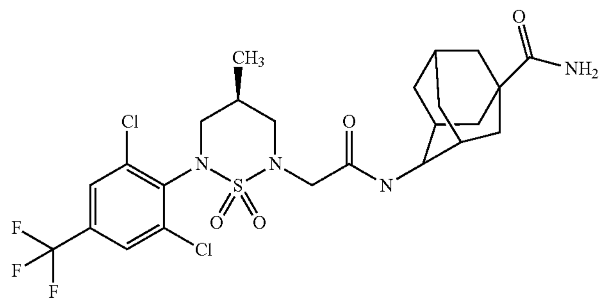 | 4-(2-((S)-6-(2,6-dichloro-4-(trifluoromethyl)phenyl)-4-methyl-1,1-dioxido-1,2,6-thiadiazinan-2-yl)acetamido)adamantan-1-carboxamide | ¹H NMR (300 MHz, CDCl₃): δ 7.68 (s, 1H), 7.66 (s, 1H), 6.94 (d, 1H, J = 7.9Hz), 5.58 (s, 1H), 5.20 (s, 1H), 4.40-4.34 (m, 1H), 4.13-3.90 (m, 3H), 3.79-3.73 (m, 1H), 3.36-3.20 (m, 2H), 2.62-2.58 (m, 1H), 2.18-1.57 (m, 13H), 0.96 (d, 3H, J = 6.7 Hz). |
| 196 | 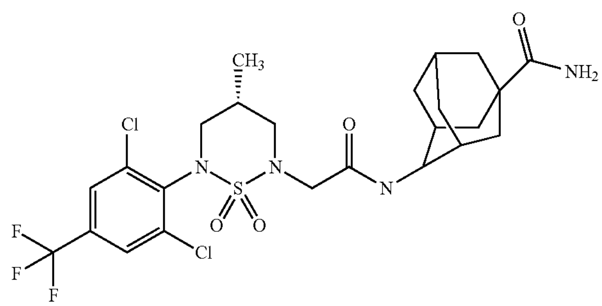 [SMILES: C[C@@H]1CN(CC(=O)NC2C3CC4CC2CC(C(N)=O)(C4)C3)S(=O)(=O)N(c2c(Cl)cc(C(F)(F)F)cc2Cl)C1] | 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide | ¹H NMR (300 MHz, CDCl₃): δ 7.68 (s, 1H), 7.65 (s, 1H), 6.95 (d, 1H, J = 8.0 Hz), 5.51 (s, 1H), 5.16 (s, 1H), 4.40-4.34 (m, 1H), 4.13-3.91 (m, 3H), 3.79-3.73 (m, 1H), 3.36-3.21 (m, 2H), 2.62-2.56 (m, 1H), 2.18-1.56 (m, 13H), 0.97 (d, 3H, J = 6.7 Hz). |
| 197 | 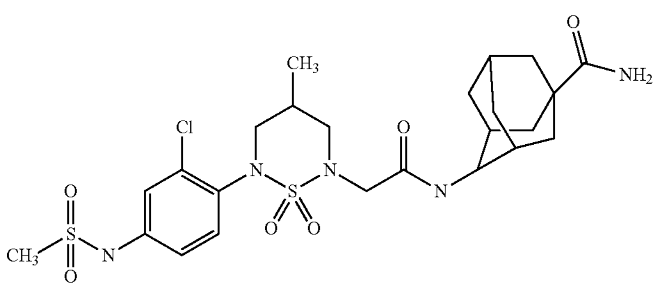 [SMILES: CC1CN(CC(=O)NC2C3CC4CC2CC(C(N)=O)(C4)C3)S(=O)(=O)N(c2ccc(NS(C)(=O)=O)cc2Cl)C1] | 4-(2-(6-(2-chloro-4-(methylsulfonamido)phenyl)-4-methyl-1,1-dioxido-1,2,6-thiadiazinan-2-yl)acetamido)adamantan-1-carboxamide | ¹H NMR (300MHz, DMSO) δ 10.13 (s, 1H), 7.77 (d, J = 7.0Hz, 1H), 7.35 (d, J = 8.8Hz, 1H), 7.30 (d, J = 2.0Hz, 1H), 7.16 (dd, J = 8.8Hz, 2.0Hz, 1H), 7.00 (s, 1H), 6.72 (s,1H), 4.08 (d, J = 16.5Hz, 1H), 3.88 (d, J = 16.5Hz, 1H) 3.84-3.82 (m, 1H), 3.57-3.42 (m, 4H), 3.27-3.20 (m, 1H), 3.03 (s, 3H), 1.89-1.74 (m, 11H), 1.44-1.40 (m, 2H), 0.84 (d, J = 6.6H z, 3H) |
| 198 | 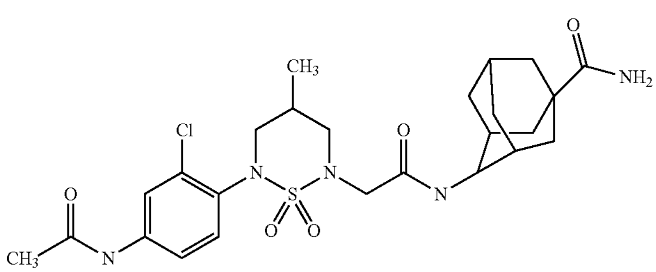 [SMILES: CC(=O)Nc1ccc(N2CC(C)CN(CC(=O)NC3C4CC5CC3CC(C(N)=O)(C5)C4)S2(=O)=O)c(Cl)c1] | 4-(2-(6-(4-acetamido-2-chlorophenyl)-4-methyl-1,1-dioxido-1,2,6-thiadiazinan-2-yl)acetamido)adamantan-1-carboxamide | ¹H NMR (300 MHz, DMSO) δ 10.23 (s, 1H), 7.93-7.92 (m, 1H), 7.77 (d, J = 7.5Hz, 1H) 7.45-7.44 (m, 2H), 6.99 (s, 1H), 4.10 (d, J = 16.4Hz, 1H), 3.88 (d, J = 16.4Hz, 1H), 3.82-3.81 (m, 1H), 3.57-3.55 (m, 4H) 3.24-3.20 (m, 1H) 2.05 (s, 3H) 1.88-1.73 (m, 11H), 1.43-1.40 (m, 2H), 0.83 (d, J = 6.6Hz, 3H) |

TABLE 29-continued

| No | Structure | IUPAC Name | NMR |
|---|---|---|---|
| 199 | 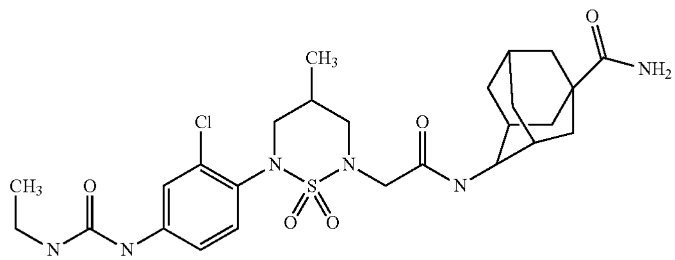 [SMILES: CCNC(=O)Nc1ccc(N2CC(C)CN(CC(=O)NC3C4CC5CC3CC(C(N)=O)(C5)C4)S2(=O)=O)c(Cl)c1] | 4-(2-(6-(2-chloro-4-(3-ethylureido)phenyl)-4-methyl-1,1-dioxido-1,2,6-thiadiazinan-2-yl)acetamido)adamantan-1-carboxamide | $^1$H NMR (300MHz, DMSO) δ 8.88 (s, 1H), 7.80 (d, J = 2.3Hz, 1H), 7.77 (d, J = 7.5 Hz, 1H), 7.35 (d, J = 8.7Hz, 1H), 7.22 (dd, J = 8.7, 2.3Hz, 1H), 7.00 (s, 1H), 6.73 (s, 1H), 6.36 (t, J = 5.4Hz, 1H), 4.09 (d, J = 16.1Hz, 1H), 3.87 (d, J = 16.1Hz, 1H), 3.83-3.82 (m, 1H) 3.52-3.40 (m, 4H) 3.23-3.18 (m, 1H) 3.09 (qu, J = 6.8Hz, 2H) 1.89-1.74 (m, 11H), 1.44-1.40 (m, 2H), 1.04 (t, J = 7.2Hz, 3H), 0.83 (d, J = 6.5 Hz, 3H) |

TABLE 30

| No | Structure | IUPAC Name | NMR |
|---|---|---|---|
| 200 | 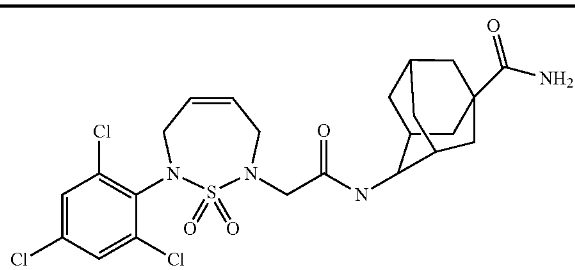 | 4-(2-(1,1-dioxido-7-(2,4,6-trichlorophenyl)-6,7-dihydro-1,2,7-thiadiazepine-2(3H)-yl)acetamido)adamantan-1-carboxamide | $^1$H NMR (300MHz, CDCl$_3$): δ 7.41 (s, 2H), 6.87 (d, J = 7.8Hz, 1H), 6.02-5.94 (m, 1H), 5.85-5.70 (m, 1H), 5.55 (s, 1H), 5.23 (s, 1H), 4.18 (m, 2H), 4.11-4.00 (m, 5H), 2.12-1.58 (m, 13H) |
| 201 | 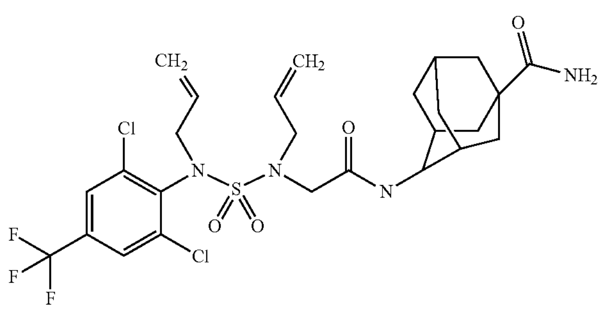 [SMILES: C=CCN(CC(=O)NC1C2CC3CC1CC(C(N)=O)(C3)C2)S(=O)(=O)N(CC=C)c1c(Cl)cc(C(F)(F)F)cc1Cl] | 4-(2-(allyl(N-allyl-N-(2,6-dichloro-4-(trifluoromethyl)phenyl)sulfamoyl)amino)acetamido)adamantan-1-carboxamide | $^1$H NMR (300 MHz, CDCl$_3$): δ 7.41 (s, 2H), 6.87 (d, J = 7.8Hz, 1H), 6.02-5.94 (m, 1H), 5.85-5.70 (m, 1H), 5.55 (s, 1H), 5.23 (s, 1H), 4.18 (m, 2H), 4.11-4.00 (m, 5H), 2.12-1.58 (m, 13H) |
| 202 | 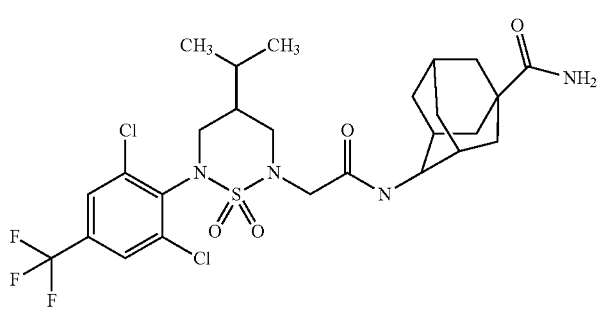 [SMILES: CC(C)C1CN(CC(=O)NC2C3CC4CC2CC(C(N)=O)(C4)C3)S(=O)(=O)N(c2c(Cl)cc(C(F)(F)F)cc2Cl)C1] | 4-(2-(6-(2,6-dichloro-4-(trifluoromethyl)phenyl)-4-isopropyl-1,1-dioxido-1,2,6-thiadiazinan-2-yl)acetamido)adamantan-1-carboxamide | $^1$H NMR (300 MHz, DMSO) δ 7.67-7.66 (m, 2H), 6.96 (d, J = 7.9Hz, 1H), 5.56 (s, 1H), 5.28 (s, 1H), 4.32 (d, J = 17.1, 1H), 4.11-4.09 (m, 3H), 3.70 (d, J = 17.1Hz 1H), 3.41-3.40 (m, 1H), 3.30-3.29 (m, 1H), 2.00-1.99 (m, 1H), 1.61-1.60 (m, 4H) 1.20-1.19 (m, 6H) |

TABLE 30-continued

| No | Structure | IUPAC Name | NMR |
|---|---|---|---|
| 203 | 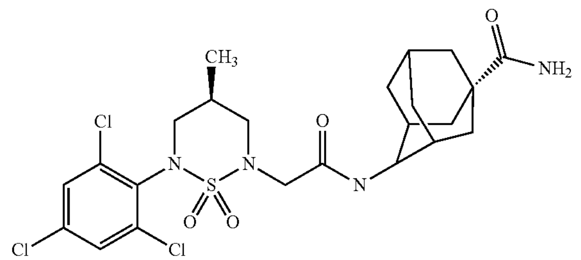 | 4-(2-((S)-4-methyl-1,1-dioxido-6-(2,4,6-trichlorophenyl)-1,2,6-thiadiazinan-2-yl)acetamido)adamantan-1-carboxamide | LCMS MH+ 563 |
| 204 | 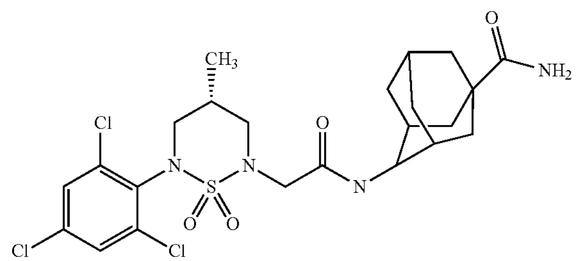 | 4-(2-((R)-4-methyl-1,1-dioxido-6-(2,4,6-trichlorophenyl)-1,2,6-thiadiazinan-2-yl)acetamido)adamantan-1-carboxamide | LCMS MH+ 563 |
| 205 | 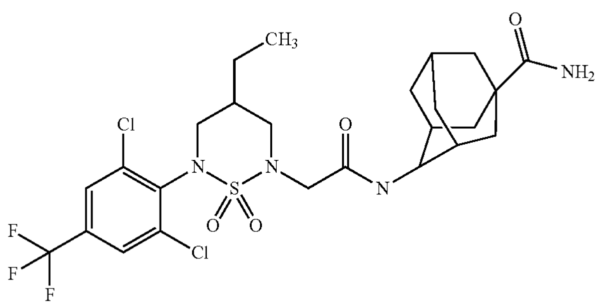 [SMILES: CCC1CN(CC(=O)NC2C3CC4CC2CC(C(N)=O)(C4)C3)S(=O)(=O)N(c2c(Cl)cc(C(F)(F)F)cc2Cl)C1] | 4-(2-(6-(2,6-dichloro-4-(trifluoromethyl)phenyl)-4-ethyl-1,1-dioxido-1,2,6-thiadiazinan-2-yl)acetamido)adamantan-1-carboxamide | $^1$H NMR (300MHz, CDCl$_3$): δ 7.68 (s, 1H), 7.65 (s, 1H), 6.96 (d, J = 8.1Hz, 1H), 5.57 (s, 1H), 5.22 (s, 1H), 4.38-4.32 (m, 1H), 4.11-3.81 (m, 3H), 3.77-3.71 (m, 1H), 3.41-3.27 (m, 2H) 2.36 (m, 1H), 2.15-1.54 (m, 13H), 1.35-1.25 (q, J = 7.6Hz, 2H), 0.98-0.93 (t, J = 7.5Hz, 3H) |
| 206 | 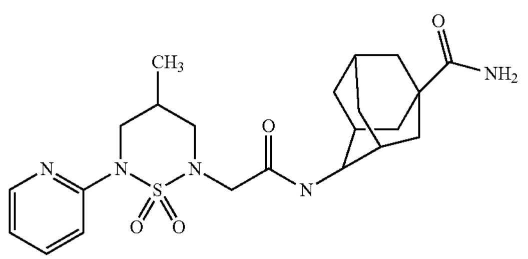 [SMILES: CC1CN(CC(=O)NC2C3CC4CC2CC(C(N)=O)(C4)C3)S(=O)(=O)N(c2ccccn2)C1] | 4-(2-(4-methyl-1,1-dioxido-6-(pyridine-2-yl)-1,2,6-thiadiazinan-2-yl)acetamido)adamantan-1-carboxamide | $^1$H NMR (300MHz, CDCl$_3$) δ 8.38- 8.36 (m, 1H), 7.67-7.66 (m, 1H), 7.4 3-7.42 (m, 1H), 7.13-7.12 (m, 1H), 6.93 (d, J = 8.0Hz, 1H), 5.54 (s, 1H), 5.27 (s, 1H), 4.15-4.14 (m, 1H), 4.00-3.99 (m, 1H), 3.76-3.75 (m, 3H), 3.23-3.22 (m, 1H), 2.82-2.80 (m, 1H), 1.88-1.87 (m, 14H) 0.99 (d, J = 6.6Hz, 3H) |

TABLE 31

| No | Structure | IUPAC Name | NMR |
|---|---|---|---|
| 207 | 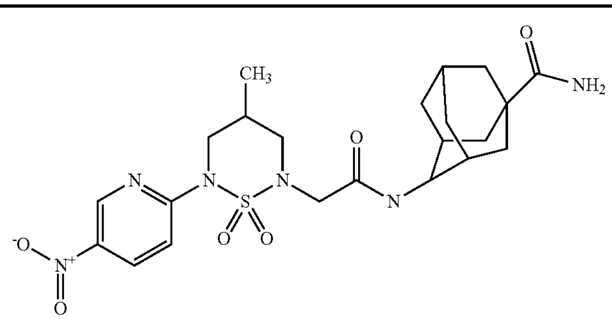 | 4-(2-(4-methyl-6-(5-nitropyridine-2-yl)-1,1-dioxido-1,2,6-thiadiazinan-2-yl)acetamido)adamantan-1-carboxamide | $^1$H NMR (300MHz, CDCl$_3$) δ 8.38-8.36 (m, 1H), 7.67-7.66 (m, 1H), 7.43-7.42 (m, 1H), 7.13-7.12 (m, 1H), 6.93 (d, J = 8.0Hz, 1H), 5.54 (s, 1H), 5.27 (s, 1H) 4.15-4.14 (m, 1H), 4.00-3.99 (m, 1H) 3.76-3.75 (m, 3H), 3.23-3.22 (m, 1H) 2.82-2.80 (m, 1H), 1.88-1.87 (m, 14H), 0.99 (d, J = 6.6Hz, 3H) |

TABLE 31-continued

| No | Structure | IUPAC Name | NMR |
|---|---|---|---|
| 208 | 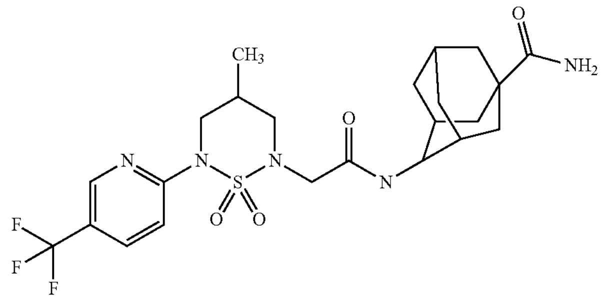 [SMILES: CC1CN(CC(=O)NC2C3CC4CC2CC(C(N)=O)(C4)C3)S(=O)(=O)N(c2ccc(C(F)(F)F)cn2)C1] | 4-(2-(4-methyl-1,1-dioxido-6-(5-(trifluoromethyl)pyridine-2-yl)-1,2,6-thiadiazinan-2-yl)acetamido)adamantan-1-carboxamide | $^1$H NMR (300 MHz, CDCl$_3$) δ 8.63-8.62 (m, 1H), 7.89 (dd, J = 8.7Hz, 2.1Hz, 1H) 7.63 (d, J = 8.6Hz, 1H), 6.83 (d, J = 7.9Hz, 1H), 5.56 (s, 1H), 5.37 (s, 1H), 4.37-4.34 (m, 1H), 4.01-4.00 (m, 1H), 3.77-3.76 (m, 2H), 3.63 (d, J = 17.1Hz, 1H), 3.25-3.23 (m, 1H), 2.70-2.69 (m, 1H), 1.80-1.76 (m, 14H) 1.02 (d, J = 6.7Hz, 3H) |
| 209 | 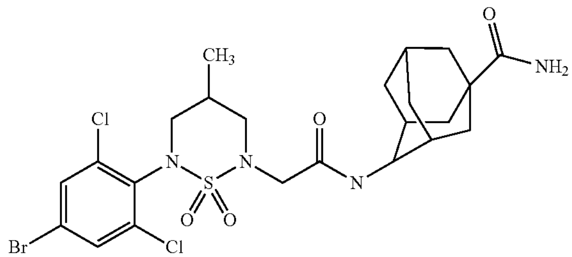 [SMILES: CC1CN(CC(=O)NC2C3CC4CC2CC(C(N)=O)(C4)C3)S(=O)(=O)N(c2c(Cl)cc(Br)cc2Cl)C1] | 4-(2-(6-(4-bromo-2,6-dichlorophenyl)-4-methyl-1,1-dioxido-1,2,6-thiadiazinan-2-yl)acetamido)adamantan-1-carboxamide | $^1$H NMR (300 MHz, CDCl$_3$): δ 7.57 (d, J = 2.3Hz, 1H), 7.54 (d, J = 2.2Hz, 1H) 6.96 (d, J = 8.2Hz, 1H), 5.21 (s,1H), 4.39-4.32 (m, 1H), 4.09-3.87 (m, 3H), 3.76-3.70 (m, 1H), 3.33-3.17 (m, 2H), 2.58 (m, 1H), 2.13-1.55 (m, 13H), 0.94 (d, J = 6.7Hz, 3H) |
| 210 | 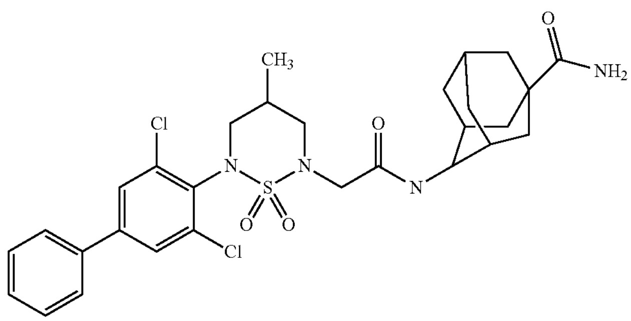 [SMILES: CC1CN(CC(=O)NC2C3CC4CC2CC(C(N)=O)(C4)C3)S(=O)(=O)N(c2c(Cl)cc(-c3ccccc3)cc2Cl)C1] | 4-(2-(6-(3,5-dichloro-[1,1'-biphenyl]-4-yl)-4-methyl-1,1-dioxido-1,2,6-thiadiazinan-2-yl)acetamido)adamantan-1-carboxamide | $^1$H NMR (300MHz, CDCl$_3$): δ 7.62-7.41 (m, 7H), 7.02 (d, J = 7.7Hz, 1H) 5.58 (s, 1H), 5.25 (s, 1H), 4.45-4.39 (m, 1H), 4.15-4.03 (m, 3H), 3.80-3.75 (m, 1H), 3.25-3.36 (m, 2H), 2.64 (m, 1H), 2.16-1.55 (m, 13H), 0.96 (d, J = 6.6Hz, 3H) |
| 211 | 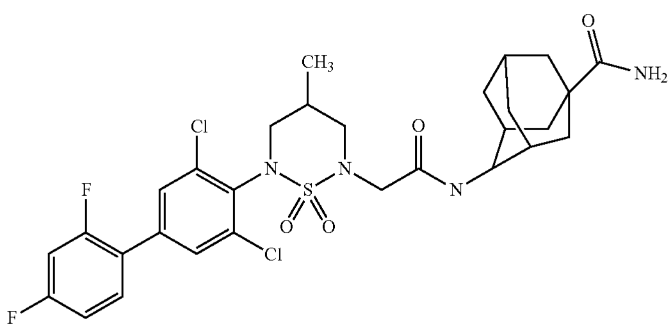 [SMILES: CC1CN(CC(=O)NC2C3CC4CC2CC(C(N)=O)(C4)C3)S(=O)(=O)N(c2c(Cl)cc(-c3ccc(F)cc3F)cc2Cl)C1] | 4-(2-(6-(3,5-dichloro-2',4'-difluoro-[1,1'-biphenyl]-4-yl)-4-methyl-1,1-dioxido-1,2,6-thiadiazinan-2-yl)acetamido)adamantan-1-carboxamide | $^1$H NMR (300 MHz, CDCl$_3$): δ 7.53 (m, 2H), 7.41-7.33 (m, 1H), 7.04-6.90 (m, 3H), 5.57 (s, 1H), 5.28 (s, 1H), 4.44-4.38 (m, 1H), 4.14-3.90 (m, 3H), 3.80-3.74 (m, 1H), 3.35-3.25 (m, 2H), 2.62 (m, 1H), 2.15-1.42 (m, 13H), 0.96 (d, J = 6.6Hz, 3H) |
| 212 | 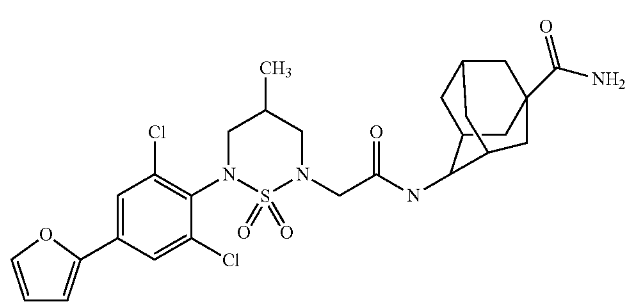 [SMILES: CC1CN(CC(=O)NC2C3CC4CC2CC(C(N)=O)(C4)C3)S(=O)(=O)N(c2c(Cl)cc(-c3ccco3)cc2Cl)C1] | 4-(2-(6-(2,6-dichloro-4-(furan-2-yl)phenyl)-4-methyl-1,1-dioxido-1,2,6-thiadiazinan-2-yl)acetamido)adamantan-1-carboxamide | $^1$H NMR (300 MHz, CDCl$_3$): δ 7.67 (dd, J = 1.9Hz, 1H), 7.64 (dd, J = 1.9Hz, 1H), 7.51 (m, 1H), 7.00 (d, J = 1.9Hz, 1H), 6.74-6.63 (m, 1H), 6.52-6.49 (m, 1H), 5.58 (s, 1H), 5.29 (s, 1H), 4.42-4.36 (m, 1H), 4.11-3.88 (m, 3H), 3.79-3.73 (m, 1H), 3.31-3.23 (m, 2H), 2.61 (m, 1H), 2.13-1.56 (m, 13H), 0.95 (d, J = 6.6Hz, 3H) |

TABLE 32

| No | Structure | IUPAC Name | NMR |
|---|---|---|---|
| 213 | 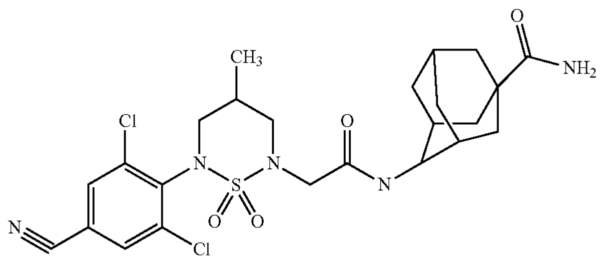 [SMILES: CC1CN(CC(=O)NC2C3CC4CC2CC(C(N)=O)(C4)C3)S(=O)(=O)N(c2c(Cl)cc(C#N)cc2Cl)C1] | 4-(2-(6-(2,6-dichloro-4-cyanophenyl)-4-methyl-1,1-dioxido-1,2,6-thiadiazinan-2-yl)acetamido)adamantan-1-carboxamide | $^1$H NMR (300 MHz, CDCl$_3$): δ 8.05 (s, 1H), 7.68 (s, 1H), 6.96 (d, J = 8.1 Hz, 1H), 5.58 (s, 1H), 5.34 (s, 1H) 4.39-4.31 (m, 1H), 4.12-3.89 (m, 3H) 3.78-3.71 (m, 1H), 3.33-3.16 (m, 2H) 2.62 (m, 1H), 2.12-1.55 (m, 13H), 0.95 (d, J = 6.6Hz, 3H) |
| 214 | 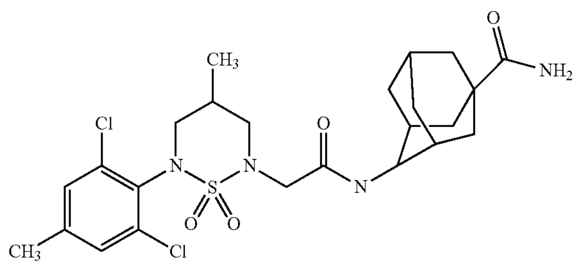 [SMILES: Cc1cc(Cl)c(N2CC(C)CN(CC(=O)NC3C4CC5CC3CC(C(N)=O)(C5)C4)S2(=O)=O)c(Cl)c1] | 4-(2-(6-(2,6-dichloro-4-methylphenyl)-4-methyl-1,1-dioxido-1,2,6-thiadiazinan-2-yl)acetamido)adamantan-1-carboxamide | $^1$H NMR (300 MHz, CDCl$_3$): δ 7.21 (s, 1H), 7.18 (s, 1H), 7.02 (d, J = 7.9Hz, 1H), 5.60 (s, 1H), 5.43 (s, 1H), 4.40-4.34 (m, 1H), 4.09-4.00 (m, 2H), 3.95-3.86 (m, 1H), 3.77-3.71 (m, 1H), 3.30-3.18 (m, 2H), 2.60 (m, 1H), 2.31 (s, 3H), 2.11-1.56 (m, 13H), 0.94 (d, J = 6.7Hz, 3H) |
| 215 | 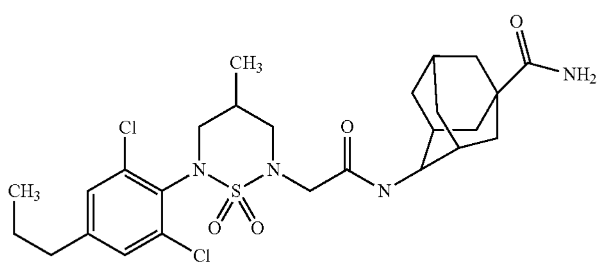 [SMILES: CCCc1cc(Cl)c(N2CC(C)CN(CC(=O)NC3C4CC5CC3CC(C(N)=O)(C5)C4)S2(=O)=O)c(Cl)c1] | 4-(2-(6-(2,6-dichloro-4-propylphenyl)-4-methyl-1,1-dioxido-1,2,6-thiadiazinan-2-yl)acetamido)adamantan-1-carboxamide | $^1$H NMR (300 MHz, CDCl$_3$): δ 7.20 (dd, J = 2.0Hz, 1H), 7.17 (d, J = 2.0Hz, 1H), 7.00 (d, J = 7.9Hz, 1H), 5.56 (s, 1H), 5.23 (s, 1H), 4.41-4.35 (m, 1H), 4.09-4.01 (m, 2H), 3.95-3.86 (m, 1H), 3.77-3.71 (m, 1H), 3.30-3.19 (m, 2H), 2.62-2.50 (m, 3H), 2.12-1.56 (m, 15H), 0.97-0.92 (m, 6H) |
| 216 | 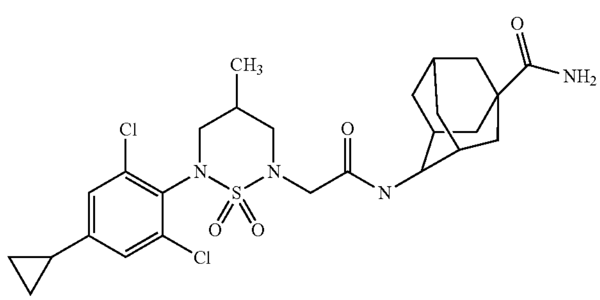 [SMILES: CC1CN(CC(=O)NC2C3CC4CC2CC(C(N)=O)(C4)C3)S(=O)(=O)N(c2c(Cl)cc(C3CC3)cc2Cl)C1] | 4-(2-(6-(2,6-dichloro-4-cyclopropylphenyl)-4-methyl-1,1-dioxido-1,2,6-thiadiazinan-2-yl)acetamido)adamantan-1-carboxamide | $^1$H NMR (300 MHz, CDCl$_3$): δ 7.06-6.99 (m, 3H), 5.55 (s, 1H), 5.24 (s, 1H), 4.40-4.34 (m, 1H), 4.08-3.85 (m, 2H), 3.77-3.71 (m, 1H), 3.29-3.17 (m, 2H), 2.59 (m, 1H), 2.13- 1.53 (m, 14H), 1.04 (m, 2H), 0.93 (d, J = 6.6Hz, 3H), 0.70 (m, 2H) |

Preparative Examples

The representative compounds among the cyclic sulfamide derivatives having an adamantyl group indicated in Tables 1-32 were synthesized as follows:

Compound 3

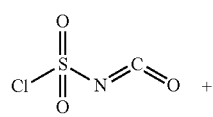

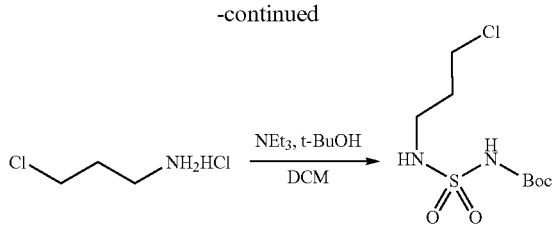

Tert-butyl alcohol (2.45 g, 33 mmol) was added to chlorosulfonyl isocyanate solution (4 g, 28.26 mmol) in CH$_2$Cl$_2$ (80 mL) at 0° C. and agitated for 30 min. Triethylamine (19.7 mL) and 3-chloropropylamine HCl (4.29 g, 33 mmol) were added to the mixture and agitated for 2 hr at room temperature, followed by extraction using CH$_2$Cl$_2$ and brine and drying over anhydrous MgSO₄. The residue was purified by silica gel column chromatography to give tert-butyl N-(3-chloropropyl)sulfamoylcarbamate (2, 4.17 g, 54%). ¹H NMR (300 MHz, CDCl₃): δ 5.25 (br, 1H), 3.67-3.62 (m, 2H), 3.28-3.26 (m, 2H), 2.09-2.01 (m, 2H), 1.51 (S, 9H).

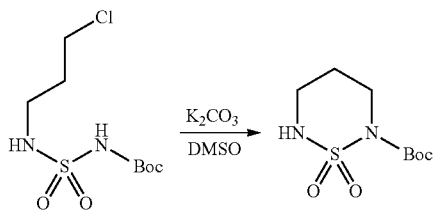

To a solution of tert-butyl N-(3-chloropropyl)sulfamoylcarbamate (2 g, 7.333 mmol) in DMSO (10 mL), was added K₂CO₃ (5.068 g, 36.665 mmol) at room temperature. The reaction mixture was agitated for 4 hr and extracted using ethyl acetate and NH₄Cl solution. The organic layer was dried over MgSO₄. The residue was purified by silica gel column chromatography to give tert-butyl 1,2,6-thiadiazinan-2-carboxylate 1,1-dioxide (689 mg, 2.92 mmol, 40%, white solid). ¹H NMR (300 MHz, CDCl₃): δ 4.47 (br, 1H), 3.95-3.91 (m, 2H), 3.55-3.49 (m, 2H), 1.89-1.82 (m, 2H), 1.54 (m, 9H).

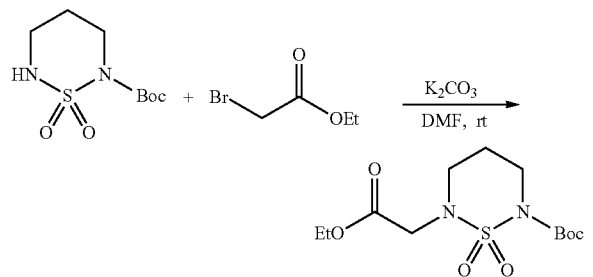

To a solution of tert-butyl 1,2,6-thiadiazinan-2-carboxylate 1,1-dioxide (2 g, 8.464 mmol), were added K₂CO₃ (2.34 g, 16.93 mmol) and ethylbromoacetate (1.7 g, 10.16 mmol). The reaction mixture was agitated for 4 hr at room temperature and extracted using ethyl acetate and brine. The organic layer was dried over MgSO₄. The residue was purified by silica gel column chromatography to give 6-(2-ethoxy-2-oxoethyl)-1,2,6-thiadiazinan-2-carboxylate 1,1-dioxide (2.2 g, 80%, white solid). ¹H NMR (500 MHz, CDCl₃): δ 4.21 (q, J=7.1 Hz, 2H), 3.98-3.96 (m, 4H), 3.68-3.66 (m, 2H), 1.89-1.85 (m, 2H), 1.51 (s, 9H), 1.28 (t, J=7.1 Hz, 3H).

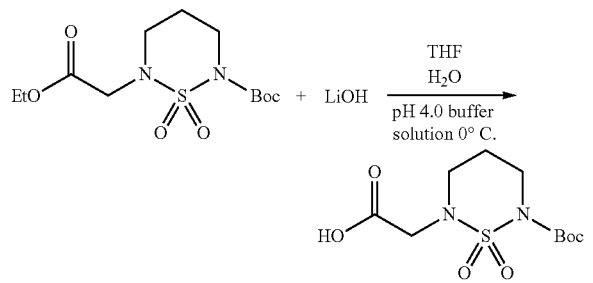

To a solution of 6-(2-ethoxy-2-oxoethyl)-1,2,6-thiadiazinan-2-carboxylate 1,1-dioxide (100 mg, 0.310 mmol) in THF (5 mL) and MeOH (5 mL), was added LiOH (39.1 mg, 0.93 mmol) in H₂O (5 mL) at 0° C. The reaction mixture was agitated for 3 hr, evaporated and extracted using ethyl acetate and a buffer solution (pH 4). The organic layer was dried over MgSO₄ to yield 2-(6-(tert-butoxycarbonyl)-1,1-dioxido-1,2,6-thiadiazinan-2-yl)acetic acid (70 mg, 77%, yellow solid). ¹H NMR (300 MHz, DMSO-d6): δ 12.75 (s, 1H), 3.93 (s, 2H), 3.81-3.77 (m, 2H), 3.59-3.55 (m, 2H), 1.82-1.78 (m, 2H), 1.44 (s, 9H).

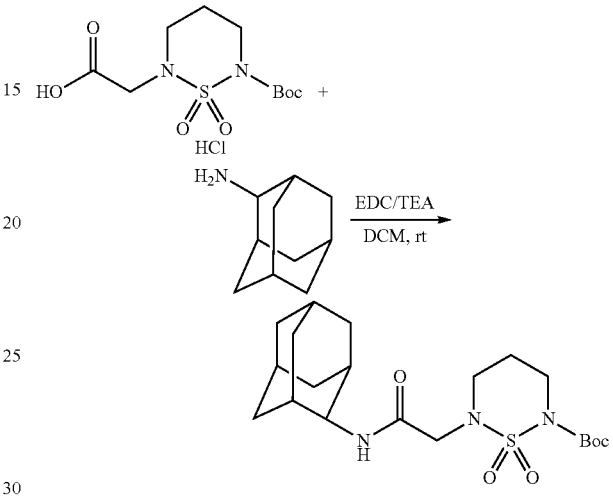

To a solution of 2-(6-(tert-butoxycarbonyl)-1,1-dioxido-1,2,6-thiadiazinan-2-yl)acetic acid (60 mg, 0.204 mmol) in CH₂Cl₂ (5 mL), were added 2-adamantan amine HCl (57.5 mg, 0.306 mmol), TEA (41.3 mg, 0.408 mmol) and EDCI (117.3 mg, 0.612 mmol). The reaction mixture was agitated for 5 hr at room temperature and extracted using CH₂Cl₂ and brine. The organic layer was dried over MgSO₄. The residue was purified by silica gel column chromatography to give tert-butyl 6-(2-(adamantan-2-yl amino)-2-oxoethyl)-1,2,6-thiadiazinan-2-carboxylate 1,1-dioxide (5.30 mg, 35%). ¹H NMR (300 MHz, CDCl₃): δ 6.90 (brd, 1H), 4.06 (m, 1H), 4.00 (t, J=5.8 Hz, 2H), 3.83 (s, 2H), 3.66 (t, J=5.8 Hz, 2H), 1.92-1.63 (m, 15H), 1.52 (s, 9H).

Compound 5

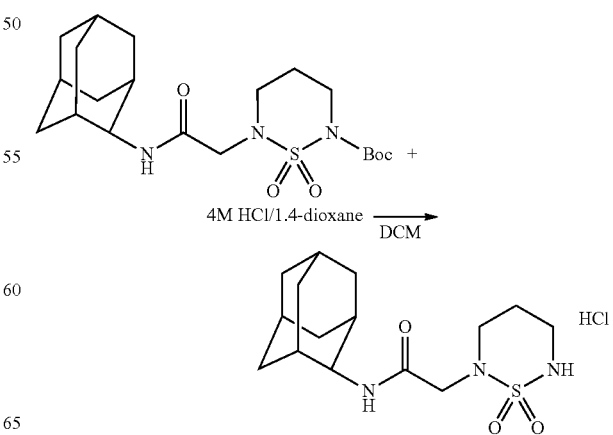

To a solution of tert-butyl 6-(2-(adamantan-2-yl amino)-2-oxoethyl)-1,2,6-thiadiazinan-2-carboxylate 1,1-dioxide (150 mg, 0.351 mmol) in $CH_2Cl_2$ (5 mL), was added an excessive amount of 4 M HCl in 1.4-dioxane. The reaction mixture was agitated for 4 hr at room temperature and evaporated to give N-(adamantan-2-yl)-2-(1,1-dioxido-1,2,6-thiadiazinan-2-yl) acetamide hydrochloride (120 mg, 92%, white solid). $^1$H NMR (300 MHz, DMSO-$d_6$): δ 7.06-7.57 (brd, 1H), 7.00 (t, J=6.9 Hz, 1H), 3.85-3.82 (m, 1H), 3.59 (s, 2H), 3.33-3.23 (m, 4H), 1.90-1.48 (m, 16H).

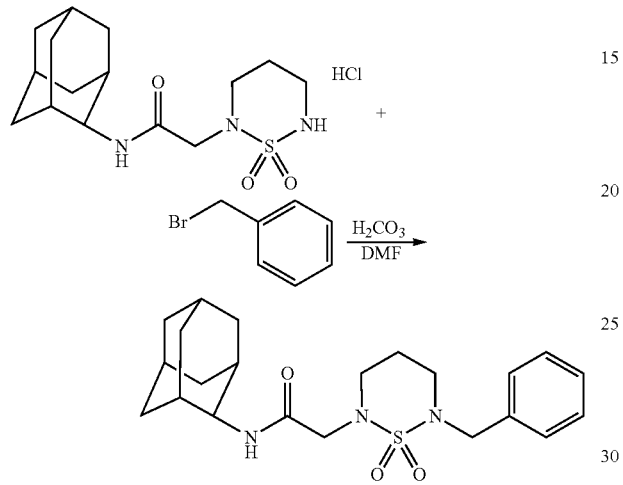

To N-(adamantan-2-yl)-2-(1,1-dioxido-1,2,6-thiadiazinan-2-yl)acetamide hydrochloride (50 mg, 0.135 mmol) in DMF (1 mL), were added $K_2CO_3$ (93.3 mg, 0.675 mmol) and (bromomethyl)benzene (46.2 mg, 0.27 mmol). The reaction mixture was agitated for 4 hr at room temperature and extracted with ethyl acetate and brine. The organic layer was dried over $MgSO_4$ and the residue was purified by silica gel column chromatography to yield N-(adamantan-2-yl)-2-(6-benzyl-1,1-dioxido-1,2,6-thiadiazinan-2-yl)acetamide (53 mg, 94%, white solid). $^1$H NMR (300 MHz, DMSO-$d_6$): δ 7.72-7.69 (brd, 1H), 7.39-7.28 (m, 5H), 4.17 (s, 2H), 3.86-3.83 (m, 1H), 3.79 (s, 2H), 3.46-3.42 (m, 2H), 3.17-3.14 (m, 2H), 1.93-1.89 (m, 2H), 1.80-1.67 (m, 12H), 1.52-1.48 (m, 2H).

Compound 15

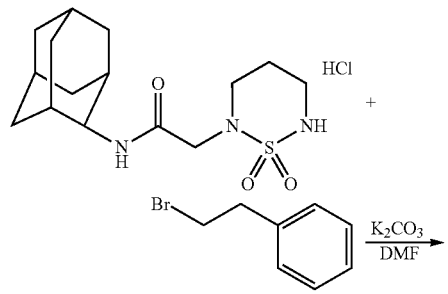

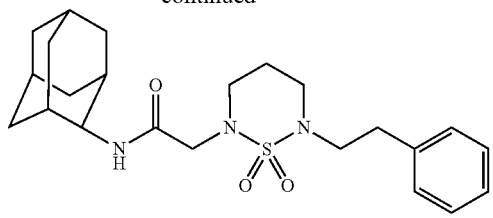

To N-(adamantan-2-yl)-2-(1,1-dioxido-1,2,6-thiadiazinan-2-yl)acetamide hydrochloride (50 mg, 0.135 mmol) in DMF (1 mL), were added $K_2CO_3$ (93.3 mg, 0.675 mmol) and (2-bromoethyl)benzene (50 mg, 0.27 mmol). The reaction mixture was agitated for 4 hr at room temperature and extracted with ethyl acetate and brine. The organic layer was dried over $MgSO_4$ and the residue was purified by silica gel column chromatography to yield N-(adamantan-2-yl)-2-(1,1-dioxido-6-phenethyl-1,2,6-thiadiazinan-2-yl)acetamide (8 mg, 13%, white solid). $^1$H NMR (300 MHz, DMSO-$d_6$): δ 7.33-7.19 (m, 5H), 7.01-6.98 (brd, 1H), 4.06-4.047 (m, 1H), 3.71 (s, 2H), 3.53-3.49 (m, 2H), 3.38-3.33 (m, 4H), 2.94-2.87 (m, 2H), 1.92-1.60 (m, 14H).

Compound 2

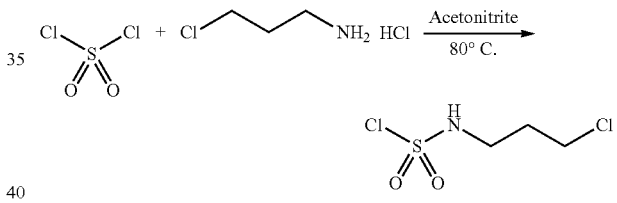

To sulfuryl chloride (5 g, 30.05 mmol) in acetonitrile (30 mL), was added 3-chloropropyl amine hydrochloride (486 mg, 5.00 mmol). The reaction mixture was allowed to react at 80° C., evaporated and then extracted with diethyl ether and $H_2O$, followed by evaporation of the organic layer under vacuum, to give 3-chloropropylsulfamoyl chloride that was used without further purification.

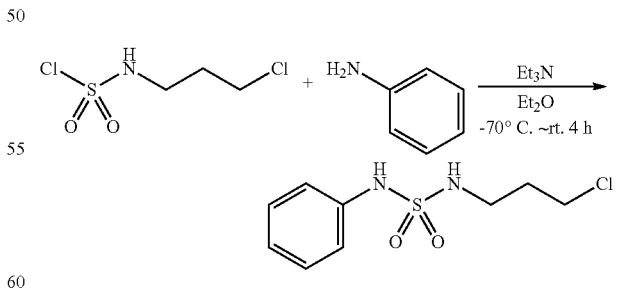

To 3-chloropropylsulfamoyl chloride (8, 1.5 g, 7.81 mmol) in ether (20 mL), were added aniline (436.4 mg, 4.686 mmol) and triethyl amine (1.58 g, 15.62 mmol) at −78° C. The reaction mixture was agitated for 4 hr and extracted with ether and $H_2O$. The organic layer was evaporated and dried under vacuum to give the sulfamide derivatives.

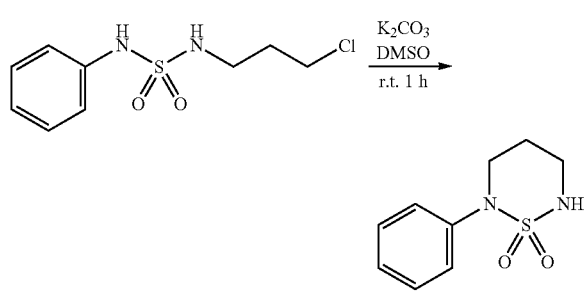

To the sulfamide derivatives (1.625 g, 6.53 mmol) in DMSO (15 mL), was added K₂CO₃ (903 mg, 6.53 mmol). The reaction mixture was agitated for 2 hr at room temperature and extracted with ethyl acetate and NH₄Cl. The organic layer was dried over MgSO₄ and the residue was crystallized using ether and n-hexane to give 2-phenyl-1,2,6-thiadiazinan 1,1-dioxide (490 mg, 2.31 mmol, white solid). ¹H NMR (300 MHz, DMSO-de): δ 7.42-7.24 (m, 5H), 3.64-3.61 (m, 2H), 3.40-3.34 (m, 2H), 2.51-2.49 (m, 2H).

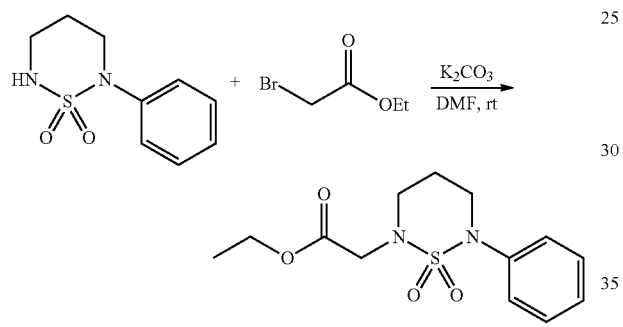

To 2-phenyl-1,2,6-thiadiazinan 1,1-dioxide (400 mg, 1.89 mmol) in DMSO (15 mL), were added K₂CO₃ (522.4 mg, 3.78 mmol) and ethyl bromoacetate (379.1 mg, 2.27 mmol). The reaction mixture was agitated for 4 hr and extracted with ethyl acetate and brine. The organic layer was dried over MgSO₄ and the residue was purified by silica gel column chromatography to yield ethyl 2-(1,1-dioxido-6-phenyl-1,2,6-thiadiazinan-2-yl)acetate (468 mg, 1.56 mmol, 83%, white solid). ¹H NMR (300 MHz, CDCl₃): δ 7.45-7.34 (m, 3H), 7.30-7.25 (m, 1H), 4.28-4.20 (q, J=7.1 Hz, 2H), 4.03 (s, 2H), 3.82-3.73 (m, 4H), 1.99-1.91 (m, 2H), 1.30 (t, J=7.1 Hz, 3H).

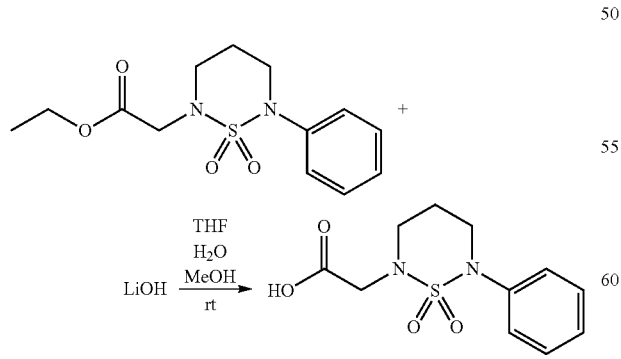

To ethyl 2-(1,1-dioxido-6-phenyl-1,2,6-thiadiazinan-2-yl) acetate (260 mg, 0.872 mmol) in THF (5 mL) and MeOH (5 mL), was added LiOH (182.9 mg, 4.36 mmol) in H₂O (5 mL). The reaction mixture was agitated for 3 hr at room temperature and evaporated. The residue was introduced into ice water, its pH was adjusted down to 1 with 2 N HCl, and extracted with ethyl acetate. The organic layer was dried over MgSO₄ to give 2-(1,1-dioxido-6-phenyl-1,2,6-thiadiazinan-2-yl)acetic acid (230 mg, 97%, yellow solid). ¹H NMR (300 MHz, DMSO-d₆): δ 12.81 (s, 1H), 7.43-7.26 (m, 5H), 3.96 (s, 2H), 3.68-3.62 (m, 4H), 1.92-1.85 (m, 2H).

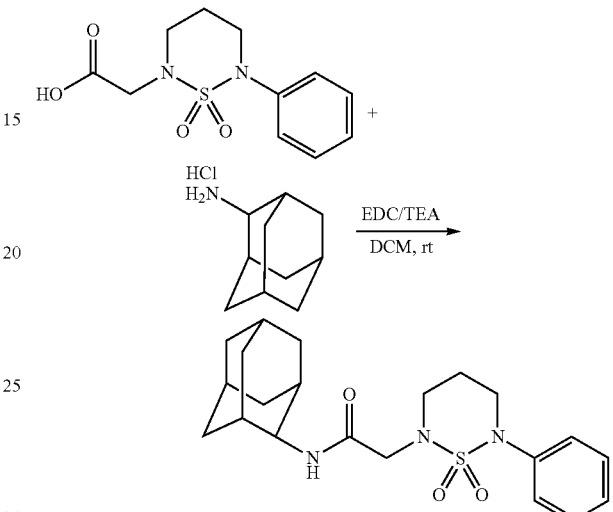

To 2-(1,1-dioxido-6-phenyl-1,2,6-thiadiazinan-2-yl)acetic acid (100 mg, 0.37 mmol) in DCM (5 mL), were added 2-adamantan amine HCl (105 mg, 0.56 mmol), TEA (74.9 mg, 0.74 mmol) and EDCI (212.8 mg, 1.11 mmol). The reaction mixture was agitated for 5 hr at room temperature and extracted using CH₂Cl₂ and brine. The organic layer was dried over MgSO₄. The residue was purified by silica gel column chromatography to give N-(adamantan-2-yl)-(1,1-dioxido-6-phenyl-1,2,6-thiadiazinan-2-yl)acetamide (80 mg, 54%). ¹H NMR (300 MHz, CDCl₃): δ 7.41-7.26 (m, 5H), 7.02-6.99 (brd, 1H), 4.07 (m, 1H), 3.94 (s, 2H), 3.81-3.74 (m, 4H), 2.03-1.94 (m, 4H), 1.85-1.74 (m, 10H), 1.66-1.60 (m, 3H).

Compound 60

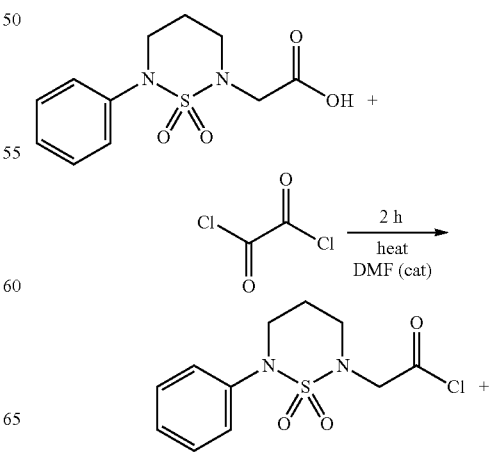

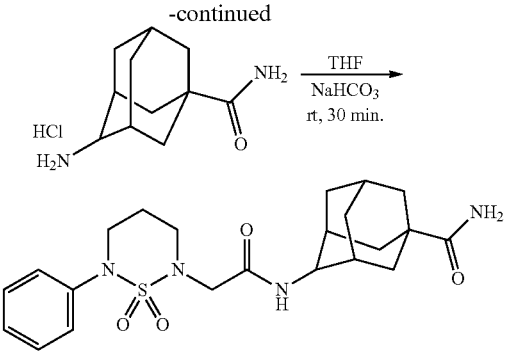

2-(6-phenyl-1,2,6-thiadiazinan-2-yl)acetic acid and 1,1-dioxide (60 mg, 0.222 mmol) in oxalyl dichloride (2 mL) was agitated for 2 hr at 50° C. and dissolved in THF (2 mL). To the resultant, was slowly added 4-amino-tricyclo[3,3,1,13,7]decane-1-carboxaminde (50 mg, 0.264 mmol) in NaHCO₃ solution (2 mL). The reaction mixture was agitated for 30 min at room temperature and extracted with ethyl acetate and brine. The organic layer was dried over MgSO₄. The residue was purified by silica gel column chromatography to give 4-(2-(1,1-dioxido-6-phenyl-1,2,6-thiadiazinan-2-yl)acetamido) adamantan-1-carboxamide (16 mg, 11%). $^1$H NMR (300 MHz, CDCl₃): δ 7.41-7.30 (m, 5H), 6.96 (brd, J=7.1 Hz, NH), 5.69 (br, NH2), 5.25 (br, NH2), 4.00-3.98 (m, 1H), 3.94-3.92 (m, 2H), 3.81-3.74 (m, 4H), 2.17-1.68 (m, 15H).

Compound 59

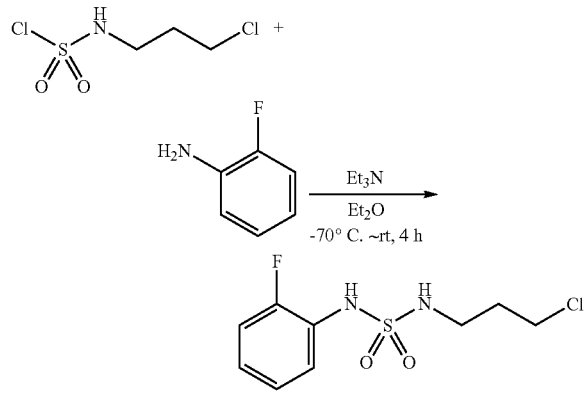

To 3-chloropropylsulfamoyl chloride (1.5 g, 7.81 mmol) in ether (20 mL), were dropwisely added 2-fluoroaniline (520.7 mg, 4.686 mmol) and triethyl amine (1.58 g, 15.62 mmol) at −76° C. The reaction mixture was agitated for 4 hr and extracted with H₂O/ether/EA. The organic layer was dried over MgSO₄ and concentrated to obtain the sulfamide (1.45 g) that was used without further purification for the next reaction.

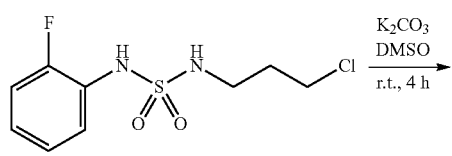

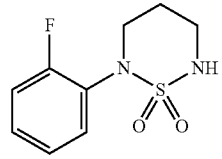

K₂CO₃ (751 mg, 5.436 mmol was added to the sulfamide obtained (1.45 g, 5.436 mmol) in DMSO (15 mL) and agitated for 4 hr. After the completion of the reaction, the resultant was concentrated under reduced pressure, extracted with EA/NH₄Cl, dried over MgSO₄ and concentrated. The residue was purified by column chromatography (EtOAc:Hex=1:3) to yield 2-(2-fluorophenyl)-1,2,6-thiadiazinan 1,1-dioxide (804 mg, 3.491 mmol, 64%, oil). $^1$H NMR (300 MHz, DMSO-d₆): δ 7.57-7.51 (m, 1H), 7.39-7.20 (m, 4H), 3.64-3.60 (m, 2H), 3.44-3.38 (m, 2H), 1.85-1.77 (m, 2H). LC/MS MH⁺231.

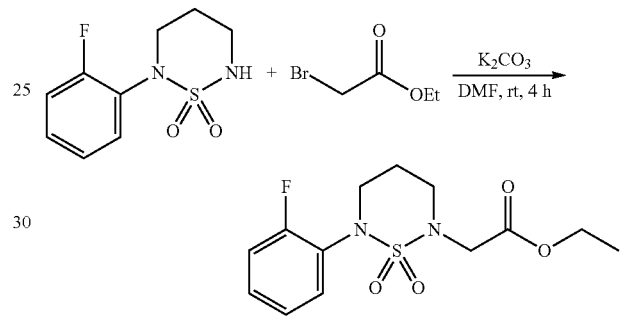

K₂CO₃ (599 mg, 4.34 mmol) and ethyl bromoacetate (434 mg, 2.60 mmol) were added to 2-(2-fluorophenyl)-1,2,6-thiadiazinan 1,1-dioxide (500 mg, 2.17 mmol) in DMF (10 mL), and agitated for 4 hr. After the completion of the reaction, the resultant was concentrated under reduced pressure, extracted with EA/NH₄Cl, dried over MgSO₄ and concentrated. The residue was purified by column chromatography (EtOAc: Hex=1:3) to yield ethyl 2-(6-(2-fluorophenyl)-1,2,6-thiadiazinan-2-yl)acetate 1,1-dioxide (460 mg, 1.45 mmol, 67%, yellow solid). $^1$H NMR (300 MHz, CDCl₃): δ 7.62-7.56 (m, 1H), 7.31-7.23 (m, 1H), 7.17-7.09 (m, 2H), 4.24 (q, J=7.1 Hz, 2H), 4.04 (s, 2H), 3.81-3.76 (m, 4H), 1.99-1.91 (m, 2H), 1.30 (t, J=7.1 Hz, 3H). LCMS MH⁺ 317.

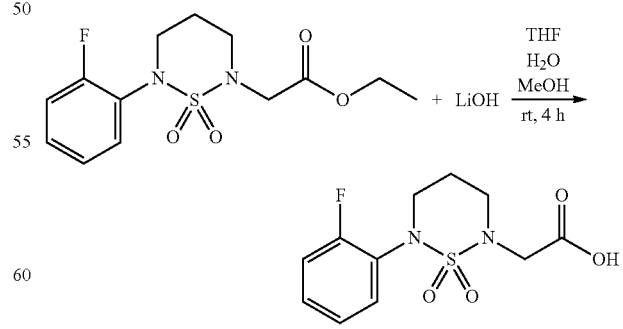

To ethyl 2-(6-(2-fluorophenyl)-1,2,6-thiadiazinan-2-yl) acetate 1,1-dioxide (460 mg, 1.454 mmol) in THF (10 mL) and MeOH (10 mL), was added LiOH (305 mg, 7.27 mmol) in H₂O (10 mL). The mixture was allowed to react for 4 hr.

The resultant was concentrated, introduced to ice, its pH was adjusted down to 1 with 2 N HCl, and extracted with EtOAc. The organic layer was dried over MgSO₄ and then concentrated to give 2-(6-(2-fluorophenyl)-1,2,6-thiadiazinan-2-yl) acetic acid 1,1-dioxide (376 mg, 89%). ¹H NMR (300 MHz, DMSO-d₆): δ 7.55-7.50 (m, 1H), 7.40-7.19 (m, 3H), 3.94 (s, 2H), 3.67-3.64 (m, 4H), 1.90-1.87 (m, 2H). LCMS MH⁺ 289.

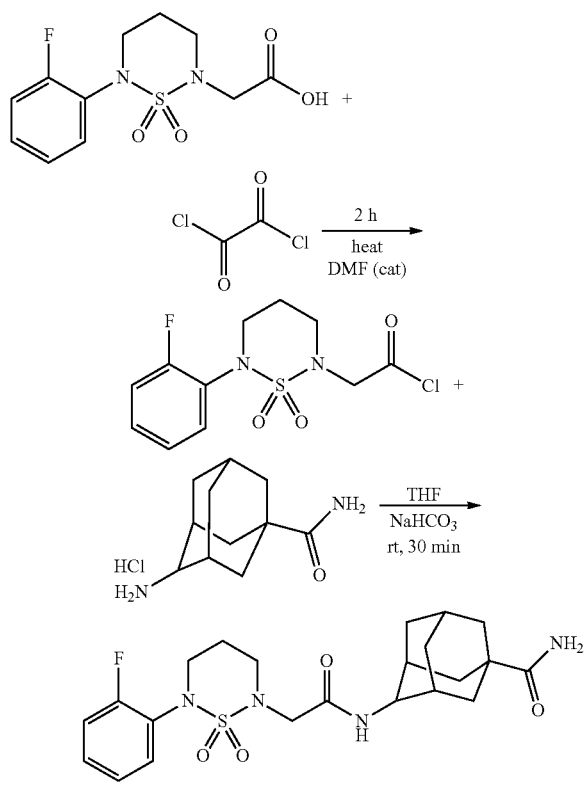

The reactions were undertaken as the above-described procedures.

¹H NMR (300 MHz, CDCl₃): δ 7.46-7.41 (m, 1H), 7.34-7.26 (m, 1H), 7.18-7.12 (m, 2H), 6.98-6.94 (br, NH), 5.67-5.59 (br, NH₂), 5.34-5.26 (s, NH₂), 4.07-3.96 (m, 1H), 3.95-3.92 (m, 2H), 3.81-3.77 (m, 4H), 2.17-1.58 (m, 15H). LCMS MH⁺465.

Compound 69

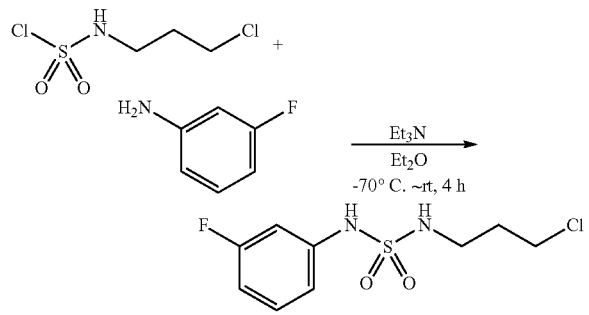

To 3-chloropropylsulfamoyl chloride (1.5 g, 7.81 mmol) in ether (20 mL), were dropwisely added 3-fluoroaniline (520.7 mg, 4.686 mmol) and triethyl amine (1.58 g, 15.62 mmol) at -76° C. The reaction mixture was agitated for 4 hr and extracted with H₂/ether/EA. The organic layer was dried over MgSO₄ and concentrated to obtain the sulfamide (1.4 g) that was used without further purification for the next reaction.

K₂CO₃ (725 mg, 5.25 mmom) was added to the sulfamide obtained (1.4 g, 5.25 mmol) in DMSO (15 mL) and agitated for 4 hr. After the completion of the reaction,

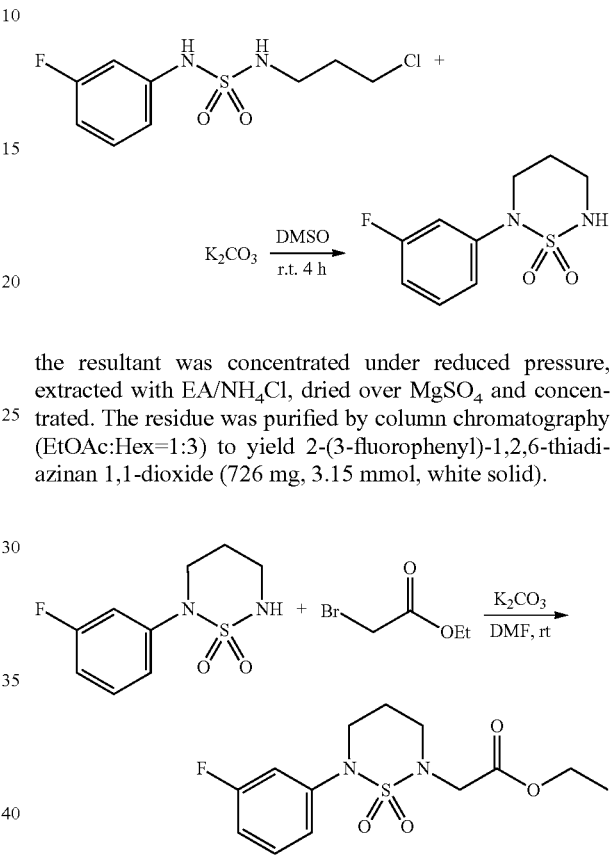

the resultant was concentrated under reduced pressure, extracted with EA/NH₄Cl, dried over MgSO₄ and concentrated. The residue was purified by column chromatography (EtOAc:Hex=1:3) to yield 2-(3-fluorophenyl)-1,2,6-thiadiazinan 1,1-dioxide (726 mg, 3.15 mmol, white solid).

¹H NMR (300 MHz, CDCl₃): δ 7.37-7.29 (m, 1H), 7.23-7.15 (m, 2H), 7.02-6.96 (m, 1H), 4.24 (q, J=7.1 Hz, 2H), 4.02 (s, 2H), 3.81-3.72 (m, 4H), 1.99-1.92 (m, 2H), 1.31 (t, J=7.1 Hz, 2H).

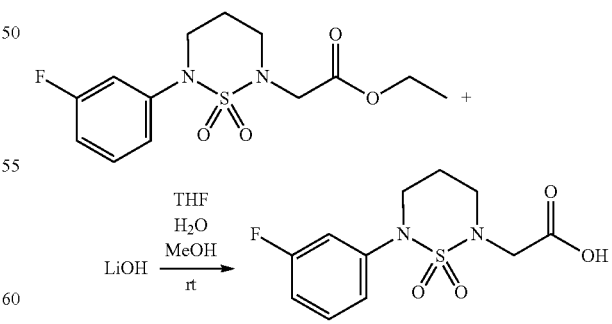

To ethyl 2-(6-(3-fluorophenyl)-1,2,6-thiadiazinan-2-yl) acetate 1,1-dioxide (360 mg, 1.138 mmol) in THF (5 mL) and MeOH (5 mL), was added LiOH (239 mg, 5.69 mmol) in H₂O (5 mL). The mixture was allowed to react for 4 hr. The resultant was concentrated, introduced to ice, its pH was adjusted down to 2 with 2 N HCl, and extracted with EtOAc. The organic layer was dried over MgSO$_4$ and then concentrated to give 2-(6-(3-fluorophenyl)-1,2,6-thiadiazinan-2-yl) acetic acid 1,1-dioxide (260 mg, 80%, yellow solid). $^1$H NMR (300 MHz, DMSO-d$_6$): δ 7.47-7.39 (m, 1H), 7.25-7.10 (m, 3H), 3.95 (s, 2H), 3.70-3.61 (m, 4H), 1.91-1.83 (m, 2H).

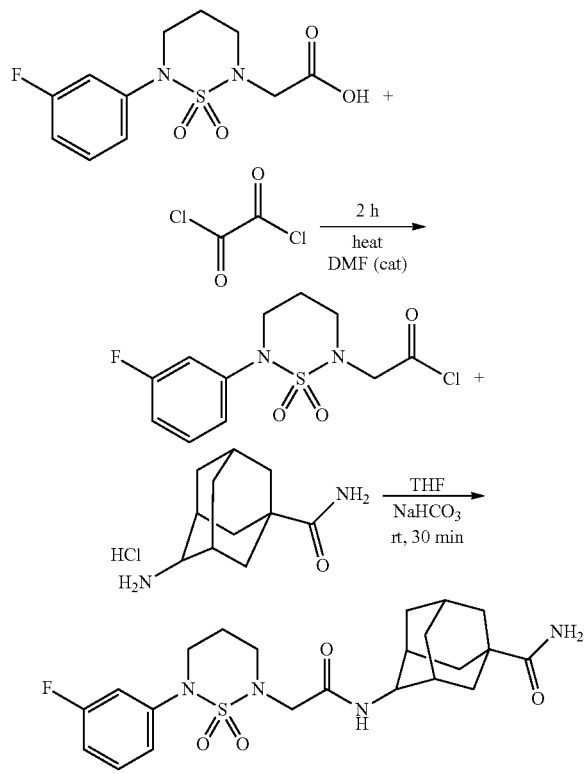

The reactions were undertaken as the above-described procedures.

$^1$H NMR (300 MHz, CDCl$_3$): δ 7.38-7.31 (m, 1H), 7.16-6.99 (m, 3H), 6.94 (brd, J=7.8 Hz, NH), 5.58 (br, NH$_2$), 5.35 (br, NH$_2$), 4.07-3.99 (m, 1H), 3.93-3.91 (m, 2H), 3.80-3.75 (m, 4H), 2.15-1.58 (m, 15H). LC/MS MH$^+$ 465.

Compound 44

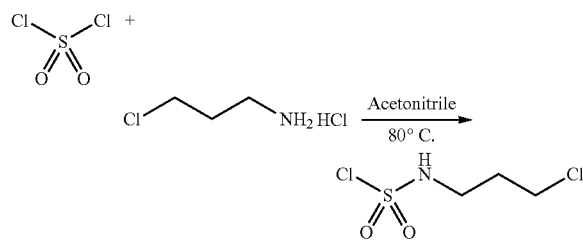

To sulfuryl chloride (5 g, 30.05 mmol) in acetonitrile (30 mL), was added 3-chloropropyl amine hydrochloride (486 mg, 5.00 mmol). The reaction mixture was allowed to react over 18 hr at 75-80° C. After the completion of the reaction, the resultant was concentrated under reduced pressure, extracted with ether and then kept under vacuum for a long time to remove remained sulfuryl chloride, giving 3-chloropropylsulfamoyl chloride that was used without further purification.

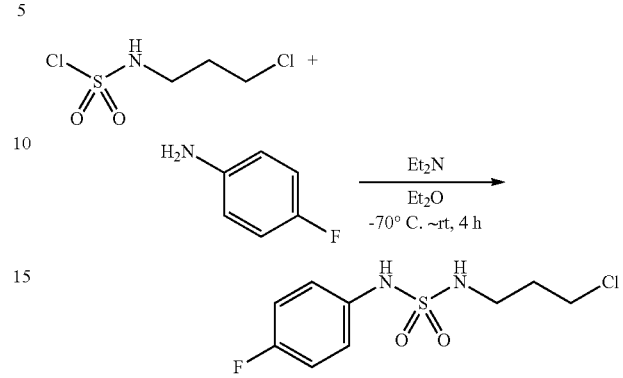

To 3-chloropropylsulfamoyl chloride (1.5 g, 7.81 mmol) in ether (20 mL), were dropwisely added 4-fluoroaniline (520.7 mg, 4.686 mmol) and triethyl amine (1.58 g, 15.62 mmol) at −76° C. The reaction mixture was agitated for 4 hr and extracted with H$_2$O/ether/EA. The organic layer was dried over MgSO$_4$ and concentrated to obtain the sulfamide (1.4 g) that was used without further purification for the next reaction.

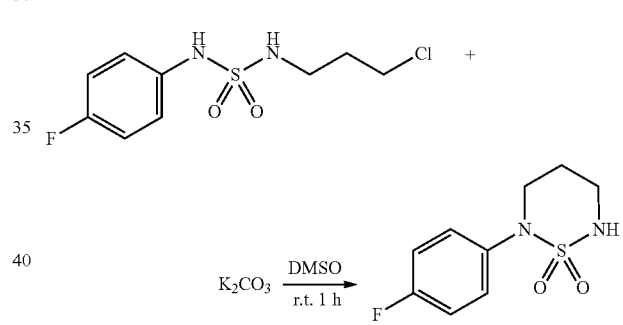

K$_2$CO$_3$ (725 mg, 5.25 mmol) was added to the sulfamide obtained (1.4 g, 5.25 mmol) in DMSO (15 mL) and agitated for 2 hr. After the completion of the reaction, the resultant was concentrated under reduced pressure, extracted with EA/NH$_4$Cl, dried over MgSO$_4$ and concentrated. The residue was purified by column chromatography (EtOAc:Hex=1:3) to yield 2-(4-fluorophenyl)-1,2,6-thiadiazinan 1,1-dioxide (726 mg, 3.15 mmol, white solid). $^1$H NMR (300 MHz, DMSO-d$_6$): δ 7.38-7.29 (m, 2H), 7.25-7.18 (m, 2H), 3.59-3.32 (m, 2H), 3.38-3.32 (m, 2H), 1.84-1.77 (m, 2H).

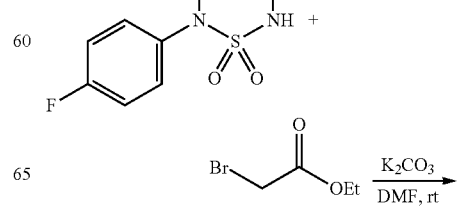

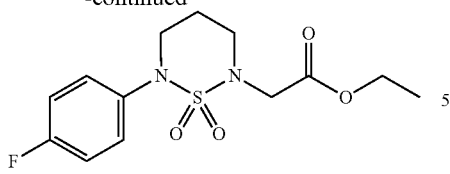
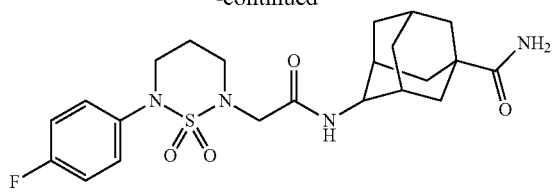

K$_2$CO$_3$ (864 mg, 6.254 mmol) and ethyl bromoacetate (626.3 mg, 3.75 mmol) were added to 2-(4-fluorophenyl)-1,2,6-thiadiazinan 1,1-dioxide (720 mg, 3.127 mmol) in DMF (10 mL), and agitated for 4 hr. After the completion of the reaction, the resultant was concentrated under reduced pressure, extracted with EA/NH$_4$Cl, dried over MgSO$_4$ and concentrated. The residue was purified by column chromatography (EtOAc:Hex=1:3) to yield ethyl 2-(6-(4-fluorophenyl)-1,2,6-thiadiazinan-2-yl)acetate 1,1-dioxide (800 mg, 2.53 mmol, 80%, yellow solid).

$^1$H NMR (300 MHz, CDCl$_3$): δ 7.44-7.39 (m, 2H), 7.08-7.02 (m, 2H), 4.24 (q, J=7.1 Hz, 2H), 4.01 (s, 2H), 3.77-3.72 (m, 4H), 1.99-1.91 (m, 2H), 1.30 (t, J=7.1 Hz, 3H). LC/MS MH$^+$ 317.16.

2-(6-(4-fluorophenyl)-1,2,6-thiadiazinan-2-yl)acetic acid 1,1-dioxide, 1,1-dioxide (50 mg, 0.164 mmol), 4-amino-tricyclo[3,3,1,13,7]decane-1-carboxamide (60 mg, 0.26 mmol), EDCI (99.5 mg, 0.519 mmol) and DIPEA (67 mg, 0.519 mmol) were dissolved in DMF and DCM (5 mL). The mixture was agitated for 5 hr at room temperature and underwent work up with DCM/NaCl. The resultant was dried over MgSO$_4$, concentrated and purified by column chromatography (MC:MeOH=5:95) to give KR-66971 (E-15 mg) and KR-66970 (Z-3 mg).

$^1$H NMR (300 MHz, CDCl$_3$): δ 7.43-7.32 (m, 2H), 7.10-7.01 (m, 2H), 6.90-9.95 (m, NH), 4.04 (m, 1H), 3.82-3.64 (m, 6H), 2.36-1.12 (m, 15H). LC/MS MH$^+$ 465

$^1$H NMR (300 MHz, CDCl$_3$): δ 7.43-7.30 (m, 2H), 7.10-7.03 (m, 2H), 6.90-9.95 (m, NH), 4.04 (m, 1H), 3.79-3.64 (m, 6H), 2.15-1.12 (m, 15H). LC/MS MH$^+$ 465

Compound 89

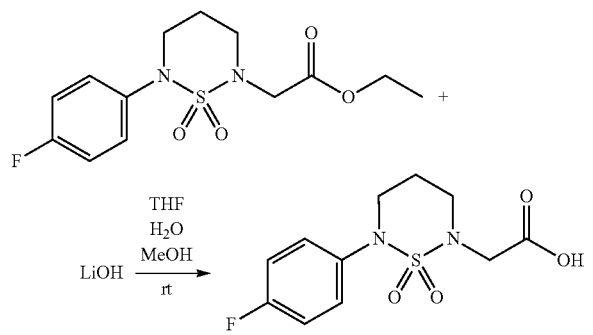

To ethyl 2-(6-(4-fluorophenyl)-1,2,6-thiadiazinan-2-yl)acetate 1,1-dioxide (700 mg, 2.21 mmol) in THF (10 mL) and MeOH (10 mL), was added LiOH (464 mg, 11.05 mmol) in H$_2$O (10 mL). The mixture was allowed to react for 4 hr. The resultant was concentrated, introduced to ice, its pH was adjusted down to 1 with 2 N HCl, and extracted with EtOAc. The organic layer was dried over MgSO$_4$ and then concentrated to give 2-(6-(4-fluorophenyl)-1,2,6-thiadiazinan-2-yl)acetic acid 1,1-dioxide (590 mg, 92%, white solid).

$^1$H NMR (300 MHz, DMSO-d$_6$): δ 12.97 (s, 1H), 7.41-7.36 (m, 2H), 7.26-7.19 (m, 2H), 3.95 (s, 2H), 3.64-3.60 (m, 4H), 1.90-1.83 (m, 2H). LC/MS MH$^+$ 289

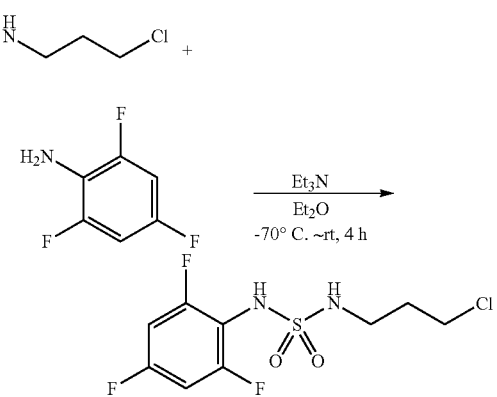

The reactions were undertaken as the above-described procedures without further purification for the next reaction.

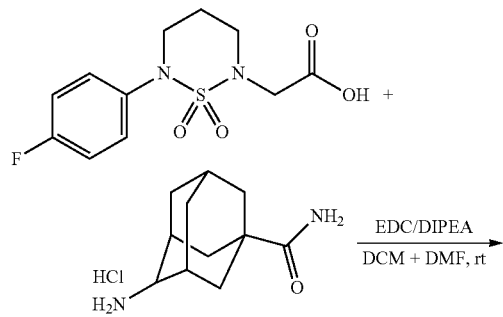

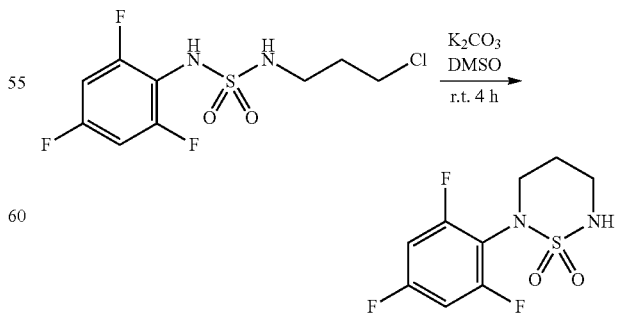

The compound was synthesized by the above-described procedures.

¹H NMR (300 MHz, DMSO-d6): δ 7.32~7.26 (m, 2H+NH), 3.71 (m, 2H), 3.40 (m, 2H), 1.77 (m, 2H). LC/MS MH⁺ 267

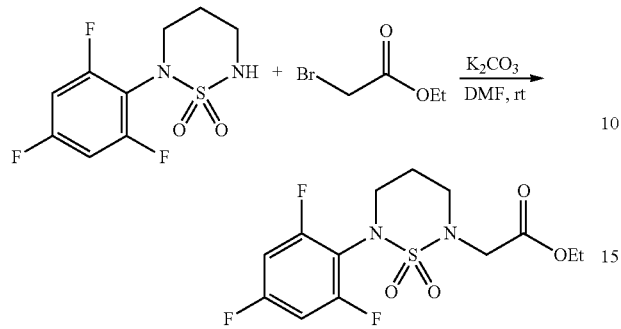

The compound was synthesized by the above-described procedures.

¹H NMR (300 MHz, CDCl₃): δ 6.77~6.70 (m, 2H), 4.23 (q, J=7.1 Hz, 2H), 4.06 (s, 2H), 3.92~3.88 (m, 2H), 3.84~3.80 (m, 2H), 1.97~1.89 (m, 2H), 1.30 (t, J=7.1 Hz, 3H). LC/MS MH⁺ 353

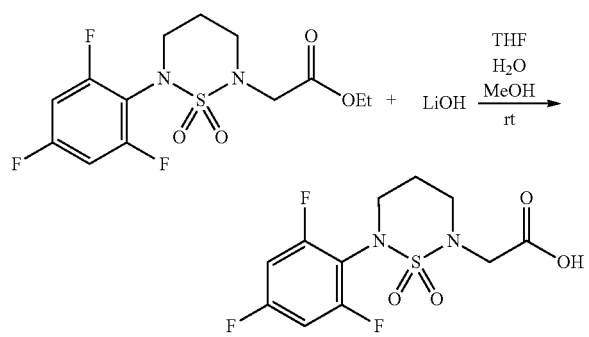

The compound was synthesized by the above-described procedures.

¹H NMR (300 MHz, DMSO-d6): δ 12.81 (br, OH), 7.37~7.29 (m, 2H), 3.94 (s, 2H), 3.76~3.71 (m, 4H), 1.87~4.80 (m, 2H). LC/MS MH⁺ 324

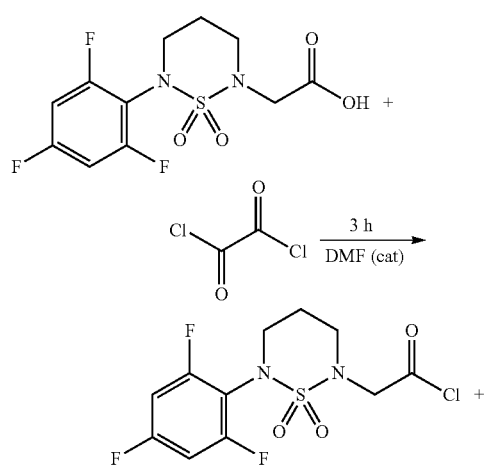

-continued

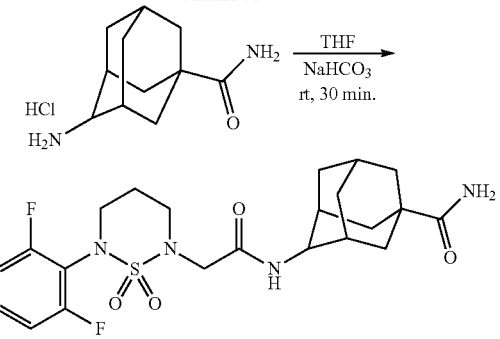

The compound was synthesized by the above-described procedures.

¹H NMR (300 MHz, CDCl₃): δ 6.95 (brd, J=7.9 Hz, NH), 6.78~6.72 (m, 2H), 5.57 (br, NH2), 5.28 (br, NH2), 4.07~4.04 (m, 1H), 3.93 (s, 2H), 3.87~3.81 (m, 4H), 2.09~1.61 (m, 15H). ksh-05-0092-E-cdcl₃, mass spectrum m/e (relative intensity): 501.05 (MH+)

¹H NMR (300 MHz, CDCl₃): δ 6.91 (brd, J=7.0 Hz, NH), 6.79~6.72 (m, 2H), 5.65 (br, NH2), 5.23 (br, NH2), 4.01~3.98 (m, 1H), 3.90 (s, 2H), 3.87~3.80 (m, 4H), 2.17~4.73 (m, 15H). LC/MS MH⁺ 501

Compound 88

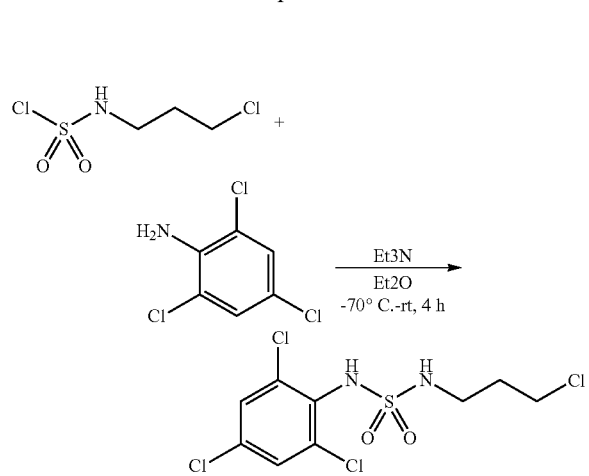

The reactions were undertaken as the above-described procedures without further purification for the next reaction.

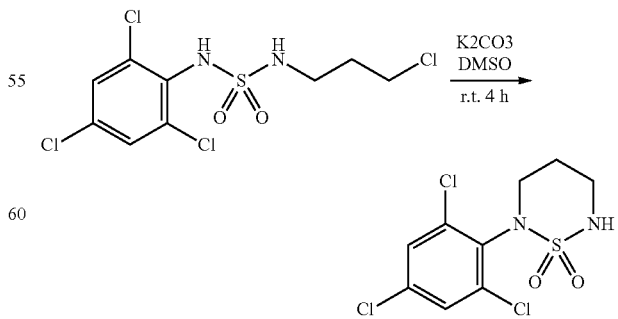

The compound was synthesized by the above-described procedures.

117

¹H NMR (300 MHz, DMSO-d6): δ 7.40 (s, 2H), 6.80~6.75 (brm, NH), 3.77~3.45 (m, 4H), 1.82~4.74 (m, 2H) LC/MS MH⁺ 316

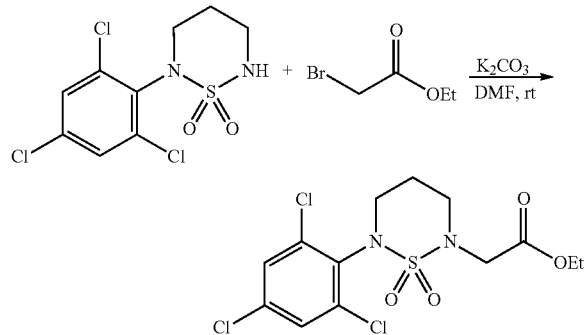

The compound was synthesized by the above-described procedures.

¹H NMR (300 MHz, CDCl₃): δ 7.39 (s, 2H), 4.23 (q, J=7.1 Hz, 2H), 4.15 (s, 2H), 3.95~3.91 (m, 2H), 3.84~3.80 (m, 2H), 2.20~1.95 (m, 2H), 1.30 (t, J=7.1 Hz, 3H). LC/MS MH⁺ 402

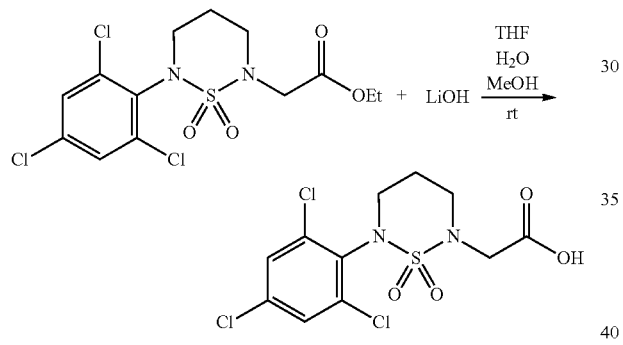

The compound was synthesized by the above-described procedures.

¹H NMR (300 MHz, DMSO-d6): δ 12.80 (br, OH), 7.79 (s, 2H), 4.04 (s, 2H), 3.77~3.72 (m, 4H), 1.92~1.87 (m, 2H). LC/MS MH⁺ 374

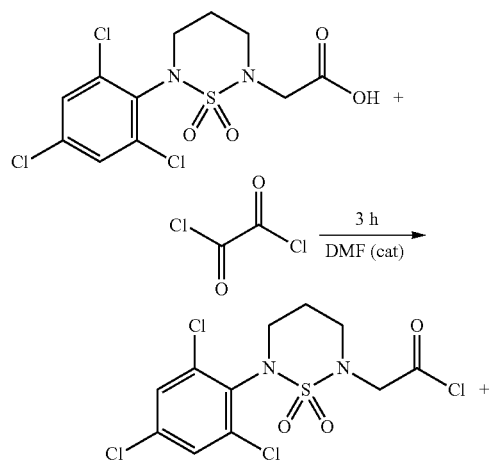

118

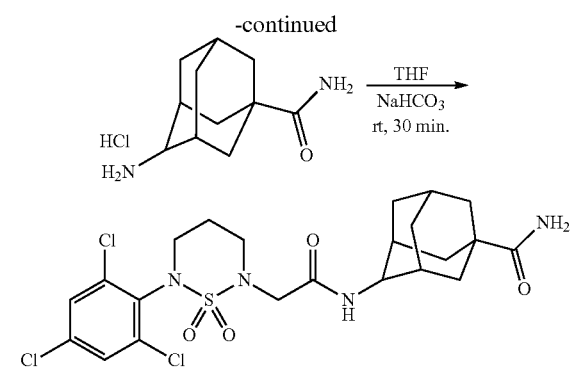

The compound was synthesized by the above-described procedures.

¹H NMR (300 MHz, CDCl₃): δ 7.41 (s, 2H), 6.97 (brd, J=7.8 Hz, NH), 5.57 (br, NH2), 5.25 (br, NH2), 4.15~4.03 (m, 3H), 3.87~3.83 (m, 4H), 2.09~4.42 (m, 15H). LC/MS MH+ 550

¹H NMR (300 MHz, CDCl₃): δ 7.41 (s, 2H), 6.94 (brd, J=7.0 Hz, NH), 5.56 (br, NH2), 5.22 (br, NH2), 4.18~4.14 (m, 1H), 4.00 (s, 2H), 3.87~3.82 (m, 2H), 3.71~3.41 (m, 2H), 2.14~4.61 (m, 15H). LC/MS MH⁺ 550

Compound 124

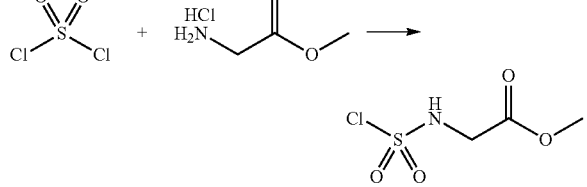

To 3-chloropropylamine hydrochloride (10.0 g, 76.9 mmol) in acetonitrile (150 mL), was dropwisely added sulfuryl chloride (62.2 g, 461.4 mmol). The mixture was heated under reflux for 18 hr. After the completion of the reaction, the resultant was concentrated to yield the title compound (12.5 g, y=85%).

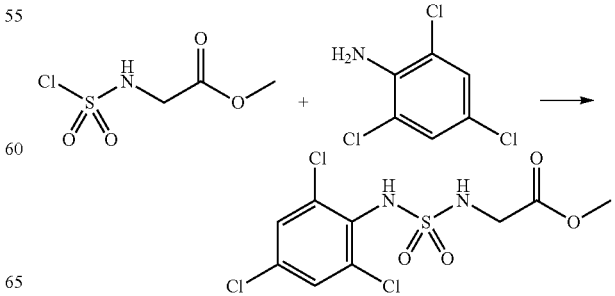

Trichloroaniline (1.5 g, 7.6 mmol) and TEA (3.7 mL, 22.8 mmol) were added to methyl 2-((chlorosulfonyl)amino)acetate (2.5 g, 12.1 mmol) in dichloromethane (80 mL) and agitated for 5 hr at room temperature. Following the completion of the reaction, the resultant was extracted with EtOAc after addition of water, dried (Na$_2$SO$_4$), filtered and concentrated under reduced pressure. The resultant was purified by column chromatography (EtOAc/hexane 1:1) to yield the compound (1.0 g, y=38%, oil). $^1$H NMR (300 MHz, DMSO-d$_6$): δ 9.37 (s, 1H), 7.82 (t, J=6 Hz, 1H), 3.90 (d, J=6 Hz, 2H), 3.72 (s, 3H). LC/MS MH$^+$ 348.91

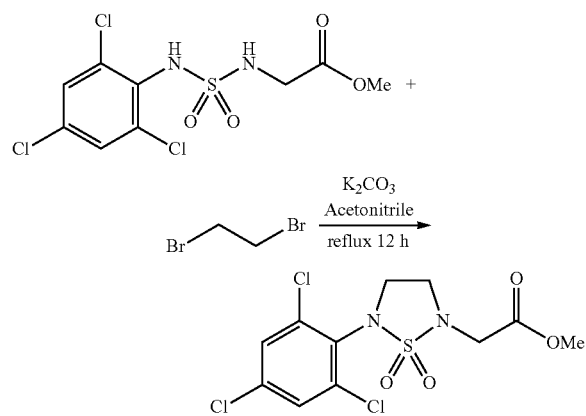

Methyl 2-(N-(2,4,6-trichlorophenyl)sulfamoylamino)acetate (300 mg, 0.863 mmol) in CH$_3$CN (10 mL) was reacted with K$_2$CO$_3$ (239 mg, 1.726 mmol) and 1,2-dibromoethane (325 mg, 1.726 mmol) for 12 hr with agitation under reflux. The resultant was extracted with EA/NaCl, dried over MgSO$_4$, concentrated and purified by column chromatography (EtOAc:Hex=1:3) to give the compound (210 mg, 0.562 mmol, 65%). $^1$H NMR (300 MHz, CDCl$_3$): δ 7.44 (s, 2H), 3.93 (s, 2H), 3.93-3.90 (m, 2H), 3.87-3.81 (m, 2H), 3.80 (s, 3H). LC/MS MH$^+$ 373

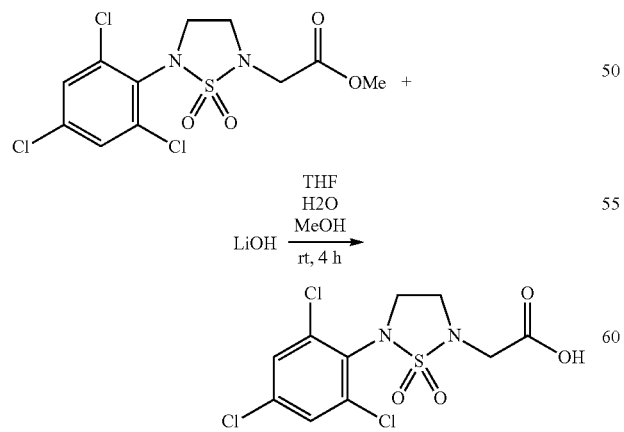

The reactions were undertaken as the above-described procedures.

$^1$H NMR (300 MHz, DMSO-d$_6$): δ 12.93 (br, OH), 7.85 (s, 2H), 3.87 (s, 2H), 3.82-3.80 (m, 2H), 3.77-3.75 (m, 2H).

(E)-N-[5-(aminocarbonyl)tricyclo[3,3,1,13,7]dec-2-yl]-2-(5-(2,4,6-trichlorophenyl)-1,1-dioxo-1,2,5-thiazolidine-2-yl)acetamide

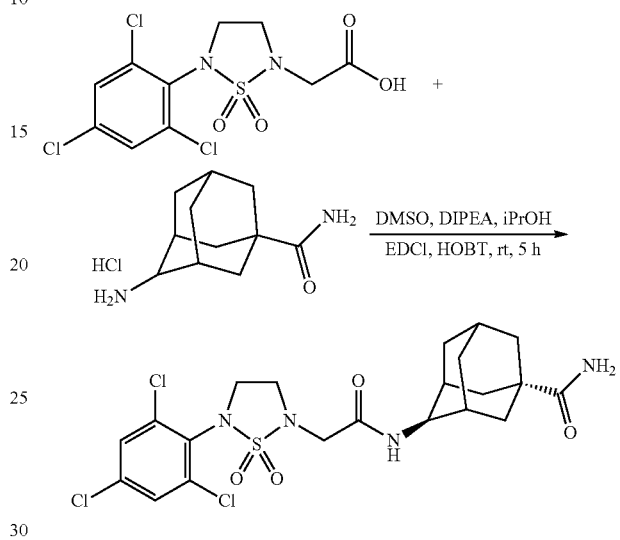

The E-isomer was synthesized by the similar procedures to the above-described procedures.

$^1$H NMR (300 MHz, CDCl$_3$): δ 7.46 (s, 2H), 7.16 (brd, J=7.7 Hz, NH), 5.56 (br, NH2), 5.22 (br, NH2), 4.10-4.07 (m, 1H), 3.98-3.89 (m, 2H), 3.87 (s, 2H), 3.79-3.74 (m, 2H), 2.10-1.57 (m, 13H).

(Z)—N-[5-(aminocarbonyl)tricyclo[3,3,1,13,7]dec-2-yl]-2-(5-(2,4,6-trichlorophenyl)-1,1-dioxo-1,2,5-thiazolidine-2-yl)acetamide

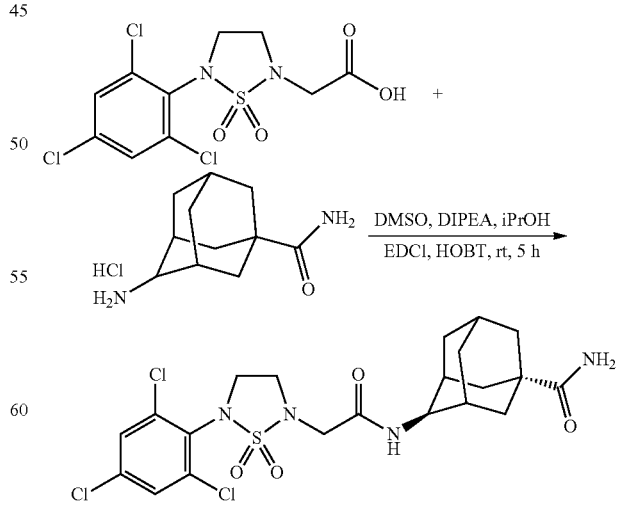

The E-isomer was synthesized by the similar procedures to the above-described procedures.

¹H NMR (300 MHz, CDCl₃): δ 7.46 (s, 2H), 7.26-7.22 (m, NH), 5.79 (br, NH₂), 5.12 (br, NH₂), 4.06-4.02 (m, 1H), 3.95-3.91 (m, 2H), 3.89 (s, 2H), 3.80-3.76 (m, 2H), 2.17-1.62 (m, 13H). LC/MS MH⁺ 535

Compound 122

Synthesis of methyl 2-(7-(2,4,6-trichlorophenyl)-1,2,7-thiadiazepan-2-yl)acetate, 1-1-dioxide

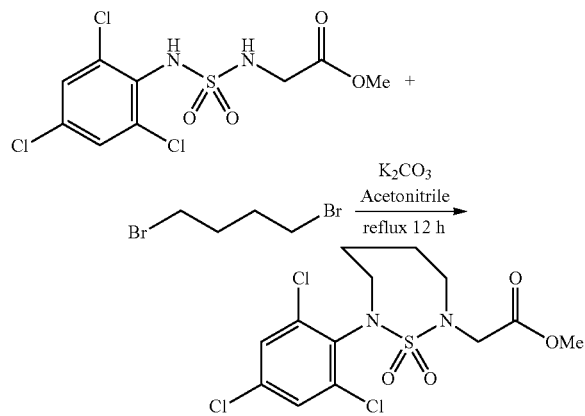

Methyl 2-(N-(2,4,6-trichlorophenyl)sulfamoylamino)acetate (300 mg, 0.863 mmol) in CH₃CN (10 mL) was reacted with K₂CO₃ (239 mg, 1.726 mmol) and 1,4-dibromobutane (187 mg, 0.863 mmol) for 12 hr with agitation under reflux. The resultant was extracted with EA/NaCl, dried over MgSO₄, concentrated and purified by column chromatography (EtOAc:Hex=1:3) to give the title compound (170 mg, 0.423 mmol, 49%). ¹H NMR (300 MHz, CDCl₃): δ 7.41 (s, 2H), 4.11 (s, 2H), 3.76 (s, 3H), 3.66-3.62 (m, 2H), 3.52-3.49 (m, 2H), 2.11-2.09 (m, 2H), 1.99-1.95 (m, 2H).

2-(7-(2,4,6-trichlorophenyl)-1,2,7-thiadiazepan-2-yl)acetic acid, 1-1-dioxide

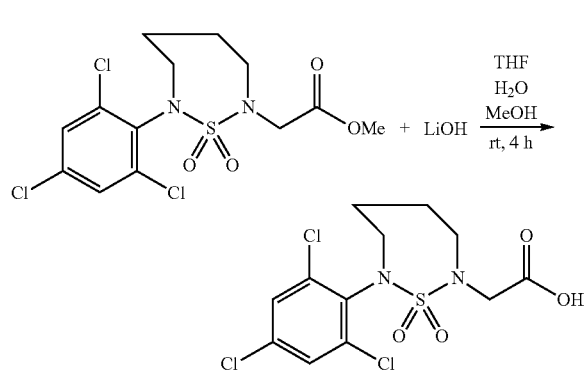

The title compound was synthesized by the similar procedures to the above-described procedures.

¹H NMR (300 MHz, DMSO-d₆): δ 8.70 (br, OH), 7.40 (s, 2H), 4.15 (s, 2H), 3.65-3.61 (m, 2H), 3.50-3.40 (m, 2H), 2.17-2.04 (m, 2H), 1.97-1.96 (m, 2H).

(E)-N-[5-(aminocarbonyl)tricyclo[3,3,1,13,7]dec-2-yl]-2-(7-(2,4,6-trichlorophenyl)-1,1-dioxo-1,2,7-thiadiazepan-2-yl)acetamide

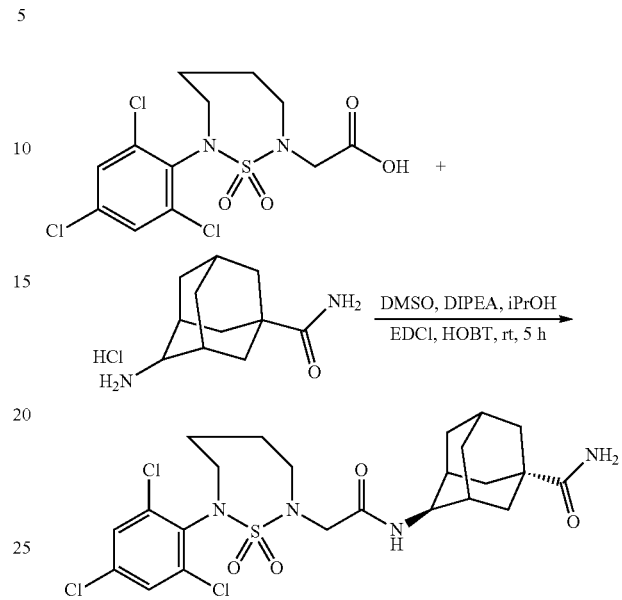

The title compound was synthesized by the similar procedures to the above-described procedures.

¹H NMR (300 MHz, CDCl₃): δ 7.43 (s, 2H), 6.94 (brd, J=8.0 Hz, NH), 5.57 (br, NH₂), 5.30 (br, NH₂), 4.04-4.01 (m, 1H), 3.95 (s, 2H), 3.55-3.52 (m, 2H), 3.42-3.38 (m, 2H), 2.23-2.17 (m, 2H), 2.04-1.55 (m, 15H). LC/MS MH⁺ 563

Compound 123

Methyl 2-(methyl(N-methyl-N-(2,4,6-trichlorophenyl)sulfamoyl)amino)acetate

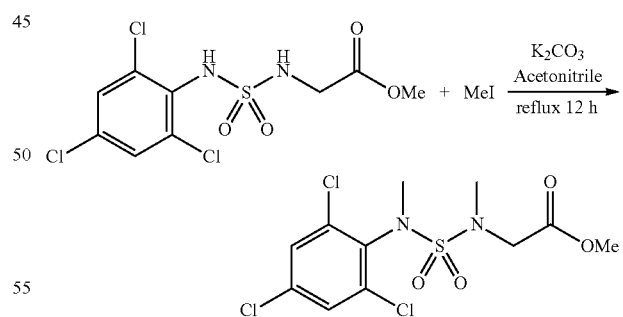

Methyl 2-(N-(2,4,6-trichlorophenyl)sulfamoylamino)acetate (300 mg, 0.863 mmol) in CH₃CN (10 mL) was reacted with K₂CO₃ (239 mg, 1.726 mmol) and MeI (367 mg, 2.589 mmol) for 12 hr with agitation under reflux. The resultant was extracted with EA/NaCl, dried over MgSO₄, concentrated and purified by column chromatography (EtOAc:Hex=1:3) to give the title compound (300 mg, 0.799 mmol, 92%). ¹H NMR (300 MHz, CDCl₃): δ 7.39 (s, 2H), 4.10 (s, 2H), 3.77 (s, 3H), 3.16 (s, 3H), 3.09 (s, 3H).

123

2-(methyl(N-methyl-N-(2,4,6-trichlorophenyl)sulfamoyl)amino)acetic acid

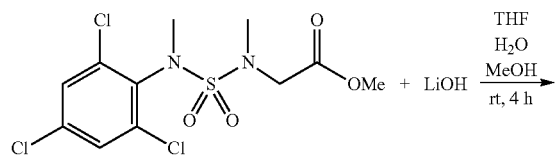

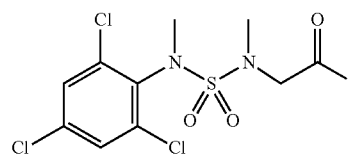

The title compound was synthesized by the similar procedures to the above-described procedures.

$^1$H NMR (300 MHz, DMSO-d$_6$): δ 12.88 (br, OH), 7.82 (s, 2H), 4.04 (s, 2H), 3.07 (s, 3H), 3.00 (s, 3H).

N-2,4,6-trichlorophenyl-N'-methyl-N-acetamide-N'-methyl-(E)-[5-(amino carbonyl)tricyclo[3,3,1,13,7]dec-2-yl]sulfamide

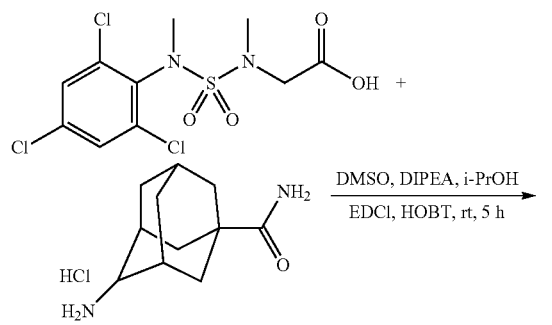

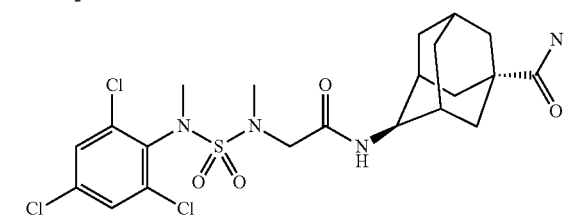

The title compound was synthesized by the similar procedures to the above-described procedures.

$^1$H NMR (300 MHz, CDCl$_3$): δ 7.43 (s, 2H), 6.85 (brd, J=7.8 Hz, NH), 5.57 (br, NH$_2$), 5.27 (br, NH$_2$), 4.05-4.02 (m, 1H), 3.92 (s, 2H), 3.22 (s, 3H), 3.09 (s, 3H), 2.16-1.57 (m, 13H). LC/MS MH$^+$ 537

124

Compound 128

Methyl 2-(3-methyl-6-(2,4,6-trichlorophenyl)-1,2,6-thiadiazinan-2-yl)acetate, 1-1-dioxide

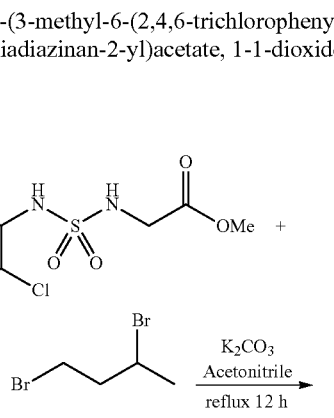

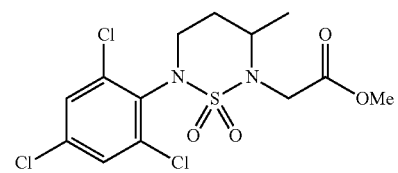

Methyl 2-(N-(2,4,6-trichlorophenyl)sulfamoylamino)acetate (300 mg, 0.863 mmol) in CH$_3$CN (10 mL) was reacted with K$_2$CO$_3$ (239 mg, 1.726 mmol) and 1,3-dibromobutane (373 mg, 1.726 mmol) for 12 hr with agitation under reflux. The resultant was extracted with EA/NaCl, dried over MgSO$_4$, concentrated and purified by column chromatography (EtOAc:Hex=1:3) to give the compound (230 mg, 0.572 mmol, 66%). $^1$H NMR (300 MHz, CDCl$_3$): δ 7.40 (d, J=2.4 Hz, 1H), 7.38 (d, J=2.4 Hz, 1H), 4.60-4.50 (m, 1H), 4.38-4.32 (m, 1H), 4.27-4.17 (m, 1H), 3.78-3.73 (m, 1H), 3.76 (s, 3H), 3.29-3.22 (m, 1H), 2.07-1.93 (m, 1H), 1.68-1.61 (m, 1H), 1.32 (t, J=6.9 Hz, 3H).

2-(3-methyl-6-(2,4,6-trichlorophenyl)-1,2,6-thiadiazinan-2-yl)acetic acid, 1-1-dioxide

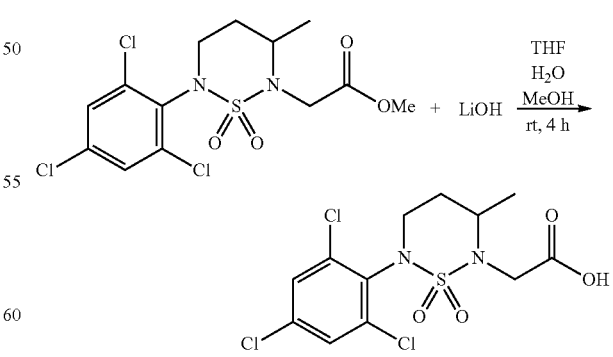

$^1$H NMR (300 MHz, DMSO-d6): δ 12.72 (br, OH), 7.80 (d, J=2.3 Hz, 1H), 7.76 (d, J=2.3 Hz, 1H), 4.33-4.28 (m, 1H), 4.05-3.88 (m, 2H+1H), 3.36-3.31 (m, 1H), 2.03-1.88 (m, 1H), 1.63-1.58 (m, 1H), 1.23 (d, J=6.8 Hz, 3H).

(E)-N-[5-(aminocarbonyl)tricyclo[3,3,1,13,7]dec-2-yl]-2-(3-methyl-6-(2,4,6-trichlorophenyl)-1,1-dioxo-1,2,6-thiadiazinan-2-yl)acetamide

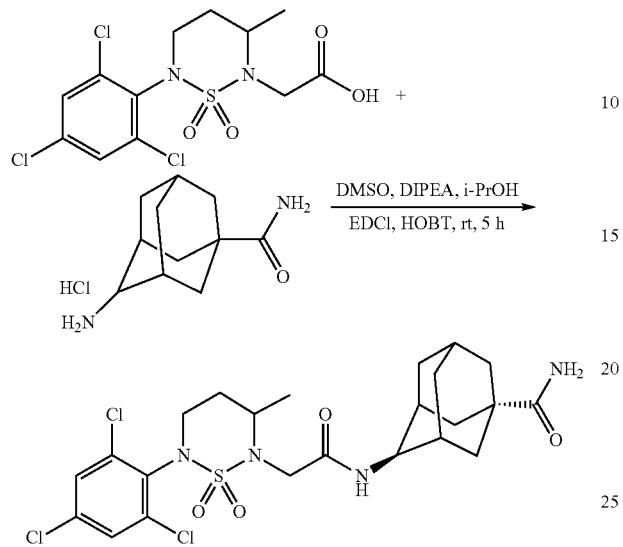

The title compound was synthesized by the similar procedures to the above-described procedures.

¹H NMR (300 MHz, CDCl₃): δ 7.42 (d, J=2.4 Hz, 1H), 7.39 (d, J=2.4 Hz, 1H), 6.99 (brd, J=7.7 Hz, NH), 5.56 (br, NH2), 5.22 (br, NH2), 4.61-4.50 (m, 1H), 4.28-4.18 (m, 1H+1H), 4.05-4.02 (m, 1H), 3.65-3.59 (m, 1H), 3.31-3.24 (m, 1H), 2.14-1.54 (m, 15H), 1.33 (d, J=6.9 Hz, 3H). LC/MS MH⁺ 563

Compound 156

Methyl 2-(4-methyl-1,1-dioxido-6-(2,4,6-trichlorophenyl)-1,2,6-thiadiazinan-2-yl)acetate

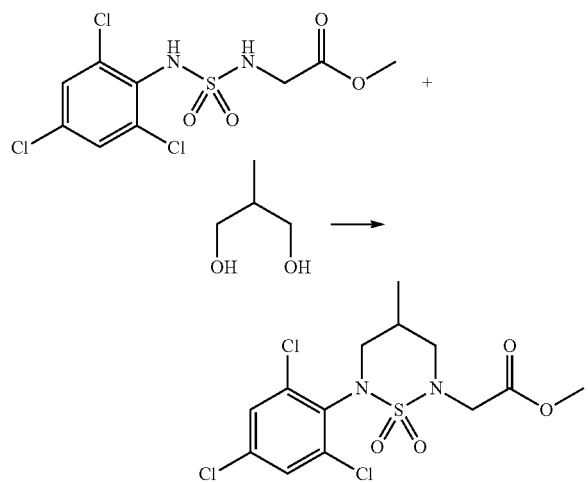

To methyl 2-(N-(2,4,6-trichlorophenyl)sulfamoylamino)acetate (3.0 g, 8.3 mmol), 2-methylpropan-1,3-diol (1.18 mL, 8.3 mmol) and PPh₃ (5.4 g, 20.7 mmol), was dropwisely added DIAD (4 mL, 20.7 mmol) with adjustment of external temperature to 0° C. The reaction mixture was agitated for 3 hr at room temperature, extracted with EtOAc, dried (Na₂SO₄), filtered and concentrated under reduced pressure, followed by column chromatography (MeOH/DCM 1%), finally giving the title compound (2.3 g, y=65%, solid). ¹H NMR (300 MHz, CDCl₃): δ 7.41 (d, J=2.4 Hz, 1H), 7.37 (d, J=2.4 Hz, 1H), 4.44 (d, J=17 Hz, 1H), 4.37-3.86 (m, 5H), 3.59-3.41 (m, 1H), 3.38-3.13 (m, 1H), 2.75-2.53 (m, 1H), 1.32 (t, J=7.1 Hz, 3H), 0.94 (t, J=7.1 Hz, 3H).

2-(4-methyl-1,1-dioxido-6-(2,4,6-trichlorophenyl)-1,2,6-thiadiazinan-2-yl)acetic acid

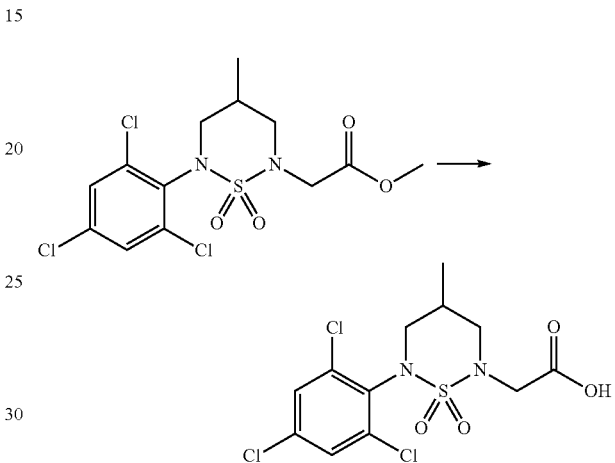

To methyl 2-(4-methyl-1,1-dioxido-6-(2,4,6-trichlorophenyl)-1,2,6-thiadiazinan-2-yl)acetate (2.3 g, 5.4 mmol) in THF (12 mL) and MeOH (12 mL), was dropwisely added LiOH (1.1 g, 27.0 mmol) in H₂O. The reaction mixture was agitated for 3 hr at room temperature. After the completion of the reaction, the resultant was concentrated and its pH was adjusted down to 3 with 2 N HCl after the addition of water. The resultant was extracted with EtOAc, dried over Na₂SO₄, filtered and concentrated under reduced pressure, giving the title compound (2.0 g, y=83%, solid). ¹H NMR (300 MHz, CDCl₃) δ 7.42 (d, J=2.4 Hz, 1H), 7.38 (d, J=2.4 Hz, 1H), 4.53 (d, J=17 Hz, 1H), 4.16-3.88 (m, 4H), 3.40-3.38 (m, 1H), 3.20-3.15 (m, 1H), 2.57-2.11 (m, 1H), 0.93 (d, J=7.1 Hz, 3H).

4-(2-(4-methyl-1,1-dioxido-6-(2,4,6-trichlorophenyl)-1,2,6-thiadiazinan-2-yl)acetamido)adamantan-1-carboxamide To 4-aminoadamantan-1-carboxamide hydrochloride (900 mg, 3.9 mmol) in DMSO (40 mL) and i-prOH (50 mL), were added DIPEA (2.5 g, 19.5 mmol), 2-(4-methyl-1,1-dioxido-6-(2,4,6-trichlorophenyl)-1,2,6-thiadiazinan-2-yl)acetic acid (1.8 g, 4.7 mmol), EDC (894 mg, 4.7 mmol) and HOBT (632 mg, 4.7 mmol), and then agitated for 5 hr at room temperature. After the addition of water, the resultant extracted with EtOAc, dried (Na₂SO₄), filtered and concentrated under reduced pressure, followed by column chromatography (MeOH/DCM 5%), finally giving the title compound (solid, 980 mg, y=64%) E-form. ¹H NMR (300 MHz, DMSO-d6) δ 7.41 (d, J=2.4 Hz, 1H), 7.39 (d, J=2.4 Hz, 1H), 5.58 (s, 1H), 5.35 (s, 1H), 4.35 (d, J=17 Hz, 1H), 4.08-4.00 (m, 2H), 3.91-3.85 (m, 1H), 3.73 (d, J=17 Hz, 1H), 3.30-3.17 (m, 2H), 2.70-2.54 (m, 1H), 2.17-1.54 (m, 13H); LC/MS MH⁺ 563

Compound 175

Ethyl 2-(4-methylene-1,1-dioxido-6-(2,4,6-trichlorophenyl)-1,2,6-thiadiazinan-2-yl)acetate

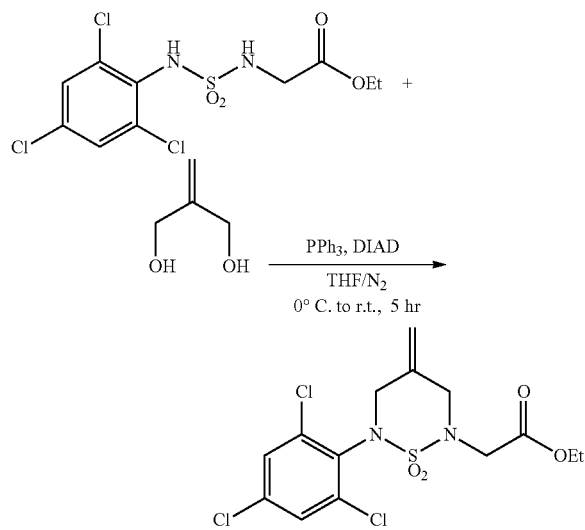

Ethyl 2-((N-(2,4,6-trichlorophenyl)sulfamoyl)amino)acetate (300 mg, 0.83 mmol), 2-methylenepropane-1,3-diol (73 mg, 0.83 mmol) and triphenylphosphine (544 mg, 2.08 mmol) were dissolved in anhydrous THF (30 mL) in a reactor, and then cooled down −20° C. after removal of air in the reactor by purging nitrogen gas. DIAD (420 mg, 2.08 mmol) was dropwisely added to the reaction mixture and agitated for 5 hr at room temperature. The resultant was concentrated under reduced pressure and purified by column chromatography (dichloromethane:hexane:ethyl acetate=5:4:1), finally yielding the title compound (305 mg, 89%, white solid). $^1$H NMR (300 MHz, CDCl$_3$): δ 7.40 (s, 2H), 5.25 (s, 1H), 5.16 (s, 1H), 4.36 (s, 2H), 4.27-4.20 (m, 4H), 4.08 (s, 2H), 1.33-1.28 (t, 3H, J=7.1, 7.1 Hz).

2-(4-methylene-1,1-dioxido-6-(2,4,6-trichlorophenyl)-1,2,6-thiadiazinan-2-yl)acetic acid

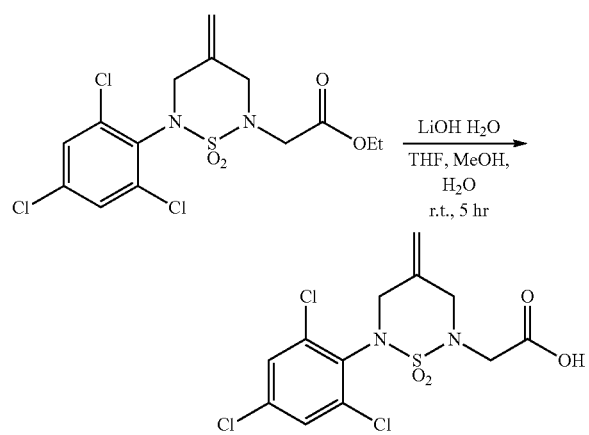

To ethyl 2-(4-methylene-1,1-dioxido-6-(2,4,6-trichlorophenyl)-1,2,6-thiadiazinan-2-yl)acetate (305 mg, 0.74 mmol) in THF (10 mL) and MeOH (10 mL), was added LiOH monohydrate (155 mg, 3.69 mmol) in water (3 mL) and agitated for 5 hr at room temperature. After addition of ethyl acetate (30 mL) and water (30 mL), pH of the resultant was adjusted to 3 with 1 N HCl and extracted to the organic layer. The resultant was dried over MgSO$_4$, concentrated under reduced pressure, and crystallized with ethyl acetate (1 mL) and hexane (10 mL), giving the compound of interest (253 mg, 89%, white solid). $^1$H NMR (300 MHz, CDCl$_3$): δ 7.42 (s, 2H), 5.26 (s, 1H), 5.16 (s, 1H), 4.41 (s, 2H), 4.33 (s, 2H), 4.09 (s, 2H).

4-(2-(4-methylene-1,1-dioxido-6-(2,4,6-trichlorophenyl)-1,2,6-thiadiazinan-2-yl)acetamido)adamantan-1-carboxamide (E form)

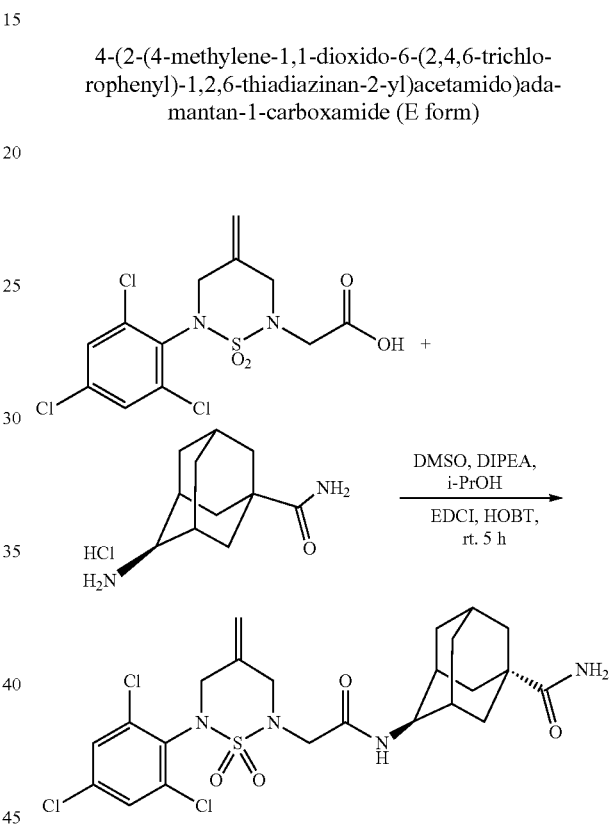

To adamantyl amine hydrochloride (127 mg, 0.55 mmol) in DMSO (700 mg), were successively added DIPEA (357 mg, 2.75 mmol), i-PrOH (10 mL), 2-(4-methylene-1,1-dioxido-6-(2,4,6-trichlorophenyl)-1,2,6-thiadiazinan-2-yl)acetic acid (253 mg, 0.66 mmol), EDCI (211 mg, 1.10 mmol) and HOBt (169 mg, 1.10 mmol), and agitated for 12 hr at room temperature. After concentration at 50° C. under reduced pressure, the resultant was added with saturated NH$_4$Cl solution (20 mL), kept to stand for 1 hr for crystallization, filtered and washed three times with water (20 mL). The filtered solid was purified by column chromatography (dichloromethane:methanol=97:3) to yield the compound of interest (122 mg, 39%, white solid). $^1$H NMR (300 MHz, CDCl$_3$): δ 7.42 (s, 2H), 6.93 (d, 1H J=8.0 Hz), 5.58 (s, 1H), 5.29 (m, 2H), 5.21 (s, 1H), 4.29 (s, 2H), 4.26 (s, 2H), 4.06 (m, 1H), 3.97 (s, 2H), 2.17-1.58 (m, 13H).

Compound 176

Ethyl 2-(6,6-dioxido-7-(2,4,6-trichlorophenyl)-6-thia-5,7-diazaspiro[2,5]-octane-5-yl)acetate

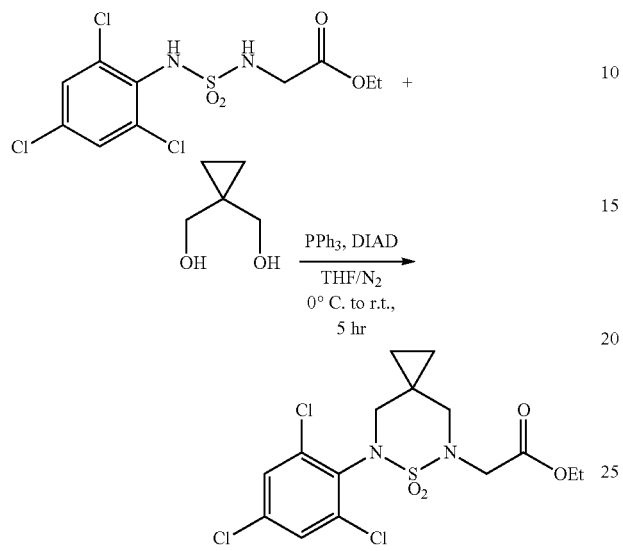

Ethyl 2-((N-(2,4,6-trichlorophenyl)sulfamoyl)amino)acetate (380 mg, 1.05 mmol), cyclopropane-1,1-diyldimethanol (107 mg, 1.05 mmol) and triphenylphosphine (689 mg, 2.63 mmol) were dissolved in anhydrous THF (30 mL) in a reactor, and then cooled down −20° C. after removal of air in the reactor by purging nitrogen gas. DIAD (532 mg, 2.63 mmol) was dropwisely added to the reaction mixture and agitated for 5 hr at room temperature. The resultant was concentrated under reduced pressure and purified by column chromatography (dichloromethane:hexane:ethyl acetate=5:4:1), finally yielding the title compound (198 mg, 44%, white solid). $^1$H NMR (300 MHz, CDCl$_3$): δ 7.39 (s, 2H), 4.39 (s, 2H), 4.26-4.19 (q, 2H, J=7.1, 7.1, 7.1 Hz), 3.73 (s, 2H), 3.57 (s, 2H), 1.32-1.27 (t, 3H, J=7.1, 7.1 Hz), 0.66-0.64 (m, 4H).

2-(6,6-dioxido-7-(2,4,6-trichlorophenyl)-6-thia-5,7-diazaspiro[2,5]-octane-5-yl)acetic acid

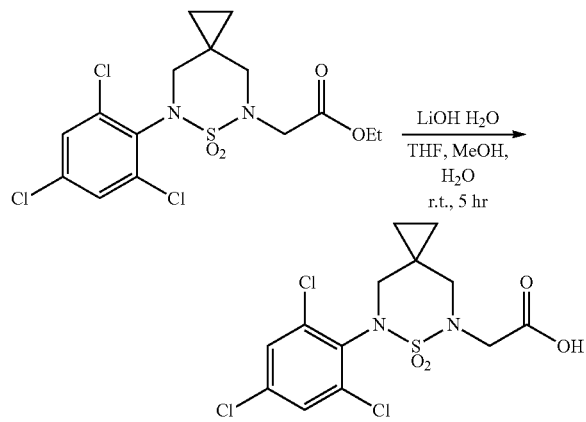

To ethyl 2-(6,6-dioxido-7-(2,4,6-trichlorophenyl)-6-thia-5,7-diazaspiro[2,5]-octane-5-yl)acetate (60 mg, 0.14 mmol) in THF (5 mL) and MeOH (5 mL), was added LiOH monohydrate (25 mg, 0.58 mmol) in water (1 mL) and agitated for 5 hr at room temperature. After addition of ethyl acetate (30 mL) and water (30 mL), pH of the resultant was adjusted to 3 with 1 N HCl and extracted to the organic layer. The resultant was dried over MgSO$_4$, concentrated under reduced pressure, and crystallized with ethyl acetate (1 mL) and hexane (10 mL), giving the compound of interest (50 mg, 89%, white solid). $^1$H NMR (300 MHz, CDCl$_3$): δ 7.39 (s, 2H), 4.39 (s, 2H), 3.73 (s, 2H), 3.57 (s, 2H), 0.66-0.64 (m, 4H).

4-(2-(6,6-dioxido-7-(2,4,6-trichlorophenyl)-6-thia-5,7-diazaspiro[2,5]octane-5-yl)acetamido)adamantan-1-carboxamide (E form)

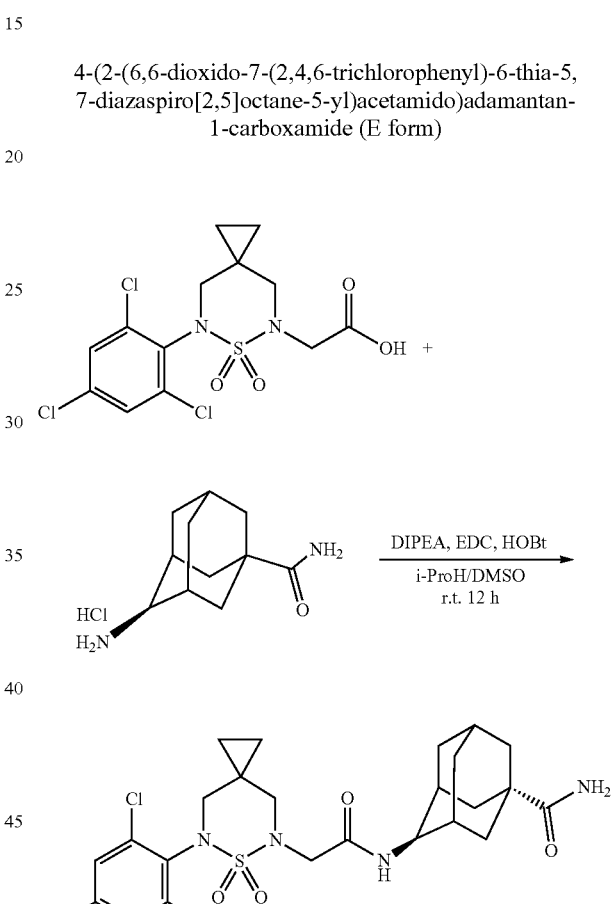

To adamantyl amine hydrochloride (26 mg, 0.11 mmol) in DMSO (700 mg), were successively added DIPEA (78 mg, 0.60 mmol), i-PrOH (10 mL), 2-(6,6-dioxido-7-(2,4,6-trichlorophenyl)-6-thia-5,7-diazaspiro[2.5]octane-5-yl)acetic acid (50 mg, 0.13 mmol), EDCI (46 mg, 0.22 mmol) and HOBt (37 mg, 0.22 mmol), and agitated for 12 hr at room temperature. After concentration at 50° C. under reduced pressure, the resultant was added with saturated NH$_4$Cl solution (20 mL), kept to stand for 1 hr for crystallization, filtered and washed three times with water (20 mL). The filtered solid was purified by column chromatography (dichloromethane:methanol=97:3) to yield the compound of interest (40 mg, 63%, white solid).

Compound 177

Ethyl 2-(4,4-dimethyl-1,1-dioxido-6-(2,4,6-trichlorophenyl)-1,2,6-thia-diazinan-2-yl)acetate

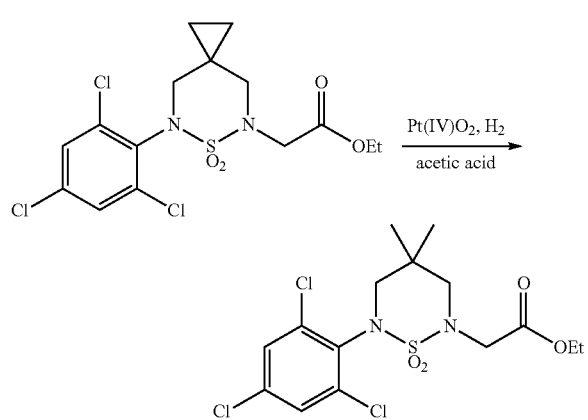

Ethyl 2-(6,6-dioxido-7-(2,4,6-trichlorophenyl)-6-thia-5,7-diazaspiro[2.5]-octane-5-yl)acetate (50 mg, 0.12 mmol) and Pt(IV)O$_2$ (54 mg, 0.24 mmol) were dissolved in acetic acid (10 mL) in a reactor and then air in the reactor was removed by introducing hydrogen gas, followed by shaking for 14 hr under 50 psi. The resultant was washed with ethyl acetate and filtered over celite. To the filtrate, was added water (50 mL) and neutralized using 1 N NaOH, followed by extraction to obtain the organic layer. The resultant was dried over MgSO$_4$, concentrated under reduced pressure, and purified by column chromatography (hexane:ethyl acetate=8:2), giving the compound of interest (46 mg, 77%, light apricot-colored solid). $^1$H NMR (300 MHz, CDCl$_3$): δ 7.38 (s, 2H), 4.26-4.19 (q, 2H, J=7.1, 7.1, 7.1 Hz), 4.17 (s, 2H), 3.65 (s, 2H), 3.49 (s, 2H), 1.32-1.27 (t, 3H, J=7.1, 7.1 Hz), 1.22 (s, 6H).

2-(4,4-dimethyl-1,1-dioxido-6-(2,4,6-trichlorophenyl)-1,2,6-thia-diazinan-2-yl)acetatic acid To ethyl 2-(4,4-dimethyl-1,1-dioxido-6-(2,4,6-trichlorophenyl)-1,2,6-thia-diazinan-2-yl)acetate (140 mg, 0.33 mmol) in THF (10 mL) and MeOH (10 mL), was dropwisely added LiOH monohydrate (25 mg, 0.58 mmol) in water (2 mL) and agitated for 5 hr at room temperature. After addition of ethyl acetate (30 mL) and water (30 mL), pH of the resultant was adjusted to 3 with 1 N HCl and extracted to the organic layer. The resultant was dried over MgSO$_4$, concentrated under reduced pressure, and crystallized with ethyl acetate (1 mL) and hexane (10 mL), giving the compound of interest (125 mg, 95%, white solid). $^1$H NMR (300 MHz, CDCl$_3$): δ 7.38 (s, 2H), 4.17 (s, 2H), 3.65 (s, 2H), 3.49 (s, 2H), 1.22 (s, 6H).

4-(2-(4,4-dimethyl-1,1-dioxido-6-(2,4,6-trichlorophenyl)-1,2,6-thiadiazinan-2-yl) acetamido)adamantan-1-carboxamide (E form)

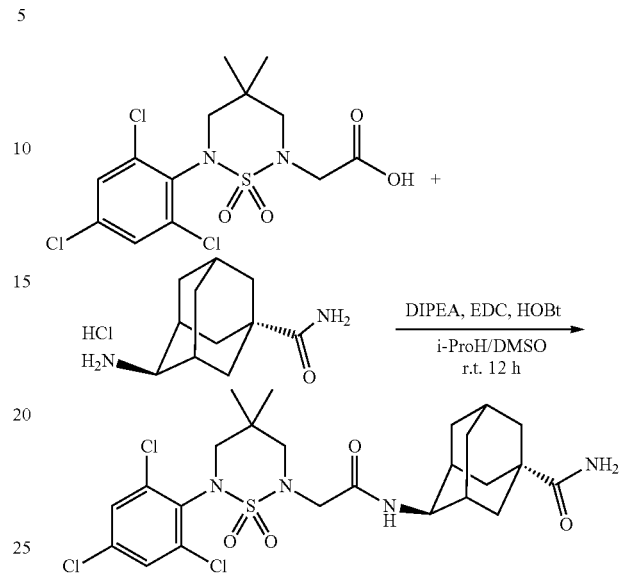

To adamantyl amine hydrochloride (60 mg, 0.26 mmol) in DMSO (800 mg), were successively added DIPEA (169 mg, 1.30 mmol), i-PrOH (10 mL), 2-(4,4-dimethyl-1,1-dioxido-6-(2,4,6-trichlorophenyl)-1,2,6-thiadiazinan-2-yl)acetic acid (123 mg, 0.31 mmol), EDCI (100 mg, 0.52 mmol) and HOBt (80 mg, 0.52 mmol), and agitated for 12 hr at room temperature. After concentration at 50° C. under reduced pressure, the resultant was added with saturated NH$_4$Cl solution (20 mL), kept to stand for 1 hr for crystallization, filtered and washed three times with water (20 mL). The filtered solid was purified by column chromatography (dichloromethane:methanol=97:3) to yield the compound of interest (67 mg, 37%, white solid). $^1$H NMR (300 MHz, CDCl$_3$): δ 7.40 (s, 2H), 7.01-6.98 (d, 1H, J=8.0 Hz), 5.55 (s, 1H), 5.23 (s, 1H), 4.07 (s, 2H), 4.05 (m, 1H), 3.68 (s, 2H), 3.46 (s, 2H), 2.09-1.25 (m, 13H), 1.24 (s, 6H).

Compound 183

First pathway for synthesis of ethyl 2-(6-(2,6-dichloro-4(trifluoromethyl)phenyl)-4-methyl-1,1-dioxido-1,2,6-thiadiazinan-2-yl)acetate

Ethyl 2-((chlorosulfonyl)amino)acetate

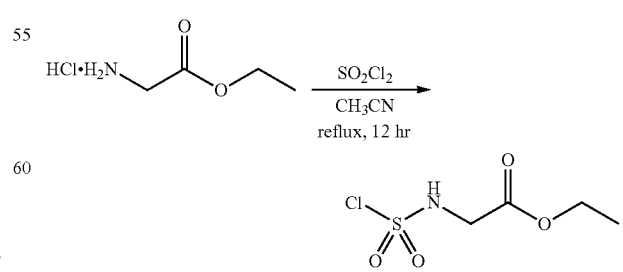

To glycine ethylester hydrochloride (5.00 g, 35.8 mmol) in CH$_3$CN (200 mL), was added sulfuryl chloride (29.00 g, 214.8 mmol), refluxed for 12 hr, and concentrated under reduced pressure. To the reaction mixture, was diethyl ether (100 mL), concentrated under reduced pressure (2×), and dried under vacuum. The resultant was used without further purification.

Ethyl 2-((N-2,6-dichloro-4-(trifluoromethyl)phenyl)sulfamoyl)amino)acetate

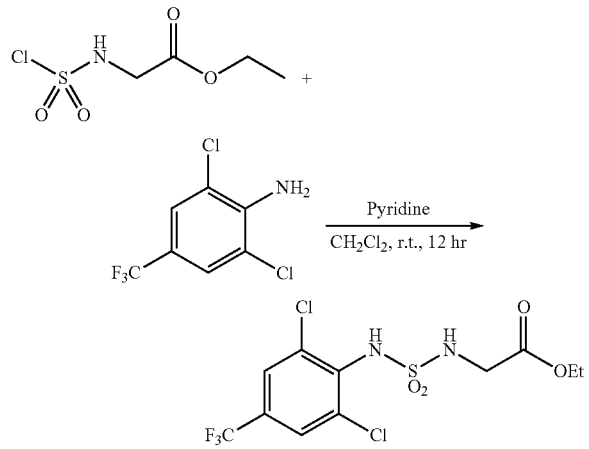

Ethyl 2-((chlorosulfonyl)amino)acetate (3.60 g, 17.9 mmol) was dissolved in CH$_2$Cl$_2$ (100 mL) and cooled to −20° C. To the solution of ethyl 2-((chlorosulfonyl)amino)acetate, was dropwisely added 2,6-dichloro-4-(trifluoromethyl) aniline (2.50 g, 10.7 mmol) and pyridine (2.53 g, 32.1 mmol) in CH$_2$Cl$_2$ (70 mL) and agitated for 12 hr at room temperature. The reaction mixture was added with water (100 mL) for extraction to obtain the organic layer. The resultant was dried over MgSO$_4$, concentrated under reduced pressure, and purified by column chromatography (hexane:ethyl acetate=7:3), giving the compound of interest (2.11 g, 16%, yellow solid). $^1$H NMR (300 MHz, CDCl$_3$): δ 7.41 (s, 1H), 6.58 (s, 1H, NH), 5.22 (brs, 1H, NH), 4.31-4.24 (q, J=7.14, 7.17, 7.11 Hz, 2H), 4.08-4.06 (d, J=7.14 Hz, 2H, —OCH2CH3), 1.34-1.29 (t, 3H, J=7.11, 7.17 Hz, —OCH2CH3).

Ethyl 2-(6-(2,6-dichloro-4-(trifluoromethyl)phenyl)-4-methyl-1,1-dioxido-1,2,6-thiadiazinan-2-yl)acetate

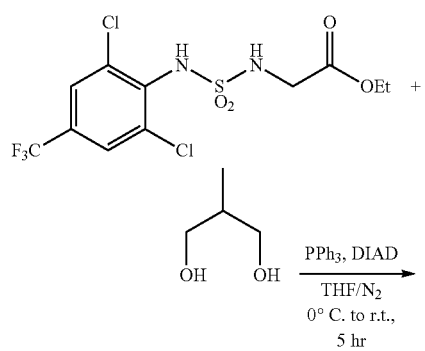

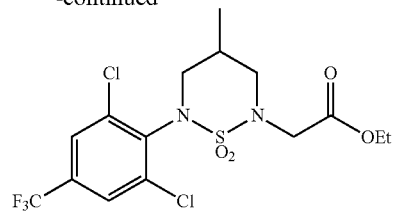

Ethyl 2-((N-(2,6-dichloro-4-(trifluoromethyl)phenyl)sulfamoyl)amino)acetate (300 mg, 0.76 mmol), 2-methylpropane-1,3-diol (75 mg, 0.76 mmol) and triphenylphosphine (498 mg, 1.90 mmol) were dissolved in anhydrous THF (30 mL), and then cooled down −20° C. after removal of air in the reactor by purging nitrogen gas. DIAD (384 mg, 1.90 mmol) was dropwisely added to the reaction mixture and agitated for 5 hr at room temperature. The resultant was concentrated under reduced pressure and purified by column chromatography (dichloromethane:hexane:ethyl acetate=5:4:1), finally yielding the title compound (225 mg, 66%, light yellow solid). $^1$H NMR (300 MHz, CDCl$_3$): δ 7.65 (s, 1H), 7.63 (s, 1H), 4.44-4.38 (m, 1H), 4.30-4.17 (m, 2H), 4.11-4.03 (m, 1H), 3.98-3.87 (m, 2H), 3.53-3.44 (m, 1H), 3.24-3.17 (m, 1H), 2.59 (m, 1H), 1.31 (t, 3H, J=7.1 Hz), 0.94 (d, 3H, J=6.7 Hz).

Second pathway for synthesis of ethyl 2-(6-(2,6-dichloro-4(trifluoromethyl)phenyl)-4-methyl-1,1-dioxido-1,2,6-thiadiazinan-2-yl)acetate Methyl Chlorosulfonylcarbamate

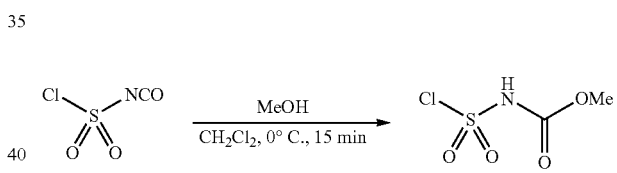

To chlorosulfonyl isocyanate (32.52 g, 0.23 mol) in CH$_2$Cl$_2$ (60 mL), was added dropwisely MeOH (8.10 g, 0.25 mol) in CH$_2$Cl$_2$ (60 mL) at 0° C. With maintaining the temperature of 0° C., the reaction mixture was agitated for 15 min and concentrated under reduced pressure. The resultant was dried in vacuo to yield the compound of interest (39.90 g, 100%, white solid), which was used with no further purification.

Methyl N-(2,6-dichloro-4-(trifluoromethyl)phenyl)sulfamoylcarbamate

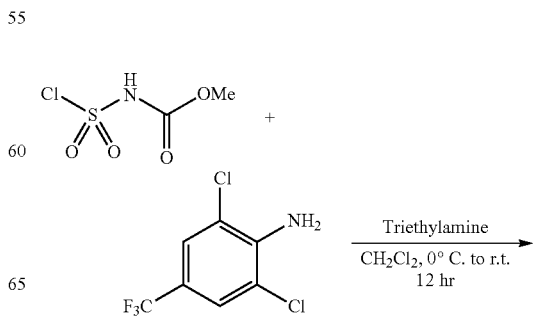

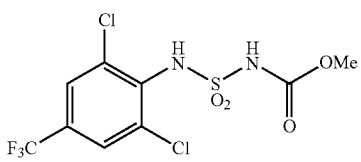

Methyl chlorosulfonylcarbamate (27.90 g, 0.16 mol) was dissolved in CH$_2$Cl$_2$ (100 mL) and cooled to −20° C. To the solution of methyl chlorosulfonylcarbamate, was dropwisely added 2,6-dichloro-4-(trifluoromethyl)aniline (2.50 g, 10.7 mmol) and triethylamine (2.53 g, 32.1 mmol) in CH$_2$Cl$_2$ (70 mL) and agitated for 12 hr at room temperature. The reaction mixture was added with water (100 mL) for extraction to obtain the organic layer. The resultant was dried over MgSO$_4$, concentrated under reduced pressure, and purified by column chromatography (hexane:ethyl acetate=7:3), giving the compound of interest (2.11 g, 6%, yellow solid). $^1$H NMR (300 MHz, CDCl$_3$): δ 7.57 (s, 2H), 3.84 (s, 3H).

Methyl 6-(2,6-dichloro-4-(trifluoromethyl)phenyl)-4-methyl-1,2,6-thia-diazinan-2-carboxylate 1,1-dioxide

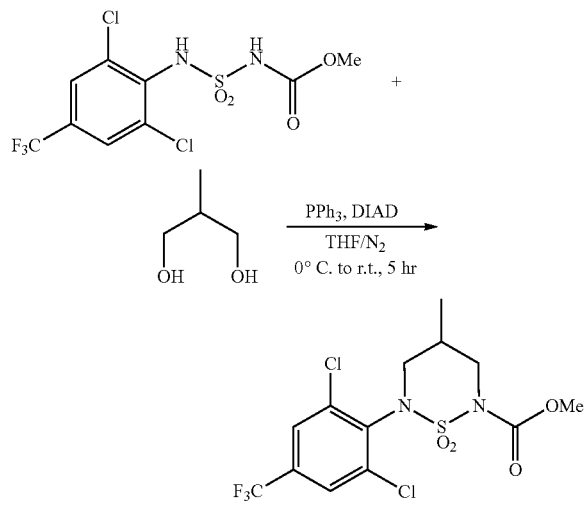

Methyl N-(2,6-dichloro-4-(trifluoromethyl)phenyl)sulfamoylcarbamate (6.00 g, 16.34 mmol), 2-methylpropane-1,3-diol (2.21 g, 24.51 mmol) and triphenylphosphine (10.71 g, 40.85 mmol) were dissolved in anhydrous THF (100 mL) in a reactor, and then cooled down −20° C. after removal of air in the reactor by purging nitrogen gas. DIAD (8.2 g, 40.8 mmol) was dropwisely added to the reaction mixture and agitated for 5 hr at room temperature. The resultant was concentrated under reduced pressure and purified by column chromatography (dichloromethane:hexane:ethyl acetate=5:4:1), finally yielding the title compound (3.9 g, 70%, white solid). $^1$H NMR (300 MHz, CDCl$_3$): δ 7.66 (s, 2H), 4.45-4.39 (m, 1H), 3.88 (s, 3H), 3.84-3.75 (m, 2H), 3.54-3.37 (m, 1H), 2.72-2.69 (m, 1H), 1.02 (d, 3H, J=6.7 Hz).

2-(2,6-dichloro-4-(trifluoromethyl)phenyl)-4-methyl-1,2,6-thiadiazinan 1,1-dioxide

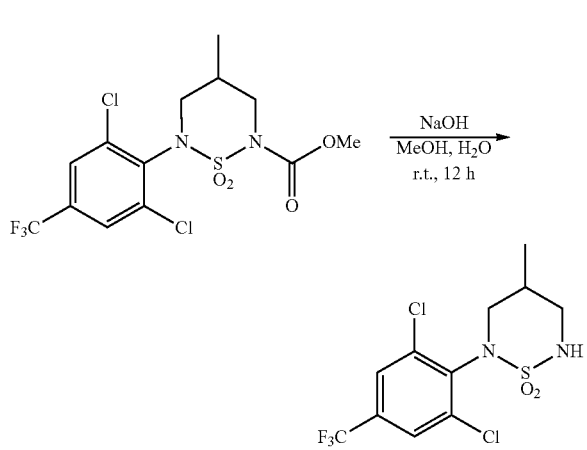

To methyl 6-(2,6-dichloro-4-(trifluoromethyl)phenyl)-4-methyl-1,2,6-thia-diazinan-2-carboxylate 1,1-dioxide (3.58 g, 8.50 mmol) in MeOH (60 mL), was dropwisely added 1 N NaOH (85 mL, 85 mmol) and agitated for 12 hr at room temperature. Following concentration under reduced pressure, ethyl acetate (30 mL) and water (30 mL) were added to the resultant to obtain the organic layer. The organic layer was dried over MgSO$_4$ and crystallized using ethyl acetate (10 mL) and hexane (70 mL), giving the compound of interest (2.96 g, 96%, white solid). $^1$H NMR (300 MHz, CDCl$_3$): δ 7.65 (s, 2H), 4.48-4.43 (m, 1H), 4.04-3.96 (m, 1H), 3.61-3.55 (m, 2H), 3.42-3.36 (m, 1H), 2.32 (m, 1H), 0.97 (d, 3H, J=6.8 Hz).

Ethyl 2-(6-(2,6-dichloro-4-(trifluoromethyl)phenyl)-4-methyl-1,1-dioxido-1,2,6-thiadiazinan-2-yl acetate

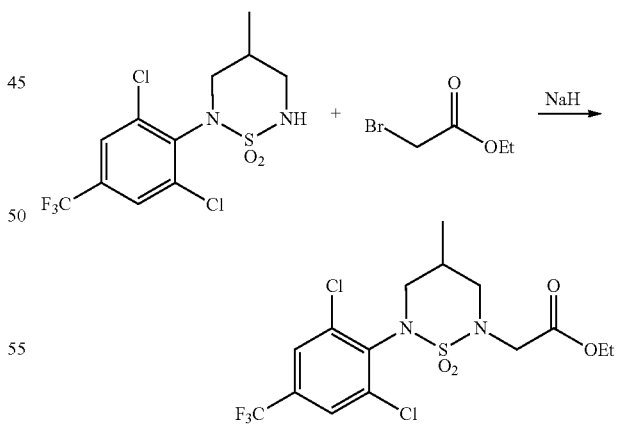

2-(2,6-dichloro-4-(trifluoromethyl)phenyl)-4-methyl-1,2,6-thiadiazinan 1,1-dioxide (2.96 g, 8.15 mmol) and ethyl bromoacetate (2.04 g, 12.23 mmol) were dissolved THF (100 mL) and cooled to 0° C. To the reaction mixture, was dropwisely added 60% NaH in mineral oil (0.98 g, 24.45 mmol) and agitated for 1 hr at 0° C. The resultant was slowly added with water (30 mL) to quench residual NaH and its organic layer was concentrated under reduced pressure. The residue was extracted using ethyl acetate (150 mL) and H₂O (100 mL) to obtain the organic layer. The organic layer was dried over MgSO₄, concentrated under reduced pressure and purified by column chromatography (hexane:ethyl acetate=7:3) to yield the compound of interest (2.92 g, 80%, light yellow solid). ¹H NMR (300 MHz, CDCl₃): δ 7.65 (s, 1H), 7.63 (s, 1H), 4.44-4.38 (m, 1H), 4.30-4.17 (m, 2H), 4.11-4.03 (m, 1H), 3.98-3.87 (m, 2H), 3.53-3.44 (m, 1H), 3.24-3.17 (m, 1H), 2.59 (m, 1H), 1.31 (t, 3H, =7.1 Hz), 0.94 (d, 3H, =6.7 Hz).

2-(6-(2,6-dichloro-4-(trifluoromethyl)phenyl)-4-methyl-1,1-dioxido-1,2,6-thiadiazinan-2-yl)acetic acid

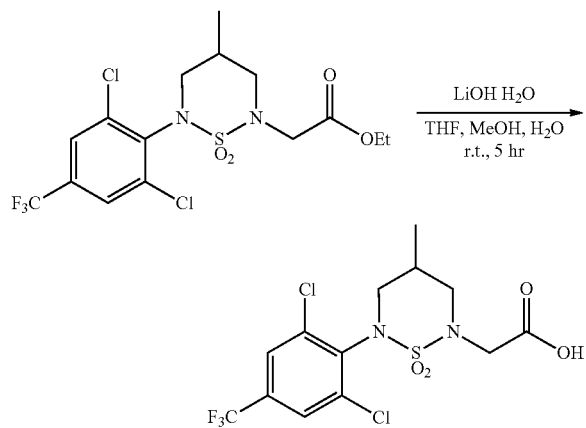

To ethyl 2-(6-(2,6-dichloro-4-(trifluoromethyl)phenyl)-4-methyl-1,1-dioxido-1,2,6-thiadiazinan-2-yl acetate (220 mg, 0.45 mmol) in THF (10 mL) and MeOH (10 mL), was dropwisely added LiOH monohydrate (94 mg, 0.45 mmol) in water (3 mL) and agitated for 5 hr at room temperature. After addition of ethyl acetate (30 mL) and water (30 mL), pH of the resultant was adjusted to 3 with 1 N HCl and extracted to obtain the organic layer. The resultant was dried over MgSO₄, concentrated under reduced pressure, and crystallized with ethyl acetate (1 mL) and hexane (10 mL), giving the compound of interest (163 mg, 86%, white solid). ¹H NMR (300 MHz, CDCl₃): δ 7.67 (s, 1H), 7.64 (s, 1H), 4.53-4.47 (m, 1H), 4.12-3.91 (m, 3H), 3.46-3.42 (m, 1H), 3.26-3.19 (m, 1H), 2.59 (m, 1H), 0.96 (d, 3H, J=6.7 Hz).

4-(2-((S)-6-(2,6-dichloro-4-(trifluoromethyl)phenyl)-4-methyl-1,1-dioxido-1,2,6-thiadiazinan-2-yl)acetamido)adamantan-1-carboxamide (E form)

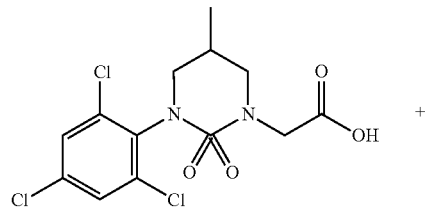

+

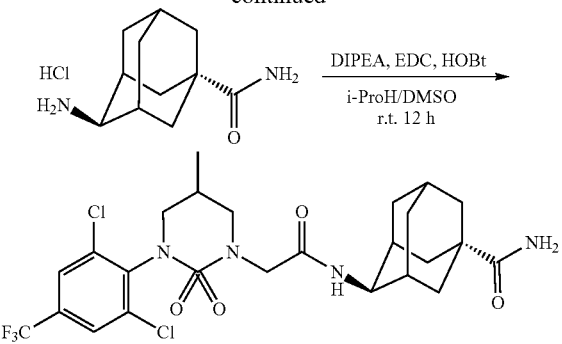

To adamantyl amine hydrochloride (74 mg, 0.32 mmol) in DMSO (800 mg), were successively added DIPEA (208 mg, 1.60 mmol), i-PrOH (25 mL), 2-(6-(2,6-dichloro-4-(trifluoromethyl)phenyl)-4-methyl-1,1-dioxido-1,2,6-thiadiazinan-2-yl) acetic acid (160 mg, 0.38 mmol), EDCI (123 mg, 0.64 mmol) and HOBt monohydrate (124 mg, 0.64 mmol), and agitated for 12 hr at room temperature. After concentration at 50° C. under reduced pressure, the resultant was added with saturated NH₄Cl solution (20 mL), kept to stand for 1 hr for crystallization, filtered and washed three times with water (20 mL). The filtered solid was purified by column chromatography (dichloromethane:methanol=97:3) to yield the compound of interest (113 mg, 49%, white solid). ¹H NMR (300 MHz, CDCl₃): δ 7.69 (s, 1H), 7.65 (s, 1H), 6.95 (d, 1H, J=6.8 Hz), 5.58 (s, 1H), 5.29 (s, 1H), 4.40-4.34 (m, 1H), 4.12-3.90 (m, 3H), 3.78-3.72 (m, 1H), 3.33-3.21 (m, 2H), 2.62-2.59 (m, 1H), 2.14-1.58 (m, 13H), 0.97 (d, 3H, J=6.0 Hz). LC/MS MH⁺ 597

Compound 195

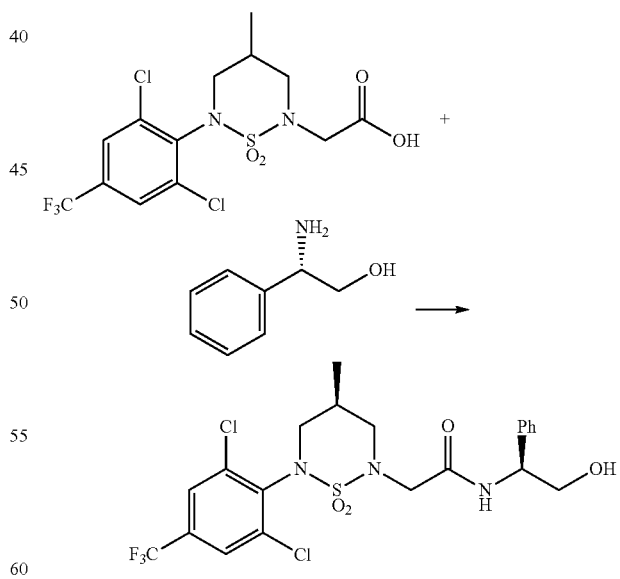

To 2-(6-(2,6-dichloro-4-(trifluoromethyl)phenyl)-4-methyl-1,1-dioxido-1,2,6-thiadiazinan-2-yl)acetic acid (2.49 g, 5.94 mmol) in CH₂Cl₂ (30 mL), were successively added DIPEA (2.30 g, 17.82 mmol), (S)-(+)-2-phenylglycinol (0.97 g, 7.08 mmol), EDCI (1.70 g, 8.85 mmol) and HOBt (1.20 g, 8.85 mmol), and agitated for 12 hr at room temperature. To the reaction mixture, was added NH₄Cl solution (40 mL) to extract the organic layer. The organic layer was dried over MgSO₄ and concentrated under reduced pressure. The residue was purified by column chromatography (hexane:ethyl acetate=1:3) to yield the compound of interest (1.12 g, 35%, white solid). ¹H NMR (300 MHz, CDCl₃): δ 7.67 (s, 1H), 7.65 (s, 1H), 7.40-7.23 (m, 5H), 5.12 (m, 1H), 4.42-4.36 (m, 1H), 4.06-4.02 (m, 1H), 3.93-3.78 (m, 4H), 3.25-3.16 (m, 2H), 2.54-2.50 (m, 2H), 0.92 (d, 3H, J=6.7 Hz).

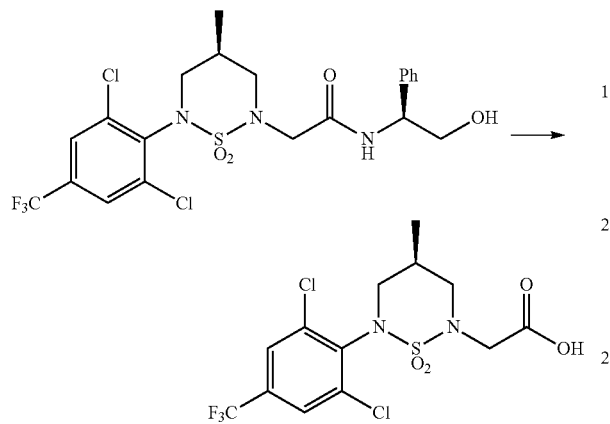

To 2-((S)-6-(2,6-dichloro-4-(trifluoromethyl)phenyl)-4-methyl-1,1-dioxido-1,2,6-thiadiazinan-2-yl)-N—((S)-2-hydroxy-1-phenylethyl)acetamide (600 mg, 1.11 mmol) in 1,4-dioxane (30 mL) and H₂O (30 mL), was added 1 M H₂SO₄ (25 mL) and agitated for 4 days at 90° C. The reaction mixture was treated with saturated NaHCO₃ aqueous solution to adjust its pH to 3, and then extracted with ethyl acetate (50 mL×2). The extracted organic layer was washed with H₂O (100 mL×1) and brine (100 mL×1), dried over MgSO₄ and concentrated under reduced pressure. The resultant was dried under vacuum to yield the compound of interest (360 mg, 77%, white solid). ¹H NMR (300 MHz, CDCl₃): δ 7.66 (s, 1H), 7.64 (s, 1H), 4.52-4.46 (m, 1H), 4.12-3.90 (m, 3H), 3.51-3.42 (m, 1H), 3.27-3.19 (m, 1H), 2.58 (m, 1H), 0.956 (d, 3H, J=6.7 Hz).

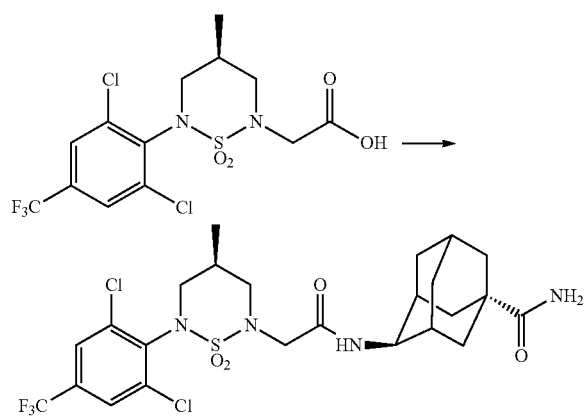

To adamantyl amine hydrochloride (196 mg, 0.85 mmol) in DMSO (600 mg), were successively added DIPEA (552 mg, 4.25 mmol), i-PrOH (30 mL), (S)-2-(6-(2,6-dichloro-4-(trifluoromethyl)phenyl)-4-methyl-1,1-dioxido-1,2,6-thiadiazinan-2-yl)acetic acid (360 mg, 0.85 mmol), EDCI (328 mg, 1.71 mmol) and HOBt (231 mg, 1.71 mmol), and agitated for 12 hr at room temperature. After concentration at 50° C. under reduced pressure, the resultant was added with saturated NH₄Cl solution (30 mL), kept to stand for 1 hr for crystallization, filtered and washed three times with water (25 mL). The filtered solid was purified by column chromatography (dichloromethane:methanol=97:3) to yield the compound of interest (182 mg, 36%, white solid). ¹H NMR (300 MHz, CDCl₃): δ 7.68 (s, 1H), 7.66 (s, 1H), 6.94 (d, 1H, J=7.9 Hz), 5.58 (s, 1H), 5.20 (s, 1H), 4.40-4.34 (m, 1H), 4.13-3.90 (m, 3H), 3.79-3.73 (m, 1H), 3.36-3.20 (m, 2H), 2.62-2.58 (m, 1H), 2.18-1.57 (m, 13H), 0.96 (d, 3H, J=6.7 Hz). LC/MS MH⁺ 597

Compound 196

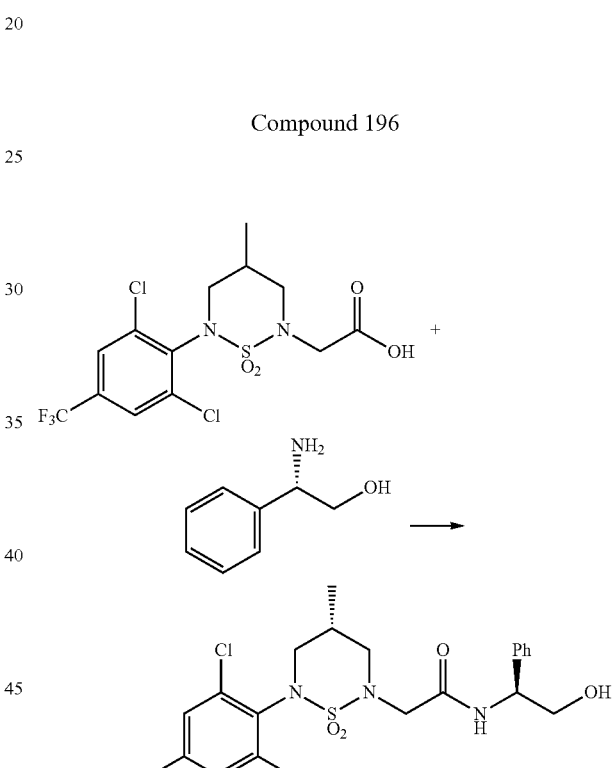

To 2-(6-(2,6-dichloro-4-(trifluoromethyl)phenyl)-4-methyl-1,1-dioxido-1,2,6-thiadiazinan-2-yl)acetic acid (2.49 g, 5.94 mmol) in CH₂Cl₂ (30 mL), were successively added DIPEA (2.30 g, 17.82 mmol), (S)-(+)-2-phenylglycinol (0.97 g, 7.08 mmol), EDCI (1.70 g, 8.85 mmol) and HOBt (1.20 g, 8.85 mmol), and agitated for 12 hr at room temperature. To the reaction mixture, was added NH₄Cl solution (40 mL) to extract the organic layer. The organic layer was dried over MgSO₄ and concentrated under reduced pressure. The residue was purified by column chromatography (hexane:ethyl acetate=1:3) to yield the compound of interest (0.94 g, 29%, white solid). ¹H NMR (300 MHz, CDCl₃): δ 7.66 (s, 1H), 7.65 (s, 1H), 7.38-7.26 (m, 5H), 5.12 (m, 1H), 4.38-4.32 (m, 1H), 4.08-4.04 (m, 1H), 3.98-3.84 (m, 4H), 3.42-3.35 (m, 1H), 3.28-3.20 (m, 1H), 2.64 (m, 1H), 2.29 (m, 1H), 0.97 (d, 3H, J=6.7 Hz).

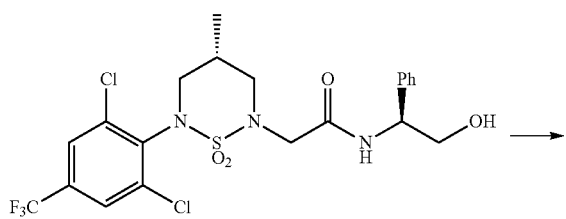

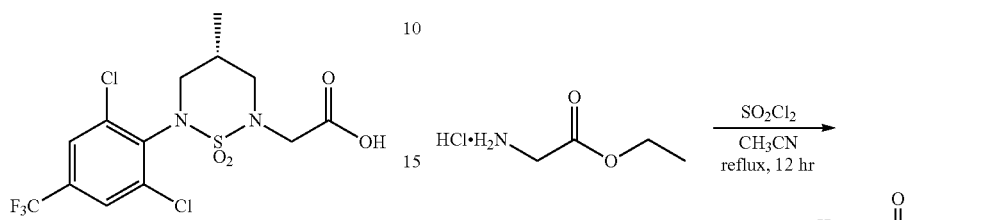

To 2-((R)-6-(2,6-dichloro-4-(trifluoromethyl)phenyl)-4-methyl-1,1-dioxido-1,2,6-thiadiazinan-2-yl)-N—((S)-2-hydroxy-1-phenylethyl)acetamide (940 mg, 1.74 mmol) in 1,4-dioxane (45 mL) and $H_2O$ (45 mL), was added 1 M $H_2SO_4$ (35 mL) and agitated for 4 days at 90° C. The reaction mixture was treated with saturated $NaHCO_3$ aqueous solution to adjust its pH to 3, and then extracted with ethyl acetate (50 mL×2). The extracted organic layer was washed with $H_2O$ (100 mL×1) and brine (100 mL×1), dried over $MgSO_4$ and concentrated under reduced pressure. The resultant was dried under vacuum to yield the compound of interest (360 mg, 77%, white solid). $^1H$ NMR (300 MHz, $CDCl_3$): δ 7.67 (s, 1H), 7.64 (s, 1H), 4.51-4.45 (m, 1H), 4.12-3.90 (m, 3H), 3.49-3.40 (m, 1H), 3.26-3.19 (m, 1H), 2.58 (m, 1H), 0.95 (d, 3H, J=6.6 Hz).

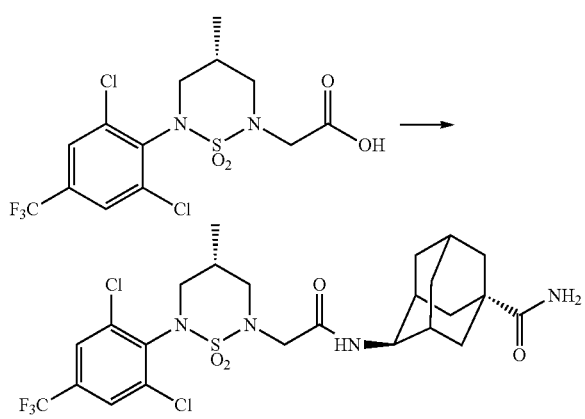

To adamantyl amine hydrochloride (288 mg, 1.25 mmol) in DMSO (900 mg), were successively added DIPEA (821 mg, 6.25 mol), i-PrOH (45 mL), (R)-2-(6-(2,6-dichloro-4-(trifluoromethyl)phenyl)-4-methyl-1,1-dioxido-1,2,6-thiadiazinan-2-yl)acetic acid (527 mg, 1.25 mmol), EDCI (479 mg, 2.50 mmol) and HOBt (338 mg, 2.50 mmol), and agitated for 12 hr at room temperature. After concentration at 50° C. under reduced pressure, the resultant was added with saturated $NH_4Cl$ solution (25 mL), kept to stand for 1 hr for crystallization, filtered and washed three times with water (20 mL). The filtered solid was purified by column chromatography (dichloromethane:methanol=97:3) to yield the compound of interest (384 mg, 51%, white solid). $^1H$ NMR (300 MHz, $CDCl_3$): δ 7.68 (s, 1H), 7.65 (s, 1H), 6.95 (d, 1H, J=8.0 Hz), 5.51 (s, 1H), 5.16 (s, 1H), 4.40-4.34 (m, 1H), 4.13-3.91 (m, 3H), 3.79-3.73 (m, 1H), 3.36-3.21 (m, 2H), 2.62-2.56 (m, 1H), 2.18-1.56 (m, 13H), 0.97 (d, 3H, J=6.7 Hz). LC/MS $MH^+$ 597

Compound 172

Ethyl 2-((chlorosulfonyl)amino)acetate

To glycine ethylester hydrochloride (5.00 g, 35.8 mmol) in $CH_3CN$ (200 mL), was added sulfuryl chloride (29.00 g, 214.8 mmol), refluxed for 12 hr, and concentrated under reduced pressure. To the reaction mixture, was diethyl ether (100 mL), concentrated under reduced pressure (2×), and dried under vacuum. The resultant was used without further purification.

Ethyl 2-((N-2,4,6-trichlorophenyl)sulfamoyl)amino)acetate

Ethyl 2-((chlorosulfonyl)amino)acetate (18.50 g, 91.75 mmol) was dissolved in $CH_2Cl_2$ (200 mL) and cooled to −20° C. To the solution of ethyl 2-((chlorosulfonyl)amino)acetate, was dropwisely added 2,4,6-trichloroaniline (7.21 g, 36.7 mmol) and triethylamine (18.57 g, 183.50 mmol) in dichloromethane (120 mL) and agitated for 12 hr at room temperature. The reaction mixture was added with water (100 mL) for extraction to obtain the organic layer. The resultant was dried over $MgSO_4$, concentrated under reduced pressure, and purified by column chromatography (hexane:ethyl acetate=7:3), giving the compound of interest (2.12 g, 16%, yellow solid). $^1H$ NMR (300 MHz, $CDCl_3$): δ 7.41 (s, 2H), 6.58 (s, 1H), 5.22 (brs, 1H), 4.31-4.24 (q, J=7.14, 7.17, 7.11 Hz, 2H), 4.08-4.06 (d, 2H, J=5.5 Hz), 1.34-1.29 (t, 3H, J=7.1, 7.2 Hz).

Ethyl 2-(4-hydroxy-1,1-dioxido-6-(2,4,6-trichlorophenyl)-1,2,6-thiadiazinan-2-yl)acetate

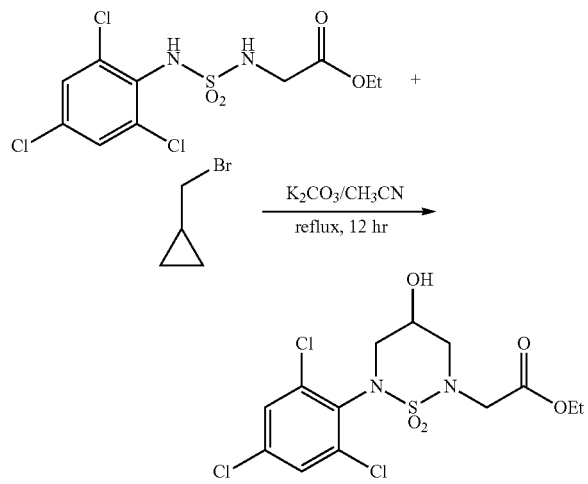

Ethyl 2-((N-2,4,6-trichlorophenyl)sulfamoyl)amino)acetate (1.00 g, 2.88 mmol) and epibromohydrin (0.79 g, 5.75 mmol) were anhydrous acetonitrile (50 mL). To the reaction mixture, was added $K_2CO_3$ (1.19 g, 8.63 mmol) and refluxed for 12 hr at 85° C. The resultant was treated with ethyl acetate (200 mL) and saturated brine (200 mL) to extract the organic layer. The organic layer was dried over $MgSO_4$, concentrated under reduced pressure, and recrystallized using ethyl acetate, giving the compound of interest (0.42 g, 36%, light apricot-colored solid). $^1H$ NMR (300 MHz, $CDCl_3$): δ 7.80-7.77 (m, 2H), 5.40 (brs, 1H), 4.31 (s, 2H), 4.15-4.07 (m, 3H), 3.83-3.57 (m, 4H), 1.20-1.16 (t, 3H, J=7.1, 7.1 Hz).

Ethyl 2-(1,1-dioxido-4-oxo-6-(2,4,6-trichlorophenyl)-1,2,6-thiadiazinan-2-yl)acetate

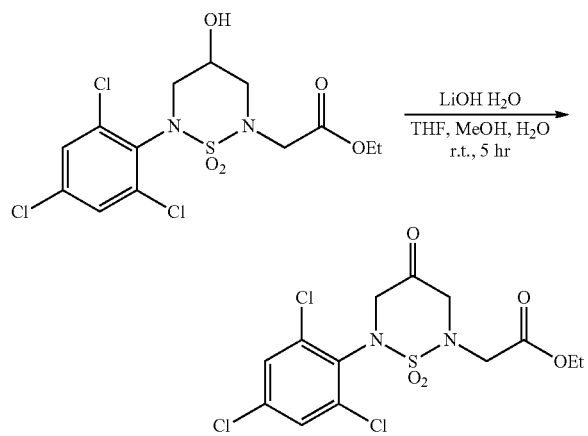

To ethyl 2-(4-hydroxy-1,1-dioxido-6-(2,4,6-trichlorophenyl)-1,2,6-thiadiazinan-2-yl)acetate (400 mg, 0.96 mmol) in dichloromethane (20 mL), was added Dess-Martin periodinane (1.30 g, 3.07 mmol) and agitated for 5 hr at room temperature. The resultant was washed with ethyl acetate (50 mL) and the white solid formed thus was filtered through celite upon washing with ethyl acetate (50 mL). The filtrate was concentrated under reduced pressure, and purified by column chromatography (hexane:ethyl acetate=7:3), giving the compound of interest (344 mg, 86%, white solid). $^1H$ NMR (300 MHz, DMSO-$d_6$): δ 7.83 (s, 2H), 4.45 (s, 2H), 4.40 (s, 2H), 4.25 (s, 2H), 4.18-4.10 (q, 2H, J=7.1, 7.1, 7.1 Hz), 1.22-1.17 (t, 3H, J=7.1, 7.1 Hz).

Ethyl 2-(4,4-difluoro-1,1-dioxido-6-(2,4,6-trichlorophenyl)-1,2,6-thiadiazinan-2-yl)acetate

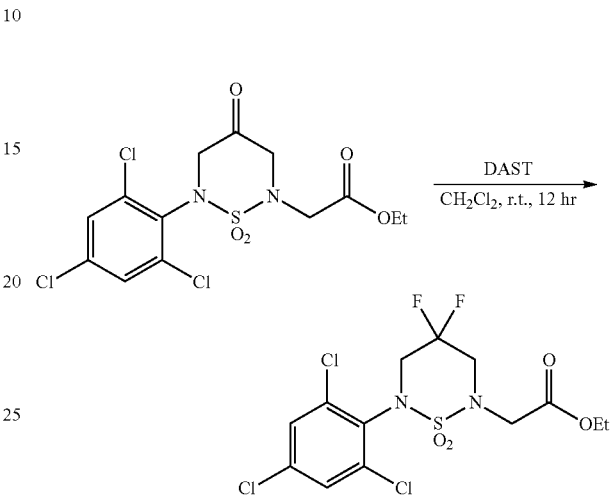

To ethyl 2-(1,1-dioxido-4-oxo-6-(2,4,6-trichlorophenyl)-1,2,6-thiadiazinan-2-yl)acetate (50 mg, 0.12 mmol) in dichloromethane (10 mL), was added DAST (97 mg, 0.60 mmol) and agitated for 12 hr at room temperature. The reaction mixture was slowly quenched with saturated $NaHCO_3$, diluted with dichloromethane (20 mL), and added with water (30 mL), followed by extraction of the organic layer. The organic layer was dried over $MgSO_4$, concentrated under reduced pressure and purified by column chromatography (hexane:ethyl acetate=7:3) to yield the compound of interest (40 mg, 75%, yellow solid). $^1H$ NMR (300 MHz, $CDCl_3$): δ 7.43 (s, 2H), 4.34 (s, 2H), 4.28-4.21 (q, 2H, J=7.1, 7.1, 7.2 Hz), 4.17-4.03 (m, 4H), 1.32-1.25 (t, 3H, J=7.1, 7.1 Hz).

2-(4,4-difluoro-1,1-dioxido-6-(2,4,6-trichlorophenyl)-1,2,6-thiadiazinan-2-yl)acetic acid

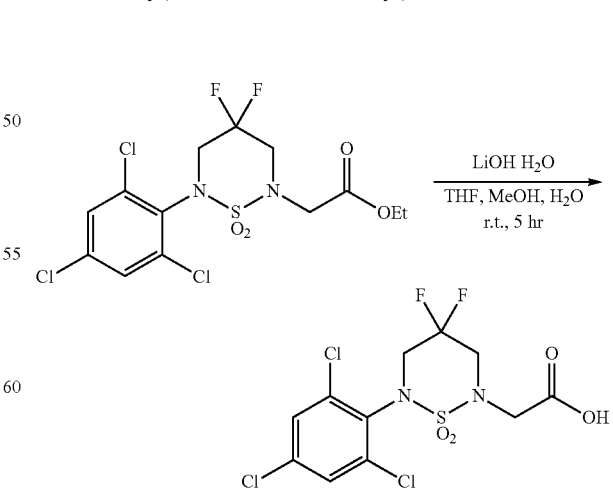

To ethyl 2-(4,4-difluoro-1,1-dioxido-6-(2,4,6-trichlorophenyl)-1,2,6-thiadiazinan-2-yl)acetate (40 mg, 0.10 mmol) in THF (10 mL) and MeOH (10 mL), was dropwisely added LiOH monohydrate (21 mg, 0.50 mmol) in water (3 mL) and agitated for 5 hr at room temperature. After addition of ethyl acetate (30 mL) and water (30 mL), pH of the resultant was adjusted to 3 with 1 N HCl and extracted to obtain the organic layer. The organic layer was dried over MgSO$_4$, concentrated under reduced pressure, and crystallized with ethyl acetate (1 mL) and hexane (10 mL), giving the compound of interest (33 mg, 80%, white solid). $^1$H NMR (300 MHz, CDCl$_3$): δ 7.44 (s, 2H), 4.35 (s, 2H), 4.14-4.03 (m, 4H).

4-(2-(4,4-difluoro-1,1-dioxido-6-(2,4,6-trichlorophenyl)-1,2,6-thiadiazinan-2-yl)acetamido)adamantan-1-carboxamide (E form)

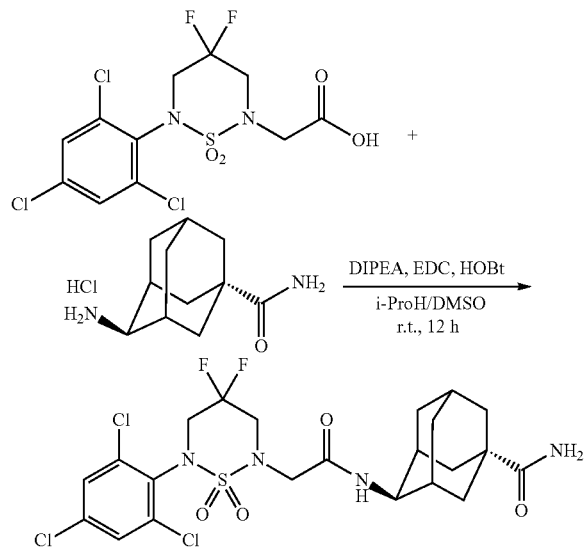

To adamantyl amine hydrochloride (16 mg, 0.07 mmol) in DMSO (500 mg), were successively added DIPEA (46 mg, 0.35 mmol), i-PrOH (5 mL), 2-(4,4-difluoro-1,1-dioxido-6-(2,4,6-trichlorophenyl)-1,2,6-thiadiazinan-2-yl)acetic acid (33 mg, 0.08 mmol), EDCI (27 mg, 0.14 mmol) and HOBt (21 mg, 0.14 mmol), and agitated for 12 hr at room temperature. After concentration at 50° C. under reduced pressure, the resultant was added with saturated NH$_4$Cl solution (10 mL), kept to stand for 1 hr for crystallization, filtered and washed three times with water (10 mL). The filtered solid was purified by column chromatography (dichloromethane:methanol=97:3) to yield the compound of interest (18 mg, 38%, white solid). $^1$H NMR (300 MHz, CDCl$_3$): δ 7.44 (s, 2H), 6.67 (d, 1H J=8.0 Hz), 5.54 (s, 1H), 5.24 (s, 1H), 4.21 (s, 2H), 4.14-4.01 (m, 5H), 2.10-1.56 (m, 13H).

Experimental Examples

Pharmacological Tests

The compounds prepared above and their pharmaceutically acceptable add addition salts were tested for their 11β-HSD1 inhibition activity as follows:

(1) Enzyme Sources

The full-length cDNA molecule coding for human or mouse 11β-HSD1 was inserted into pcDNA (Promega) as mammalian expression vectors and transformed into CHO cells for 5 hr using Lipofectamine plus (Invitrogen) in accordance with manufacturer's manual, followed by stabilization for 48 hr. The CHO cells were incubated with 0.8 μg/ml puromycin (Sigma) once every three days for two weeks to obtain human or mouse 11β-HSD1 overexpressing cells. The cells were grown and frozen, and thawed for enzyme inhibition tests.

(2) Measurement of Enzyme Inhibition Constant

The in vitro inhibitory activities of the novel compounds to human 11β-HSD1 were evaluated in accordance with homogenous time-resolved fluorescence (HTRF).

The human or mouse 11β-HSD1 overexpressing cells were subcultured at the number of 2.5×10$^4$ cells in 96-well plate and stabilized for 24 hr. The cells in each well were incubated with 100 μl of medium containing 160 nM cortisone (Sigma) and diluted compound for 3 hr at 37° C. in an incubator. Then, samples of the medium (10 μl) were transferred to 384-well plate and the amounts of cortisol produced were measured using a cortisol kit (Cisbio international) in accordance with manufacturer's instruction. The control group was incubated with 160 nM cortisone and 0.1% DMSO. The background value was obtained with no use of cells from samples containing 160 nM cortisone and 0.1% DMSO. The % inhibitory activity was calculated as follows:

Ratio=Fluorescent value measured at 665 nm/Fluorescent value measured at 620 nm×10$^4$   1.

Delta F value=(Ratio of compounds−Ratio of negative)/Ratio of negative×100   2.

Normalized value=Delta F value of compounds−Delta F value of control   3.

% inhibition=Normalized value of compounds/Normalized value of background×100   4.

The inhibitory potentials of compounds were calculated as IC$_{50}$ values, which are summarized in Table 33.

TABLE 33

| No. of Compounds | IC$_{50}$(nM) to 11β-HSD-1 | IC$_{50}$(nM) to 11β-HSD-2 |
|---|---|---|
| Compound 3 | 363 | >10,000 |
| Compound 5 | 360 | >10,000 |
| Compound 14 | 1660 | >10,000 |
| Compound 2 | 12 | >10,000 |
| Compound 24 | 3370 | >10,000 |
| Compound 60 | 17 | >10,000 |
| Compound 59 | 14 | >10,000 |
| Compound 69 | 3 | >10,000 |
| Compound 44 | 79 | >10,000 |
| Compound 89 | 20 | >10,000 |
| Compound 88 | 0.2 | >10,000 |
| Compound 124 | 187 | >10,000 |
| Compound 122 | 0.4 | >10,000 |
| Compound 123 | 0.8 | >10,000 |
| Compound 128 | 0.1 | >10,000 |
| Compound 156 | 1.0 | >10,000 |
| Compound 175 | 14 | >10,000 |
| Compound 176 | 5 | >10,000 |
| Compound 177 | 5 | >10,000 |
| Compound 183 | 4.8 | >10,000 |
| Compound 195 | — | >10,000 |
| Compound 196 | 1.3 | >10,000 |
| Compound 172 | — | >10,000 |

As indicated in Table 33 showing HTRF analysis results to human 11β-HSD-1 and 11β-HSD-2, the compounds of the present invention exhibit inhibitory activity to human 11β-HSD-1. The inhibitory activity was shown to be specific in the senses that the compounds of the present invention inhibited the activity of 11β-HSD-1 but did not inhibit the activity of 11β-HSD-2.

Consequently, it would be appreciated that the cyclic sulfamide derivatives with an adamantyl group and their pharmaceutically acceptable salts having significant inhibition activity to 11β-HSD1 are very useful in prevention or treatment of 11β-HSD-associated diseases including insulin-dependent diabetes (type 1 diabetes), insulin-independent diabetes (type 2 diabetes) and immune diseases.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A sulfamide derivative having an adamantyl group represented by the following Formula 1, or its pharmaceutically acceptable salt:

Chemical Formula 1

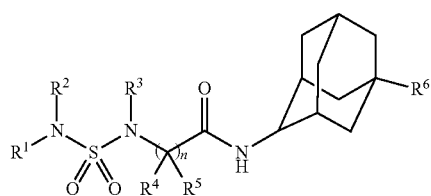

wherein $R^1$ represents H; $C_1$-$C_4$ alkyl; cyano $C_1$-$C_4$ alkyl; $C_3$-$C_8$ cycloalkyl; benzyl unsubstituted or substituted with halogen, $C_1$-$C_4$ alkyl or $OCX_3$ (X is halogen); phenylethyl; $C_1$-$C_6$ alkoxycarbonyl; phenylacetyl; naphthyl; or phenyl unsubstituted or substituted with halogen, $C_1$-$C_4$ alkyl, $C_3$-$C_8$ cycloalkyl, $C_1$-$C_6$ alkoxy, $CX_3$ (X is halogen), $OCX_3$ (X is halogen), cyano, nitro, acetamido, ethylureido, phenyl or 5-10 membered heteroaryl; $R^2$ and $R^3$ bind together to form a ring structure, the ring structure is

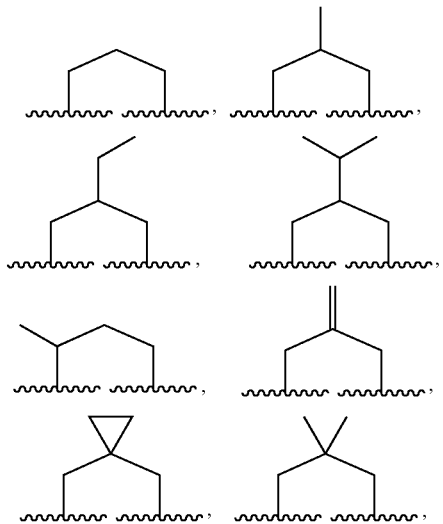

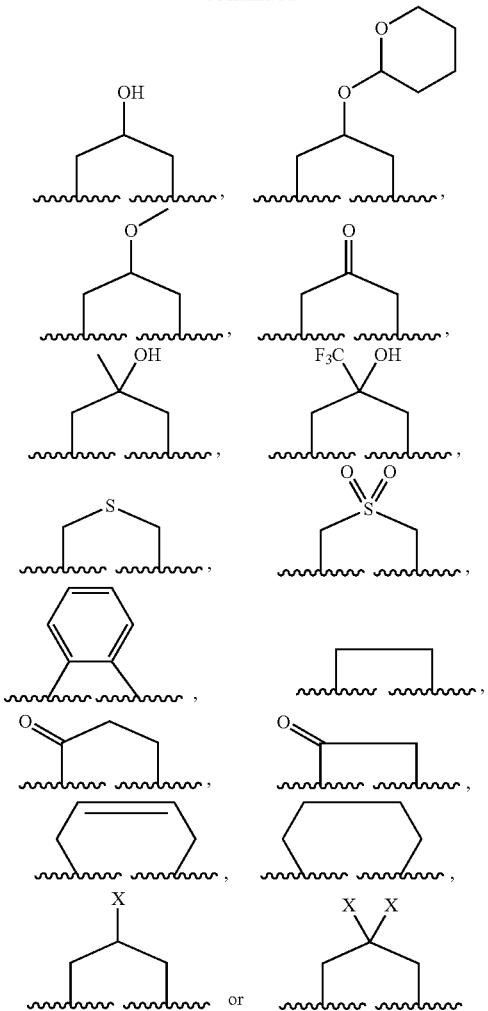

(X is halogen); $R^4$ and $R^5$ independently represent H; or $C_1$-$C_4$ alkyl; $R^6$ represents H; OH; $COOR^7$; or $CONR^7R^7$; $R^7$ represents H; or $C_1$-$C_4$ alkyl; and n represents an integer of 1.

2. The sulfamide derivative or its pharmaceutically acceptable salt according to claim 1, wherein $R^1$ represents phenyl unsubstituted or substituted with halogen, $C_1$-$C_4$ alkyl or $CF_3$, $OCF_3$, cyano, nitro, acetamido, ethylureido, phenyl or 5-10 membered heteroaryl.

3. The sulfamide derivative or its pharmaceutically acceptable salt according to claim 1, wherein the derivative represented by the Formula 1 is selected from the group consisting of:

(1) N-(adamantan-2-yl)-2-(1,1-dioxido-6-(2-oxo-2-phenylethyl)-1,2,6-thiadiazinan-2-yl)acetamide;
(2) N-(adamantan-2-yl)-2-(1,1-dioxido-6-phenyl-1,2,6-thiadiazinan-2-yl)acetamide;
(3) tert-butyl 6-(2-(adamantan-2-ylamino)-2-oxoethyl)-1,2,6-thiadiazinan-2-carboxylate-1,1-dioxide;
(4) N-(adamantan-2-yl)-2-(1,1-dioxido-1,2,6-thiadiazinan-2-yl)acetamide hydro chloride;
(5) N-(adamantan-2-yl)-2-(6-benzyl-1,1-dioxido-1,2,6-thiadiazinan-2-yl)acetamide;
(6) N-(adamantan-2-yl)-2-(6-(4-fluorobenzyl)-1,1-dioxido-1,2,6-thiadiazinan-2-yl)acetamide;
(7) N-(adamantan-2-yl)-2-(1,1-dioxido-6-(4-(trifluoromethoxy)benzyl)-1,2,6-thiadiazinan-2-yl)acetamide;

(8) N-(adamantan-2-yl)-2-(6-(4-chlorobenzyl)-1,1-dioxido-1,2,6-thiadiazinan-2-yl)acetamide;
(9) N-(adamantan-2-yl)-2-(6-(3-methylbenzyl)-1,1-dioxido-1,2,6-thiadiazinan-2-yl)acetamide;
(10) N-(adamantan-2-yl)-2-(6-(3-chlorobenzyl)-1,1-dioxido-1,2,6-thiadiazinan-2-yl)acetamide;
(11) N-(adamantan-2-yl)-2-(6-(3-fluorobenzyl)-1,1-dioxido-1,2,6-thiadiazinan-2-yl)acetamide;
(12) N-(adamantan-2-yl)-2-(6-(3-methoxybenzyl)-1,1-dioxido-1,2,6-thiadiazinan-2-yl)acetamide;
(13) N-(adamantan-2-yl)-2-(6-(2-chlorobenzyl)-1,1-dioxido-1,2,6-thiadiazinan-2-yl)acetamide;
(14) N-(adamantan-2-yl)-2-(6-(2-fluorobenzyl)-1,1-dioxido-1,2,6-thiadiazinan-2-yl)acetamide;
(15) N-(adamantan-2-yl)-2-(1,1-dioxido-6-phenethyl-1,2,6-thiadiazinan-2-yl)acetamide;
(16) N-(adamantan-2-yl)-2-(6-(3-fluorophenyl)-1,1-dioxido-1,2,6-thiadiazinan-2-yl)acetamide;
(17) N-(adamantan-2-yl)-2-(6-(3-chlorophenyl)-1,1-dioxido-1,2,6-thiadiazinan-2-yl)acetamide;
(18) N-(adamantan-2-yl)-2-(6-(4-fluorophenyl)-1,1-dioxido-1,2,6-thiadiazinan-2-yl)acetamide;
(19) N-(adamantan-2-yl)-2-(6-(4-chlorophenyl)-1,1-dioxido-1,2,6-thiadiazinan-2-yl)acetamide;
(20) N-(adamantan-2-yl)-2-(6-(4-methoxyphenyl)-1,1-dioxido-1,2,6-thiadiazinan-2-yl)acetamide;
(21) N-(adamantan-2-yl)-2-(6-(3-methoxyphenyl)-1,1-dioxido-1,2,6-thiadiazinan-2-yl)acetamide;
(22) N-(adamantan-2-yl)-2-(6-(2-fluorophenyl)-1,1-dioxido-1,2,6-thiadiazinan-2-yl)acetamide;
(23) N-(adamantan-2-yl)-2-(6-(3,4-dichlorophenyl)-1,1-dioxido-1,2,6-thiadiazinan-2-yl)acetamide;
(24) N-(adamantan-2-yl)-2-(1,1-dioxido-6-(p-tolyl)-1,2,6-thiadiazinan-2-yl)acetamide;
(25) N-(adamantan-2-yl)-2-(1,1-dioxido-5-phenyl-1,2,5-thiadiazolidin-2-yl)acetamide;
(26) N-(adamantan-2-yl)-2-(6-methyl-1,1-dioxido-1,2,6-thiadiazinan-2-yl)acetamide;
(27) N-(adamantan-2-yl)-2-(6-(4-chlorophenyl)-1,1-dioxido-1,2,6-thiadiazinan-2-yl)acetamide;
(28) Methyl-4-(2-(6-(4-chlorophenyl)-1,1-dioxido-1,2,6-thiadiazinan-2-yl) acetamido)adamantan-1-carboxylate;
(29) 4-(2-(6-(4-chlorophenyl)-1,1-dioxido-1,2,6-thiadiazinan-2-yl)acetamido) adamantan-1-carboxylic acid;
(30) N-(adamantan-2-yl)-2-(1,1-dioxido-6-(4-(trifluoromethyl)phenyl)-1,2,6-thiadiazinan-2-yl)acetamide;
(31) N-(adamantan-2-yl)-2-(6-(4-cyanophenyl)-1,1-dioxido-1,2,6-thiadiazinan-2-yl)acetamide;
(32) N-(adamantan-2-yl)-2-(6-(naphthalene-2-yl)-1,1-dioxido-1,2,6-thiadiazinan-2-yl)acetamide;
(33) Methyl-4-(2-(1,1-dioxido-6-phenyl-1,2,6-thiadiazinan-2-yl)acetamido)adamantan-1-carboxylate;
(34) 4-(2-(6-(4-chlorophenyl)-1,1-dioxido-1,2,6-thiadiazinan-2-yl)acetamido)adamantan-1-carboxamide;
(35) N-(adamantan-2-yl)-2-(6-cyclohexyl-1,1-dioxido-1,2,6-thiadiazinan-2-yl)acetamide;
(36) 4-(2-(1,1-dioxido-6-phenyl-1,2,6-thiadiazinan-2-yl)acetamido)adamantan-1-carboxylic acid;
(37) 2-(6-(4-chlorophenyl)-1,1-dioxido-1,2,6-thiadiazinan-2-yl)-N-(5-hydroxyadamantan-2-yl)acetamide;
(38) 2-(1,1-dioxido-6-phenyl-1,2,6-thiadiazinan-2-yl)-N-(5-hydroxyadamantan-2-yl)acetamide;
(39) 2-(1,1-dioxido-6-phenyl-1,2,6-thiadiazinan-2-yl)-N-(5-hydroxyadamantan-2-yl)acetamide;
(40) 2-(6-(4-fluorophenyl)-1,1-dioxido-1,2,6-thiadiazinan-2-yl)-N-(5-hydroxyadamantan-2-yl)acetamide;
(41) 2-(6-(2-fluorophenyl)-1,1-dioxido-1,2,6-thiadiazinan-2-yl)-N-(5-hydroxyadamantan-2-yl)acetamide;
(42) 4-(2-(6-(2-fluorophenyl)-1,1-dioxido-1,2,6-thiadiazinan-2-yl)acetamido)adamantan-1-carboxamide;
(43) 4-(2-(6-(2-fluorophenyl)-1,1-dioxido-1,2,6-thiadiazinan-2-yl)acetamido)adamantan-1-carboxamide;
(44) 4-(2-(6-(4-fluorophenyl)-1,1-dioxido-1,2,6-thiadiazinan-2-yl)acetamido)adamantan-1-carboxamide;
(45) 4-(2-(6-(4-fluorophenyl)-1,1-dioxido-1,2,6-thiadiazinan-2-yl)acetamido)adamantan-1-carboxamide;
(46) 2-(6-(3,4-dichlorophenyl)-1,1-dioxido-1,2,6-thiadiazinan-2-yl)-N-(5-hydroxyadamantan-2-yl)acetamide;
(47) 2-(6-(3-chlorophenyl)-1,1-dioxido-1,2,6-thiadiazinan-2-yl)-N-(5-hydroxyadamantan-2-yl)acetamide;
(48) N-(adamantan-2-yl)-2-(6-ethyl-1,1-dioxido-1,2,6-thiadiazinan-2-yl)acetamide;
(49) 4-(2-(6-(3,4-dichlorophenyl)-1,1-dioxido-1,2,6-thiadiazinan-2-yl)-acetamido)adamantan-1-carboxamide;
(50) 4-(2-(6-(3,4-dichlorophenyl)-1,1-dioxido-1,2,6-thiadiazinan-2-yl)-acetamido)adamantan-1-carboxamide;
(51) N-(adamantan-2-yl)-2-(1,1-dioxido-6-(prop-2-yn-1-yl)-1,2,6-thiadiazinan-2-yl)acetamide;
(52) 4-(2-(6-(3-methoxyphenyl)-1,1-dioxido-1,2,6-thiadiazinan-2-yl)-acetamido)adamantan-1-carboxamide;
(53) 4-(2-(6-(3-methoxyphenyl)-1,1-dioxido-1,2,6-thiadiazinan-2-yl)-acetamido)adamantan-1-carboxamide;
(54) 4-(2-(1,1-dioxido-6-(p-tolyl)-1,2,6-thiadiazinan-2-yl)acetamido)adamantan-1-carboxamide;
(55) 4-(2-(1,1-dioxido-6-(p-tolyl)-1,2,6-thiadiazinan-2-yl)acetamido)adamantan-1-carboxamide;
(56) 4-(2-(6-(3-chlorophenyl)-1,1-dioxido-1,2,6-thiadiazinan-2-yl)-acetamido)adamantan-1-carboxamide;
(57) N-(5-hydroxyadamantan-2-yl)-2-(6-(napthalene-2-yl)-1,1-dioxido-1,2,6-thiadiazinan-2-yl)acetamide;
(58) 2-(6-(4-cyanophenyl)-1,1-dioxido-1,2,6-thiadiazinan-2-yl)-N-(5-hydroxyadamantan-2-yl)acetamide;
(59) 4-(2-(6-(2-fluorophenyl)-1,1-dioxido-1,2,6-thiadiazinan-2-yl)-acetamido)adamantan-1-carboxamide;
(60) 4-(2-(1,1-dioxido-6-phenyl-1,2,6-thiadiazinan-2-yl)acetamido)adamantan-1-carboxamide;
(61) 4-(2-(1,1-dioxido-5-phenyl-1,2,5-thiadiazolidin-2-yl)acetamido)adamantan-1-carboxamide;
(62) 4-(2-(1,1-dioxido-6-(4-(trifluoromethyl)phenyl-1,2,6-thiadiazinan-2-yl)acetamido)adamantan-1-carboxamide;
(63) 4-(2-(6-(napthalene-2-yl)-1,1-dioxido-1,2,6-thiadiazinan-2-yl)acetamido)adamantan-1-carboxamide;
(64) 4-(2-(5-(2-fluorophenyl)-1,1-dioxido-1,2,5-thiadiazolidin-2-yl)acetamido)adamantan-1-carboxamide;
(65) 4-(2-(5-(2-chlorophenyl)-1,1-dioxido-1,2,5-thiadiazolidin-2-yl)acetamido)adamantan-1-carboxamide;
(66) 4-(2-(5-(4-fluorophenyl)-1,1-dioxido-1,2,5-thiadiazolidin-2-yl)acetamido)adamantan-1-carboxamide;
(67) N-(adamantan-2-yl)-2-(5-(2-chlorophenyl)-1,1-dioxido-1,2,5-thiadiazolidin-2-yl)acetamide;
(68) N-(adamantan-2-yl)-2-(5-(4-fluorophenyl)-1,1-dioxido-1,2,5-thiadiazolidin-2-yl)acetamide;
(69) 4-(2-(6-(3-fluorophenyl)-1,1-dioxido-1,2,6-thiadiazinan-2-yl)acetamido)adamantan-1-carboxamide;
(70) 4-(2-(6-(4-methoxyphenyl)-1,1-dioxido-1,2,6-thiadiazinan-2-yl)acetamido)adamantan-1-carboxamide;
(71) 4-(2-(6-(4-cyanophenyl)-1,1-dioxido-1,2,6-thiadiazinan-2-yl)acetamido)adamantan-1-carboxamide;
(72) 4-(2-(6-(4-chlorophenyl)-1,1-dioxido-1,2,6-thiadiazinan-2-yl)propaneamido)adamantan-1-carboxamide;

(73) 4-(2-(6-(4-chloronaphtalene-1-yl)-1,1-dioxido-1,2,6-thiadiazinan-2-yl)acetamido)adamantan-1-carboxamide;
(74) 4-(2-(6-(3,4-dichlorophenyl)-1,1-dioxido-1,2,6-thiadiazinan-2-yl)propaneamido)adamantan-1-carboxamide;
(75) 4-(2-(6-(2,4-difluorophenyl)-1,1-dioxido-1,2,6-thiadiazinan-2-yl)acetamido)adamantan-1-carboxamide;
(76) 4-(2-(6-(3,4-difluorophenyl)-1,1-dioxido-1,2,6-thiadiazinan-2-yl)acetamido)adamantan-1-carboxamide;
(77) 4-(2-(1,1-dioxido-5-(o-tolyl)-1,2,5-thiadiazolidin-2-yl)acetamido)adamantan-1-carboxamide;
(78) 4-(2-(5-(benzo[d][1,3]dioxol-5-yl)-1,1-dioxido-1,2,5-thiadiazolidin-2-yl)acetamido)adamantan-1-carboxamide;
(79) 4-(2-(6-(3,4-difluorophenyl)-1,1-dioxido-1,2,6-thiadiazinan-2-yl)propanemido)adamantan-1-carboxamide;
(80) 4-(2-(6-(2,4-difluorophenyl)-1,1-dioxido-1,2,6-thiadiazinan-2-yl)propaneamido)adamantan-1-carboxamide;
(81) 4-(2-(6-(benzo[d][1,3]dioxol-5-yl)-1,1-dioxido-1,2,6-thiadiazinan-2-yl)acetamido)adamantan-1-carboxamide;
(82) 4-(2-(6-(benzo[d][1,3]dioxol-5-yl)-1,1-dioxido-1,2,6-thiadiazinan-2-yl)propaneamido)adamantan-1-carboxamide;
(83) 4-(2-(6-(2-fluorophenyl)-1,1-dioxido-1,2,6-thiadiazinan-2-yl)acetamido)adamantan-1-carboxamide;
(84) 4-(2-(6-(2-fluorophenyl)-1,1-dioxido-1,2,6-thiadiazinan-2-yl)acetamido)adamantan-1-carboxamide;
(85) 4-(2-(6-(2,5-difluorophenyl)-1,1-dioxido-1,2,6-thiadiazinan-2-yl)acetamido) adamantan-1-carboxamide;
(86) 4-(2-(6-(2,5-difluorophenyl)-1,1-dioxido-1,2,6-thiadiazinan-2-yl)acetamido) adamantan-1-carboxamide;
(87) 4-(2-(1,1-dioxido-6-(2,4,6-trichlorophenyl)-1,2,6-thiadiazinan-2-yl)acetamido)adamantan-1-carboxamide;
(88) 4-(2-(1,1-dioxido-6-(2,4,6-trichlorophenyl)-1,2,6-thiadiazinan-2-yl)acetamido)adamantan-1-carboxamide;
(89) 4-(2-(1,1-dioxido-6-(2,4,6-trifluorophenyl)-1,2,6-thiadiazinan-2-yl)acetamido)adamantan-1-carboxamide;
(90) 4-(2-(1,1-dioxido-6-(2,4,6-trifluorophenyl)-1,2,6-thiadiazinan-2-yl)acetamido)adamantan-1-carboxamide;
(91) 4-(2-(6-(2-chlorophenyl)-1,1-dioxido-1,2,6-thiadiazinan-2-yl)acetamido)adamantan-1-carboxamide;
(92) 4-(2-(6-(2-chlorophenyl)-1,1-dioxido-1,2,6-thiadiazinan-2-yl)acetamido)adamantan-1-carboxamide;
(93) 4-(2-(6-(2-fluorophenyl)-1,1-dioxido-1,2,6-thiadiazinan-2-yl)propaneamido)adamantan-1-carboxamide;
(94) 4-(2-(6-(2-fluorophenyl)-1,1-dioxido-1,2,6-thiadiazinan-2-yl)propaneamido)adamantan-1-carboxamide;
(95) 4-(2-(6-(2-bromophenyl)-1,1-dioxido-1,2,6-thiadiazinan-2-yl)acetamido)adamantan-1-carboxamide;
(96) 4-(2-(1,1-dioxido-6-(2,4,5-trifluorophenyl)-1,2,6-thiadiazinan-2-yl)acetamido)adamantan-1-carboxamide;
(97) 4-(2-(6-(2-fluorophenyl)-1,1-dioxido-1,2,6-thiadiazinan-2-yl)methylpropaneamido)adamantan-1-carboxamide;
(98) 4-(2-(6-(2-fluorophenyl)-1,1-dioxido-1,2,6-thiadiazinan-2-yl)methylpropaneamido)adamantan-1-carboxamide;
(99) 4-(2-(6-(2,5-dichlorophenyl)-1,1-dioxido-1,2,6-thiadiazinan-2-yl)acetamido)adamantan-1-carboxamide;
(100) 4-(2-(1,1-dioxido-6-(2,4,5-trichlorophenyl)-1,2,6-thiadiazinan-2-yl)acetamido)adamantan-1-carboxamide;
(101) 4-(2-(1,1-dioxido-6-(2,4,5-trichlorophenyl)-1,2,6-thiadiazinan-2-yl)acetamido)adamantan-1-carboxamide;
(102) 4-(2-(6-(2,6-difluorophenyl)-1,1-dioxido-1,2,6-thiadiazinan-2-yl)acetamido)adamantan-1-carboxamide;
(103) 4-(2-(6-(2,6-difluorophenyl)-1,1-dioxido-1,2,6-thiadiazinan-2-yl)acetamido)adamantan-1-carboxamide;
(104) 4-(2-(6-(2-chloro-4-fluorophenyl)-1,1-dioxido-1,2,6-thiadiazinan-2-yl)acetamido)adamantan-1-carboxamide;
(105) 4-(2-(6-(4-chloro-2-fluorophenyl)-1,1-dioxido-1,2,6-thiadiazinan-2-yl)acetamido)adamantan-1-carboxamide;
(106) 4-(2-(6-(4-chloro-2-fluorophenyl)-1,1-dioxido-1,2,6-thiadiazinan-2-yl)acetamido)adamantan-1-carboxamide;
(107) 4-(2-(6-(2,5-dichlorophenyl)-1,1-dioxido-1,2,6-thiadiazinan-2-yl)acetamido)adamantan-1-carboxamide;
(108) 4-(2-(6-(2-bromophenyl)-1,1-dioxido-1,2,6-thiadiazinan-2-yl)acetamido)adamantan-1-carboxamide;
(109) 4-(2-(1,1-dioxido-6-(2,4,5-trifluorophenyl)-1,2,6-thiadiazinan-2-yl)acetamido)adamantan-1-carboxamide;
(110) 4-(2-(6-(2-chloro-4-fluorophenyl)-1,1-dioxido-1,2,6-thiadiazinan-2-yl)acetamido)adamantan-1-carboxamide;
(111) 4-(2-(1,1-dioxido-6-(2,3,5,6-tetrafluorophenyl)-1,2,6-thiadiazinan-2-yl)acetamido)adamantan-1-carboxamide;
(112) 4-(2-(1,1-dioxido-6-(2,3,5,6-tetrafluorophenyl)-1,2,6-thiadiazinan-2-yl)acetamido)adamantan-1-carboxamide;
(113) 4-(2-(6-(2,4-dichlorophenyl)-1,1-dioxido-1,2,6-thiadiazinan-2-yl)acetamido)adamantan-1-carboxamide;
(114) 4-(2-(6-(2,4-dichlorophenyl)-1,1-dioxido-1,2,6-thiadiazinan-2-yl)acetamido)adamantan-1-carboxamide;
(115) 4-(2-(6-(2-chloro-5-(trifluoromethyl)phenyl)-1,1-dioxido-1,2,6-thiadiazinan-2-yl)acetamido)adamantan-1-carboxamide;
(116) 4-(2-(6-(2-chloro-5-(trifluoromethyl)phenyl)-1,1-dioxido-1,2,6-thiadiazinan-2-yl)acetamido)adamantan-1-carboxamide;
(117) 4-(2-(6-(4-chloro-2-(trifluoromethyl)phenyl)-1,1-dioxido-1,2,6-thiadiazinan-2-yl)acetamido)adamantan-1-carboxamide;
(118) 4-(2-(6-(4-chloro-2-(trifluoromethyl)phenyl)-1,1-dioxido-1,2,6-thiadiazinan-2-yl)acetamido)adamantan-1-carboxamide;
(119) 4-(2-(6-(2,3-dichlorophenyl)-1,1-dioxido-1,2,6-thiadiazinan-2-yl)acetamido)adamantan-1-carboxamide;
(120) 4-(2-(6-(2,3-dichlorophenyl)-1,1-dioxido-1,2,6-thiadiazinan-2-yl)acetamido)adamantan-1-carboxamide;
(121) 4-(2-(6-(2,6-dichlorophenyl)-1,1-dioxido-1,2,6-thiadiazinan-2-yl)acetamido)adamantan-1-carboxamide;

(122) 4-(2-(1,1-dioxido-7-(2,4,6-trichlorophenyl)-1,2,7-thiadiazepane-2-yl)acetamido)adamantan-1-carboxamide;
(123) 4-(2-(methyl(N-methyl-N-(2,4,6-trichlorophenyl)sulfamoyl)amino)acetamido)adamantan-1-carboxamide;
(124) 4-(2-(1,1-dioxido-5-(2,4,6-trichlorophenyl)-1,2,5-thiadiazolidin-2-yl)acetamido)adamantan-1-carboxamide;
(125) 4-(2-(1,1-dioxido-5-(2,4,6-trichlorophenyl)-1,2,5-thiadiazolidin-2-yl)acetamido)adamantan-1-carboxamide;
(126) 4-(2-(ethyl(N-ethyl-N-(2,4,6-trichlorophenyl)sulfamoyl)amino)acetamido) adamantan-1-carboxamide;
(127) 4-(2-(methyl(N-methyl-N-(2,4,5-trichlorophenyl)sulfamoyl)amino)acetamido)adamantan-1-carboxamide;
(128) 4-(2-(3-methyl-1,1-dioxido-6-(2,4,6-trichlorophenyl)-1,2,6-thiadiazinan-2-yl)acetamido)adamantan-1-carboxamide;
(129) 4-(2-((N-(2-fluorophenyl)-N-methylsulfamoyl)(methyl)amino)acetamido) adamantan-1-carboxamide;
(130) 4-(2-(methyl(N-methyl-N-(2,4,6-trifluorophenyl)sulfamoyl)amino)acetamido)adamantan-1-carboxamide;
(131) 4-(2-(1,1-dioxido-6-(o-tolyl)-1,2,6-thiadiazinan-2-yl)acetamido)adamantan-1-carboxamide;
(132) 4-(2-(6-(2-ethylphenyl)-1,1-dioxido-1,2,6-thiadiazinan-2-yl)acetamido)adamantan-1-carboxamide;
(133) 4-(2-(6-(3-chloro-2-methylphenyl)-1,1-dioxido-1,2,6-thiadiazinan-2-yl)acetamido)adamantan-1-carboxamide;
(134) 4-(2-(6-(4-chloro-2-methylphenyl)-1,1-dioxido-1,2,6-thiadiazinan-2-yl)acetamido)adamantan-1-carboxamide;
(135) 4-(2-(6-(3-fluoro-2-methylphenyl)-1,1-dioxido-1,2,6-thiadiazinan-2-yl)acetamido)adamantan-1-carboxamide;
(136) 4-(2-(6-(4-fluoro-2-methylphenyl)-1,1-dioxido-1,2,6-thiadiazinan-2-yl)acetamido)adamantan-1-carboxamide;
(137) 4-(2-(6-(2-fluoro-6-methylphenyl)-1,1-dioxido-1,2,6-thiadiazinan-2-yl)acetamido)adamantan-1-carboxamide;
(138) 4-(2-(6-(2,6-dichloro-3-methylphenyl)-1,1-dioxido-1,2,6-thiadiazinan-2-yl) acetamido)adamantan-1-carboxamide;
(139) 4-(2-(1,1-dioxido-6-(3,4,5-trichlorophenyl)-1,2,6-thiadiazinan-2-yl)acetamido)adamantan-1-carboxamide;
(140) 4-(2-(6-(2-chloro-4,6-dimethylphenyl)-1,1-dioxido-1,2,6-thiadiazinan-2-yl) acetamido)adamantan-1-carboxamide;
(141) 4-(2-(6-(2-fluorophenyl)-1,1-dioxido-4-((tetrahydro-2H-pyran-2-yl)oxy)-1,2,6-thiadiazinan-2-yl)acetamido)adamantan-1-carboxamide;
(142) 4-(2-(6-(2-fluorophenyl)-4-hydroxy-1,1-dioxido-1,2,6-thiadiazinan-2-yl)acetamido)adamantan-1-carboxamide;
(143) 4-(2-(6-mesityl-1,1-dioxido-1,2,6-thiadiazinan-2-yl)acetamido)adamantan-1-carboxamide;
(144) 4-(2-(6-(2,5-dimethylphenyl)-1,1-dioxido-1,2,6-thiadiazinan-2-yl)acetamido)adamantan-1-carboxamide;
(145) 4-(2-(6-(2,4-dimethylphenyl)-1,1-dioxido-1,2,6-thiadiazinan-2-yl)acetamido)adamantan-1-carboxamide;
(146) 4-(2-(6-([1,1'-Biphenyl]-2-yl)-1,1-dioxido-1,2,6-thiadiazinan-2-yl)acetamido)adamantan-1-carboxamide;
(147) 4-(2-(6-(2-methoxy-6-methylphenyl)-1,1-dioxido-1,2,6-thiadiazinan-2-yl)acetamido)adamantan-1-carboxamide;
(148) 4-(2-(6-(4-methoxy-2,6-dimethylphenyl)-1,1-dioxido-1,2,6-thiadiazinan-2-yl)acetamido)adamantan-1-carboxamide;
(149) 4-(2-(6-(2-cyanophenyl)-1,1-dioxido-1,2,6-thiadiazinan-2-yl)acetamido) adamantan-1-carboxamide;
(150) 4-(2-(6-(2,6-dibromo-4-methylphenyl)-1,1-dioxido-1,2,6-thiadiazinan-2-yl)acetamido)adamantan-1-carboxamide;
(151) 4-(2-(6-(2,4-dichloro-6-methylphenyl)-1,1-dioxido-1,2,6-thiadiazinan-2-yl)acetamido)adamantan-1-carboxamide;
(152) 4-(2-(6-(4-bromo-2-chloro-6-methylphenyl)-1,1-dioxido-1,2,6-thiadiazinan-2-yl)acetamido)adamantan-1-carboxamide;
(153) 4-(2-(6-(2,4-dimethoxyphenyl)-1,1-dioxido-1,2,6-thiadiazinan-2-yl)acetamido)adamantan-1-carboxamide;
(154) 4-(2-(6-(2-acetamidophenyl)-1,1-dioxido-1,2,6-thiadiazinan-2-yl)acetamido)adamantan-1-carboxamide;
(155) 4-(2-(6-(2,3-dihydro-1H-inden-4-yl)-1,1-dioxido-1,2,6-thiadiazinan-2-yl)acetamido)adamantan-1-carboxamide;
(156) 4-(2-(4-methyl-1,1-dioxido-6-(2,4,6-trichlorophenyl)-1,2,6-thiadiazinan-2-yl)acetamido)adamantan-1-carboxamide;
(157) 4-(2-(6-(4-bromo-2,6-dimethylphenyl)-1,1-dioxido-1,2,6-thiadiazinan-2-yl)acetamido)adamantan-1-carboxamide;
(158) 4-(2-(6-(2-bromo-4,6-dimethylphenyl)-1,1-dioxido-1,2,6-thiadiazinan-2-yl)acetamido)adamantan-1-carboxamide;
(159) 4-(2-(6-(2,6-dibromo-4-fluorophenyl)-1,1-dioxido-1,2,6-thiadiazinan-2-yl)acetamido)adamantan-1-carboxamide;
(160) 4-(2-(6-(2-bromo-6-chloro-4-fluorophenyl)-1,1-dioxido-1,2,6-thiadiazinan-2-yl)acetamido)adamantan-1-carboxamide;
(161) 4-(2-(6-(2-bromo-6-chloro-4-fluorophenyl)-1,1-dioxido-1,2,6-thiadiazinan-2-yl)acetamido)adamantan-1-carboxamide;
(162) 4-(2-(1,1-dioxido-6-(2,4,6-trichlorophenyl)-1,4,2,6-dithiadiazinan-2-yl)acetamido)adamantan-1-carboxamide;
(163) 4-(2-(1,1,4,4-tetraoxido-6-(2,4,6-trichlorophenyl)-1,4,2,6-dithiadiazinan-2-yl)acetamido)adamantan-1-carboxamide;
(164) 4-(2-(4-chloro-1,1-dioxido-6-(2,4,6-trichlorophenyl)-1,2,6-thiadiazinan-2-yl)acetamido)adamantan-1-carboxamide;
(165) 4-(2-(6-(2-bromo-4-chloro-6-fluorophenyl)-1,1-dioxido-1,2,6-thiadiazinan-2-yl)acetamido)adamantan-1-carboxamide;
(166) 4-(2-(6-(2-bromo-4,6-dichlorophenyl)-1,1-dioxido-1,2,6-thiadiazinan-2-yl)acetamido)adamantan-1-carboxamide;
(167) 4-(2-(4-hydroxy-1,1-dioxido-6-(2,4,6-trichlorophenyl)-1,2,6-thiadiazinan-2-yl)acetamido)adamantan-1-carboxamide;

(168) 4-(2-(1,1-dioxido-4-oxo-6-(2,4,6-trichlorophenyl)-1,2,6-thiadiazinan-2-yl)acetamido)adamantan-1-carboxamide;
(169) 4-(2-(4-methoxy-1,1-dioxido-6-(2,4,6-trichlorophenyl)-1,2,6-thiadiazinan-2-yl)acetamido)adamantan-1-carboxamide;
(170) 4-(2-(6-(2,6-dichloro-4-(trifluoromethoxy)phenyl)-1,1-dioxido-1,2,6-thiadiazinan-2-yl)acetamido)adamantan-1-carboxamide;
(171) 4-(2-(6-(2,6-dichloro-4-(trifluoromethyl)phenyl)-1,1-dioxido-1,2,6-thiadiazinan-2-yl)acetamido)adamantan-1-carboxamide;
(172) 4-(2-(4,4-difluoro-1,1-dioxido-6-(2,4,6-trichlorophenyl)-1,2,6-thiadiazinan-2-yl)acetamido)adamantan-1-carboxamide;
(173) 4-(2-(4-hydroxy-4-methyl-1,1-dioxido-6-(2,4,6-trichlorophenyl)-1,2,6-thiadiazinan-2-yl)acetamido)adamantan-1-carboxamide;
(174) 4-(2-(4-hydroxy-1,1-dioxido-6-(2,4,6-trichlorophenyl)-4-(trifluoromethyl)-1,2,6-thiadiazinan-2-yl)acetamido)adamantan-1-carboxamide;
(175) 4-(2-(4-methylene-1,1-dioxido-6-(2,4,6-trichlorophenyl)-1,2,6-thiadiazinan-2-yl)acetamido)adamantan-1-carboxamide;
(176) 4-(2-(6,6-dioxido-7-(2,4,6-trichlorophenyl)-6-thia-5,7-diazaspiro[2,5]octane-5-yl)acetamido)adamantan-1-carboxamide;
(177) 4-(2-(4,4-dimethyl-1,1-dioxido-6-(2,4,6-trichlorophenyl)-1,2,6-thiadiazinan-2-yl) acetamido)adamantan-1-carboxamide;
(178) 4-(2-(6-(2-chloro-4-(trifluoromethyl)phenyl)-1,1-dioxido-1,2,6-thiadiazinan-2-yl)acetamido)adamantan-1-carboxamide;
(179) 4-(2-(6-(4-bromo-2-(chlorophenyl)-1,1-dioxido-1,2,6-thiadiazinan-2-yl)acetamido)adamantan-1-carboxamide;
(180) 4-(2-(6-(2-bromo-4-(chlorophenyl)-1,1-dioxido-1,2,6-thiadiazinan-2-yl)acetamido)adamantan-1-carboxamide;
(181) 4-(2-(4-methyl-1,1-dioxido-6-phenyl-1,2,6-thiadiazinan-2-yl)acetamido)adamantan-1-carboxamide;
(182) 4-(2-(6-(2-bromo-4-chloro-6-fluorophenyl)-4-methyl-1,1-dioxido-1,2,6-thiadiazinan-2-yl)acetamido)adamantan-1-carboxamide;
(183) 4-(2-(6-(2,6-dichloro-4-(trifluoromethyl)phenyl)-4-methyl-1,1-dioxido-1,2,6-thiadiazinan-2-yl)acetamido)adamantan-1-carboxamide;
(184) 4-(2-(6-(2,6-dichloro-4-(trifluoromethyl)phenyl)-4-methylene-1,1-dioxido-1,2,6-thiadiazinan-2-yl)acetamido)adamantan-1-carboxamide;
(185) 4-(2-(4-methylene-1,1-dioxido-6-phenyl-1,2,6-thiadiazinan-2-yl)acetamido)adamantan-1-carboxamide;
(186) 4-(2-(6-(2-bromo-4-chloro-6-fluorophenyl)-4-methylene-1,1-dioxido-1,2,6-thiadiazinan-2-yl)acetamido)adamantan-1-carboxamide;
(187) 4-(2-(6-(4-chloro-2-iodophenyl)-4-methyl-1,1-dioxido-1,2,6-thiadiazinan-2-yl)acetamido)adamantan-1-carboxamide;
(188) 4-(2-(6-(2-iodophenyl)-4-methyl-1,1-dioxido-1,2,6-thiadiazinan-2-yl)acetamido)adamantan-1-carboxamide;
(189) 4-(2-(1,1-dioxido-4-oxo-5-(2,4,6-trichlorophenyl)-1,2,5-thiadiazolidin-2-yl) acetamido)adamantan-1-carboxamide;
(190) 4-(3-(4-methyl-1,1-dioxido-6-(2,4,6-trichlorophenyl)-1,2,6-thiadiazinan-2-yl)propaneamido)adamantan-1-carboxamide;
(191) 4-(2-(1,1-dioxido-5-oxo-6-(2,4,6-trichlorophenyl)-1,2,6-thiadiazinan-2-yl)acetamido)adamantan-1-carboxamide;
(192) 4-(2-(6-(2-chloro-4-nitrophenyl)-4-methyl-1,1-dioxido-1,2,6-thiadiazinan-2-yl)acetamido)adamantan-1-carboxamide;
(193) 4-(2-(6-(4-chloro-2-nitrophenyl)-4-methyl-1,1-dioxido-1,2,6-thiadiazinan-2-yl)acetamido)adamantan-1-carboxamide;
(194) 4-(2-(2,2-dioxidobenzo[c][1,2,5]thiadiazol-1(3H)-yl)acetamido)adamantan-1-carboxamide;
(195) 4-(2-((S)-6-(2,6-dichloro-4-(trifluoromethyl)phenyl)-4-methyl-1,1-dioxido-1,2,6-thiadiazinan-2-yl)acetamido)adamantan-1-carboxamide;
(196) 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide;
(197) 4-(2-(6-(2-chloro-4-(methylsulfonamido)phenyl)-4-methyl-1,1-dioxido-1,2,6-thiadiazinan-2-yl)acetamido)adamantan-1-carboxamide;
(198) 4-(2-(6-(4-acetamido-2-chlorophenyl)-4-methyl-1,1-dioxido-1,2,6-thiadiazinan-2-yl)acetamido)adamantan-1-carboxamide;
(199) 4-(2-(6-(2-chloro-4-(3-ethylureido)phenyl)-4-methyl-1,1-dioxido-1,2,6-thiadiazinan-2-yl)acetamido)adamantan-1-carboxamide;
(200) 4-(2-(1,1-dioxido-7-(2,4,6-trichlorophenyl)-6,7-dihydro-1,2,7-thiadiazepine-2(3H)-yl)acetamido)adamantan-1-carboxamide;
(201) 4-(2-(allyl(N-allyl-N-(2,6-dichloro-4-(trifluoromethyl)phenyl)sulfamoyl)amino)acetamido)adamantan-1-carboxamide;
(202) 4-(2-(6-(2,6-dichloro-4-(trifluoromethyl)phenyl)-4-isopropyl-1,1-dioxido-1,2,6-thiadiazinan-2-yl)acetamido)adamantan-1-carboxamide;
(203) 4-(2-((S)-4-methyl-1,1-dioxido-6-(2,4,6-trichlorophenyl)-1,2,6-thiadiazinan-2-yl)acetamido)adamantan-1-carboxamide;
(204) 4-(2-((R)-4-methyl-1,1-dioxido-6-(2,4,6-trichlorophenyl)-1,2,6-thiadiazinan-2-yl)acetamido)adamantan-1-carboxamide;
(205) 4-(2-(6-(2,6-dichloro-4-(trifluoromethyl)phenyl)-4-ethyl-1,1-dioxido-1,2,6-thiadiazinan-2-yl)acetamido)adamantan-1-carboxamide;
(206) 4-(2-(4-methyl-1,1-dioxido-6-(pyridine-2-yl)-1,2,6-thiadiazinan-2-yl)acetamido)adamantan-1-carboxamide;
(207) 4-(2-(4-methyl-6-(5-nitropyridine-2-yl)-1,1-dioxido-1,2,6-thiadiazinan-2-yl)acetamido)adamantan-1-carboxamide;
(208) 4-(2-(4-methyl-1,1-dioxido-6-(5-(trifluoromethyl)pyridine-2-yl)-1,2,6-thiadiazinan-2-yl)acetamido)adamantan-1-carboxamide;
(209) 4-(2-(6-(4-bromo-2,6-dichlorophenyl)-4-methyl-1,1-dioxido-1,2,6-thiadiazinan-2-yl)acetamido)adamantan-1-carboxamide;
(210) 4-(2-(6-(3,5-dichloro-[1,1'-biphenyl]-4-yl)-4-methyl-1,1-dioxido-1,2,6-thiadiazinan-2-yl)acetamido)adamantan-1-carboxamide;
(211) 4-(2-(6-(3,5-dichloro-2',4'-difluoro-[1,1'-biphenyl]-4-yl)-4-methyl-1,1-dioxido-1,2,6-thiadiazinan-2-yl)acetamido)adamantan-1-carboxamide;
(212) 4-(2-(6-(2,6-dichloro-4-(puran-2-yl)phenyl)-4-methyl-1,1-dioxido-1,2,6-thiadiazinan-2-yl)acetamido)adamantan-1-carboxamide;

(213) 4-(2-(6-(2,6-dichloro-4-cyanophenyl)-4-methyl-1,1-dioxido-1,2,6-thiadiazinan-2-yl)acetamido)adamantan-1-carboxamide;

(214) 4-(2-(6-(2,6-dichloro-4-methylphenyl)-4-methyl-1,1-dioxido-1,2,6-thiadiazinan-2-yl)acetamido)adamantan-1-carboxamide;

(215) 4-(2-(6-(2,6-dichloro-4-propylphenyl)-4-methyl-1,1-dioxido-1,2,6-thiadiazinan-2-yl)acetamido)adamantan-1-carboxamide; and (216) 4-(2-(6-(2,6-dichloro-4-cyclopropylphenyl)-4-methyl-1,1-dioxido-1,2,6-thiadiazinan-2-yl)acetamido)adamantan-1-carboxamide.

4. The sulfamide derivative or its pharmaceutically acceptable salt according to claim 1, wherein the derivative represented by the following Formula 1 is selected from the group consisting of 4-(2-(6-(3-fluorophenyl)-1,1-dioxido-1,2,6-thiadiazinan-2-yl)acetamido)adamantan-1-carboxamide; 4-(2-(1,1-dioxido-6-(2,4,6-trichlorophenyl)-1,2,6-thiadiazinan-2-yl)acetamido)adamantan-1-carboxamide (E); 4-(2-(1,1-dioxido-7-(2,4,6-trichlorophenyl)-1,2,7-thiadiazepane-2-yl)acetamido)adamantan-1-carboxamide; 4-(2-(methyl(N-methyl-N-(2,4,6-trichlorophenyl)sulfamoyl)amino)acetamido)adamantan-1-carboxamide; 4-(2-(4-methyl-1,1-dioxido-6-(2,4,6-trichlorophenyl)-1,2,6-thiadiazinan-2-yl)acetamido)adamantan-1-carboxamide; 4-(2-(4-methyl-1,1-dioxido-6-(2,4,6-trichlorophenyl)-1,2,6-thiadiazinan-2-yl)acetamido)adamantan-1-carboxamide; 4-(2-(6-(2,6-dichloro-4-(trifluoromethyl)phenyl)-4-methyl-1,1-dioxido-1,2,6-thiadiazinan-2-yl)acetamido)adamantan-1-carboxamide; 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide; 4-(2-((S)-4-methyl-1,1-dioxido-6-(2,4,6-trichlorophenyl)-1,2,6-thiadiazinan-2-yl) acetamido)adamantan-1-carboxamide; and 4-(2-((R)-4-methyl-1,1-dioxido-6-(2,4,6-trichlorophenyl)-1,2,6-thiadiazinan-2-yl)acetamido)adamantan-1-carboxamide.

5. The sulfamide derivative or its pharmaceutically acceptable salt according to claim 4, wherein the derivative represented by the Formula 1 is selected from the group consisting of 4-(2-(4-methyl-1,1-dioxido-6-(2,4,6-trichlorophenyl)-1,2,6-thiadiazinan-2-yl)acetamido)adamantan-1-carboxamide; 4-(2-(6-(2,6-dichloro-4-(trifluoromethyl)phenyl)-4-methyl-1,1-dioxido-1,2,6-thiadiazinan-2-yl)acetamido) adamantan-1-carboxamide; 4-(2-((R)-6-(2,6-dichloro-4-(trifluoromethyl)phenyl)-4-methyl-1,1-dioxido-1,2,6-thiadiazinan-2-yl)acetamido)adamantan-1-carboxamide; 4-(2-((S)-4-methyl-1,1-dioxido-6-(2,4,6-trichlorophenyl)-1,2,6-thiadiazinan-2-yl)acetamido)adamantan-1-carboxamide; and 4-(2-((R)-4-methyl-1,1-dioxido-6-(2,4,6-trichlorophenyl)-1,2,6-thiadiazinan-2-yl)acetamido)adamantan-1-carboxamide.

6. The sulfamide derivative or its pharmaceutically acceptable salt according to claim 1, wherein the pharmaceutically acceptable salt comprises hydrochloric acid salt, sulfuric acid salt, acetic acid salt, trifluoroacetic acid salt, phosphoric acid salt, fumaric acid salt, maleic acid salt, citric acid salt, methane sulfonic acid salt or lactic acid salt.

7. A pharmaceutical composition which comprises as an active ingredient the sulfamide derivative having an adamantyl group or its pharmaceutically acceptable salt of claim 1.

8. A method for treating a 11β-HSD1-related disease selected from the group consisting of diabetes, obesity, dyslipidemia, hypertension, cognitive impairment, arthritis, osteoporosis, glaucoma and diseases caused by hvpoimmunity, which comprises administering the composition of claim 7 to a subject.

* * * * *